United States Patent
Kameyama

(10) Patent No.: US 8,108,083 B2
(45) Date of Patent: Jan. 31, 2012

(54) VEHICULAR SYSTEM WHICH RETRIEVES HOSPITALITY INFORMATION PROMOTING IMPROVEMENT OF USER'S CURRENT ENERGY VALUE BASED ON DETECTED TEMPORAL CHANGE OF BIOLOGICAL CONDITION

(75) Inventor: Shogo Kameyama, Chiryu (JP)

(73) Assignee: Denso Corporation, Kariya, Aichi-Pref. (JP)

( * ) Notice: Subject to any disclaimer, the term of this patent is extended or adjusted under 35 U.S.C. 154(b) by 1038 days.

(21) Appl. No.: 11/652,107

(22) Filed: Jan. 11, 2007

(65) Prior Publication Data

US 2007/0192038 A1    Aug. 16, 2007

(30) Foreign Application Priority Data

Feb. 13, 2006   (JP) ................... 2006-035812

(51) Int. Cl.
  G06F 17/00    (2006.01)
  G01C 21/00    (2006.01)
  G01C 21/36    (2006.01)
  B60K 28/02    (2006.01)
(52) U.S. Cl. ............ 701/1; 701/409; 701/538; 701/540; 702/1; 702/19; 180/272
(58) Field of Classification Search ........... 701/1, 29, 701/31, 35, 36, 45, 49, 200, 206, 208, 209; 702/1, 19; 340/988–990, 995.1, 995.14, 340/995.16, 995.18, 995.19, 995.27, 438, 340/439; 180/271, 272
See application file for complete search history.

(56) References Cited

U.S. PATENT DOCUMENTS

| 5,521,580 | A  | * | 5/1996  | Kaneko et al. ............... 340/439 |
| 5,573,006 | A  |   | 11/1996 | Shimotani et al. |
| 5,666,953 | A  | * | 9/1997  | Wilk ............................. 600/407 |
| 5,993,401 | A  | * | 11/1999 | Inbe et al. ...................... 601/46 |
| 6,599,243 | B2 | * | 7/2003  | Woltermann et al. ......... 600/300 |
| 6,957,207 | B2 |   | 10/2005 | Sasaki |
| 6,982,635 | B2 | * | 1/2006  | Obradovich .................. 340/439 |
| 7,027,621 | B1 | * | 4/2006  | Prokoski ....................... 382/118 |
| 7,187,292 | B2 | * | 3/2007  | Hayashi et al. ............... 340/576 |
| 7,292,152 | B2 | * | 11/2007 | Torkkola et al. .............. 340/576 |

(Continued)

FOREIGN PATENT DOCUMENTS

JP   09-044800   2/1997

(Continued)

OTHER PUBLICATIONS

Japanese Office Action dated Jan. 27, 2010, issued in corresponding Japanese Application No. 2006-035812, with English translation.

*Primary Examiner* — Jack W Keith
*Assistant Examiner* — Edward Pipala
(74) *Attorney, Agent, or Firm* — Nixon & Vanderhye PC

(57) ABSTRACT

In a system for providing vehicular hospitality information, biological characteristic information about a user using a vehicle is acquired. Then, in accordance with a predetermined correlation between the biological characteristic information and stored hospitality information, hospitality information matching the acquired biological characteristic information is retrieved and outputted. Accordingly, in accordance with a character, mental condition, or physical condition of each user, appropriate information can be provided timely and sensitively.

27 Claims, 80 Drawing Sheets

U.S. PATENT DOCUMENTS

| | | |
|---|---|---|
| 7,468,673 B2 * | 12/2008 | Sultan et al. .................. 340/576 |
| 7,532,964 B2 * | 5/2009 | Fujita et al. ..................... 701/36 |
| 2001/0049471 A1 | 12/2001 | Suzuki et al. |
| 2003/0060937 A1 * | 3/2003 | Shinada et al. ................... 701/1 |
| 2003/0073886 A1 | 4/2003 | Yanagidaira et al. |
| 2003/0195701 A1 * | 10/2003 | Ohler ............................ 701/209 |
| 2004/0093155 A1 * | 5/2004 | Simonds et al. ............. 701/200 |
| 2005/0137753 A1 * | 6/2005 | Basson et al. ..................... 701/1 |
| 2005/0278093 A1 * | 12/2005 | Kameyama ..................... 701/36 |
| 2006/0006990 A1 * | 1/2006 | Obradovich ................. 340/439 |
| 2006/0011399 A1 * | 1/2006 | Brockway et al. ............ 180/272 |
| 2006/0271258 A1 * | 11/2006 | Salmeen et al. ................ 701/45 |
| 2007/0032929 A1 * | 2/2007 | Yoshioka et al. ............... 701/35 |
| 2007/0158128 A1 * | 7/2007 | Gratz et al. ................... 180/287 |
| 2007/0219746 A1 * | 9/2007 | Vancil et al. ................. 702/182 |
| 2007/0225882 A1 * | 9/2007 | Yamaguchi et al. ............ 701/36 |
| 2007/0296601 A1 * | 12/2007 | Sultan et al. .................. 340/576 |
| 2008/0030313 A1 * | 2/2008 | Obradovich ................. 340/439 |
| 2008/0091309 A1 * | 4/2008 | Walker .............................. 701/1 |
| 2009/0132099 A1 * | 5/2009 | Kriger .............................. 701/1 |

FOREIGN PATENT DOCUMENTS

| | | |
|---|---|---|
| JP | 2000-020090 | 1/2000 |
| JP | 2000-193473 | 7/2000 |
| JP | 2000-351339 | 12/2000 |
| JP | 2001-194161 | 7/2001 |
| JP | 2001-317951 | 11/2001 |
| JP | 2001-357498 | 12/2001 |
| JP | 2002-056500 | 2/2002 |
| JP | 2002-071373 | 3/2002 |
| JP | 2005-338934 | 12/2005 |
| JP | 2006-048171 | 2/2006 |

* cited by examiner

MAIN HOSPITALITY PROCESS
- S101 — READ FLAG SCENE
- S102 — SET CURRENT SCENE
- S103 — READ THEME
- S104 — EXTRACT FUNCTION
- S105 — EXECUTE APPLICATION
- RETURN

350

| SCN1 | SCN2 | SCN3 | SCN4 | SCN5 | SCN6 |
|---|---|---|---|---|---|
| 1 | 1 | 1 | 0 | 0 | 0 |

351

| | |
|---|---|
| OBJ111 | APPLICATION 111-1 |
| | APPLICATION 111-2 |
| | ⋮ |
| OBJ121 | APPLICATION 121-1 |
| | APPLICATION 121-2 |
| | ⋮ |
| OBJ131 | APPLICATION 131-1 |
| | APPLICATION 131-2 |

FIG. 7A

| | OBJ111 | VEHI. EXTE. LIGHT | VEHI. INTE. LIGHT | POWER WINDOW (CLOSING) | NOISE CAN-CELLER | CAR AUDIO | VIDEO | MOBILE PHONE | DISTURBANCE TYPE | DETECTION UNIT |
|---|---|---|---|---|---|---|---|---|---|---|
| VEHI. INTE. BRIGHT-NESS | VEHI. EXTE. BRIGHTNESS | 5 | 3 | 0 | 0 | 0 | 0 | 0 | VEHI. EXTE. LIGHT DECREASE | VEHI. EXTE. LIGHT AMOUNT SENSOR |
| | EXTE. LIGHT | 0 | 0 | 0 | 0 | 0 | 0 | 0 | VEHI. INTE. LIGHT DECREASE | ILLUMINATION SENSOR 539 |
| | INTE. LIGHT | 0 | 0 | 2 | 0 | 0 | 0 | 0 | VEHI. INTE. LIGHT DECREASE | ILLUMINATION SENSOR 539 |
| NOISE SHIELD | SHIELD | 0 | 0 | 0 | 0 | 0 | 0 | 0 | VEHI. INTE. NOISE INCREASE | VEHI. EXTE. NOISE SENSOR 562 |
| | NOISE CANCEL | 0 | 0 | 0 | 0 | 0 | 0 | 0 | VEHI. INTE. NOISE INCREASE | NOISE DETEC. MICROPHONE 2011 |
| | ENTERTAINMENT | 5 | 3 | 0 | 0 | 5 | 0 | 5 | NONE OR MEN. PHYS. CONDITION | MEN./PHYS. CONDITION DETEC. PORTION |
| | INFORMATION | 0 | 0 | 0 | 0 | 0 | 0 | 0 | NONE OR MEN. PHYS. CONDITION | MEN./PHYS. CONDITION DETEC. PORTION |
| | VEHI. INTE. ENVIRONMENT | 0 | 0 | 0 | 0 | 0 | 0 | 0 | INCREASE/DECREASE OF VEHI. INTE. TEMP. | ROOM TEMP SENSOR 563, SUNSHINE SENSOR 564 |

| VEHI. EXTE. LIGHT LEVEL | VEHI. INTE. LIGHT LEVEL | NOISE LEVEL | MUSIC SOUND LEVEL |
|---|---|---|---|
| 8 | 5 | 0 | 5 |

| OBJ211 | | VEHI. EXTE. LIGHT | VEHI. INTE. LIGHT | POWER WINDOW (CLOSING) | NOISE CAN- CELLER | CAR AUDIO | VIDEO | MOBILE PHONE | DISTURBANCE TYPE | DETECTION UNIT |
|---|---|---|---|---|---|---|---|---|---|---|
| VEHI. INTE. BRIGHT- NESS | VEHI. EXTE. BRIGHTNESS | 5 | 3 | 0 | 0 | 0 | 0 | 0 | VEHI. EXTE. LIGHT DECREASE | VEHI. EXTE. LIGHT AMOUNT SENSOR |
| | EXTE. LIGHT | 0 | 0 | 0 | 0 | 0 | 0 | 0 | VEHI. INTE. LIGHT DECREASE | ILLUMINATION SENSOR 539 |
| | INTE. LIGHT | 0 | 0 | 0 | 0 | 0 | 0 | 0 | VEHI. INTE. LIGHT DECREASE | ILLUMINATION SENSOR 539 |
| NOISE SHIELD | SHIELD | 0 | 0 | 5 | 0 | 0 | 0 | 0 | VEHI. INTE. NOISE INCREASE | VEHI. EXTE. NOISE SENSOR 562 |
| | NOISE CANCEL | 0 | 0 | 0 | 0 | 0 | 0 | 0 | VEHI. INTE. NOISE INCREASE | NOISE DETEC. MICROPHONE 2011 |
| | ENTERTAINMENT | 5 | 3 | 0 | 0 | 0 | 0 | 5 | NONE OR MEN./ PHYS. CONDITION | MEN./PHYS. CONDITION DETEC. PORTION |
| | INFORMATION | 0 | 0 | 0 | 0 | 0 | 0 | 0 | NONE OR MEN./ PHYS. CONDITION | MEN./PHYS. CONDITION DETEC. PORTION |
| | VEHI. INTE. ENVIRONMENT | 0 | 0 | 0 | 0 | 0 | 0 | 0 | INCREASE/ DECREASE OF VEHI. INTE. TEMP. | ROOM TEMP. SENSOR 563, SUNSHINE SENSOR 564 |

| VEHI. EXTE. LIGHT LEVEL | VEHI. INTE. LIGHT LEVEL | NOISE LEVEL | MUSIC SOUND LEVEL |
|---|---|---|---|
| 6 | 4 | 0 | 4 |

FIG. 9A

| OBJ241 OBJ242 | VEHI. EXTE. LIGHT | VEHI. INTE. LIGHT | POWER WINDOW (CLOSING) | NOISE CAN-CELLER | CAR AUDIO | VIDEO | MOBILE PHONE | DISTURBANCE TYPE | DETECTION UNIT |
|---|---|---|---|---|---|---|---|---|---|
| VEHI. EXTE. BRIGHTNESS | 5 (or 0) | 0 | 0 | 0 | 0 | 0 | 0 | VEHI. EXTE. LIGHT DECREASE | VEHI. EXTE. LIGHT AMOUNT SENSOR |
| VEHI. INTE. BRIGHT-NESS / EXTE. LIGHT | 0 | 3 | 0 | 0 | 0 | 0 | 0 | VEHI. INTE. LIGHT DECREASE | ILLUMINATION SENSOR 539 |
| INTE. LIGHT | 0 | 5 | 0 | 0 | 0 | 0 | 0 | VEHI. INTE. LIGHT DECREASE | ILLUMINATION SENSOR 539 |
| NOISE SHIELD / SHIELD | 0 | 0 | 5 | 0 | 0 | 0 | 0 | VEHI. INTE. NOISE INCREASE | VEHI. EXTE. NOISE SENSOR 562 |
| NOISE CANCEL | 0 | 0 | 0 | 3 | 0 | 0 | 0 | VEHI. INTE. NOISE INCREASE | NOISE DETEC. MICROPHONE 2011 |
| ENTERTAINMENT | 0 | 0 | 0 | 0 | 5 | 0 | 0 | NONE OR MEN. PHYS. CONDITION | MEN./PHYS. CONDITION DETEC. PORTION |
| INFORMATION | 0 | 0 | 0 | 0 | 0 | 5 | 0 | NONE OR MEN. PHYS. CONDITION | MEN./PHYS. CONDITION DETEC. PORTION |
| VEHI. INTE. ENVIRONMENT | 0 | 0 | 0 | 0 | 0 | 0 | 0 | INCREASE/ DECREASE OF VEHI. INTE. TEMP. | ROOM TEMP. SENSOR 563, SUNSHINE SENSOR 564 |

| VEHI. EXTE. LIGHT LEVEL | VEHI. INTE. LIGHT LEVEL | NOISE LEVEL | MUSIC SOUND LEVEL |
|---|---|---|---|
| 10 (or 0) | 6 | 9 | 6 |

| OBJ311 | CAR NAVI-GATION | VEHI. GPS | MOBILE PHONE | MOBILE PHONE GPS | AIR CON. | HORN | LIGHT | DISTURBANCE TYPE | DETECTION UNIT |
|---|---|---|---|---|---|---|---|---|---|
| VEHI. POSITION | 0 | 0 | 5 | 0 | 0 | 3 | 4 | LONG DISTANCE | VEHICLE GPS 533, MOBILE PHONE GPS 554 |
| ROOM TEMP. | 0 | 0 | 0 | 0 | 0 | 0 | 0 | ROOM TEMP. INCREASE/DECREASE | ROOM TEMP. SENSOR 563, SUNSHINE SENSOR 564 |
| INFORMATION | 0 | 0 | 0 | 0 | 0 | 0 | 0 | NONE (MEN./PHYS. CONDITION) | MEN./PHYS. CONDITION DETEC. PORTION |

| OBJ331 | CAR NAVI-GATION | VEHI. GPS | MOBILE PHONE | MOBILE PHONE GPS | AIR CON. | HORN | LIGHT | DISTURBANCE TYPE | DETECTION UNIT |
|---|---|---|---|---|---|---|---|---|---|
| VEHI. POSITION | 0 | 0 | 0 | 0 | 0 | 0 | 0 | LONG DISTANCE | VEHICLE GPS 533, MOBILE PHONE GPS 554 |
| ROOM TEMP. | 0 | 5 | 0 | 0 | 0 | 0 | 0 | ROOM TEMP. INCREASE/DECREASE | ROOM TEMP. SENSOR 563, SUNSHINE SENSOR 564 |
| INFORMATION | 0 | 5 | 0 | 0 | 0 | 0 | 0 | NONE (MEN./PHYS. CONDITION) | MEN./PHYS. CONDITION DETEC. PORTION |

| OBJ441 | CAR NAVI-GATION | CAR AUDIO | AIR CON. | VEHI. INTE. LIGHT | STEERING ADJUSTMENT | SEAT ADJUSTMENT | DISTURBANCE TYPE | DETECTION UNIT |
|---|---|---|---|---|---|---|---|---|
| VEHI. INTE. ACCOMMODATION | 0 | 0 | 0 | 0 | 4 | 5 | NONE (OR POSITIONAL RELATIONSHIP) | USER DETEC. SENSOR 565 |
| VEHI. INTE. BRIGHTNESS | 0 | 0 | 0 | 4 | 0 | 0 | VEHI. INTE. LIGHT DECREASE | ILLUMINATION SENSOR 539 |
| VEHI. INTE. ENVIRONMENT | 0 | 0 | 4 | 0 | 0 | 0 | ROOM TEMP. INCREASE/DECREASE | ROOM TEMP. SENSOR 563, SUNSHINE SENSOR 564 |
| ENTERTAINMENT | 0 | 4 | 0 | 0 | 0 | 0 | NONE OR MEN./PHYS. CONDITION | MEN./PHYS. CONDITION DETEC. PORTION |
| INFORMATION | 5 | 0 | 0 | 0 | 0 | 0 | NONE OR MEN./PHYS. CONDITION | MEN./PHYS. CONDITION DETEC. PORTION |

| OBJ141 OBJ142 | VEHI. EXTE. LIGHT | VEHI. INTE. LIGHT | POWER WINDOW (CLOSING) | NOISE CAN- CELLER | CAR AUDIO | VIDEO | AIR CON. | SEAT VIBRA- TION | FRA- GRANCE | AWAKE- NING | DISTURBANCE TYPE | DETECTION UNIT |
|---|---|---|---|---|---|---|---|---|---|---|---|---|
| VEHI. EXTE. BRIGHTNESS | 5 (or 0) | 0 | 0 | 0 | 0 | 0 | 0 | 0 | 0 | 0 | VEHI. EXTE. LIGHT DECREASE | VEHI. EXTE. LIGHT AMOUNT SENSOR |
| EXTE. LIGHT | 0 | 3 | 0 | 0 | 0 | 0 | 0 | 0 | 0 | 0 | VEHI. INTE. LIGHT DECREASE | ILLUMINATION SENSOR 539 |
| INTE. LIGHT | 0 | 5 | 0 | 0 | 0 | 0 | 0 | 0 | 0 | 0 | VEHI. INTE. LIGHT DECREASE | ILLUMINATION SENSOR 539 |
| SHIELD | 0 | 0 | 5 | 0 | 0 | 0 | 0 | 0 | 0 | 0 | VEHI. INTE. NOISE INCREASE | VEHI. EXTE. NOISE SENSOR 562 |
| NOISE CANCEL | 0 | 0 | 0 | 4 | 0 | 0 | 0 | 0 | 0 | 0 | VEHI. INTE. NOISE INCREASE | NOISE DETEC. MICROPHONE 2011 |
| ENTER- TAINMENT | 0 | 0 | 0 | 0 | 5 | 4 | 0 | 2 | 0 | 0 | NONE (OR MEN./ PHYS. CONDITION) | MEN./PHYS. CONDITION DETEC. PORTION |
| VEHICLE INTE. ENVIRON- MENT | 0 | 0 | 0 | 0 | 0 | 0 | 4 | 3 | 3 | 0 | ROOM TEMP. INCREASE/ DECREASE (MEN./PHYS. CONDITION) | ROOM TEMP. SENSOR 563 SUNSHINE SENSOR 564 MEN./PHYS. CONDITION DETEC. PORTION |
| AB- NORMALITY | 0 | 0 | 0 | 5 | 5 | 0 | 0 | 0 | 0 | 3 | (MEN./PHYS. CONDITION) | MEN./PHYS. CONDITION DETEC. PORTION |

| SONG ID 1 | SONG NAME 1 | GENRE CODE 1 | CHARACTER CODE 1 | AGE CODE 1 | SEX CODE 1 | MUSIC DATA 1 | SONG MODE 1 |
|---|---|---|---|---|---|---|---|
| SONG ID 2 | SONG NAME 2 | GENRE CODE 2 | CHARACTER CODE 2 | AGE CODE 2 | SEX CODE 2 | MUSIC DATA 2 | SONG MODE 2 |
| SONG ID 3 | SONG NAME 3 | GENRE CODE 3 | CHARACTER CODE 3 | AGE CODE 3 | SEX CODE 3 | MUSIC DATA 3 | SONG MODE 3 |
| SONG ID 4 | SONG NAME 4 | GENRE CODE 4 | CHARACTER CODE 4 | AGE CODE 4 | SEX CODE 4 | MUSIC DATA 4 | SONG MODE 4 |
| ⋮ | ⋮ | ⋮ | ⋮ | ⋮ | ⋮ | ⋮ | ⋮ |

CHARACTER CODE (SKC)

SKC1: ACTIVE
SKC2: GENTLE
SKC3: OPTIMISTIC
SKC4: PESSIMISTIC
SKC5: DECADENT
SKC6: PHYSICAL
SKC7: INTELLIGENT
SKC8: ROMANTICIST

GENRE CODE (JC)

JC1: CLASSIC
JC2: JAZZ
JC3: ROCK
JC4: POPS
JC5: JAPANESE MUSIC
JC6: WORLD MUSIC
JC7: MOOD

AGE CODE (AC)

AC1: INFANT (TO 5 YEARS)
AC2: CHILD (6 TO 11)
AC3: JUNIOR (12 TO 17)
AC4: YOUTH (18 TO 27)
AC5: MIDDLE AGE (28 TO 37)
AC6: SENIOR (38 TO 45)
AC7: MATURE AGE (46 TO 63)
AC8: OLD AGE (64 TO OVER)
AC9: REGARDLESS OF AGE

SEX CODE (SC)

SC1: MALE
SC2: FEMALE
SC3: REGARDLESS OF SEX

SONG MODE

AG: UPLIFTING, ACTIVATING
ST: REFRESHING
SF: MILD, SOOTHING
HL: HEALING, $\alpha$-WAVE

FIG. 19

| CHARACTER CODE | LIGHT COLOR CODE | LIGHTING PATTERN CONTROL DATA | |
|---|---|---|---|
| SKC1 | CC1 | CD1 (RED FLASH) | 402 |
| SKC2 | CC2 | CD2 (UMBER/FADE) | |
| SKC3 | CC3 | CD3 (BLUE CONTINUOUS FLASHING) | |
| ⋮ | ⋮ | ⋮ | |

FIG. 20

| DATE | USER | SEX | AGE | SONG ID | 403 |
|---|---|---|---|---|---|
| DATE1 | AY | M | 48 | ID301 | RD 1 |
| DATE2 | BX | F | 40 | ID211 | RD 2 |
| DATE3 | CZ | M | 21 | ID33 | RD 3 |
| ⋮ | ⋮ | ⋮ | ⋮ | | |

USER AY (COMPLIATION PERIOD: NEAREST ONE MONTH)

| JC1 : 32 | SKC1 : 4 | AC1 : 0 | SC1 : 51 |
| JC2 : 6 | SKC2 : 7 | AC2 : 0 | SC2 : 7 |
| JC3 : 11 | SKC3 : 21 | AC5 : 34 | SC3 : 32 |
| | SKC4 : 4 | AC6 : 21 | |

| USER | TRAVEL DISTANCE L | ORDINARY WAY (OW) /EXPRESS WAY (EW) | | |
|---|---|---|---|---|
| NUMBER OF HORNS $N_h$ | NUMBER OF BRAKES $N_B$ | NUMBER OF LANE CHANGES $N_{LC}$ | AVERAGE SPEED $V_N$ | AVERAGE ACCELERATION $A_N$ |

- STEERING
- LANE KEEPING $(N_h)_Q : \{(N_h)_O \times \beta_1 + (N_h)_E \times \alpha_1\}/L$ $(N_B)_Q : \{(N_B)_O \times \beta_2 + (N_B)_E \times \alpha_2\}/L$ $(N_{LC})_Q : \{(N_{LC})_O \times \beta_3 + (N_{LC})_E \times \alpha_3\}/L$ $(V_N)_Q : (V_N)_O \times \beta_4 + (V_N)_E \times \alpha_4$ $(A_N)_Q : (A_N)_O \times \beta_5 + (A_N)_E \times \alpha_5$ $\Sigma Ch = (N_h)_Q + (N_B)_Q + (N_{LC})_Q + (V_N)_Q + (A_N)_Q$

| $\Sigma Ch$ | $A_1 < \Sigma Ch \leq A_2$ | $A_2 < \Sigma Ch \leq A_3$ | $A_3 < \Sigma Ch \leq A_4$ |
|---|---|---|---|
| | GENTLE (SKC2) OPTIMISTIC (SKC3) ROMANTICIST (SKC8) | INTELLIGENT (SKC7) DECADENT (SKC5) | ACTIVE (SKC1) PHYSICAL (SKC2) PESSIMISTIC (SKC3) |
| REDUCTION FACTOR | $\delta_1$ | $\delta_2$ | $\delta_3$ |

| FIG. 51A |
|----------|
| FIG. 51B |

| Biometric Condition Parameter / Specified Condition | Control | Blood Press. Change | Blood Press. Direc. | Body Temp. Change | Body Temp. Direc. | Skin Resis. Change | Skin Resis. Direc. | Facial Express. Meaning | Facial Express. Change | Posture Change | Posture Speed |
|---|---|---|---|---|---|---|---|---|---|---|---|
| NORMAL | | NORMAL | NORMAL | NORMAL | NORMAL | NORMAL | NORMAL | NORMAL | NORMAL | NORMAL | NORMAL |
| DISTRACTION | MINIMUM | RAPID | CHANGE | NORMAL | NORMAL | RAPID | INCR. | FACE DIREC. | RAPID INCR. | INCR. AND DECR. | NORMAL |
| SLIGHTLY POOR PHYSICAL | SMALL | SLOW | NORMAL | SLOW | NORMAL | NORMAL | NORMAL | DISPLEA-SURE | SLIGHT INCR. | SLIGHT INCR. | NORMAL |
| CONDITION/DISPLEASURE SERIOUS PHYSICAL CONDITION | LARGE | SLOW | NORMAL | SLOW | NORMAL | SLOW | INCR. | DISPLEA-SURE | INCR. | INCR. AND DECR. | DECR. |
| EXCITATION (INSTABILITY) | MEDIUM | RAPID | CHANGE | RAPID | CHANGE | RAPID | DECR. | EXCI-TATION | RAPID INCR. | RAPID INCR. | INCR. |
| SLIGHTLY POOR PHYSICAL CONDITION AND DISTRACTION | SMALL | RAPID | CHANGE | SLOW | NORMAL | RAPID | INCR. | FACE DIREC./ DISPLEA-SURE | INCR. | INCR. AND DECR. | NORMAL |
| DISTRACTION AND SERIOUS PHYSICAL CONDITION | LARGE | RAPID | CHANGE | SLOW | NORMAL | SLOW | INCR. | DISPLEA-SURE | INCR. | INCR. AND DECR. | DECR. |
| SLIGHTLY POOR PHYSICAL CONDITION AND EXCITATION | MEDIUM | RAPID | NORMAL | RAPID | NORMAL | RAPID | DECR. | EXCI-TATION | RAPID INCR. | RAPID INCR. | INCR. |
| SERIOUS PHYSICAL CONDITION AND EXCITATION | LARGE | RAPID | NORMAL | RAPID | NORMAL | RAPID | DECR. | EXCI-TATION/ DISPLEA-SURE | RAPID INCR. | INCR. AND DECR. | DECR. |

FIG. 51B

| LINE OF SIGHT | | | PUPIL | STEERING | | MATCHING COUNTER | |
|---|---|---|---|---|---|---|---|
| CHANGE | SPEED | PATTERN | DIAMETER | ERROR | SPEED | (MATCHED NUMBER) | (TOTAL DEVIA. POINT) |
| NORMAL | NORMAL | NORMAL | NORMAL | NORMAL | NORMAL | $N_0$ | $\nu_0$ |
| RAPID INCR. | NORMAL | CHANGE | CHANGE | INCR. | NORMAL | $N_1$ | $\mu_1$ |
| DECR. | NORMAL | NORMAL | NORMAL | NORMAL | NORMAL | $N_2$ | $\mu_2$ |
| LARGE DECR. | LARGE DECR. | CHANGE | NORMAL | INCR. | DECR. | $N_3$ | $\mu_3$ |
| LARGE DECR. | RAPID INCR. | CHANGE | OPEN | INCR. | INCR. | $N_4$ | $\mu_4$ |
| RAPID INCR. | NORMAL | CHANGE | CHANGE | INCR. | NORMAL | $N_{12}$ | $\mu_{12}$ |
| LARGE DECR. | LARGE DECR. | CHANGE | CHANGE | INCR. | DECR. | $N_{13}$ | $\mu_{13}$ |
| LARGE DECR. | RAPID INCR. | CHANGE | OPEN | INCR. | INCR. | $N_{24}$ | $\mu_{24}$ |
| LARGE DECR. | LARGE DECR. | CHANGE | OPEN | INCR. | INCR. | $N_{34}$ | $\mu_{34}$ |

1601

FIG. 52A
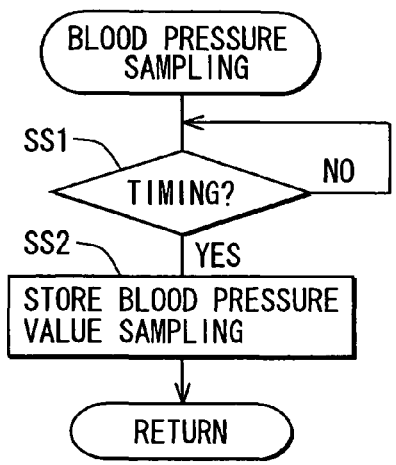
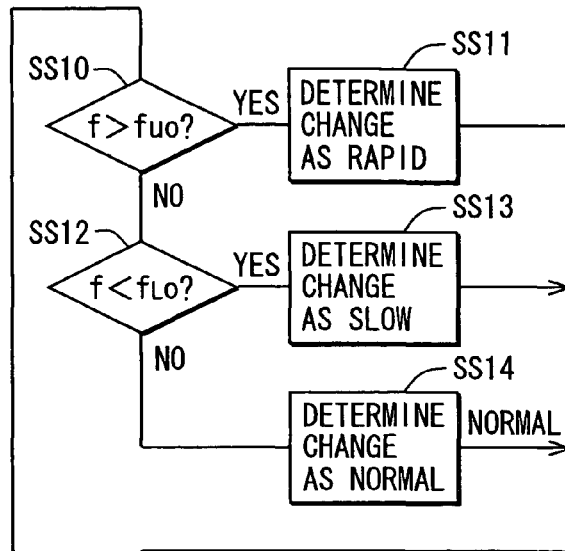
FIG. 52B
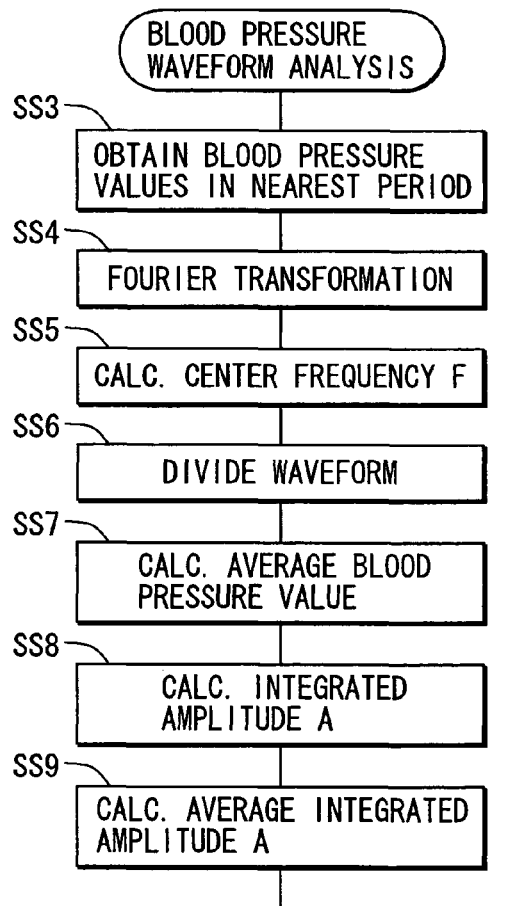
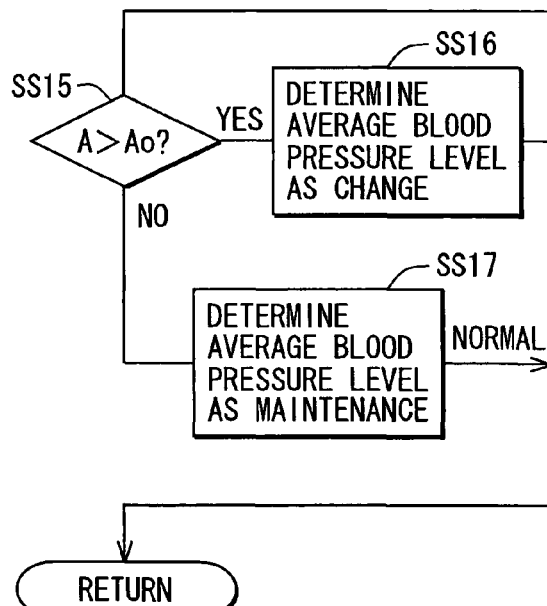

FIG. 54A
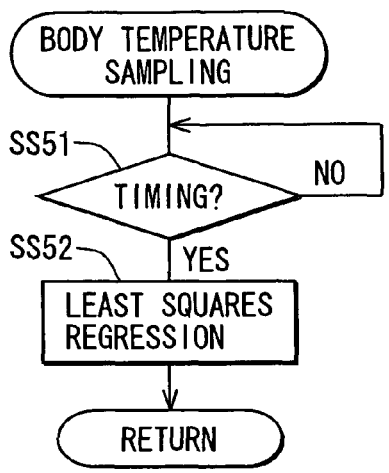
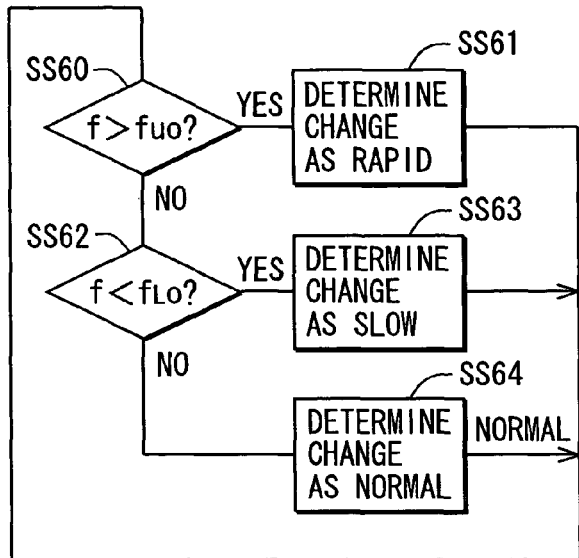
FIG. 54B
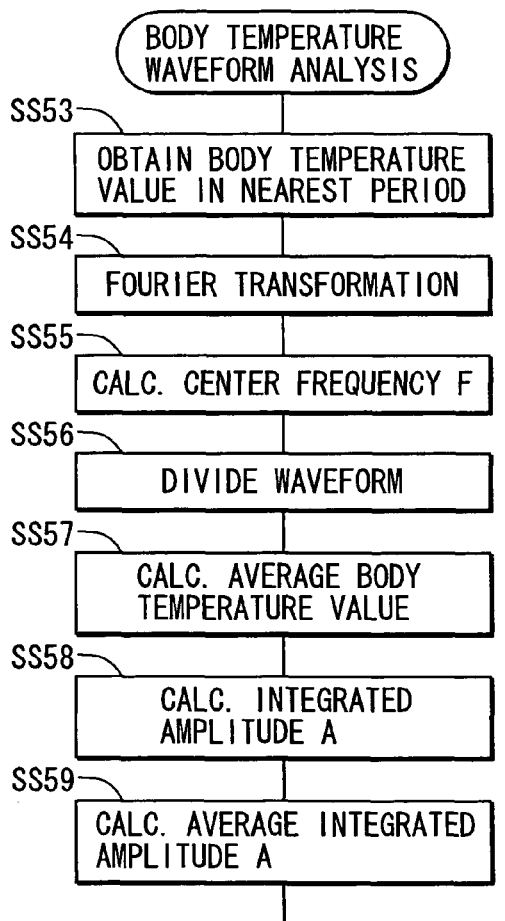
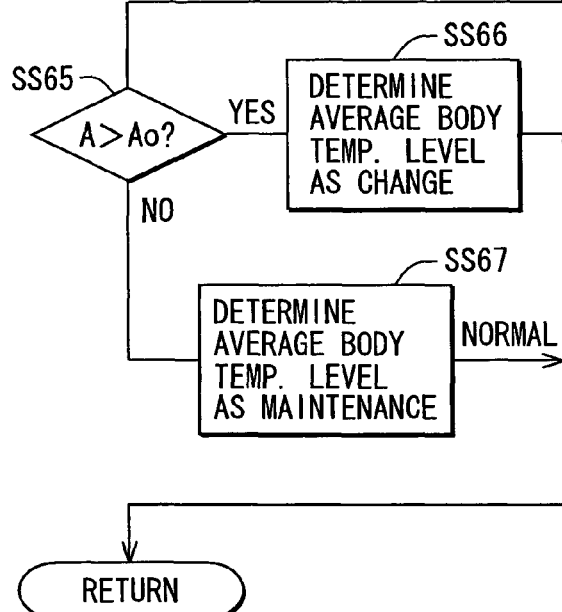

FIG. 55A
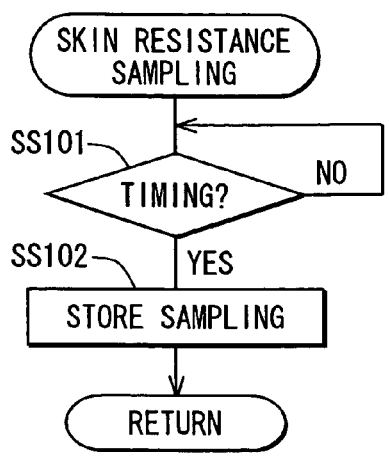
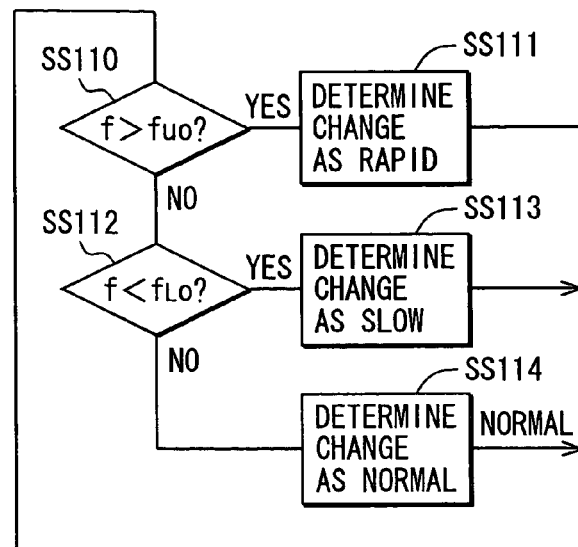
FIG. 55B
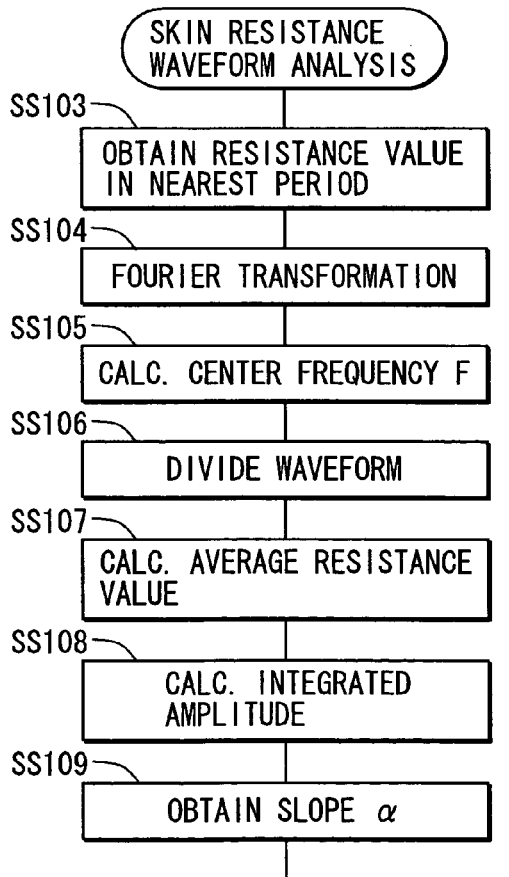
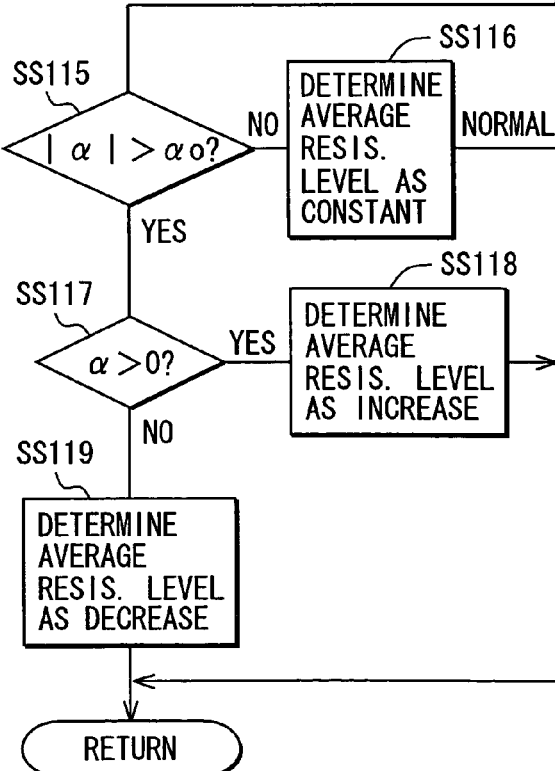

FIG. 57A
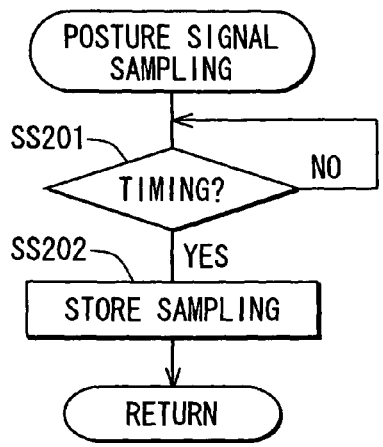
FIG. 57B
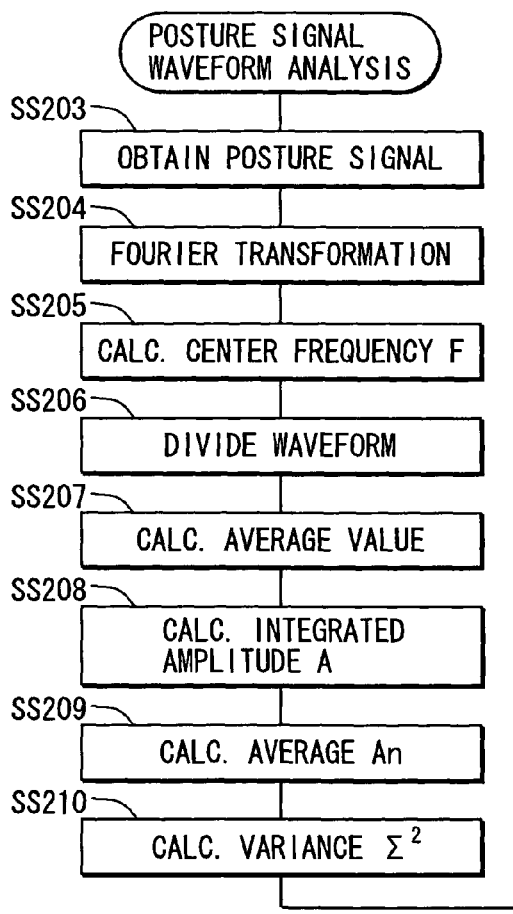
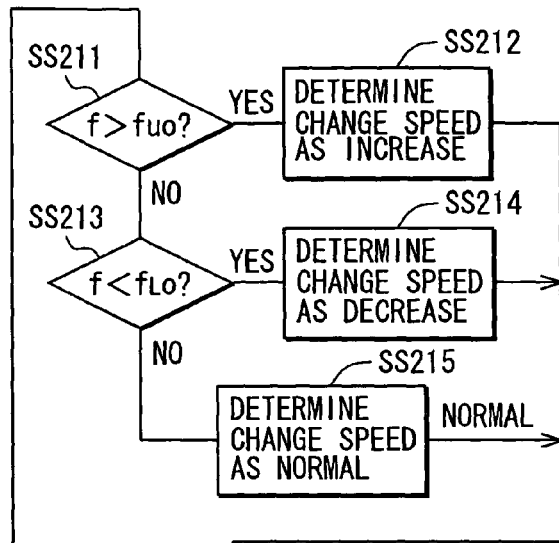
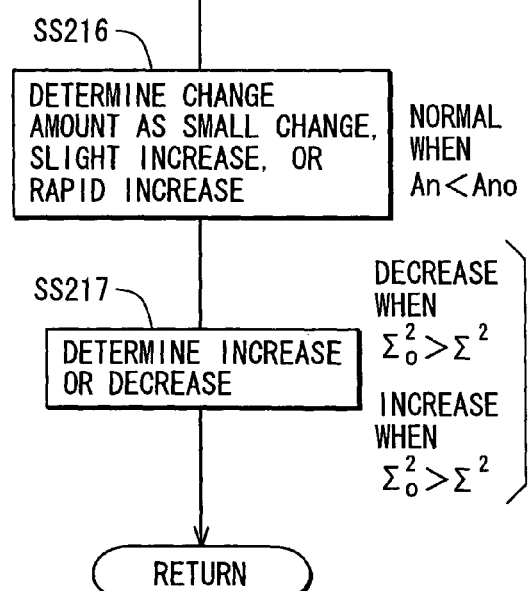

WHEN FRONT POSTURE IS STABLE: NEUTRAL POINT
WHEN POSTURE IS SHIFTED LEFT: SHIFT TO +
WHEN POSTURE IS SHIFTED RIGHT: SHIFT TO −

FIG. 60A
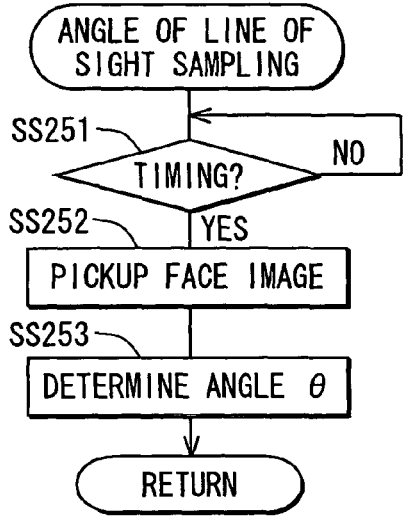
FIG. 60B
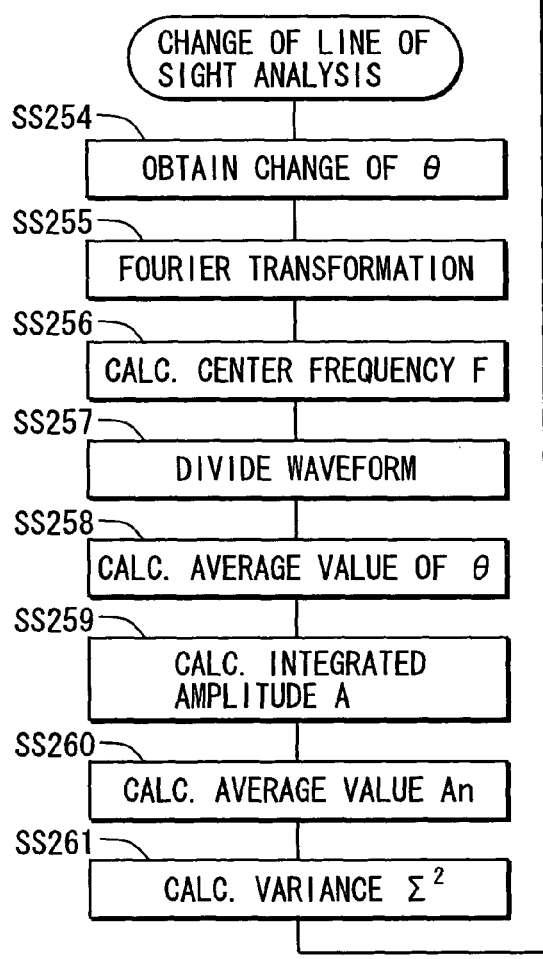
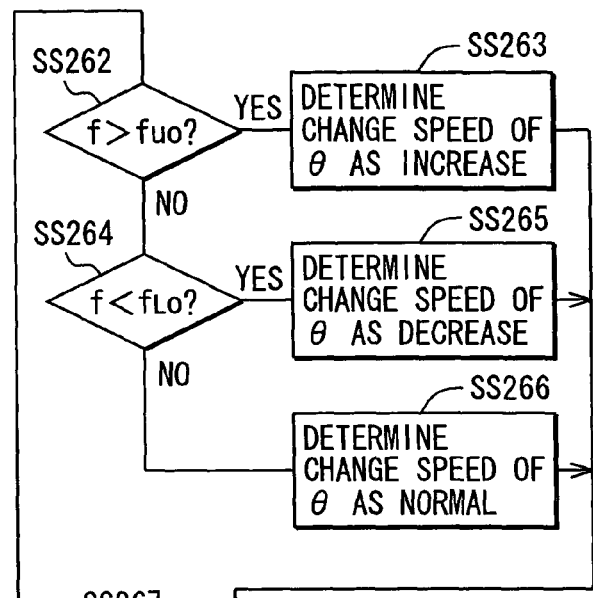
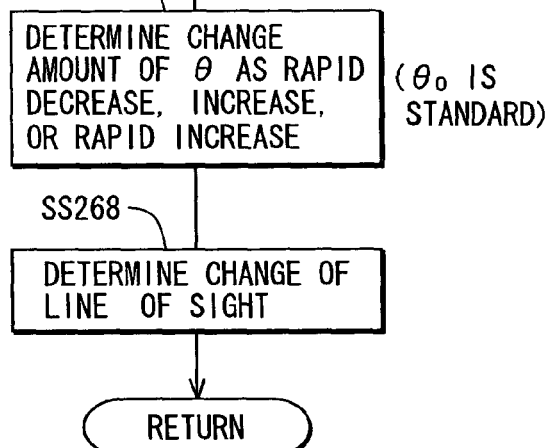

FIG. 61A
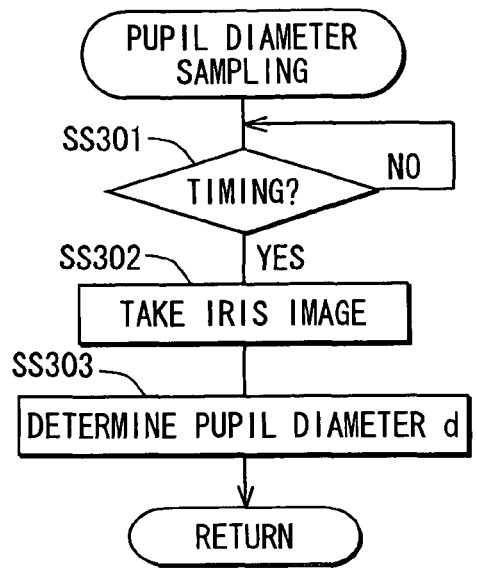
FIG. 61B
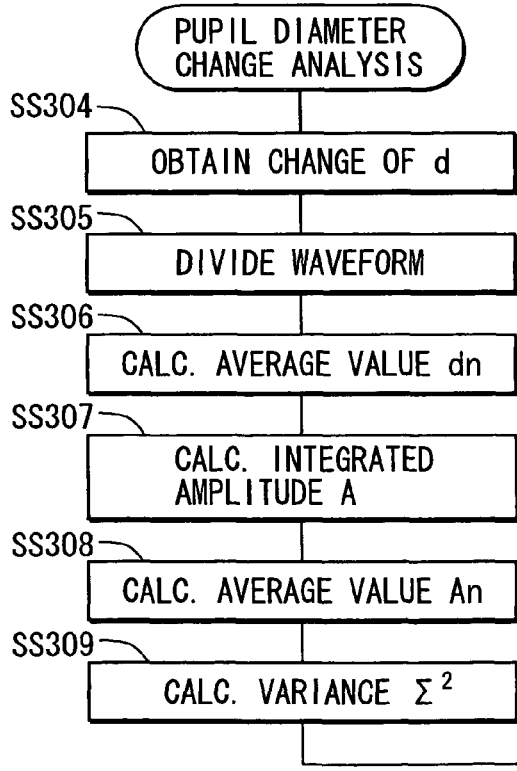
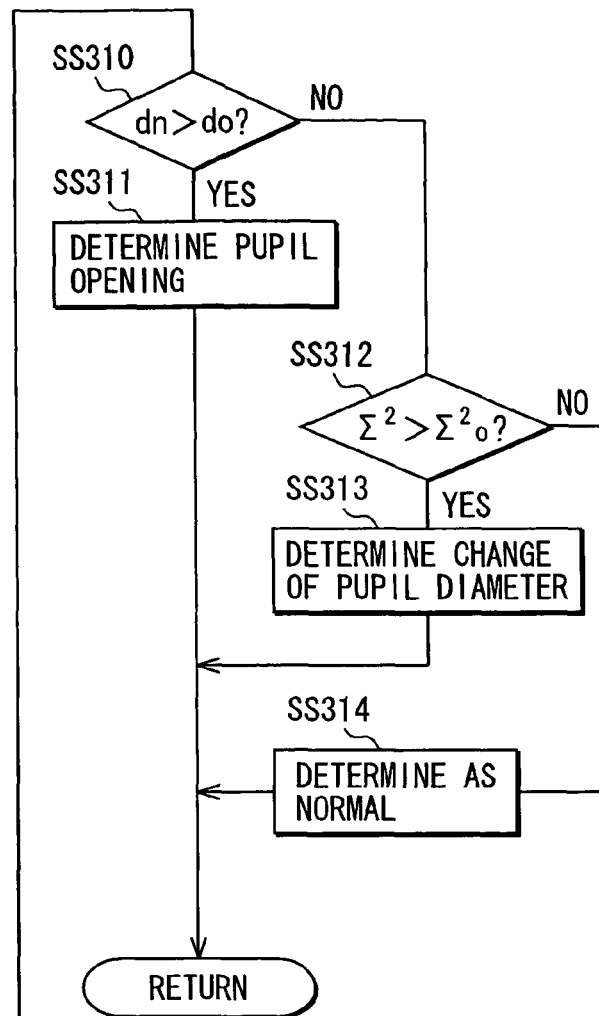

FIG. 62A
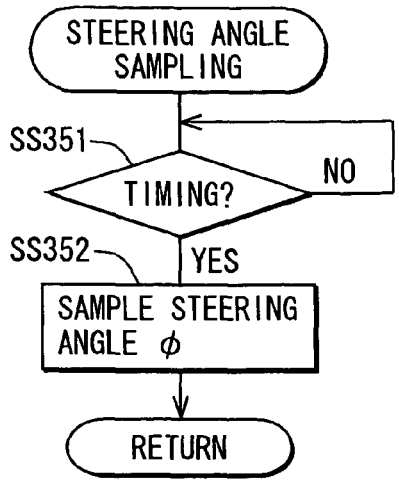
FIG. 62B
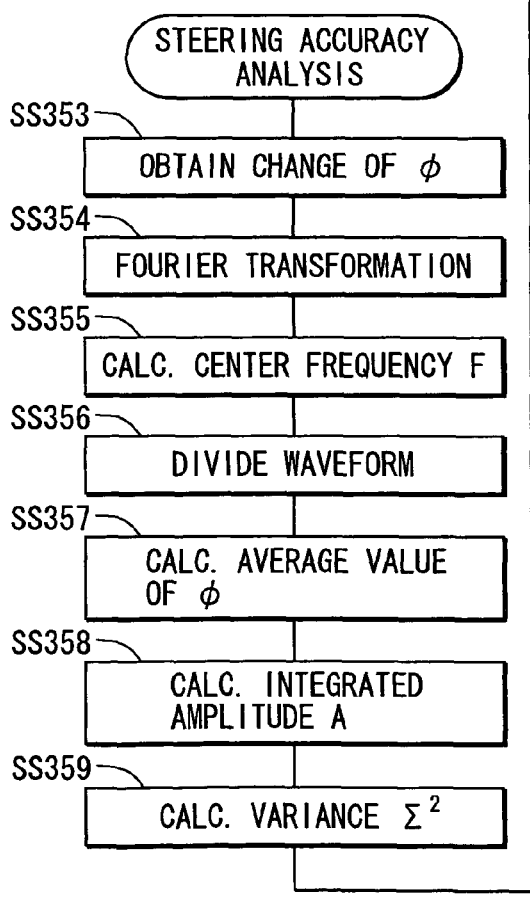
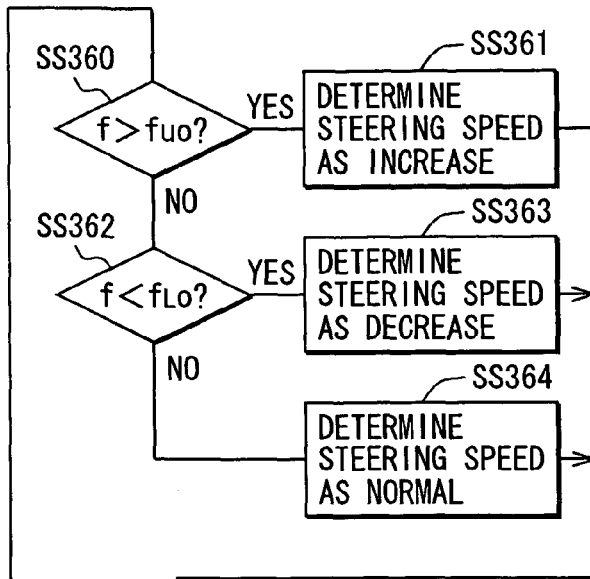
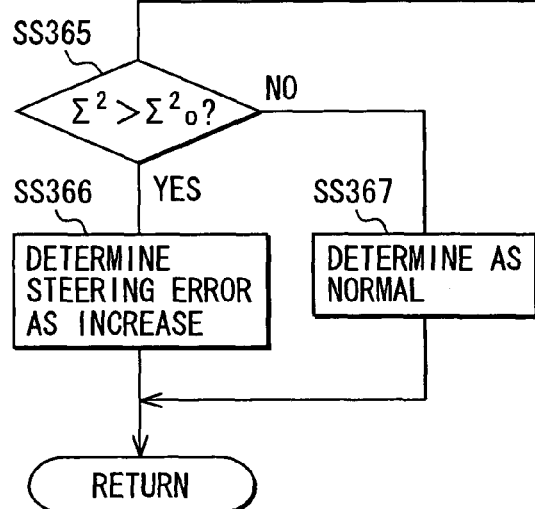

CENTER OF LANE POSITION
CENTER OF VEHICLE WIDTH POSITION

FIG. 67

| | DETECTION ITEM | VISION | AUDITION | TACTILITY OR AIR-CONDITIONING | OLFACTION |
|---|---|---|---|---|---|
| | — | MAINTENANCE | MAINTENANCE | MAINTENANCE | MAINTENANCE |
| A | SLIGHTLY POOR PHYSICAL CONDITION | DECREASE LESS REQUIRED LIGHT (ASSIST RECOGNITION) | DECREASE SOUND OTHER THAN WARNING SOUND/IMPORTANT SOUND | ABSORB IMPACT INCREASE ASSIST AMOUNT HIGH TEMPERATURE/HUMIDITY | — |
| B | SERIOUS PHYSICAL CONDITION | DARK WHITE (WARM) | LOW SOUND VOLUME, EASY | — | RELAXING FRAGRANCE |
| C | DISTRACTION | FLASH REFLECTION LIGHT (SIMULATIVE WAVELENGTH) | WARNING SOUND INCREASE AV SOUND VOLUME | IMPULSE VIBRATION (STEERING WHEEL, SEAT) | AWAKENING (HARD) |
| D | EXCITATION (INSTABILITY) | BLUE (COLD COLOR) | EASY | SLOW RHYTHM VIBRATION (SEAT), LOW TEMPERATURE | — |

FIG. 68

| | DETECTION ITEM | VISION | AUDITION | AIR CONDITIONING | VIBRATION | OLFACTION |
|---|---|---|---|---|---|---|
| | — | MAINTENANCE | MAINTENANCE | MAINTENANCE | MAINTENANCE | MAINTENANCE |
| A | SLIGHTLY POOR PHYSICAL CONDITION | RED LIGHT OUTPUT | REQUIRED SOUND LOADING +3 LOW TONE SOUND +1 HIGH TONE SOUND −1 | SET TEMPERATURE +1 START HUMIDIFICATION | MAINTENANCE | MAINTENANCE |
| B | SERIOUS PHYSICAL CONDITION | LIGHTING LEVEL −1 TO LIGHTING COLOR +1 | CHANGE SONG → LEVEL −1 TO → TURN-OFF | MAINTENANCE | TURN-OFF | FRAGRANCE +1 |
| C | DISTRACTION | LIGHTING COLOR −1 LIGHTING PATTERN 1 LIGHTING LEVEL +1 | OUTPUT WARNING SOUND IMMEDIATELY LEVEL +1 | MAINTENANCE | FREQUENCY +3 AMPLITUDE +3 | FRAGRANCE 0 AWAKENING +5 |
| D | EXCITATION (INSTABILITY) | LIGHTING COLOR −1 | CHANGE SONG | SET TEMPERATURE −1 | FREQUENCY −1 AMPLITUDE −1 | MAINTENANCE |

| VEHICLE INTERIOR LIGHTING LEVEL | LIGHTING COLOR | AIR-CONDITIONING SETTING | SEAT VIBRATION (AMPLITUDE) | SEAT VIBRATION (FREQUENCY) | FRAGRANCE | AWAKENING | MUSIC SOUND LEVEL | REQUIRED SOUND LOADING | OUTPUT WARNING SOUND |
|---|---|---|---|---|---|---|---|---|---|
| 7 | 6 | 4 | 3 | 2 | 5 | 0 | 6 | 5 | 7 |

~371a

VEHICLE          USER

"HOW IS THE LEVEL OF THE AIR CONDITIONER?" → "A LITTLE TOO HOT."   : AIR-CONDITIONING SETTING 4 TO 3

"DO YOU LIKE THE FRAGRANCE?" → "TOO HARD."   : FRAGRANCE 5 TO 4

"IS THE SOUND NOISY?" → "RAISE THE VOLUME EXTREMELY."   : MUSIC SOUND 6 TO 7

"ARE YOU RELAXED?" → "A LITTLE NERVOUS."   : LIGHTING COLOR 6 TO 7
    LIGHTING LEVEL 7 TO 6
    SEAT VIBRATION AMPLITUDE 3 TO 2

| VEHICLE INTERIOR LIGHTING LEVEL | LIGHTING COLOR | AIR-CONDITIONING SETTING | SEAT VIBRATION (AMPLITUDE) | SEAT VIBRATION (FREQUENCY) | FRAGRANCE | AWAKENING | MUSIC SOUND LEVEL | REQUIRED SOUND LOADING | OUTPUT WARNING SOUND |
|---|---|---|---|---|---|---|---|---|---|
| 6 | 7 | 3 | 2 | 2 | 4 | 0 | 7 | 5 | 7 |

EMERGENCY

| VEHICLE INTERIOR LIGHTING LEVEL | LIGHTING COLOR | AIR-CONDITIONING SETTING | SEAT VIBRATION (AMPLITUDE) | SEAT VIBRATION (CYCLE) | FRAGRANCE | AWAKENING | MUSIC SOUND LEVEL | REQUIRED SOUND LOADING | OUTPUT WARNING SOUND |
|---|---|---|---|---|---|---|---|---|---|
| 7 | 6 | 4 | 3 | 2 | 5 | 0 | 6 | 6 | 9 |

ABNORMALITY (SERIOUS PHYSICAL CONDITION)

| VEHICLE INTERIOR LIGHTING LEVEL | LIGHTING COLOR | AIR-CONDITIONING SETTING | SEAT VIBRATION (AMPLITUDE) | SEAT VIBRATION (CYCLE) | FRAGRANCE | AWAKENING | MUSIC SOUND LEVEL | REQUIRED SOUND LOADING | OUTPUT WARNING SOUND |
|---|---|---|---|---|---|---|---|---|---|
| 7 | 6 | 4 | 3 | 2 | 5 | 7 | 6 | 8 | 9 |

AUDIO

| LEVEL | HIGH TONE SOUND | LOW TONE SOUND |
|---|---|---|
| 6 | 5 | 5 |

FULL COLOR LIGHTING

| LIGHTING LEVEL | LIGHTING COLOR | LIGHTING PATTERN |
|---|---|---|
| 7 | 6 | 0 |

(0: CONTINUOUS LIGHTING)
(1: FLASH LIGHTING)

FIG. 73A

| | 440 |
|---|---|
| USER ID/PERSONAL IDENTIFICATION NUMBER | 401 |
| BIOMETRICS MASTER DATA | 432 |
| MUSIC SELECTION DATA | 403 |
| MUSIC SELECTION STATISTICS DATA | 404 |
| DETERMINATION TABLE | 601 |
| QUESTION DATA | 433 |
| USER DEFAULT SETTING DATA | 434 |
| USER METAL/PHYSICAL CONDITION DETERMINATION THRESHOLD | 435 |
| STRESS REFLECTION OPERATION STATISTICS DATA | 405 |

FIG. 73B

| OPERATION ID 1 | CONTROL DIRECTION 1 | QUESTION DATA 1 |
|---|---|---|
| OPERATION ID 2 | CONTROL DIRECTION 2 | QUESTION DATA 2 |
| ⋮ | ⋮ | ⋮ |

FIG. 72

| R | R | G | B | MIXED COLOR |
|---|---|---|---|---|
| 0 | 1 | 1 | 1 | WHITE |
| 1 | 1 | 0.5 | 1 | PALE PURPLE |
| 2 | 1 | 0 | 1 | PURPLE |
| 3 | 0.5 | 0 | 1 | BLUISH PURPLE |
| 4 | 0 | 0 | 1 | BLUE |
| 5 | 0.5 | 0.5 | 1 | PALE BLUE |
| 6 | 1 | 1 | 1 | WHITE |
| 7 | 1 | 1 | 0.5 | PALE ORANGE |
| 8 | 1 | 1 | 0 | ORANGE |
| 9 | 1 | 0 | 0 | RED |
| 10 | 1 | 0.5 | 0.5 | PINK |
| 11 | 1 | 1 | 1 | WHITE |
| 12 | 0.5 | 1 | 1 | LEMON |
| 13 | 0 | 1 | 1 | YELLOW |
| 14 | 0 | 1 | 0 | PALE GREEN |

FIG. 77

| FIG. 77A |
|---|
| FIG. 77B |

| SLIGHTLY POOR PHYSICAL CONDITION | WEIGHTING FACTOR | | | | | | | |
|---|---|---|---|---|---|---|---|---|
| | (W1) | W2 | W3 | W4 | W5 | W6 | W7 | W8 |
| IN-VIVO CONDITION PARAMETER | BLOOD PRESSURE | DIREC. | BODY TEMPERATURE | | SKIN RESISTANCE | DIREC. | FACIAL EXPRESSION | |
| | CHANGE | | CHANGE | DIREC. | CHANGE | | MEANING | CHANGE |
| CONTRIBUTION | 「2」(SLOW) | 「1」(CHANGE) | 「2」(SLOW) | 「0」(MAINTE.) | 「1」(SLOW) | 「0」(MAINTE.) | 「2」(DISPLE.) | 「1」(INCR.) |
| $\Delta \mu / \Delta \nu$ | $\Delta \mu_1$ | $\Delta \mu_2$ | $\Delta \mu_3$ | $\Delta \nu_4$ | $\Delta \mu_5$ | $\Delta \nu_6$ | $\Delta \mu_7$ | $\Delta \mu_8$ |

* 「2」 ····· ABNORMAL (POSITIVE CONTRIBUTION)    ($\Delta \mu > 0$)
  「1」 ····· NEUTRAL (NEGATIVE CONTRIBUTION)
  「0」 ····· NORMAL (NEGATIVE CONTRIBUTION)

$\Delta \mu_1 > \Delta \mu_3 > \Delta \mu_8 > \Delta \mu_7 > \Delta \mu_{10}$ $\Delta \nu_4 > \Delta \nu_9 > \Delta \nu_6 \; \Delta \nu_{12} > \Delta \nu_{15} > \Delta \nu_{14}$ $\nu = \Delta \nu_4 + \Delta \nu_9 + \Delta \nu_6 + \Delta \nu_{12} + \Delta \nu_{15} + \Delta \nu_{14}$ ······(7)

$\mu = \Delta \mu_1 + \Delta \mu_3 + \Delta \mu_8 + \Delta \mu_7 + \Delta \mu_{10}$ ······(8)

WHEN WEIGHTING FACTOR IS USED $\nu = W_4 \Delta \nu_4 + W_9 \Delta \nu_9 + W_6 \Delta \nu_6 + W_{12} \Delta \nu_{12} + W_{15} \Delta \nu_{15} + W_{14} \Delta \nu_{14}$ ······(9)

$\mu = W_1 \Delta \mu_1 + W_3 \Delta \mu_3 + W_8 \Delta \mu_8 + W_7 \Delta \mu_7 + W_{10} \Delta \mu_{10}$ ······(10)

FIG. 77B

| $W_9$ | $W_{10}$ | $W_{11}$ | $W_{12}$ | $W_{13}$ | $W_{14}$ | $W_{15}$ | $W_{16}$ |
|---|---|---|---|---|---|---|---|
| POSTURE | | LINE OF SIGHT | | | PUPIL | STEERING | |
| CHANGE | SPEED | CHANGE | SPEED | PATTERN | DIAMETER | ERROR | SPEED |
| 「2」(SLI. INCR.) | 「0」(NORMAL) | 「2」(DECR.) | 「1」(DECR.) | 「2」(CHANGE) | 「1」(CHANGE) | 「0」(NORMAL) | 「0」(NORMAL) |
| $\Delta\mu_9$ | $\Delta\nu_{10}$ | $\Delta\mu_{11}$ | $\Delta\mu_{12}$ | $\Delta\nu_{13}$ | $\Delta\mu_{14}$ | $\Delta\nu_{15}$ | $\Delta\nu_{16}$ |

FIG. 82

|  |  | BODY | | MENTALITY | |
|---|---|---|---|---|---|
|  |  | +INFLUENCE | -INFLUENCE | +INFLUENCE | -INFLUENCE |
| ENERGY | EXCESS | STAMINA MAINTAINED | — | *HIGH-TENSION, VIGOR | *HIGH-TENSION, EXCITEMENT |
| ENERGY | MODERATE | EASY | *(SLEEPINESS) | COMFORTABLE | *(SLEEPINESS) |
| ENERGY | INSUFFI-CIENT | — | *HUNGRY/ THIRSTY | — | *LANGUOR, LACK OF CONCENTRATION |
| STRESS | EXCESS | — | *TIGHTNESS/ FATIGUE/ STRAIN | — | PRESSURE/ FATIGUE |
| STRESS | MODERATE | COMFORTABLE | — | COMFORTABLE | — |
| STRESS | INSUFFI-CIENT | COMFORTABLE | — | ABSENT | *LACK OF SENSE OF TENSION |
| DAMAGE | EXCESS | — | *SERIOUS ILLNESS (SERIOUS PHYSICAL CONDITION) | — | *NEUROSIS |
| DAMAGE | MEDIUM | — | *SLIGHT ILLNESS (SLIGHTLY-POOR PHYSICAL CONDITION) | — | *DEPRESSION |

| PLACE | BODY | | MENTALITY |
|---|---|---|---|
| | EATING | DRINKING | INFORMATION |
| PETROL STATION | × | △ | × |
| CONVENIENCE STORE | ○ | ○ | ○ |
| FAMILY RESTAURANT | ○ | ○ | × |
| ROADSIDE STATION | ○ | ○ | ○ |
| MUSIC SHOP | × | × | ○ |
| DEPARTMENT STORE | ○ | ○ | ○ |
| SIGHTSEEING PLACE | × | × | ○ |
| ... | ... | ... | ... |

○ : SUPPLY
△ : LITTLE SUPPLY
× : NO SUPPLY

VEHICULAR SYSTEM WHICH RETRIEVES HOSPITALITY INFORMATION PROMOTING IMPROVEMENT OF USER'S CURRENT ENERGY VALUE BASED ON DETECTED TEMPORAL CHANGE OF BIOLOGICAL CONDITION

CROSS REFERENCE TO RELATED APPLICATION

This application is based on and incorporates herein by reference Japanese Patent Application No. 2006-35812 filed on Feb. 13, 2006.

FIELD OF THE INVENTION

The present invention relates to a system for efficiently providing the vehicular hospitality information to be used for assisting an in-vehicle user in using a vehicle or for entertaining the in-vehicle user.

BACKGROUND OF THE INVENTION

JP-2003-118421 A discloses a technique for detecting biological information about a user on the premise that a condition of the user is stable so that the information is reflected by a control of a navigation apparatus. JP-2003-118421 A further discloses another technique. Correlations are stored between (i) given information such as music and images or texts selected by a user from a database and (ii) biological information about the user when selecting the given information. The correlations are used for library creation in accordance with the tendency acquired from the biological information.

The apparatus of JP-2003-118421 A involves the below problems. Stabilization of the condition of the user takes a waiting time, and thus detailed information corresponding to the constantly changing condition of the user cannot be provided. For example, JP-2003-118421 A does not disclose an idea that can stabilize the user who becomes nervous or flares due to an outer factor and guide the user to a comfortable driving. Further, the apparatus of JP-2003-118421 A is so configured as to relatively recognize what condition the biological information concretely would be by storing the results of many events and correlating the biological information with the results. Therefore, mental and physical conditions of the user (for example, emotions and physical fatigue) cannot be specified directly. In addition, the relative recognition needs the accumulation of the long-running study for and storage of those results, leading to a problem where the user cannot use such function just after his or her purchase of the vehicle.

The apparatus of JP-2003-118421 A has another problem in which it is so configured as to use the acquired correlations between the biological information and the event information only for library creation, so the user needs to determine his or her mental and physical conditions by himself or herself, and to access the matched library to acquire the information by himself or herself. Therefore, in view of voluntary hospitality (information service) from the vehicle, the above apparatus is not satisfactory.

SUMMARY OF THE INVENTION

An object of the present invention is to provide a system for providing vehicular hospitality information in which information is timely serviced in response to biological characteristic information of a user, and a function corresponding to voluntary hospitality from a vehicle is enhanced.

To achieve the above object, according to an aspect of the present invention, a system for providing vehicular hospitality information is provided as follows. User biological characteristic information acquisition means is provided to a vehicle of a user for acquiring user biological characteristic information reflecting at least one of a character, a mental condition, and a physical condition of the user. A hospitality information storage portion is provided for storing hospitality information to assist use of the vehicle by the user, or to entertain the user. Hospitality information retrieval means is provided for retrieving hospitality information matching the user biological characteristic information acquired by the user biological characteristic information acquisition means on the hospitality information storage portion in accordance with a predetermined correlation between the user biological characteristic information and the stored hospitality information. Information output means is provided to the vehicle for outputting the retrieved hospitality information. Under this structure, proper information can be timely and sensitively provided to a user based on user's character, physical condition, or mental condition.

The hospitality information retrieval means may be a car navigation system. The hospitality information storage portion is constituted as a destination database used for setting a destination in the car navigation system. The hospitality information retrieval means retrieves a destination matching a user biological characteristic specified by the user biological characteristic information acquired by the user biological characteristic information acquisition means in accordance with the user biological characteristic information. The hospitality information output means outputs the retrieved destination on a display screen of the car navigation system. A user can select a destination such as an eating place, a sightseeing place, or a passing point using a car navigation system based on a situation. In this case, the system of the present invention automatically retrieves a destination suitable for a user according to a user's character, mental condition, or physical condition and provides the user with the retrieved destination. This decreases user's time necessary for narrowing down destinations and can satisfy the user. Since the car navigation system is used, it is possible to retrieve a suitable destination from multiple candidates along potential routes within a given distance from a current position and to allow the user to reach the retrieved destination almost matching with the condition of the user.

The above structure can provide an advantage in retrieving an eating place or restaurant. Naturally, a user becomes hungry even when driving a vehicle. It is not so easy to find or retrieve an eating place suitable for a current state of the user using a car navigation system in an unfamiliar area while driving. To solve such a problem, the user biological characteristic information acquisition means may acquire hunger information reflecting a degree of hunger of the user as the user biological characteristic information, and the hospitality information retrieval means may retrieve a facility where eating is possible on the destination database when a content of the acquired hunger information satisfies a predetermined condition. Under this structure, the system determines whether a user is hungry or not and automatically retrieves a facility for eating to indicate to the user. Thus, the user can be smoothly guided to an eating place without need of operating the car navigation system in a stressed state from hunger.

Further, timing means may be included in the system. Meal time determination means is also included for determining a meal time predetermined in accordance with time information acquired by the timing means. The user biological characteristic information acquisition means acquires a determination result of a coming of the meal time as the hunger information. When being hungry, a user is apt to become silent or irritated. This outputs a relevant signal, which can be detectable from an outside. This signal can be detected as biological information; however, it is not always accurately detected. The signal may be similarly outputted from a poor physical condition or depressed mental condition, which makes it difficult to accurately detect the hungry state. In the above-mentioned structure including the timing means or the like, an attention is focused on a meal time approximately fixed to a certain time instant for breakfast, lunch, or dinner.

Further, elapsed time timing means is included for timing an elapsed time after meal of the user. The user biological characteristic information acquisition means acquires the elapsed time as the hunger information. This structure can be combined with the above-mentioned meal time determination means. In this case, an attention is focused on hunger, which is increased with an elapsed time from when a user starts driving a vehicle. Timing an elapsed time after meal of the user allows more accurate determination as to whether the user wants to have a meal.

The predetermined correlation between the user biological characteristic information and hospitality information may be retrieved using classification information defining the correlation and primarily assigned to the hospitality information in the hospitality information storage portion. In contrast, certain user biological characteristic information may be apparently correlated to certain hospitality information. For instance, when biological characteristic information relating to hunger is obtained, it is clearly correlated to facilities for eating in the destination database. In this case, a retrieval algorithm may be defined to retrieve only facilities for eating without need to previously assign classification information. In the present invention, the concept of "predetermining a correlation between user biological characteristic information and hospitality information" includes defining an algorithm to automatically retrieve facilities for eating when a user is hungry.

In contrast, classification information related to at least one of the character, the mental condition, and the physical condition of the user may be stored in the destination database to correlate with specifying information about each destination. The hospitality information retrieval means may retrieve in the destination database a destination classified by classification information relating to a user biological characteristic specified by the user biological characteristic information acquired by the user biological characteristic information acquisition means.

In this structure, the user biological characteristic information acquisition means includes a biological condition detecting portion and mental/physical condition estimate means. The biological condition detecting portion detects a predetermined biological condition of the user as a biological condition parameter which is a value parameter reflecting the biological condition. The mental/physical condition estimate mean estimates a mental or physical condition of the user in accordance with a detection state of the detected biological condition parameter. Here, the hospitality information retrieval means finds the classification information corresponding to the estimated mental or physical condition, and retrieves a destination classified by the classification information in the destination database. Under this structure, a biological condition of a user is directly detected using the biological condition detecting portion. Thus, a destination can be retrieved to highly match the user's mental or physical condition.

The biological condition detecting portion may detect the biological condition as a temporal change of the biological condition parameter which is a value parameter reflecting the biological condition. The mental/physical estimate means estimates the mental or physical condition of the user in accordance with the temporal change of the detected biological condition parameter.

The biological condition detecting portion may detect a waveform of a temporal change of the biological condition parameter. Here, the mental/physical condition estimate means can estimate the physical condition of the user in accordance with amplitude information of the waveform. For instance, when a physical condition becomes poor because of disease or fatigue, variation in a biological condition reflecting the physical condition decreases. Namely, the disease or fatigue is apt to decrease an amplitude of the waveform of the temporal change in the biological condition parameter. Thus, the physical condition can be properly detected using the amplitude information of the waveform. In contrast, the mental/physical condition estimate means may estimate the mental condition of the user in accordance with frequency information of the waveform. Whether a mental condition is stable or not typically depends on a speed of variation in a biological condition, which is reflected on frequency information of the waveform. Thus, the user's mental condition can be properly estimated based on the frequency information of the waveform.

The biological condition detecting portion may detect a temporal change of a body temperature of the user as the temporal change of the biological condition parameter. The user's physical condition or mental condition is apparently reflected on a body temperature. For instance, a poor physical condition decreases a waveform amplitude or variation width of the body temperature. A body temperature can be remotely detected using an infrared measurement such as a facial thermograph, so it can be used to estimate a user's condition in various cases where a user approaches a vehicle, rides on the vehicle, gets out the vehicle, and departs from the vehicle, without limiting to the case for driving.

Further, the biological condition detecting portion may acquire a temporal change of at least one of a facial expression and a line-of-sight of the user as the temporal change of the biological condition parameter. The user's physical condition or mental condition is significantly reflected on these two parameters, which can be remotely measured by photographing. Therefore, they can be used to estimate a user's condition in various cases where a user approaches a vehicle, rides on the vehicle, gets out the vehicle, and departs from the vehicle, without limiting to the case for driving.

Further, the biological condition detecting portion may detect a temporal change of the biological condition parameter while the user is driving. This may achieve a safe and comfortable driving. In particular, when only a driver is in a vehicle, a temporal change in a biological condition parameter during driving highlights the user's mental or physical condition reflecting stresses or the like due to driving. Thus, the condition can be properly detected.

The biological condition detecting portion may acquire a temporal change of a first biological condition parameter of one or more of blood pressure, heart rate, body temperature, skin resistance, and perspiration as the temporal change of the biological condition parameter. The first biological condition parameter indicates a change in the internal physical condition of the driver. Thus, the user's mental (or psychological)

condition or physical condition (especially, the mental condition) is reflected on the temporal change of waveform. Therefore, analyzing the temporal change of waveform facilitates proper and effective retrieval of a destination. The first biological condition parameter can be directly measured using a sensor, for instance, attached to a portion where a driver grasps a steering wheel. Thus, the temporal change can be sensitively detected. Further, for instance, a user may be frightened by a potential danger or irritated by an interruption or overtaking by another vehicle. This significantly changes the waveform (especially, amplitude) of the first biological condition parameter such as a blood pressure, heart rate, body temperature, skin resistance, and perspiration. Further, when an attention is paid to other items or dispersed, the waveform of the first biological condition parameter varies similarly. In this case, the mental/physical condition estimate means may estimate that a mental condition of the user is abnormal when a waveform frequency of the first biological condition parameter is equal to or over a predetermined level.

In contrast, the biological condition detecting portion may detect a temporal change of a second biological condition parameter of at least one of an attitude, a line-of-sight, and a facial expression of the user who is driving as the temporal change of the biological condition parameter. The second biological condition parameter indicates a change in the external physical condition of the driver. The amplitude of the change is apt to decrease by reflecting conditions such as poor condition, disease, or fatigue. Thus, the mental/physical condition estimate means may estimate that a physical condition of the user is abnormal when a waveform amplitude of the second biological condition parameter is equal to or under a predetermined level. For instance, accurate estimate of the physical condition provides an advantage in selecting kinds of facilities for eating.

Further, the waveform of the second biological condition can be also used for estimating a mental condition of a driver. For instance, in an excited condition, an attitude of a driver frequently varies, but a line-of-sight hardly varies (e.g., eyes get glassy). Further, in a mentally unstable condition, a facial expression remarkably varies. In this case, the mental/physical condition estimate means may estimate that a mental condition of the user is abnormal when a waveform frequency of the second biological condition parameter is equal to or over a predetermined level, or equal to or under a predetermined level.

Further, another biological condition parameter can be adopted to estimate a mental or physical condition using a temporal change in an aspect other than the frequency or amplitude. For instance, the biological condition detecting portion may detect a temporal change of a pupil size of a user as the temporal change of the biological condition parameter. Here, the mental/physical condition estimate means estimates that a physical condition of the user is abnormal when the detected pupil size changes by equal to or over a predetermined level. This is because fatigue destabilizes focusing eyes or adjusting light quantity to thereby frequently cause blurry eyes or flickering eyes. In contrast, in an extremely excited condition due to anger, driver's eyes open widely. In this case, the mental/physical condition estimate means estimates that a mental condition of the user is abnormal when the detected pupil size changes or increases by equal to or over a predetermined level.

Further, a plurality of the biological condition detecting portions may be provided, and the mental/physical condition estimate means may estimate a mental condition or a physical condition of the user in accordance with a combination of temporal changes of the biological condition parameters detected by the plurality of the biological condition detecting portions. This structure can increase the number of kinds of mental or physical conditions, which can be detected or specified, and increase an estimate accuracy. In this case, a determination table may be provided to store a correlation between multiple specified conditions and a combination of relevant temporal changes. Thus, the mental/physical condition estimate means collates detected multiple temporal changes in the multiple detected biological condition parameters with combinations in the determination table to specify a certain condition. This allows an effective specification process even when a great number of biological condition parameters are considered.

In the structure to retrieve facilities for eating, the specifying information about the eating facilities may be classified correspondingly with a quality of the estimated physical condition. Here, the hospitality information retrieval means retrieves an eating facility corresponding to the estimated physical condition in the destination database when a content of the acquired hunger information satisfies a predetermined condition. When it is determined that the user wants to have a meal, a facility for eating can be selectively retrieved to match with the physical condition of the user. This can provide an eating place not to result in weighing on the physical condition of the user.

Further, when the obtained user biological information includes user character specifying information to specify a character of a user, a hospitality operation information storage portion may be provided to store a correlation between (i) hospitality operation information to define operations by hospitality operation devices and (ii) a user character kind specified by the user character specifying information. Here, the hospitality determination section reads out, from the hospitality operation information storage portion, hospitality operation information corresponding to the character kind specified by the obtained user character specifying information and instructs hospitality operation devices to control operations according to the read hospitality operation information.

Under this structure, the user characters can be classified by character kinds and hospitality operations matching with the kinds of characters are individually defined. In contrast, a vehicle side specifies a character of a user, who uses a subject vehicle, based on the obtained user character specifying information and executes the corresponding hospitality operation. This allows performance of a hospitality operation dynamically and timely matching with a character of a user depending on situations. For instance, the hospitality information retrieval means retrieves an eating facility classified into eating facilities serving low-calorie foods or plain foods on the destination database when a content of the acquired hunger information satisfies a predetermined condition and the physical condition is estimated to be under a predetermined level. This structure can propose to a user a meal matching with the poor physical condition. The user is thereby moved with the considerate hospitality operation or proposal.

The hospitality information output means can be a car audio system in a vehicle. In this case, the hospitality information storage portion stores multiple music source data for reproducing in the audio system to function as a music source database, where the individual music source data are primarily correlated with the character kinds of users. Then, the hospitality information retrieval means reads out from the music source database music source data matching with the obtained user biological characteristic information and then causes the audio system to reproduce the corresponding music source. In the music source database, music sources are classified by correlating with predetermined user character kinds or physical or mental conditions. A music source corresponding to an obtained or determined character kind or a physical or mental condition is reproduced in the audio system. This allows a music source to be properly provided to the user during driving or staying in the vehicle. Further, this omits necessity of a user to select a song or music source matching with the current state of the user from a large database.

According to another aspect of the present invention, a system for providing vehicular hospitality information is provided as follows. First user biological characteristic information acquisition means is provided to a vehicle of a user for acquiring user biological characteristic information reflecting a mental condition of the user. Second user biological characteristic information acquisition means is provided to the vehicle for acquiring user biological characteristic information reflecting a physical condition of the user. A hospitality information storage portion is provided for storing hospitality information to be used for assisting the user in using the vehicle or for entertaining the user. Hospitality information retrieval means is provided for retrieving hospitality information matching user biological characteristic information acquired by the first and/or second user biological characteristic information acquisition means in accordance with a predetermined correlation between two pieces of the user biological characteristic information and the stored hospitality information. Hospitality information outputting means is provided for outputting the retrieved hospitality information, the means being provided to the vehicle.

According to another aspect of the present invention, a system for providing vehicular hospitality information is provided as follows. First user biological characteristic information acquisition means is provided to a vehicle of a user for acquiring user biological characteristic information reflecting a mental condition of the user. Second user biological characteristic information acquisition means is provided to the vehicle for acquiring user biological characteristic information reflecting a physical condition of the user. A hospitality information storage portion is provided for storing hospitality information to be used for assisting the user in using the vehicle or for entertaining the user. Hospitality information retrieval means is provided to be configured to classify the two pieces of the user biological characteristic information into at least two or more of energy, stress, and damage so as to estimate a condition of the user, and thereby to retrieve hospitality information matching the user biological characteristic information acquired by the first and/or second user biological characteristic information acquisition means on the hospitality information storage portion in accordance with a predetermined correlation between the estimated condition of the user and the stored hospitality information. Hospitality information output means is provided to the vehicle for outputting the retrieved hospitality information.

According to another aspect of the present invention, a system for providing vehicular hospitality information is provided as follows. Character acquisition means is provided to a vehicle of a user for acquiring a character of a user. User biological characteristic information acquisition means is provided for acquiring user biological characteristic information reflecting at least one of a mental condition and a physical condition. A hospitality information storage portion is provided for storing hospitality information to be used for assisting the user in using the vehicle or for entertaining the user. Hospitality information retrieval means is provided for retrieving hospitality information matching user biological characteristic information acquired by at least one of the character acquisition means and the user biological characteristic information acquisition means, on the hospitality information storage portion, in accordance with the character acquisition means and a predetermined correlation between the user biological characteristic information and the stored hospitality information. Hospitality information output means is provided to the vehicle for outputting the retrieved hospitality information.

According to yet another aspect of the present invention, a system for providing vehicular hospitality information is provided as follows. Character acquisition means is provided to a vehicle of a user for acquiring a character of the user. User biological characteristic information acquisition means is provided for acquiring user biological characteristic information reflecting at least one of a mental condition and a physical condition. A hospitality information storage portion is provided for storing hospitality information to be used for assisting the user in using the vehicle or for entertaining the user. Hospitality information retrieval means is provided for retrieving hospitality information matching a correction taste acquired by correcting a default taste, which is set based on a character acquired by the character acquisition means, by use of user biological characteristic information acquired by the user biological characteristic information acquisition means, on the hospitality information storage portion, in accordance with the character acquisition means and a predetermined correlation between the user biological characteristic information and the stored hospitality information. Hospitality information output means is provided to the vehicle for outputting the retrieved hospitality information.

BRIEF DESCRIPTION OF THE DRAWINGS

The above and other objects, features, and advantages of the present invention will become more apparent from the following detailed description made with reference to the accompanying drawings. In the drawings:

FIGS. 7A, 7B are diagrams showing a first example of a function selection table and a control appropriate value setting table;

FIGS. 8A, 8B are diagrams showing a second example of the function selection table and a control appropriate value setting table;

FIGS. 9A, 9B are diagrams showing a third example of the function selection table and a control appropriate value setting table;

FIG. 10 is a diagram showing a forth example of the function selection table;

FIG. 11 is a diagram showing a fifth example of the function selection table;

FIG. 12 is a diagram showing a sixth example of the function selection table;

FIGS. 13A, 13B are integrated representative functions of some of the function selection tables together with a control appropriate value setting table;

FIG. 18 is a conceptual diagram showing a content of a music source database;

FIG. 19 is a conceptual diagram showing an example of a structure of lighting control data of a lighting device;

FIG. 20 is a conceptual diagram showing a content of a music selection history storage unit;

FIG. 21 is a conceptual diagram showing a content of statistic information of music selection history;

FIG. 22 is a conceptual diagram showing a content of a stress reflection operation statistic storage unit;

FIG. 51, which is divided into FIGS. 51A, 51B, is a table showing one example of a determination table;

FIGS. 52A, 52B are flowcharts showing one example of obtaining blood pressure change waveform and of its analysis algorithm;

FIGS. 54A, 54B are flowcharts showing one example of obtaining a body temperature waveform and of its analysis algorithm;

FIGS. 55A, 55B are flowcharts showing one example of obtaining a skin resistance waveform and of its analysis algorithm;

FIGS. 57A, 57B are flowcharts showing one example of obtaining a posture signal waveform and of its analysis algorithm;

FIGS. 60A, 60B are flowcharts showing one example of obtaining a waveform of an angle of a line of sight and of its analysis algorithm;

FIGS. 61A, 61B are flowcharts showing one example of obtaining a pupil diameter waveform and of its analysis algorithm;

FIGS. 62A, 62B are flowcharts showing one example of obtaining a steering angle waveform and of its analysis algorithm;

FIG. 67 is a diagram showing relationship between specified conditions and hospitality operation types;

FIG. 68 is a diagram showing an example of a hospitality control amount setting table;

FIG. 69 is a diagram showing an example of changing a default control setting value by use of a question interaction method;

FIGS. 70A, 70B are examples of control appropriate value setting tables used in case of emergency or abnormality;

FIG. 71 is a diagram showing an example of detailed setting of a control appropriate value for audio and lighting;

FIG. 72 is a diagram showing relationship between mixed ratios of RGB full color lights, lighting colors, and indexes;

FIG. 73A is a diagram showing an example of a structure of data for determining hospitality;

FIG. 73B is a diagram showing an example of a structure of question data;

FIG. 77, which is divided into FIGS. 77A, 77B, is a diagram showing an example of contents of a condition specifying result table;

FIG. 82 is a diagram illustrating a condition of a user in view of energy, stress, and damage, as a table;

DETAILED DESCRIPTION OF THE PREFERRED EMBODIMENTS (Overall Structure)

Figure 1:
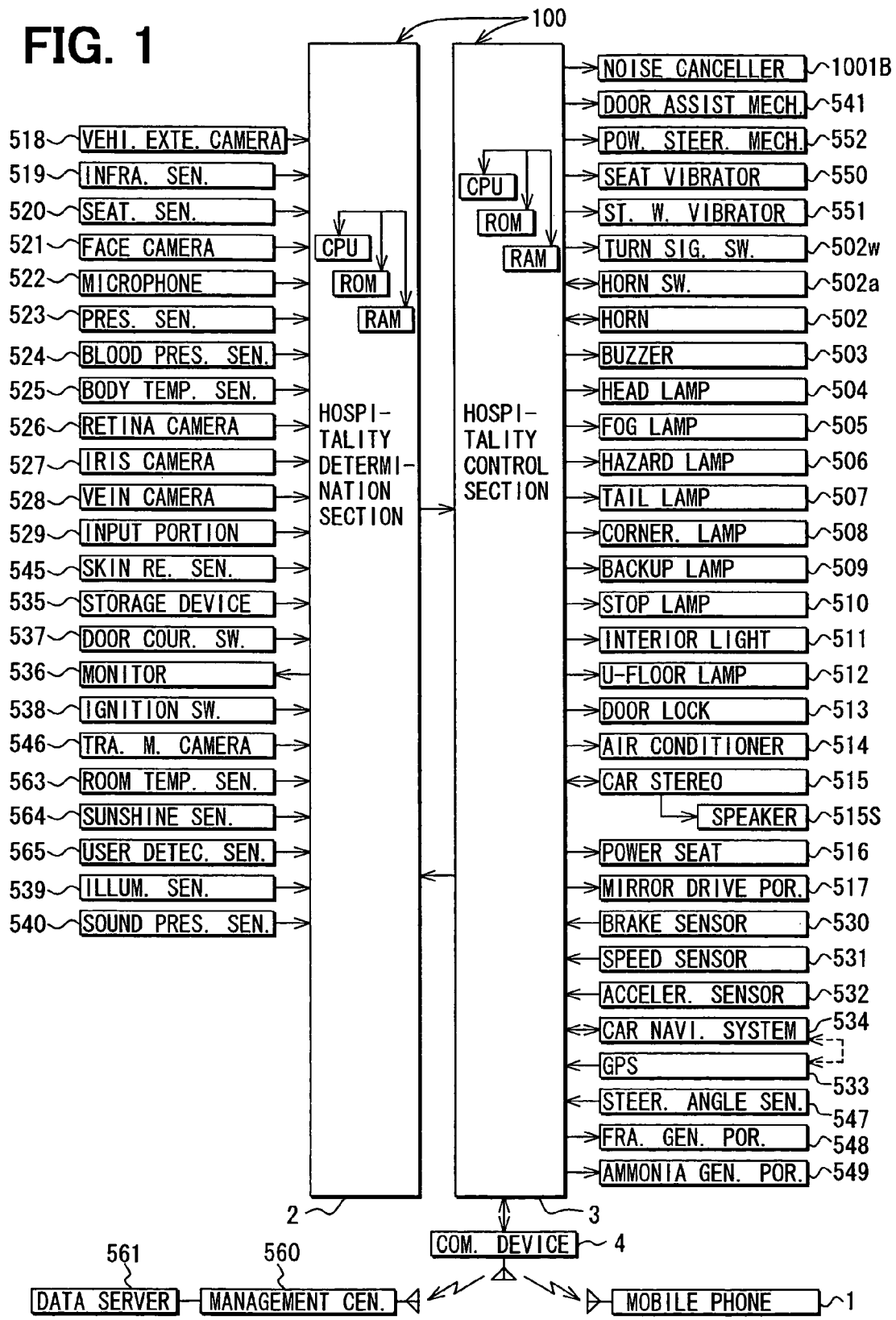
FIG. 1 is a block diagram showing one example of an electrical structure of a vehicular user hospitality system of the present invention.

Embodiments of the present invention will be explained below in reference to the appended drawings. FIG. 1 is a conceptual block diagram of a vehicular user hospitality system (hereinafter also called just a "system") 100, which includes a system for providing vehicular hospitality information as one embodiment of the present invention. The system 100 comprises a vehicle-mounted portion 100 as its main portion. The vehicle-mounted portion 100 comprises a hospitality control section 3 including a first computer connected to various hospitality operation devices 502 to 517, 534, 541, 548, 549, 550, 551, 552, and 1001B, and a hospitality determination section 2 including a second computer connected to various sensors and cameras 518 to 528. The first and second computers have CPUs, ROMs, and RAMs. The first and second computers execute control software (software program for controlling) stored in the ROMs by use of the RAMs as working memory, to achieve after-mentioned various functions.

(Hospitality Operation Devices)

Figure 50:
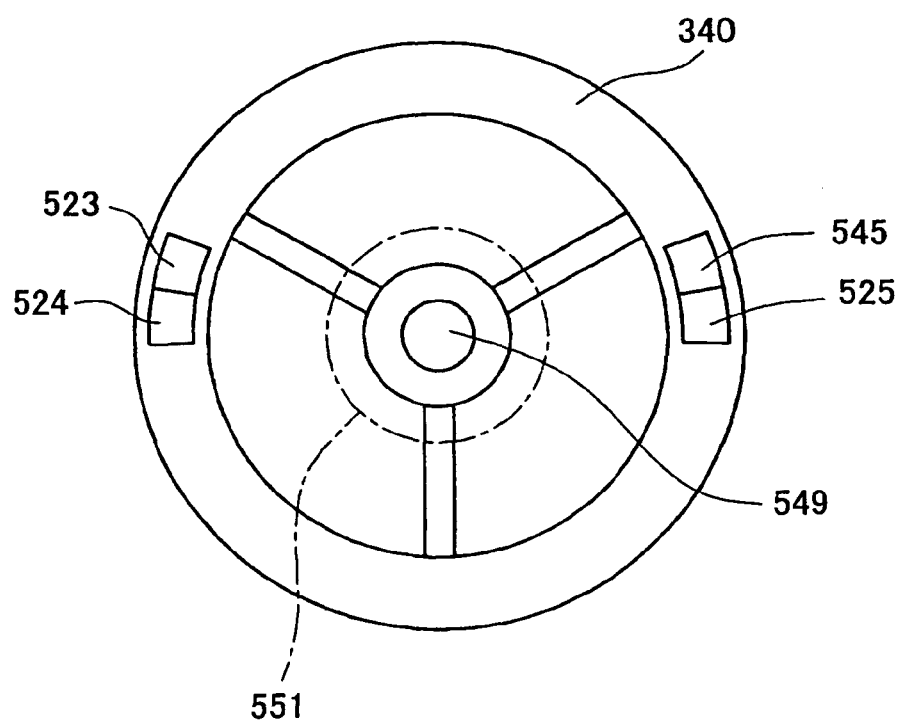
FIG. 50 is a view showing an example of mounting various sensors and hospitality operation devices to a steering wheel.
Figure 58:
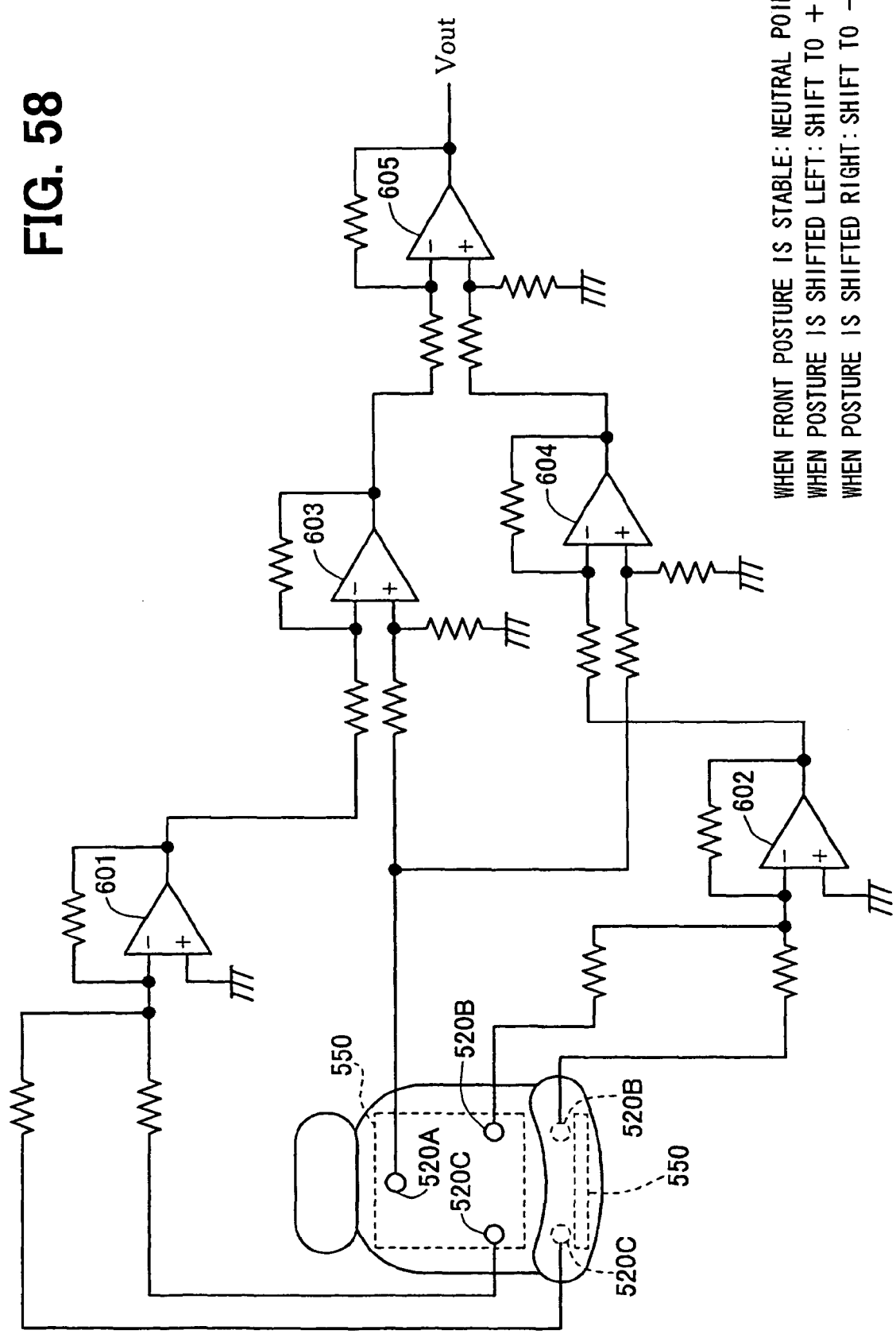
FIG. 58 is a circuit showing one example of hardware generating a posture signal waveform.

Next, hospitality operation devices will be explained below. In the system 100, motions of a user using a vehicle when the user approaches the vehicle, gets in the vehicle, drives the vehicle or stays in the vehicle, and gets out the vehicle, are divided into multiple predetermined scenes. In respective divided scenes, the hospitality operation devices 502 to 517, 534, 541, 548, 549, 550, 551, 552, and 1001B operate hospitality for assisting the use of the vehicle by the user, or for entertaining the user. In this embodiment, a horn 502 and a buzzer 503 are connected as devices for generating sound (sound wave) to outside the vehicle. As lighting devices (lamps), a head lamp 504 (its beam can be switched between high and low), a fog lamp 505, a hazard lamp 506, a tail lamp 507, a cornering lamp 508, a backup lamp 509, a stop lamp 510, an interior light 511, and an under-floor lamp 512, a door lock 513 are connected. As the other hospitality operation devices, an air conditioner 514, a car audio system (car stereo) 515, a driving portion 517 for adjusting angles of, e.g., a power seat 516 and side and rearview mirrors, a car navigation system 534, an assist mechanism (hereinafter called a door assist mechanism) 541 for opening and closing doors, a fragrance generation portion 548 for outputting fragrance, an ammonia generation portion 549 (as shown in FIG. 50, mounted to the center portion of a steering wheel 340 to output ammonia toward the face of the driver) for awaking the driver in serious physical condition (including strong sleepiness), a seat vibrator 550 (as shown in FIG. 58, embedded in a bottom portion or backrest portion of a seat) for warning the driver or awaking the driver from sleepiness, a steering wheel vibrator 551 (as shown in FIG. 50, mounted to a shaft of the steering wheel 340), a noise canceller 1001B for decreasing noise in the-vehicle, and a power steering mechanism 552 are connected.

Figure 80:
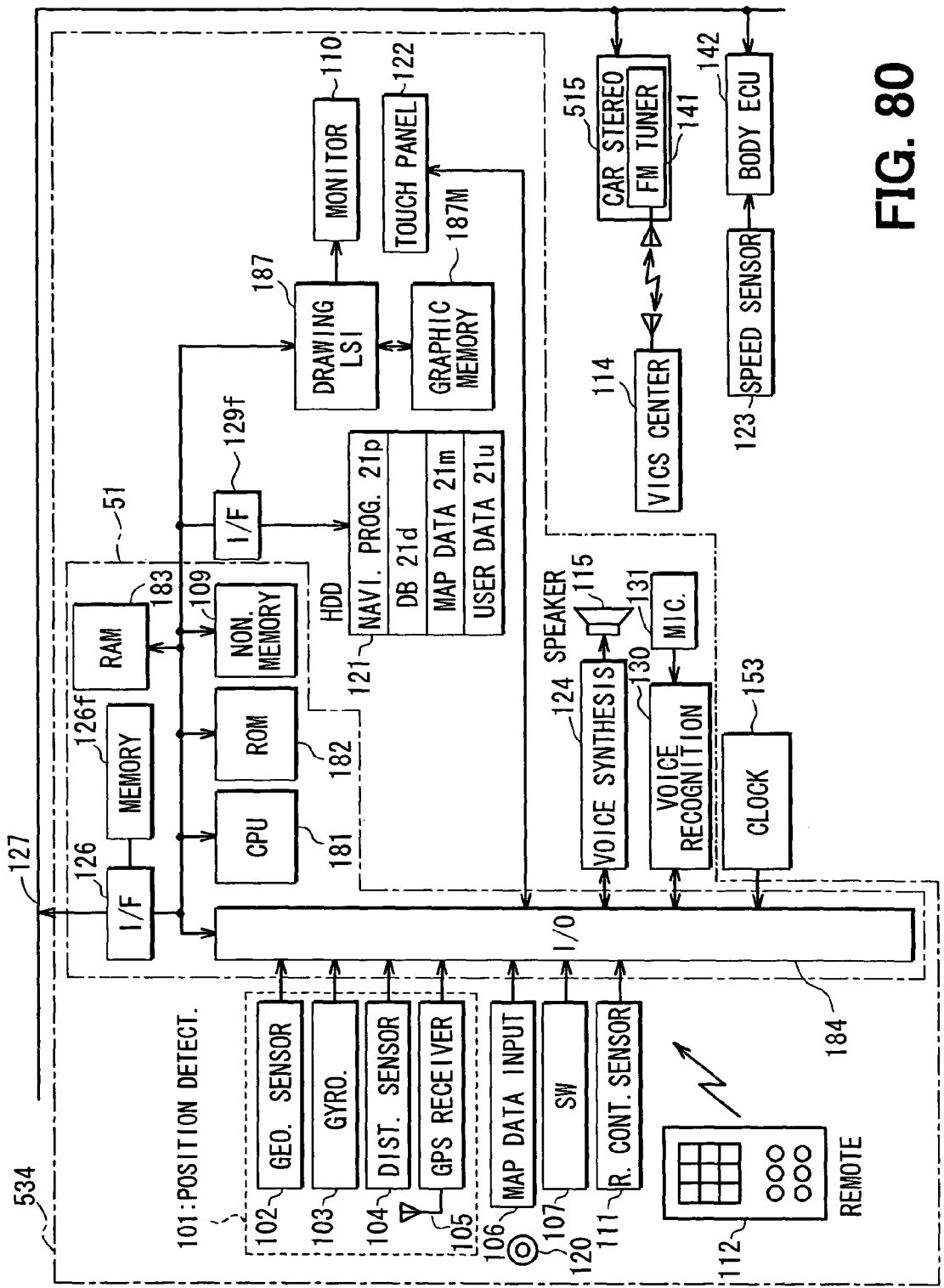
FIG. 80 is a block diagram showing an electrical structure of a car navigation system operating as a main function of a system for providing vehicular hospitality information.

FIG. 80 is a block diagram showing an example of a structure of a car navigation system 534. The car navigation system 534 operates as a function output portion of a vehicular hospitality information providing apparatus of the present invention. The car navigation system 534 comprises: a position detecting device 101; a map data input device 106, an operation switch group 107; a remote control sensor 111; a speaker 115 for, e.g., voice guidance; a nonvolatile memory 109 such as a flash memory; a monitor 110 such as an LCD; an information ECU 51 forming a main control portion to which these components are connected; a remote control terminal 112; a hard disk device (HDD) 121 forming a main storage device; and so on. Information and data required for operating the navigation system 534, such as history information of a vehicle, are stored in the nonvolatile memory 109.

The position detecting device 101 includes a well-known geomagnetic sensor 102; a gyroscope 103; a distance sensor 104; and a GPS receiver 105 for GPS. The GPS detects a position of a vehicle in accordance with a radio wave from a satellite. Because these components such as the sensors 102, 103, 104, and 105 have errors having different characteristics, these multiple sensors compensate each other. The position detecting device 101 may include part of the above sensors in accordance with their accuracies. A rotation sensor for a steering wheel, a wheel sensor for each wheel, and so on, may be used.

The operation switch group 107 can use, e.g., a mechanical switch. In this embodiment, a touch panel 122 integrated with the monitor 110 is also used as the operation switch group 107. When a touch panel area corresponding to a button image displayed on the monitor 110 is touched by a finger, an operation state can be recognized (the so-called a soft button). By use of the operation switch group 107 and remote control terminal 112, various instructions can be inputted.

Additionally, a voice recognition unit 130 can be used to input various instructions. When a voice is inputted from a microphone 131 connected to the voice recognition unit 130, a signal of the voice is voice-recognized by use of a well-known voice recognition technique. The voice signal is converted to an operation command corresponding to the recognition result.

The information ECU 51 is constituted as a normal computer. A well-known CPU 181, ROM 182, RAM 183, the above nonvolatile memory 109, and an input-output portion 184 are bus-connected to the information ECU 51. The HDD 121 is bus-connected to the information ECU 51 via an interface 129f. A display LSI 187 which outputs images to the monitor 110 in accordance with display information for maps and navigation screens, and a graphic memory 187M for display, are bus-connected to the information ECU 51. The monitor 110 is connected to the display LSI 187. The CPU 181 executes controls by use of a navigation program 21p and data stored in the HDD 121. The data is read and written from and to the HDD 121 by the CPU 181.

Map data 21m including road data and a destination database 21d are stored in the HDD 121. The user can write data 21u, e.g., for point registration. These data can be rewritten by operating the operation switch group 107 and remote terminal 112 or by inputting voice. By reading data from a storage medium 120 by use of an outer information input-output device (map data input device) 106, content of the HDD 121 can be updated. In this embodiment, the information ECU 51 is connected to a serial communications bus 127 forming a vehicle interior network via a communications interface 126 and a buffer memory 126f which stores communications data temporarily. The information ECU 51 transfers the data to and from other control devices such as a body ECU 142 and an engine control ECU (not shown).

To explain the outline of the hospitality control section 3 of FIG. 1 easily, the case where the hospitality control section 3 comprises the single ECU has been exampled hereinbefore. However, it is more natural that the hospitality control section 3 comprises multiple ECUs connected to the above network. At least part of various data in the storage device 535 used by the hospitality determination section 2 for determining hospitality, and of data to be outputted from the vehicular hospitality information providing apparatus (for example, data stored in an after-mentioned destination database 21d and music source databases 515b, 515c), may be stored in a data server outside the vehicle, and may be downloaded by use of radio communications for use in the vehicle.

The monitor 110 comprises a color liquid crystal display. On a screen of the monitor 110, a current position mark of the vehicle, the current position being inputted from the position detecting device 101, the map data 21m inputted from the HDD 121, and additional data such as guide routes to be displayed on the map, are superimposed and displayed. On the screen, menu buttons for setting a route guide, for guiding during routing, and for switching the screen, are displayed.

An FM tuner 141 mounted to a car stereo 515 receives an airwave for carrying traffic congestion information from, e.g., a VICS (Vehicle Information and Communication System) center 114. The information is transmitted to the information ECU 51 via the vehicle interior network.

In the car navigation system 534, the CPU 181 of the information ECU 51 starts the navigation program 21p. A driver selects a desired destination from the destination database 21d by operating the operation switch group 107 or remote control terminal 112 or by inputting voice to the microphone 131. For example, when the driver selects the route guide from the menu displayed on the monitor 110 so as to display a route to a destination on the monitor 110, the following process is done. When the driver inputs a destination by use of the map or destination selecting screen on the monitor 110, a current position of the vehicle is found in accordance with satellite data acquired from the GPS receiver 105. Then, an optimum route from the current position to the destination is found. The guide route is superimposed and displayed on the road map on the monitor 110 so as to guide the driver to the optimum route. As the method for setting an optimum route automatically, the Dijkstra method and so on are well known. By use of either of the monitor 110 or speaker 115, operation guidance and messages corresponding to operation states are outputted.

Figure 16:
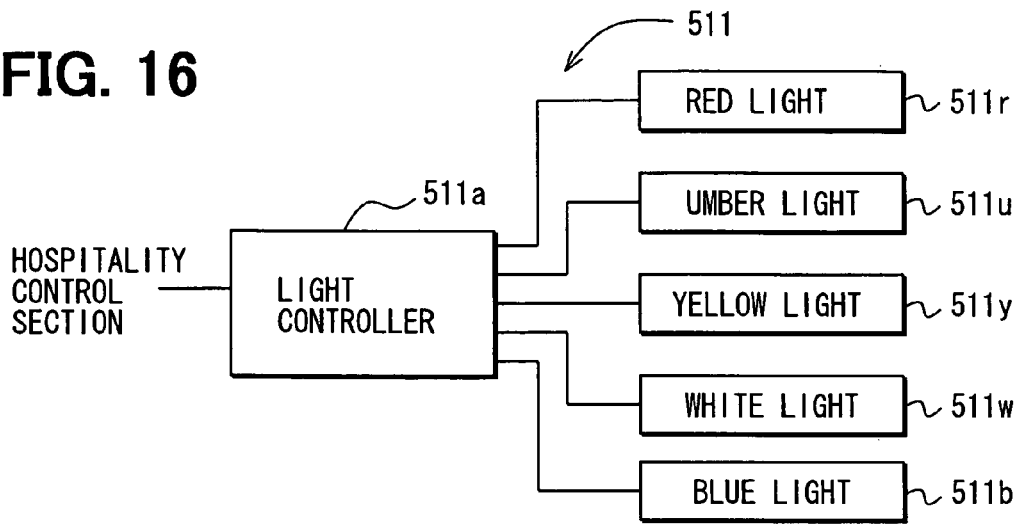
FIG. 16 is a block diagram showing one example of an electrical structure of vehicle interior lighting.

FIG. 16 shows an example of a structure of the interior light 511. The interior light 511 includes multiple light portions (in this embodiment, including a red light 511r, an umber light 511u, a yellow light 511y, a white light 511w, and a blue light 511b). In response to a control instruction signal inputted from the hospitality determination section 2 to the hospitality control section 3, these light portions are selected, and the lighting of the light portions are controlled in various lighting patterns in accordance with the control signal. FIG. 19 shows an example of a structure of light control data determined in accordance with a character type of the user. The light control data is stored in the ROM of the hospitality determination section 2, read by the control software as needed, and used. For example, with respect to an active character (SKC1, see FIG. 18), the red light 511r is selected, and flashes (only at first, then continuously lights). Additionally, with respect to a gentle character (SKC2), the umber light 511u is selected, and fades in. These are only part of the examples.

Figure 39:
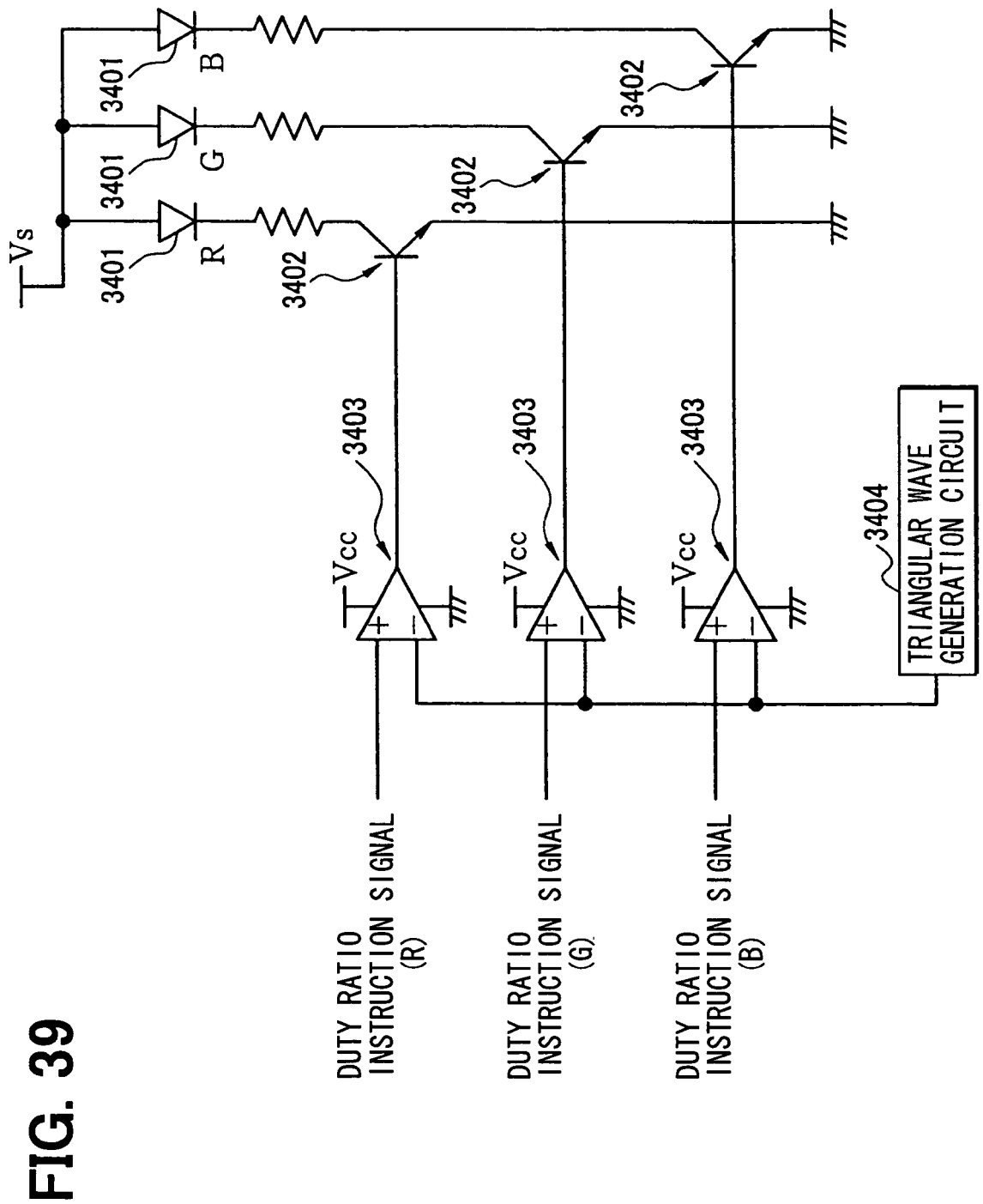
FIG. 39 is a circuit diagram showing one example of a lighting device using a light emitting diode.

The lighting device can use an incandescent lamp, a fluorescent lamp, or a lighting device using a light emitting diode. Especially, light emitting diodes of the three primary colors, red (R), green (G), and blue (B) can be combined to obtain various lights easily. FIG. 39 shows one example of a structure of the circuit. A red light emitting diode 3401 (R), a green light emitting diode 3401 (G), and a blue light emitting diode 3401 (B) are connected to a power supply (Vs), and switched and driven by transistors 3402. This switching is PWM-controlled in accordance with a duty ratio determined by a cycle of a triangular wave (a saw tooth wave may be used) inputted to a comparator 3403 and by a voltage level of an instruction signal. Each input waveform of an instruction signal to each light emitting diode 3401 can be changed separately. Light of arbitrary color can be obtained in accordance with a mixed ratio of the three emitted lights. Colors and light intensity patterns can be changed over time in accordance with an input waveform of an instruction signal. A light emitting intensity of each light emitting diode 3401 can be adjusted by a level of a driving current on the premise of continuous lighting, as well as PWM-controlled. A method in which this adjustment and the PWM control is combined, can be used.

FIG. 72 shows relationship between mixed ratios (in accordance with duty ratios) of red light (R), green light (G), and blue light (B) and viewed colors of the mixed lights. The mixed colors are provided with indexes (0 to 14), which are stored in the ROM of the hospitality control section 3 (or in a storage device 535 of the hospitality determination section 2: information required for the control may be sent to the hospitality control section 3 by communications) as control reference information. White light is frequently used. To achieve smooth switches between white light and colored light, multiple indexes of white light appear periodically in the arrangement of all the indexes. Especially, warm colors (pale orange, orange, red) are arranged after the white color (index 6) in the middle, and cold colors (light blue, blue, blue-purple) before the white color (index 6) in the middle. In accordance with physical condition and mental condition of the user, white light can be switched to warm color light or cold color light smoothly.

Figure 17:
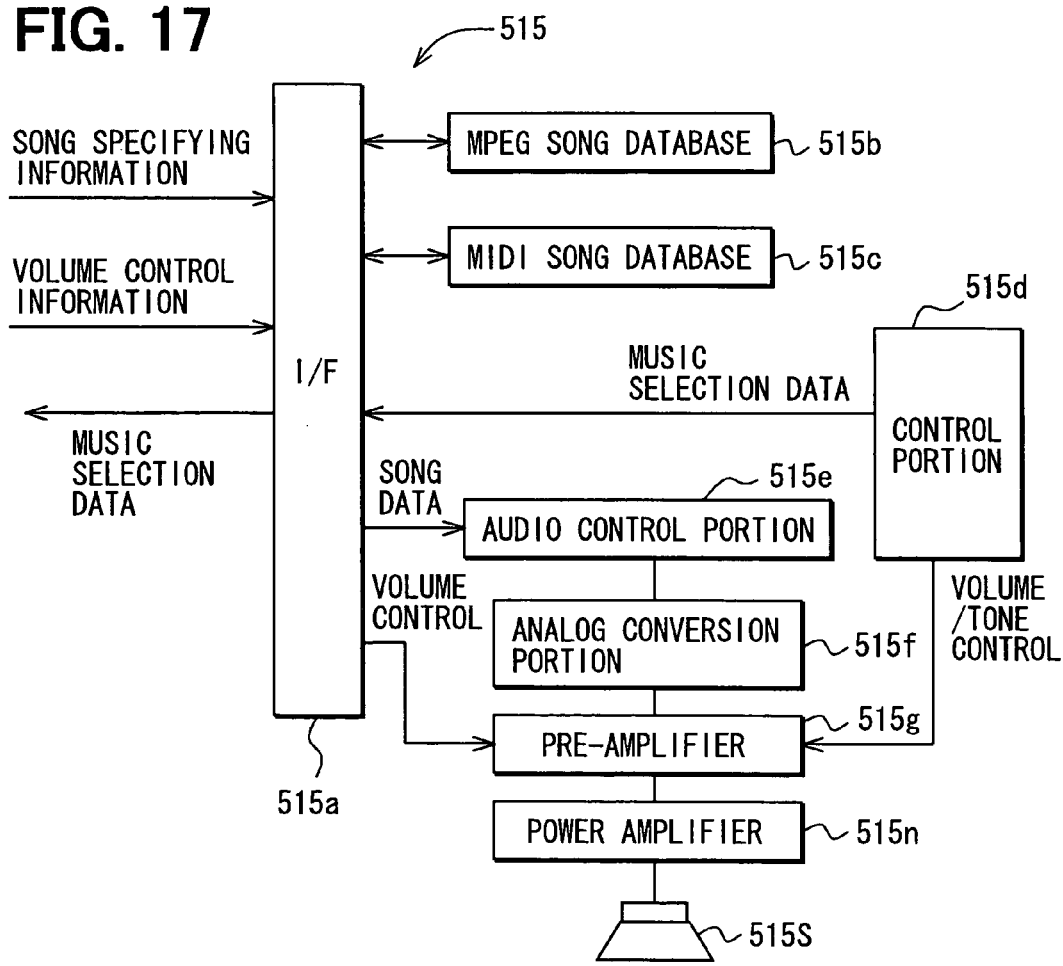
FIG. 17 is a block diagram showing one example of an electrical structure of a car audio system.

FIG. 17 shows an example of a structure of the car audio system 515. The car audio system 515 has an interface portion 515a to which hospitality song play control information such as song specifying information and volume controlling information is inputted from the hospitality determination section 2 via the hospitality control section 3. A digital audio control portion 515e, music source databases 515b, 515c in which many music source data are stored (the former is an MPEG3 database, the latter is an MIDI database) are connected to the interface portion 515a. The music source data selected in accordance with the song specifying information is sent to the audio control portion via the interface portion 515a. The music source data is decoded to digital music waveform data in the audio control portion 515e, and converted into analog in an analog conversion portion 515f. The source data is outputted from a speaker 515S at a volume specified by the hospitality song play control information, via a preamplifier 515g and a power amplifier 515h.

Figure 40:
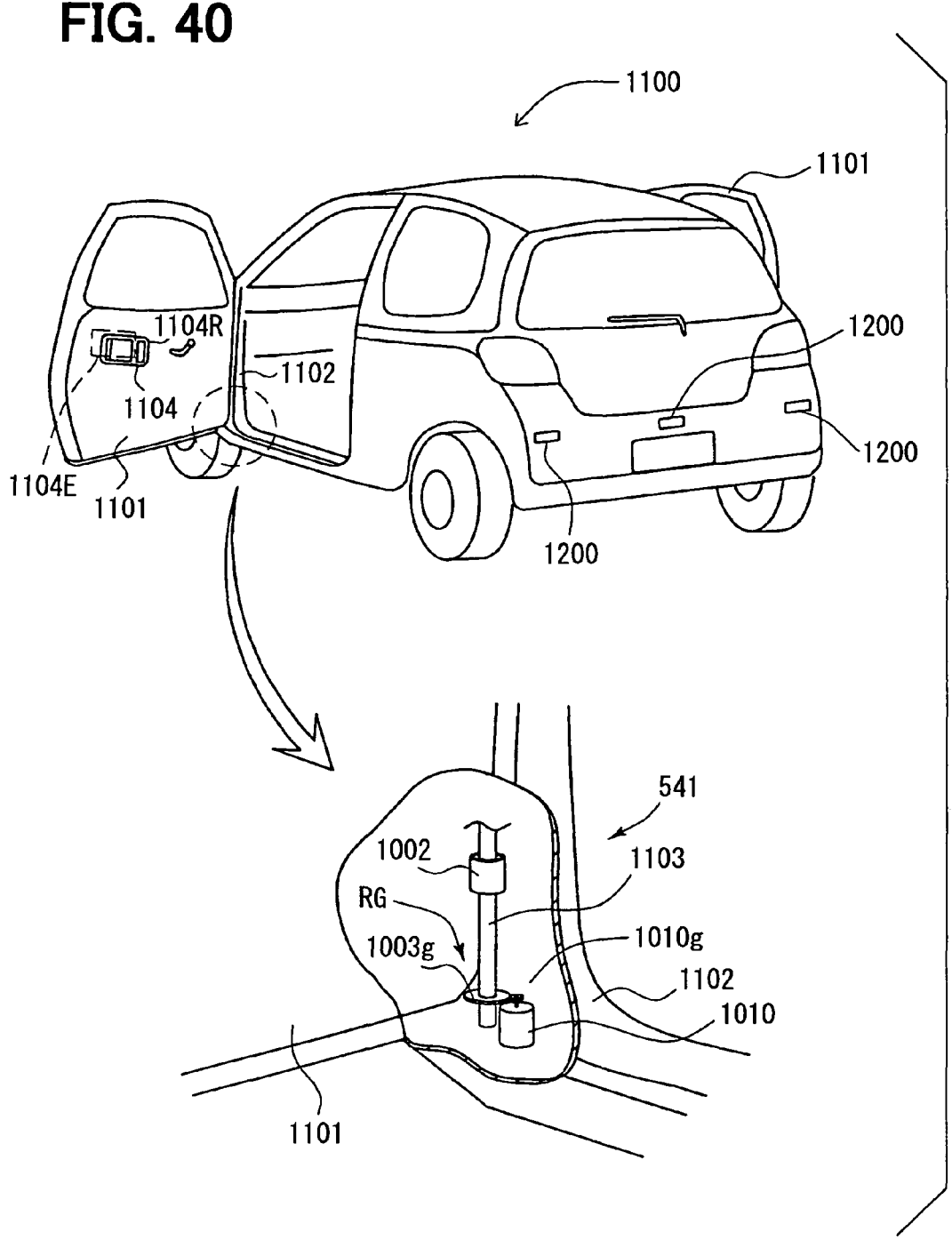
FIG. 40 is a view showing one example of a portion of a mechanical structure of a door assist mechanism.

FIG. 40 shows an overview of the door assist mechanism 541. Each of swing doors 1101 (hereinafter also called just a "door") for getting in and off a vehicle is mounted to an edge of an entrance 1102 of a vehicle 1100 via a door pivot shaft 1103. The door 1101 can be opened from a closed position where the door 1101 closes the entrance 1102 to a position of an arbitrary angle, manually. This manual door opening is assisted by a power of a motor (actuator) 1010. In this embodiment, with respect to the door pivot shaft 1103 rotating together with the door 1101, a torque of a rotary output of the motor 1010 is increased via a reduction gear mechanism RG, and directly transmitted to the pivot shaft 1103 as a rotary driving force for assisting the opening and closing of the door.

Figure 41:
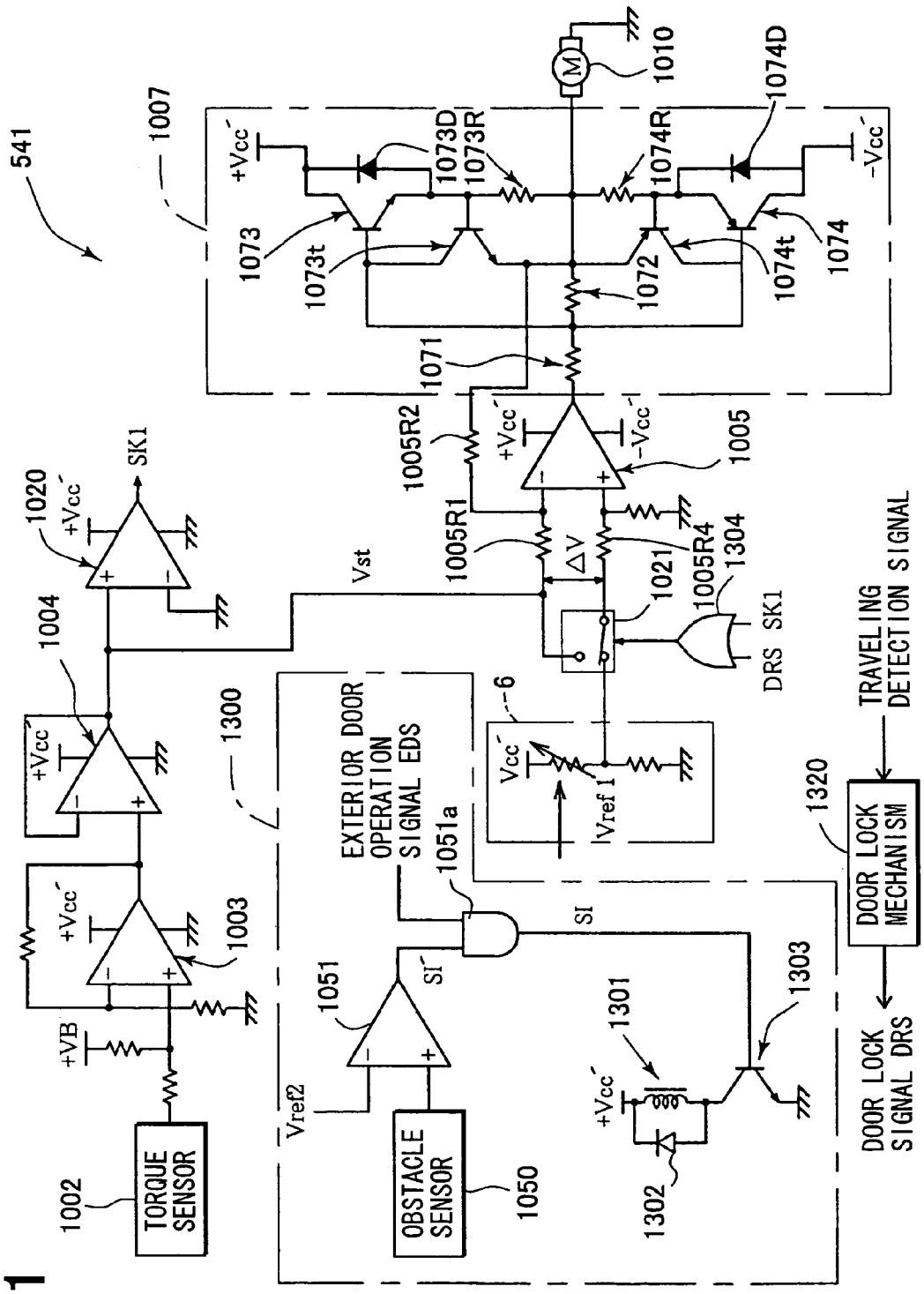
FIG. 41 is a circuit diagram of the door assist mechanism.

FIG. 41 is one example of a circuit diagram of the door assist mechanism 541. The door assist mechanism 541 has an obstacle detection unit for detecting obstacles outside the vehicle, the obstacles preventing the door from opening. In the case where no obstacle is detected, the actuator controlling unit enters normal assist mode where a forward assist force for opening the doors is generated by an actuator, when the door is opened. In the case where the obstacle detection unit detects an obstacle, when the door is opened, the actuator controlling unit controls the actuator to assist the door so that the actuator controlling unit enters collision preventing mode to prevent the door from colliding with the obstacle. In this case, the door can be opened to at least a middle position of the door pivoting section between a closed position where the door closes the entrance and a collision position where the door collides with the obstacle.

The actuator is the motor 1010 which can rotate forward and reverse directions. In this embodiment, the actuator includes a DC motor (the other types of motor such as an induction motor, a brushless motor, a stepping motor may be used). The actuator control unit rotates the motor in the forward direction in forward assist mode, and rotates the motor 1010 in the reverse direction in reverse assist mode. In this embodiment, an interactive linear control type motor driver 1007 using a push-pull transistor circuit forms the actuator control unit.

Especially, the motor driver 1007 includes a forward drive transistor 1073 connected to a positive power supply (voltage Vcc) and a reverse drive transistor 1074 connected to a negative power supply (voltage –Vcc) as its main portions. A drive instruction voltage VD is adjusted by a resistor 1071, and inputted to base terminals of the transistors 1073, 1074. The resistor 1071 is a feedback resistor for amplification, which transfers part of a current between a collector and an emitter of each transistor 1073, 1074, and returns it to a base of each transistor. When VD is positive, the forward drive transistor 1073 sends a current in proportion to VD to the motor 1010. When VD is negative, the reverse drive transistor 1074 sends a current in proportion to VD to the motor 1010. The forward assist mode is such that the motor 1010 rotates in the forward direction when VD is positive. The reverse assist mode is such that the motor 1010 rotates in the reverse direction when VD is negative. The assist force is determined by a motor current corresponding to VD. The drive transistors 1073, 1074 are provided with transistors 1073t, 1074t for over-current protection. The numerals 1073R, 1074R are detection resistors for over-current. The numerals 1073D, 1074D are fly-back diodes.

Figure 43A:
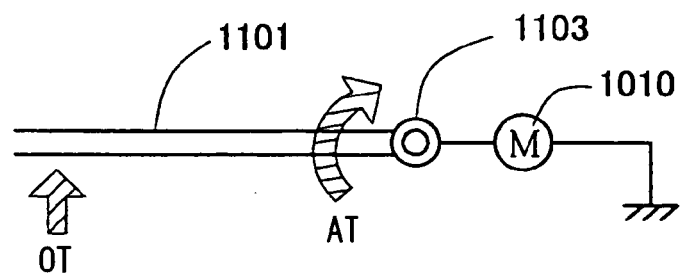
FIGS. 43A to 43C are views for explaining normal actions of the door assist mechanism of FIG. 41.
Figure 43B:
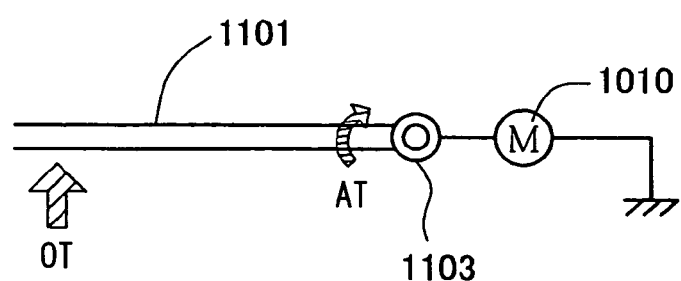
Figure 43C:
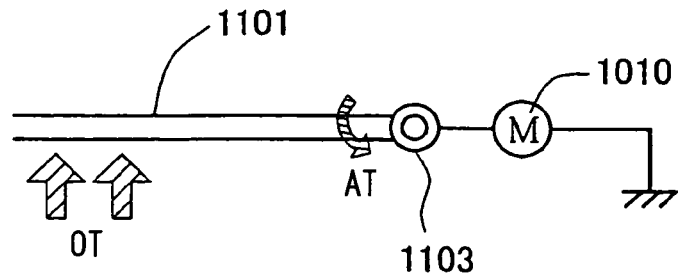

The door assist mechanism 541 is provided with an operation force detecting unit 1.002 for detecting an operation force of the door 1101. As shown in FIGS. 43A, 43B, and 43C, the actuator control unit controls the actuator 1010 so that the positive assist increases in the forward assist mode as the door operation force detected by the operation force detection unit 1002 decreases. When a person having weak strength opens the door 1101, the forward assist force by the motor 1010 functions strongly, so that the person can open the door 1101 easily. On the other hand, when a person having great strength opens the door 1101, the forward assist force functions relatively weak. For example, a sum of a door opening torque of an outer operation force and a door opening torque of the forward assist force is maintained almost constant, so that anyone can open the door 1101 by use of an almost-constant normal torque.

In the circuit of FIG. 41, the above functions are achieved as follows. The operation force detection unit 1002 is a torque sensor 1002 provided to the door pivot shaft 1103 as shown in FIG. 40. As the operation force for opening the door functions more strongly, a twist torque generated at the door pivot shaft 1103 becomes larger, so that an output voltage of the torque sensor 1002 increases. The output voltage of the torque sensor 1002 is positive when the door is opened, and the output voltage is negative when the door is closed. Accordingly, the direction of the torque can be detected by use of a sign of the voltage. In this embodiment, the output voltage of the torque sensor 1002 is amplified by a non-inverting amplifier 1003, and outputted as a torque detection voltage Vst via a voltage follower 1004.

The above torque detection voltage Vst is inputted to a differential amplifier circuit 1005. The differential amplifier circuit 1005 compares the torque detection voltage Vst to a reference voltage Vref1, amplifies a difference $\Delta V$ (=Vref1−Vst) by a predetermined gain, and outputs it as the drive instruction voltage VD for the motor 1010. When the door 1101 starts to be opened, $\Delta V$ becomes large and an output current of the motor 1010 becomes large because the torque detection voltage Vst is small at first, so that a large forward assist force functions. A torque of the forward assist force and the outer operation force are superimposed to the door pivot shaft 1103, so that the torque detection voltage Vst increases by a contribution of the forward assist force. Then, $\Delta V$ decreases. In other words, the torque of the forward assist force is returned to the door pivot shaft 1103, so that the sum torque of the outer operation force and forward assist force is reflected by the torque detection voltage Vst. To approximate the torque detection voltage Vst to vref1, the door assist drive of the motor 1010 is fed back. As a result, when the person having weak strength opens the door 1101, an assist motor current (assist torque AT) is maintained large by a decrease of the distribution of the outer operation force. When the person having great strength opens the door 1101, the assist motor current is maintained small.

As known, the door 1101 can be opened and closed by use of either a vehicle exterior operation knob 1104E or a vehicle interior operation knob 1104. When a lock button 1104R is pushed, the door cannot be opened or closed by use of the knobs 1104E, 1104 in a well known door lock mechanism 1320 shown in FIG. 41. When the door lock mechanism 1320 is locked, a door lock signal DRS is outputted, and used for stopping the motor 1010. In this embodiment, a switch 1021, which has received the door lock signal DRS, cuts off the reference voltage Vref1 from the differential amplifier circuit 1005, short-circuits an inverting input terminal and a non-inverting input terminal of the differential amplifier circuit 1005, and sets the differential input $\Delta V$ and the drive instruction voltage VD for the motor 1010 to zero forcibly, so that the motor 1010 is stopped.

In the circuit of FIG. 41, a comparator 1020 is provided for outputting an assist control signal SK1 when a sign of the torque detection voltage Vst is negative. A logical sum of the door lock signal DRS and an assist prohibition signal SK1 is inputted to a control terminal of the switch 1021 via a gate 1304. Even when the assist control signal SK1 is detected, the motor 1010 of an assist system SYS1 is stopped.

The obstacle detection unit is provided for detecting obstacles outside the vehicle, the obstacles interfering with the door 1101 when the door 1101 is opened. The obstacle detection unit can detect an obstacle facing a side surface of the door 1101. An obstacle in the direction of opening the door 1101 can be detected accurately. As such obstacle detection unit, for example, an obstacle sensor 1050 such as a known proximity switch, a reflective optical sensor (including an infrared sensor), or an ultrasonic sensor can be used.

A detection output of the obstacle sensor 1050 is compared to a threshold in the comparator 1051, and a signal showing whether an obstacle is detected is outputted in a form of a binary. In the case where the obstacle sensor 1050 detects an obstacle when the door 1101 is opened from the inside, an angle position of the door 1101 where the obstacle sensor 1050 detects the obstacle is a limit angle position. A detection signal SI' showing that there is the obstacle is outputted. The door assist control unit receives the detection signal SI' to prevent the door from opening further. In this embodiment, when the door 1101 reaches the limit angle position, a door pivot lock mechanism 1300 for obstacles is provided for preventing the door from pivoting further, as a part of the door assist control unit.

Figure 42A:
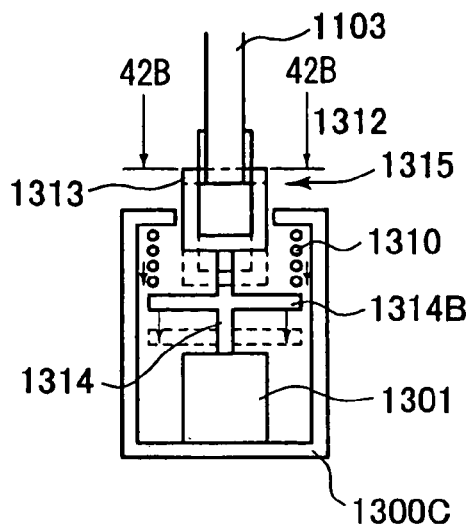
FIGS. 42A, 42B are views showing examples of a structure of a door rotation lock mechanism for obstacles.
Figure 42B:
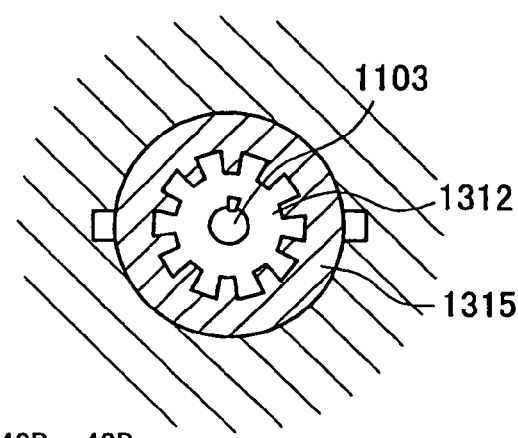

FIGS. 42A, 42B show an example of a structure of a lock portion of the lock mechanism 1300. A main portion of the lock portion includes a door engagement portion (a male spline in this embodiment) 1312 provided to the pivot shaft 1103 of the door 1101 and a vehicular engagement portion (female spline in this embodiment) 1313 fixed to the vehicle. The vehicular engagement portion 1313 is engaged detachably with the door engagement portion 1312 at an arbitrary angular phase in accordance with a pivot angle of the pivot shaft 1103, and locks the pivot of the pivot shaft 1103 at an angle phase of the engagement. The vehicular engagement portion 1313 is provided to approach or separate from the door engagement portion 1312 in the axial direction of the pivot shaft 1103. In case of the approach, locking engagement between the door engagement portion 1312 and the vehicular engagement portion 1313 is achieved. In case of the separation, the locking engagement is released. In this embodiment, this approach-separation mechanism is structured of a known solenoid mechanism (cylinder mechanism may be used). The vehicular engagement portion 1313 is mounted to a top of a driving shaft 1314 having a spring bearing portion 1314B. When the driving shaft 1314 biases a solenoid 1301 driven forward and reward in the axial direction by the solenoid 1301 contained in a case 1300C, the driving shaft 1314 is ejected, so that the vehicular engagement portion 1313 engages with the door engagement portion 1312. On the other hand, when the bias of the solenoid is released, a bias spring 1310 engaging with the spring bearing portion 1314B elastically returns. The driving shaft 1314 withdraws, so that the engagement between the door engagement portion 1312 and the vehicular engagement portion 1313 is released.

As shown in FIG. 41, when the detection signal SI' of an obstacle is outputted, a drive switch (transistor: the numeral 1302 is a flay-back diode for protection) 1303 is turned on. The solenoid 1301 is biased. The vehicular engagement portion 1313 and door engagement portion 1312 of FIG. 42A engage with each other. At this point, the door 1101 approaches an obstacle at an undefined position outside the vehicle. The spline engagement between the vehicular engagement portion 1313 and door engagement portion 1312 is achieved at an angle phase when the obstacle is detected, and locked at the angle. Namely, in accordance with an angular position of the door when the obstacle detection unit detects the obstacle (namely, in accordance with a position of the obstacle), the limit angle position is variably determined. Accordingly, regardless of a relative distance between the vehicle and obstacle, when the door approaches the obstacle, the door is prevented from opening so that the door does not collide with the obstacle. At this time, because the opening of the door 1101 is prevented even when the forward assist force of the motor 1010 generates, it is clear that the actuator controls the door assist to enter the collision avoidance mode.

When an outer door operation signal EDS shows that the door has been operated from outside the vehicle, a control mechanism of restricting the door assist (here, the door pivot lock mechanism 1300 for obstacles) regardless of a detection output of the obstacle sensor 1050, is limited. Specifically, a logical product output SI of the detection signal SI' of the obstacle sensor 1050, the signal SI' being made to be a binary by the comparator 1051, and the binary outer door operation signal EDS (when the door is operated from the outside, the signal EDS has the reverse sign to the detection signal SI), is used as a drive signal of the above drive switch 1303 to achieve the restricting function.

Instead of the mode using the swing door having the assist mechanism, an electric slide door including a known electric automatic open-close mechanism or assist mechanism can be used.

Figure 44:
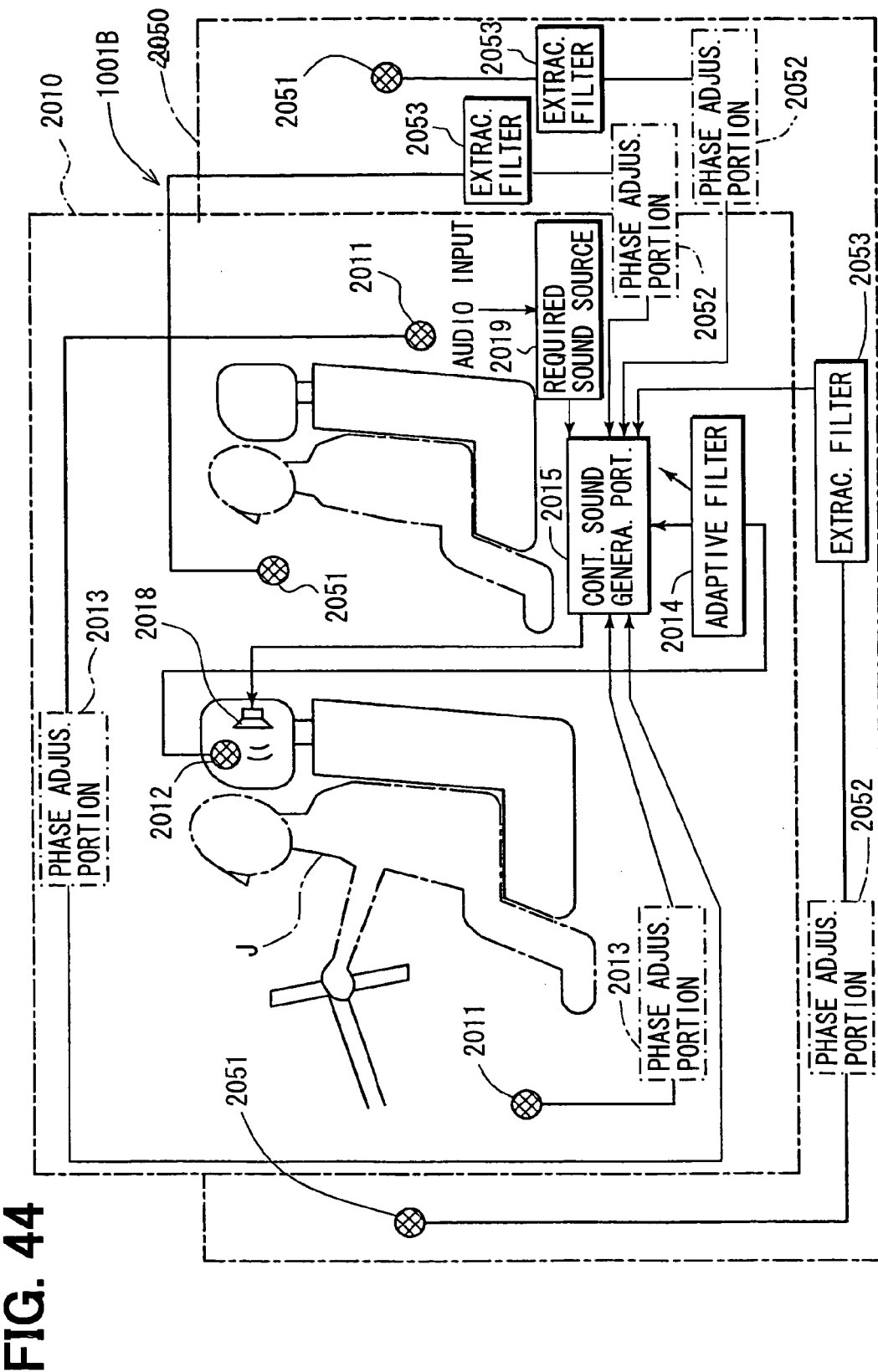
FIG. 44 is a conceptual block diagram showing an example of a structure of a noise canceller.

FIG. 44 is a functional block diagram showing an example of a structure of a noise canceller 1001B. A main portion of the noise canceller 1001B includes an active noise control mechanism body 2010 forming a noise restriction unit and a required sound emphasis portion (unit) 2050. The active noise control mechanism body 2010 has a vehicle interior noise detection microphone (noise detection microphone) 2011 for detecting a noise intruding into the vehicle and a noise control waveform synthesis portion (control sound generation portion) 2015 for synthesizing a noise control waveform having a reverse phase to a noise waveform detected by the vehicle interior noise detection microphone 2011. The noise control waveform is outputted from a noise control speaker 2018. An error detection microphone 2012 is provided for detecting a remaining noise element contained inside the vehicle after a noise control sound wave is superimposed. An adaptive filter 2014 is provided for adjusting a filter factor to decrease a level of the remaining noise.

The vehicle interior noise generated from the vehicle includes, e.g., an engine noise, a road noise, and a wind noise. Several vehicle interior noise detection microphones 2011 are distributed to positions for detecting respective vehicle interior noises. The vehicle interior noise detection microphones 2011 are positioned differently when viewed from a passenger J. Noise waveforms picked up by the microphones 2011 are quite different in phase from noise waveforms the passenger J actually hears. To adjust the phase difference, detection waveforms of the vehicle interior noise detection microphones 2011 are sent to the control sound generation portion 2015 properly via a phase adjustment portion 2013.

Next, the required sound emphasis portion 2050 includes an emphasized sound detection microphone 2051 and a required sound extraction filter 2053. An extracted waveform of the required sound is sent to the control sound generation portion 2015. In accordance with the same situation as the vehicle interior noise detection microphones 2011, a phase adjustment portion 2052 is provided properly. The emphasized sound detection microphones 2051 include a vehicle exterior microphone 2051 for collecting required sounds outside the vehicle and a vehicle interior microphone 2051 for collecting vehicle interior required sounds inside the vehicle. Both microphones can be formed of known directional microphones. The vehicle exterior microphone is such that a strong directional angular area for sound detection is directed outside the vehicle, and a weak directional angular area is directed inside the vehicle. In this embodiment, the whole of the microphone 2051 is mounted outside the vehicle. The microphone 2051 can be mounted across inside and outside the vehicle so that the weak directional angular area is mounted inside the vehicle and only the strong directional angular area is outside the vehicle. On the other hand, the vehicle interior microphone 2051 is mounted corresponding to each seat to detect a conversation sound of the passenger selectively, so that the strong directional angular area for sound detection is directed to a front of the passenger, and the weak directional angular area is directed opposite the passenger. These emphasized sound detection microphones 2051 are connected to the required sound extraction filter 2053 for sending required sound elements of the inputted waveforms (detected waveforms) preferentially. An audio input of the car audio system 515 of FIG. 1 is used as a vehicle interior required sound source 2019. An output sound from a speaker of this audio device (the speaker may use the noise control speaker 2018, or may be provided separately) is controlled not to be offset even when superimposed with the noise control waveforms.

Figure 45:
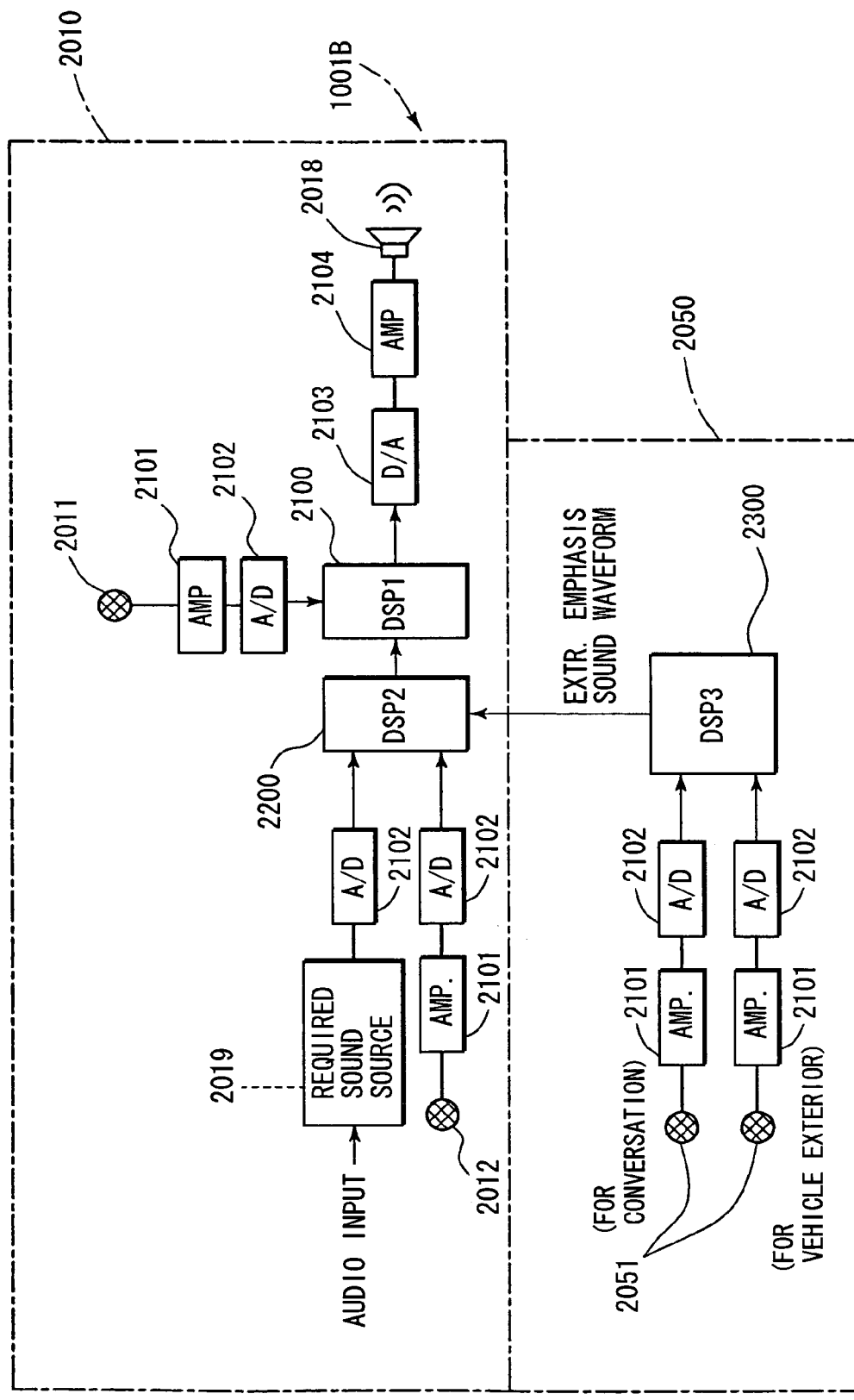
FIG. 45 is a conceptual block diagram showing an example of a structure of hardware of the noise canceller.

FIG. 45 is one example of a hardware block diagram corresponding to the functional block diagram of FIG. 44. A first DSP (Digital Signal Processor) 2100 forms a noise control waveform synthesis portion (control sound generation portion) 2015 and an adaptive filter 2014 (and a phase adjustment portion 2013). The vehicle interior noise detection microphones 2011 are connected to the first DSP 2100 via a microphone amplifier 2101 and an AD converter 2102. The noise control speaker 2018 is connected to the first DSP 2100 via a DA converter 2103 and an amplifier 2104. On the other hand, a second DSP 2200 forms an extraction portion for noise elements to be restricted. The error detection microphone 2012 is connected to the second DSP 2200 via the microphone amplifier 2101 and the AD converter 2102. The sound signal source not to be restricted, such as audio inputs, namely, the required sound source 2019 is connected to the second DSP 2200 via the AD converter 2102.

The required sound emphasis portion 2050 has a third DSP 2300 functioning as the required sound extraction filter 2053. The required sound detection microphone (emphasized sound detection microphone) 2051 is connected to the third DSP 2300 via the microphone amplifier 2101 and AD converter 2102. The third DSP 2300 functions as a digital adaptive filter. A process for setting a filter factor is explained below.

Sirens of emergency vehicles (such as an ambulance, a fire engine, and a patrol car), highway crossing signal sounds, horns of following vehicles, whistles, cries of persons (children and women) are defined as vehicle exterior required sounds (emphasized sounds) to be recognized as danger. Their sample sounds are recorded in, e.g., a disk as a library of readable and reproducible reference emphasized sound data. With respect to conversation sounds, model sounds of the respective plurality of persons are recorded as a library of the reference emphasized sound data as well. When passenger candidates of a vehicle are determined, the model sounds can be prepared as the reference emphasized sound data obtained from the phonation of the candidates. Accordingly, the emphasis accuracy of the conversation sounds can be increased when the candidates get in the vehicle.

An initial value is provided to the filter factor. An emphasized sound detection level by the emphasis sound detection microphone 2051 is set to the initial value. Next, each reference emphasized sound is read and outputted, and detected by the emphasized sound detection microphones 2051. Waveforms passing through the adaptive filter are read. Levels of the waveforms which can pass through the filter are measured. The above process is repeated until the detection level reaches a target value. The reference emphasized sounds of the vehicle exterior sounds and vehicle interior sounds (conversation) are switched one after another. Then, a training process for the filter factor is executed to optimize the detection level of the passing waveform. The required sound extraction filter 2053 having the filter factor adjusted as described above extracts a required sound from waveforms from the emphasized sound detection microphones 2051. The extracted emphasized sound waveform is sent to the second DSP 2200. The second DSP 2200 calculates a difference between an input waveform from the required sound source (audio output) 2019 and an extracted emphasized sound waveform from the third DSP 2300, from a detection waveform of the vehicle interior noise detection microphone 2011.

A filter factor of the digital adaptive filter embedded in the first DSP 2100 is initialized before use of the system. Various noises to be restricted are determined. Sample sounds of the noises are recorded in, e.g., a disk as a library of reproducible reference noises. An initial value is provided to the filter factor. A level of a remaining noise from the error detection microphone 2012 is set to the initial value. The reference noises are read sequentially and outputted, and detected by the vehicle interior noise detection microphone 2011. A detection waveform of the vehicle interior noise detection microphone 2011, the waveform passing through the adaptive filter, is read, and applied the fast Fourier transformation. Accordingly, the noise detection waveform is decomposed to fundamental sine waves each having a different wavelength. Reversed elementary waves are generated by reversing phases of respective fundamental sine waves, and synthesized again, so that a noise control waveform in anti-phase to the noise detection waveform is obtained. This noise control waveform is outputted from the noise control speaker 2018.

When a factor of the adaptive filter is determined properly, only noise elements can be extracted from a waveform of the vehicle interior noise detection microphones 2011 efficiently. The noise control waveform negative-phase-synthesized in accordance with the factor can offset the noise in the vehicle exactly. However, when the filter factor is not set properly, the waveform elements which are not offset is generated as remaining noise elements. These are detected by the error detection microphone 2012. A level of the remaining noise elements is compared to a target value. When the level is over the target value, the filter factor is updated. This process is repeated until the level is equal to or under the target value. Accordingly, the reference noises are switched one after another to execute the training process of the filter factor so that the remaining noise elements are minimized. In case of the actual usage, the remaining noise elements are regularly monitored. The filter factor is updated in real time to always minimize the remaining noise elements, and the same process as above is executed. As a result, while required sound wave elements remain, a noise level inside the vehicle decreases efficiently.

Figure 14:
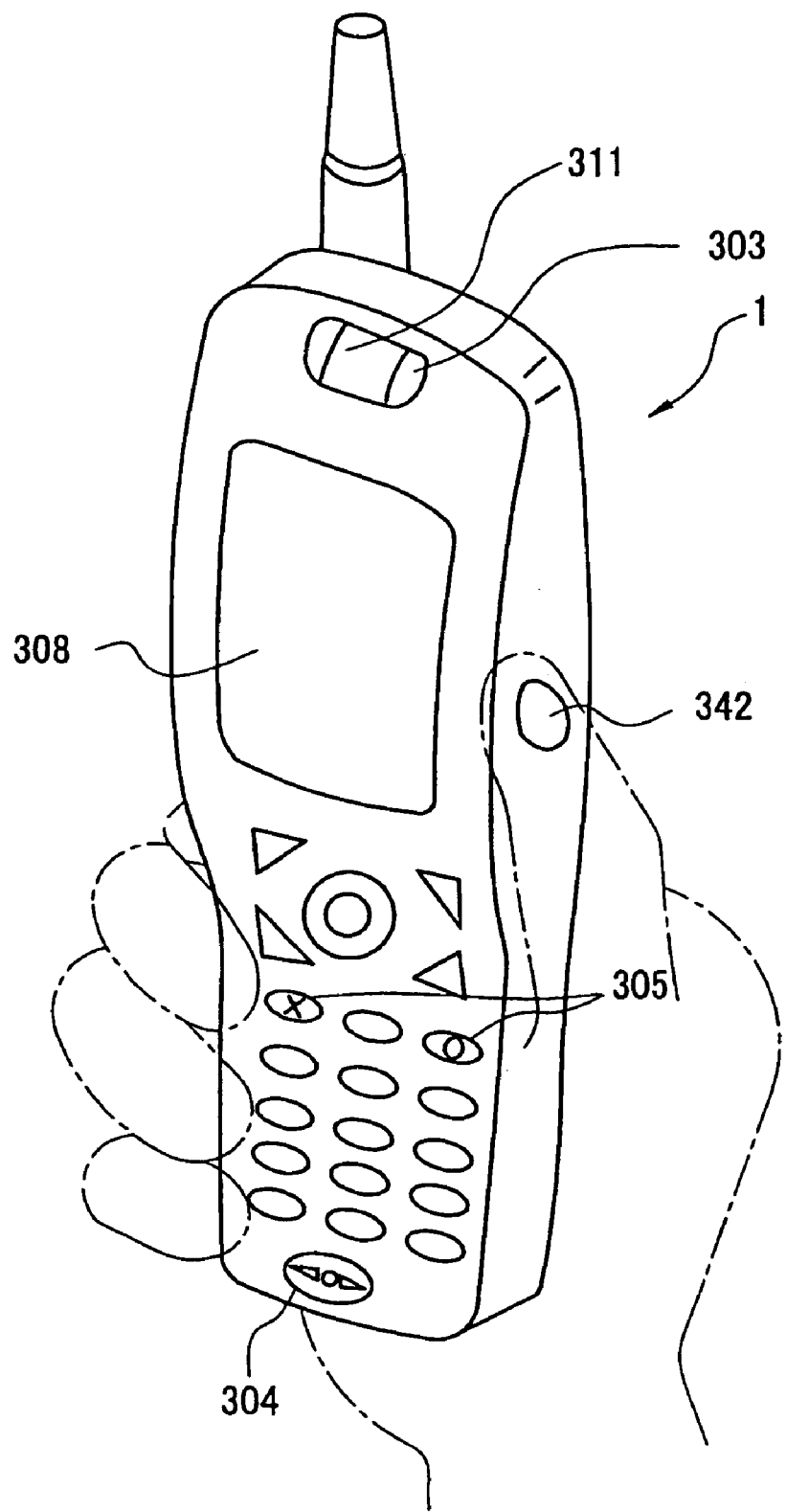
FIG. 14 is an external perspective view showing one example of a user terminal device structured as a mobile phone.

Next, a user terminal device 1 is structured as a mobile phone as shown in FIG. 14 in this embodiment (hereinafter called a "mobile phone 1"). The mobile phone 1 includes a monitor 308 having, e.g., a liquid crystal display, an input portion 305 having a keyboard, a transmitter 304, and a receiver 303. A pulse sensor (heartbeat sensor) 342 is also provided to a side of the mobile phone 1.

Figure 15:
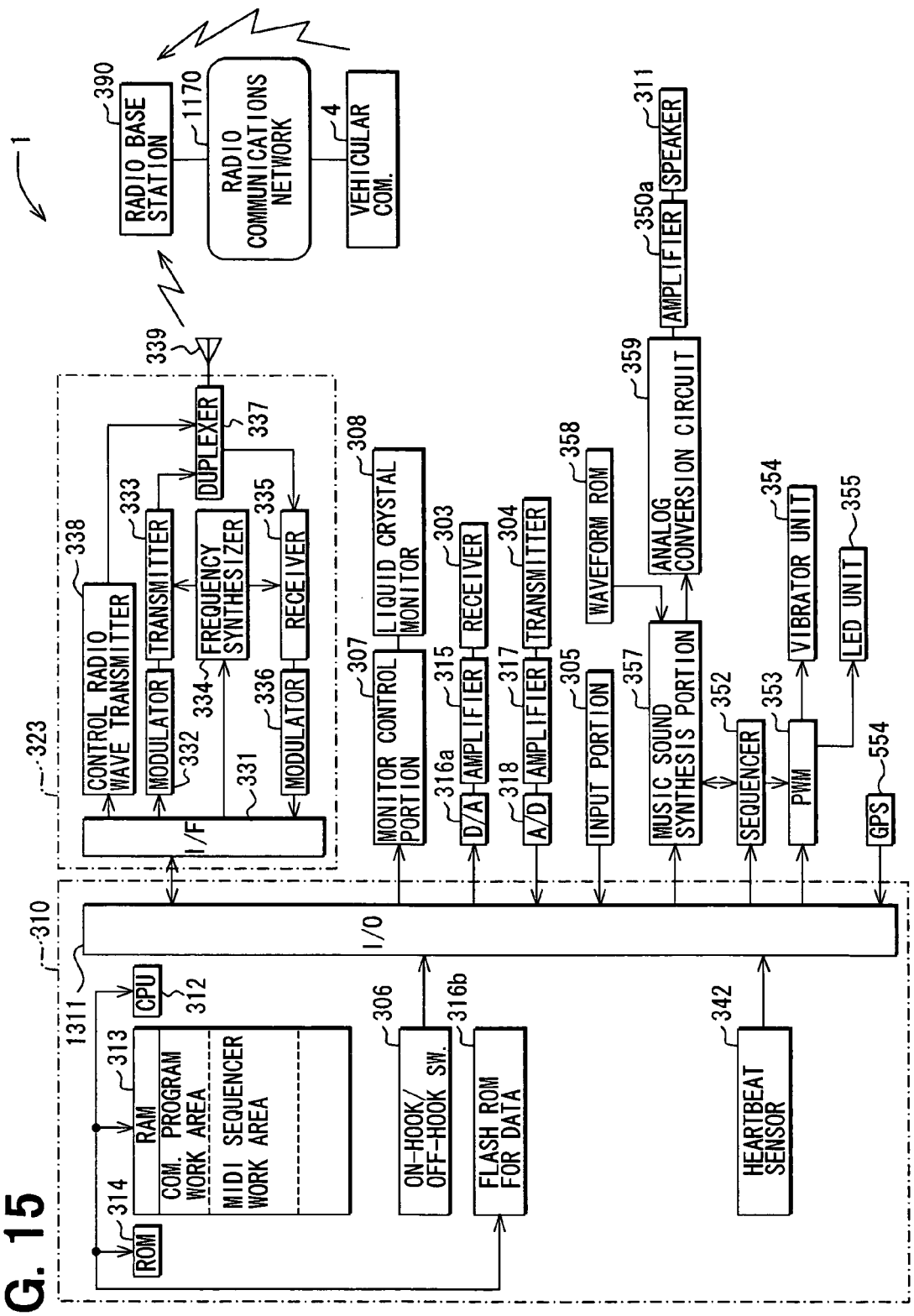
FIG. 15 is a block diagram showing one example of an electrical structure of the user terminal device.

FIG. 15 is a block diagram showing one example of an electrical structure of the mobile phone 1. A main portion of the circuit includes an input-output portion 1311 and a control portion 310 having, e.g., a CPU 312, a ROM 314, and a RAM 313 connected to the input-output portion 1311. An input portion 305, an on-hook/off-hook switch 306 are connected to the input-output portion 1311. The receiver 303 is connected to the input-output portion 1311 via an amplifier 315 and a DA converter 316*a*. The transmitter 304 is connected to the input-output portion 1311 via an amplifier 317 and an AD converter 318. A known GPS 554 for obtaining positional information of the mobile phone 1 is connected to the input-output portion 1311. The monitor 308 is connected to the input-output portion 1311 via a monitor control potion 307.

In this embodiment, to grasp a distance and directional relationship between the user terminal device 1 and the vehicle, the GPS 554 of the user terminal device 1, as well as the GPS 533 of the vehicle; is provided, so that the user terminal device 1 can acquire its positional information independently. The terminal positional information is sent to the vehicle via a radio communications network 1170. Accordingly, the vehicle can acquire accurate vehicle positional information by use of the GPS 533 connected to the vehicle and an accurate terminal position received from the user terminal device 1 and acquired by use of the GPS 554. The distance and directional relationship between the user terminal device 1 and the vehicle can be grasped extremely accurately. Change of distance and directional relationship between the user terminal device 1 and the vehicle can be grasped in real time.

Referring to FIG. 15 again, a communications device 323 is connected to the input-output portion 1311 of the mobile phone 1. The communications device 323 includes, e.g., a connection interface 331 for connecting to the control portion 310, a modulator 332 connected to the connection interface 331, a transmitter 333, a frequency synthesizer 334, a receiver 335, a demodulator 336, and a duplexer 337. A data signal from the control portion 310 is modulated by the modulator 332, and transmitted by the transmitter 333 from an antenna 339 via the duplexer 337. The reception electric wave is received by the receiver 335 via the antenna 339 and duplexer 337, demodulated by the demodulator 336, and inputted to the input-output portion 1311 of the control portion 310. In case of a call, for example, a voice signal inputted from the transmitter 304 is amplified by the amplifier 317, digitalized by the AD converter 318, and inputted to the control portion 310. The signal is outputted from the receiver 303 via the DA converter 316*a* and amplifier 315 after being processed by the control portion 310 in accordance with requirement.

A control radio wave transmitter 338 for transmitting a control radio wave is connected to the connection interface 331. The control radio wave is transmitted from the antenna 339 via the duplexer 337. When the mobile phone 1 moves to a different communications zone, a radio base station 390 of the network 1170 executes a known handover process in accordance with a received condition of the control radio wave.

Next, the following functions are provided to the mobile phone 1 for outputting ring tones and playing music. Ring tone data and music data (MPEG3 data or MIDI data: also used as ring tones) downloaded through radio reception are stored in a sound data flash ROM 316*b*. In case of MIDI data, in accordance with MIDI code, music sound data including, e.g., tone color, pitch, duration, and tempo is transmitted to a music sound synthesis portion 357. The music sound synthesis portion 357 buffers the musical sound data, reads a waveform data of a specified tone color from a waveform ROM functioning as a sound source, converts a frequency of the data so that the data has a pitch defined by the MIDI code, and outputs the data sequentially in accordance with a defined tempo as digital waveform data. The outputted digital waveform data is outputted from the speaker 311 via the analog conversion circuit 359 and amplifier 350*a*. Sound data formed of compression waveform data such as MPEG3 is outputted from the speaker 311 through a decode process and via the analog conversion circuit 359 and amplifier 350*a*. In this embodiment, timing information about sound output is inputted from the music sound synthesis portion 357 to a sequencer 352, and drives a vibrator unit 354 and an LED unit 355 in synchronization with music via a PWM unit 353. Accordingly, a hospitality effect using the sound output from the mobile phone 1 is further increased in combination with vibration and LED lighting.

(Sensors and Cameras)

Next, sensors and cameras will be explained below. The following sensors and cameras are connected to the hospitality determination section 2. Part of these sensors and cameras function as a scene estimate information obtaining unit, and as a biological condition detection unit. An vehicle exterior camera 518 takes a user approaching a vehicle, and obtains a gesture and facial expression of the user as static images and moving images. To magnify and take the user, an optical zoom method using a zoom lens and a digital zoom method for digitally magnifying a taken image can be used together. An infrared sensor 519 takes a thermography in accordance with radiant infrared rays from the user approaching the vehicle or from a face of the user in the vehicle. The infrared sensor 519 functions as a temperature measurement portion, which is the biological condition detection unit, and can estimate a physical and mental condition of the user by measuring a time changing waveform of the temperature.

A seating sensor 520 detects whether the user is seated on a seat. The seating sensor 520 can include, e.g., a contact switch embedded in the seat of the vehicle. The seating sensor 520 can include a camera taking the user who has been seated on the seat. In this case, the case where a load other than a person, such as baggage, is placed on the seat, and the case where a person is seated on a seat, can be distinguished from each other. A selectable control is possible. For example, only when a person is seated on the seat, the hospitality operation is executed. By use of the camera, a motion of the user seated on the seat can be detected, so that the detection information can be varied. To detect a motion of the user on the seat, a method using a pressure sensor mounted to the seat is also used.

In this embodiment, as shown in FIG. 58, in accordance with detection outputs of seating sensors 520A, 520B, 520C distributed and embedded in a seating portion and back-rest portion of the seat, a change of a posture of the user (driver) on the seat is detected as a waveform. The seating sensors are pressure sensors for detecting seating pressures. Especially, the standard sensor 520A is placed on the center of a back of the user who has seated facing a front. The sensors for the seating portion are a left sensor 520B placed on the left of the standard sensor 520A, and a right sensor 520C placed on the right of the standard sensor 520A. A difference between an output of the standard sensor 520A and an output of the right sensor 520C and a difference between an output of the standard sensor 520A and an output of the left sensor 520B are calculated in a differential amplifiers 603, 604. The differential outputs are inputted to a differential amplifier 605 for outputting a posture signal. The posture signal output Vout (second biological condition parameter) is almost a standard value (here, zero V) when the user is seated facing the front. When the posture inclines right, an output of the right sensor 520C increases, and an output of the left sensor 520B decreases, so that the posture signal output Vout shifts to negative. When the posture inclines left, the posture signal output Vout shifts to positive. Outputs of the right sensor 520C and left sensor 520B are added to an output of the back-rest sensor by adders 601, 602, and outputted as addition values. Differences between the seating portion sensors and the back-rest sensor may be outputted (in this case, when the driver is plunged forward, an output of the back-rest sensor decreases, and the differences increases, so that the plunge is detected as a large change of the posture).

Figure 49:
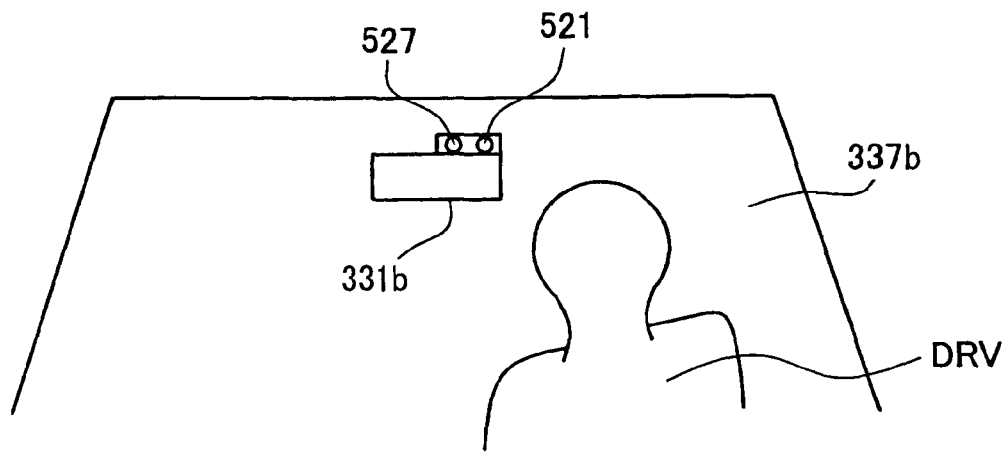
FIG. 49 is a view showing an example of a mounting position of a camera in the vehicle.
Figure 59:
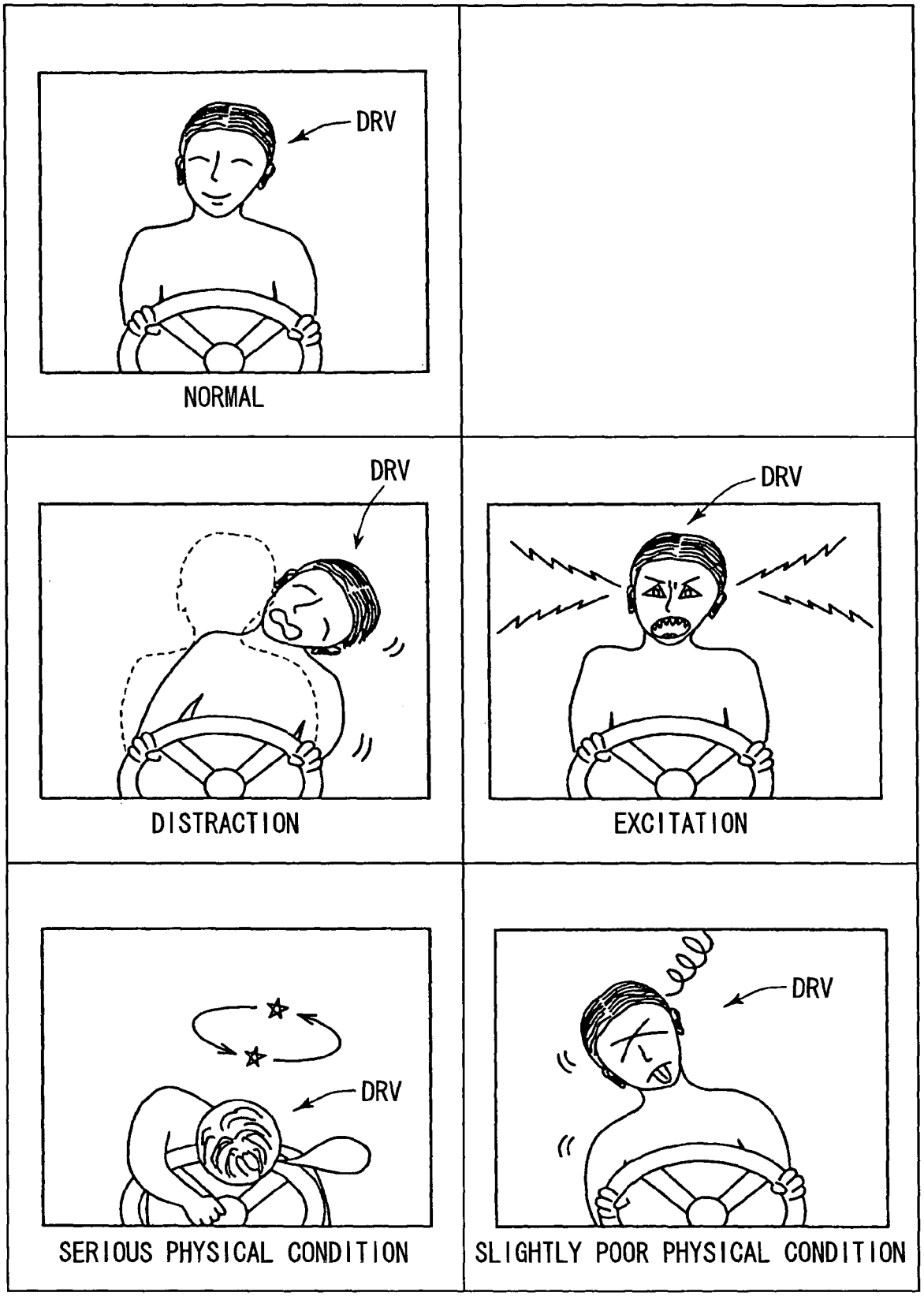
FIG. 59 is a diagram of images of various specified conditions.

A face camera 521 takes a facial expression of the user who has been seated. As shown in FIG. 49, the face camera 521 is mounted to, e.g., a rearview mirror 331b, and takes a bust of the user (driver) who has been seated on the seat, including the face, from diagonally above through a front screen 337b. An image of the face portion is extracted from the taken image. Various facial expressions of the user, shown in FIG. 59, can be specified. An order of the facial expressions is determined in accordance with the physical condition and mental condition. The facial expressions are provided with points in the order (for example, in case of the mental condition, stability is "1," distraction and anxiety are "2," excitation and anger are "3"). The facial expressions can be used as discrete numeral parameters (second biological parameter). The time change of the facial expressions can be measured as discrete waveforms. As a result, in accordance with the waveforms, the mental or physical condition can be estimated. From a shape of the image of the bust including the face and a position of the center of gravity on the image, a change of the posture of the driver can be detected. Namely, a waveform of the change of the position of the center of the gravity can be used as a change waveform of the posture (second biological condition parameter). In accordance with the waveform, the mental or physical condition can be estimated. The face camera 521 is used for user authentication by use of biometrics, in addition to the source for obtaining the user biological condition information used for the hospitality control. The face camera 521 can magnify and detect a direction of an iris of an eye to specify a direction of the face or eye (for example, when the user sees a watch frequently, the user is estimated to be upset about time). In accordance with time change waveform of an angle of the eye direction (a direction when the user faces a just front is defined as a standard direction, an angle of the shift to right and left relative to the standard direction is detected as a change of the waveform) (second biological condition parameter), the face camera 521 is used for estimating the physical or mental condition of the driver. A microphone 522 detects a voice of the user, and can function as the biological condition detection unit.

A pressure sensor 523 is mounted to a position grasped by the user, such as a steering wheel or shift lever, and detects a grip of the user and a repeating frequency of the gripping and releasing (biological condition detection unit). A blood pressure sensor 524 is mounted to a user-grasped position of the steering wheel of the vehicle (biological condition detection unit). A time change of a value of a blood pressure detected by a blood pressure sensor 524 is recorded as a waveform (first biological parameter). In accordance with the waveform, the pressure sensor 523 is used for estimating the physical and mental condition of the driver. A body temperature sensor 525, as shown in FIG. 50, includes a temperature sensor mounted to a user-grasped position of the steering wheel of the vehicle (biological condition detection unit). A time change of a temperature detected by the body temperature sensor 525 is recorded as a waveform (first biological condition parameter). The body temperature sensor 525 is used for estimating the physical and mental condition of the user in accordance with the waveform. A skin resistance sensor 545 is a known sensor for measuring a resistance value of the surface of a body due to sweat, and as shown in FIG. 50, is mounted to a user-grasped position of the steering wheel of the vehicle. A time change of a skin resistance value detected by the skin resistance sensor 545 is recorded as a waveform (first biological condition parameter). The skin resistance sensor 545 is used for estimating the physical or mental condition of the driver in accordance with the waveform.

A retina camera 526 takes a retina pattern, which is used for a user authentication by use of biometrics. An iris camera 527, as shown in FIG. 49, is mounted to, e.g., a rearview mirror 331b, and takes an image of an iris of the user. The iris is used for a user authentication by use of biometrics. When an image of an iris is used, characteristics of a pattern and color of an iris is used for the verification and authentication. Especially, a pattern of an iris is an acquired element, and has less genetic influence. Even identical twins have significantly different irises. Accordingly, by use of irises, reliable identifications can be achieved. By use of the identification using iris patterns, recognition and verification are executed rapidly, in which a ratio that a wrong person is recognized is low. In accordance with a time change of a size of a pupil of the driver taken by the iris camera (second biological condition parameter), the physical or mental condition can be estimated. A vein camera 528 takes a vein pattern of the user, which is used for the user identification by use of biometrics. A door courtesy switch 537 detects the opening and closing of the door, and is used as a scene estimate information obtaining unit for detecting a switch to a scene of getting in the vehicle and to a scene of getting off the vehicle.

An output of an ignition switch 538 for detecting an engine start is branched and inputted to the hospitality determination section 2. An illumination sensor 539 for detecting a level of an illumination inside the vehicle and a sound pressure sensor 540 for measuring a sound level inside the vehicle are connected to the hospitality determination section 2.

An input portion 529 including, e.g., a touch panel (which may use a touch panel superimposed on the monitor of the car navigation system 534: in this case, input information is transmitted from the hospitality control section 3 to the hospitality determination section 2) and a storage device 535 including, e.g., a hard disk drive functioning as a hospitality operation information storage unit are connected to the hospitality determination section 2.

On the other hand, a GPS 533 for obtaining vehicular position information (also used in the car navigation system 534), a brake sensor 530, a vehicle speed sensor 531, an acceleration sensor 532, and a steering wheel angle sensor 547 are connected to the hospitality control section 3.

The hospitality determination section 2 obtains user biological condition information including at least one of a character, mental condition, and physical condition of the user from detection information from one or two of the sensors and cameras 518 to 528. The hospitality determination section 2 determines what hospitality operation is executed in the hospitality operation device in accordance with contents of the information, and instructs the hospitality control section 3 to execute the determined hospitality operation. The hospitality control section 3 receives the instruction to cause the hospitality operation devices 502 to 517, 534, 541, 548, 549, 550, 551, 552, and 1001B to execute the hospitality operation. Namely, the hospitality determination section 2 and hospitality control section 3 operate together to change an operation of the hospitality operation devices 502 to 507, 534, 541, 548, 549, 550, 551, 552, and 1001B in accordance with the obtained user biological condition information. A radio communications device 4 forming a vehicular communications unit (host communications unit) is connected to the hospitality control section 3. The radio communications device 4 communicates via the user terminal device (mobile phone) 1 and the radio communications network 1170 (FIG. 15).

(Car Audio System)

Next, a car audio system will be explained below. An operation portion 515*d* (FIG. 17) operated by the user manually is provided to the car audio system 515. Selected music data is inputted from the operation portion 515*d* to read desired music source data and play the music. A volume/tone control signal from the operation portion 515*d* is inputted to the preamplifier 515*g*. This selected music data is sent from the interface portion 515*a* to the hospitality determination section 2 via the hospitality control section 3, and accumulated as music selection history data 403 of the storage device 535 connected to the hospitality determination section 2. In accordance with the accumulated music selection history data 403, the after-mentioned user character determination process is executed (namely, the operation portion 515*d* of the car audio system 515 forms a function of the biological condition detection unit).

FIG. 18 shows one example of a database structure of the music source data. Music source data (MPEG3 or MIDI) is stored in the database, corresponding to song IDs, song names, and genre codes. In each music source data, a character type code showing a character type (e.g., "active," "gentle," "decadent," "physical," "intelligent," or "romanticist"), age code (e.g., "infant," "child," "junior," "youth," "middle age," "senior," "mature age," "old," or "regardless of age"), and sex code ("male," "female," and "regardless of sex") of a user who has selected the song are stored. The character type code is one of pieces of the user character specifying information. The age code and sex code are sub classification unrelated to the character. Even when a character of a user can be specified, a music source not suitable for an age and sex of the user is not effective for offering hospitality to the user. To specify suitability of the music source provided to the user, the above sub classification is effective.

A song mode code corresponds to, and is stored in each music source data. The song mode shows relationship between a mental and physical condition of the user who has selected the song, and the song. In this embodiment, the song codes are classified into "uplifting," "refreshing," "mild and soothing," "healing and α wave," and so on. Because the character type code, age code, sex code, genre code, and song mode code are the data referenced when a hospitality content unique to each user is selected, these codes are named hospitality reference data collectively.

Figure 81:
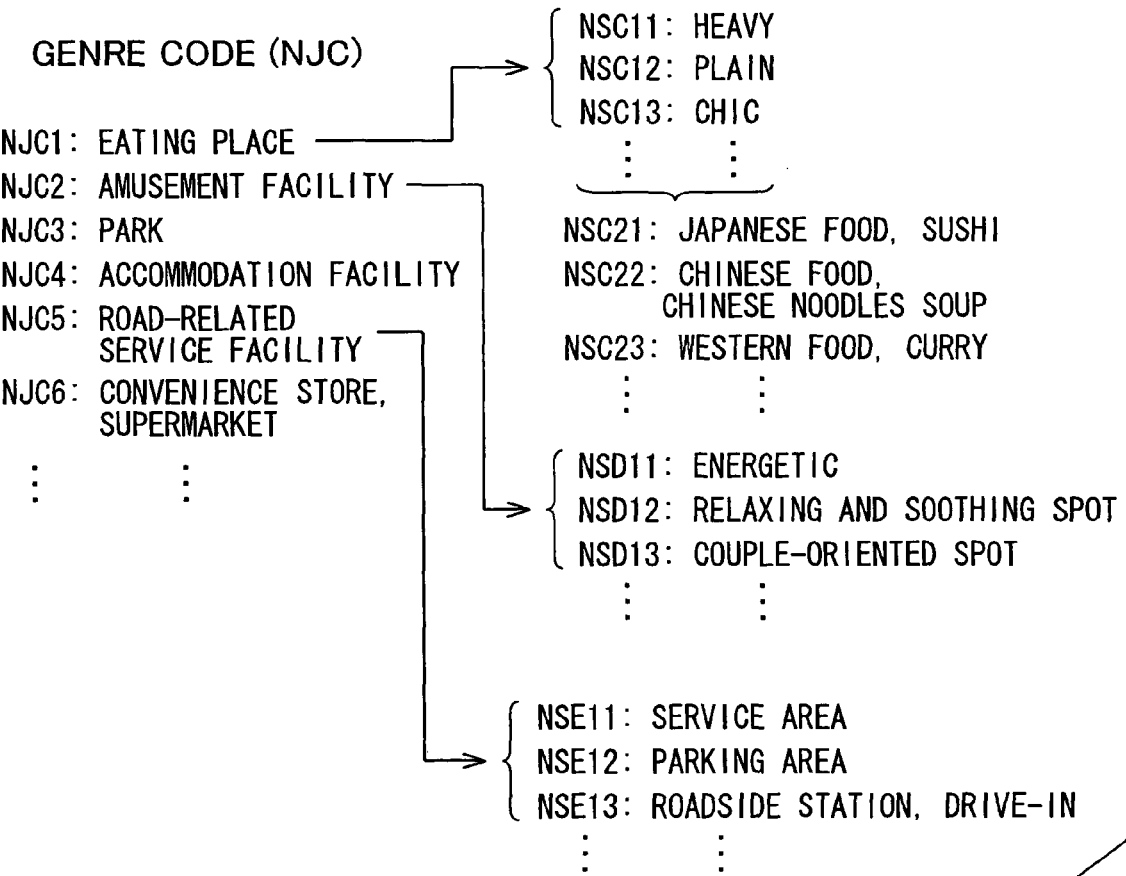
FIG. 81 is a conceptual diagram of a destination database.

FIG. 81 shows the content of the destination database 21*d* used in the car navigation system 534. As well as the above music source database, position information about each destination is provided with an ID for identifying each destination, and with classification information comprised of the same hospitality reference data as the music source database. In the classification information, a character type code, age code, and sex code are almost the same as the music source database. Some examples follow. As for the user who selects a destination, estimated codes are a character type (e.g., "active," "gentle," "optimistic," "pessimistic," "decadent," "physical," "intelligent," or "romanticist"), age code (e.g., "infant," "child," "junior," "youth," "middle age," "senior," "mature age," "old," or "regardless of age"), and sex code ("male," "female," and "regardless of sex"), which are corresponded with the position information for storing. The character type code is one of pieces of the user character specifying information. The age code and sex code are sub classifications unrelated to the character. Even when a character of the user can be specified, a destination unsuitable for an age and sex of the user is not effective for offering "hospitality" which entertains the user. To specify suitability of a destination to be suggested to the user, the above sub classifications are effective.

The genre codes are used for classifying facilities of destinations in accordance with types of the facilities. The genre codes include, e.g., "eating house," "amusement facility," "park," "accommodation facility," "road-related service facility," "convenience store," and "supermarket." The facilities such as "eating house," "road-related service facility," "convenience store," and "supermarket" are defined as facilities where eating is possible.

Each genre code has suitable sub classification codes. In consideration of "hospitality" effect, types of the sub classification codes of "eating house" are defined to select a destination related to physical and mental conditions of a user. An eating house to be selected by a user (particularly, such as youth and middle age) who is in good physical condition and has a good appetite, is provided with a sub classification code ("heavy") for prioritizing a feeling of fullness. An eating house to be selected by a user (particularly, such as female) who is not in good physical condition and has a little appetite, is provided with a sub classification code ("plain") for prioritizing light meals. An eating house to be selected by, e.g., a user who is tired and needs a change of pace and a couple who wants to go to a place with atmosphere, is provided with a sub classification code ("chic") for prioritizing atmosphere at meals.

In addition to the priority of the "hospitality effect" sub classifications based on general food types ("Japanese food such as sushi," "Chinese food such as Chinese noodles soup," and "Western food such as curry") are provided, and can be selected properly.

On the other hand, sub classification codes based on entertainment service facilities such as amusement facilities (or sightseeing spots) and parks are defined so that a destination can be selected in accordance with physical and mental conditions of a user. Some examples follow. A facility to be selected by a user (particularly, such as youth and middle age) who requests a cheerful and active service, is provided with a sub classification code ("energetic spot") for prioritizing physical or mental release. A facility to be selected by a user (particularly, such as female) who is not in good condition or is tired, is provided with a sub classification code ("relaxing and soothing") for prioritizing control of loss of bodily strength. A facility to be selected by a couple (particularly, such as female) who wants to go to a place with atmosphere, is provided with a sub classification code ("couple-oriented spot") for prioritizing atmosphere.

On the other hand, the genre code "road-related service facility" is provided with sub classifications "service area," "parking area," "roadside station," and "drive-in."

(Scenes)

Figure 2:
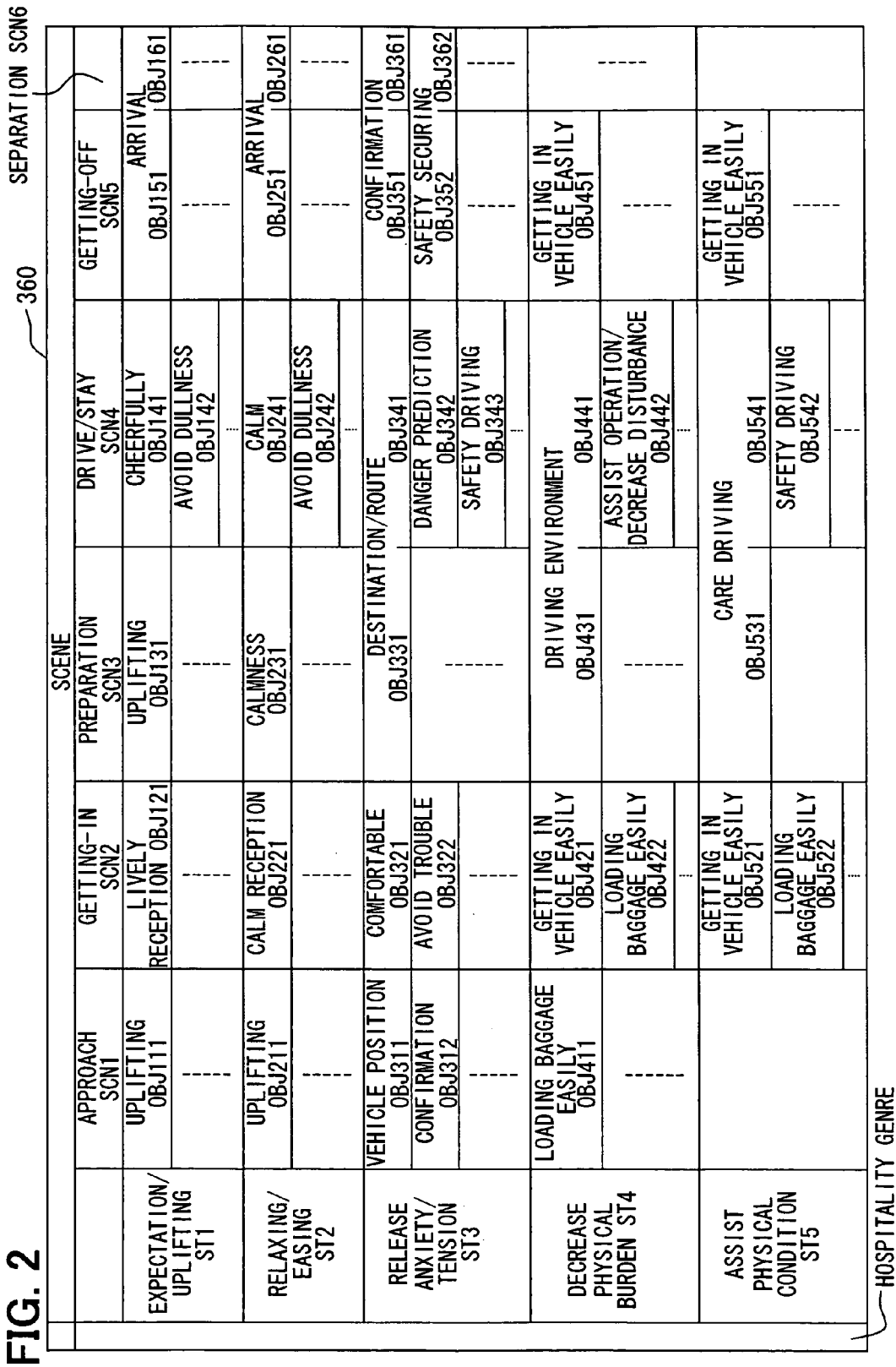
FIG. 2 is a view showing one example of a hospitality determination table.

Next, scenes will be explained below. In the ROM (or the storage device 535) of the hospitality determination section 2 of FIG. 1, as shown in FIG. 2, a hospitality determination table 360 for storing hospitality contents for each scene is stored. In this embodiment, an approach scene SCN1, a getting-in scene SCN2, a preparation scene SCN3, a drive/stay scene SCN4, a getting-off scene SCN5, and a separation scene SCN6 are set in this order sequentially. In each scene, five hospitality genres (ST) are set. In each genre, one or more hospitality themes (OBJ) are set. The genre supervises multiple themes in each scene, and belongs to the concept of the "theme" in a broad sense.

Figures 4, 5, 6:
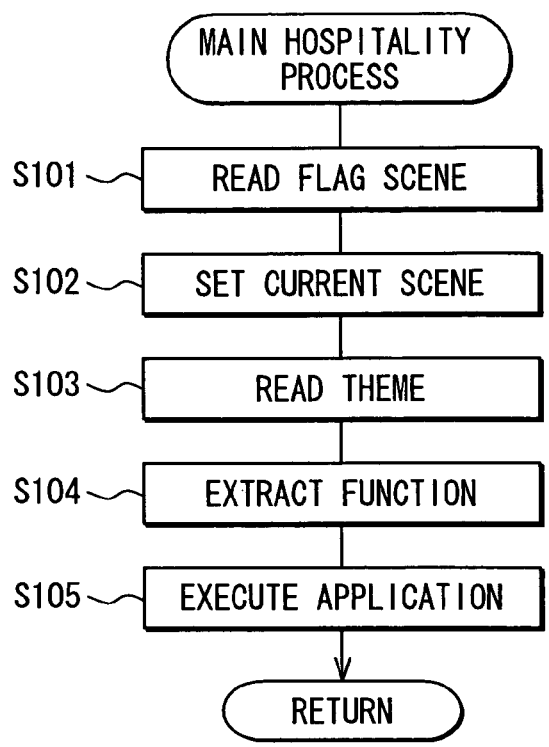
FIG. 4 is a flowchart showing a flow of a main hospitality process.
FIG. 5 is a view showing contents of scene flags.
FIG. 6 is a diagram showing a concept of a theme application library.

To specify the approach scene, as described later, the GPS 554 of a user and the GPS 533 of a vehicle specify a relative distance between the vehicle and the user outside the vehicle and a change of the distance to detect that the user has approached to inside a predetermined distance. The getting-in scene and getting-off scene are specified in accordance with a door-opening detection output of the door courtesy switch 537. Because the getting-in scene or getting-off scene cannot be specified by use of only the door opening information, a scene flag 350 is provided in the RAM of the hospitality determination section 2 as a current scene specifying information storage unit, as shown in FIG. 5. The scene flag 350 has an individual scene flag corresponding to each scene. In each scene, coming order of which is determined in the time sequence, the flag corresponding to the scene is set to "coming (flag value 1)." In the scene flag 350, to specify the last flag having a value of "1" (the last of the flag string of "1"), which scene is in progress can be specified.

The preparation scene and drive/stay scene are specified in accordance with whether the seating sensor detects a user. The period from the time that the user gets in the vehicle until the user turns on an ignition switch 538, or the period until the user is seated for over a predetermined time although the ignition switch 538 is not turned on, is recognized as the preparation scene. The switch to the separation scene is recognized when the door courtesy switch 537 detects the door closing after the getting-off scene.

The hospitality operation in each theme is controlled by an operation control application of the corresponding hospitality operation device. As shown in FIG. 6, the operation control applications are stored in the ROM (or the storage device 535) of the hospitality control section 3 in the form of the theme application library 351. The theme determined in the hospitality determination section 2 is notified to the hospitality control section 3, where the operation control application for the corresponding theme is read and executed. When the operation control application is executed, a usage priority of multiple hospitality operations supervised in each hospitality theme is determined in accordance with what level of the hospitality a user desires. In each theme (or scene), the hospitality operation is selected from the prepared hospitality operations in the descending order of the priority. Specifically, as shown in FIGS. 7A to 13B (mentioned later), function selection tables 371, 372 which define an operation priority (the greater the numeral is, the higher the priority is) of the multiple hospitality operation devices (hospitality functions) for each operation object determined in accordance with a disturbance type, are prepared for each hospitality theme, and stored in the ROM of the hospitality control section 3. Namely, the function selection tables 371, 372 specify the multiple hospitality operation devices usable in each scene, and show relationship between a disturbance on the user and the hospitality operation device preferentially used in accordance with the disturbance.

(Operations of Vehicular User Hospitality System)

Figure 46:
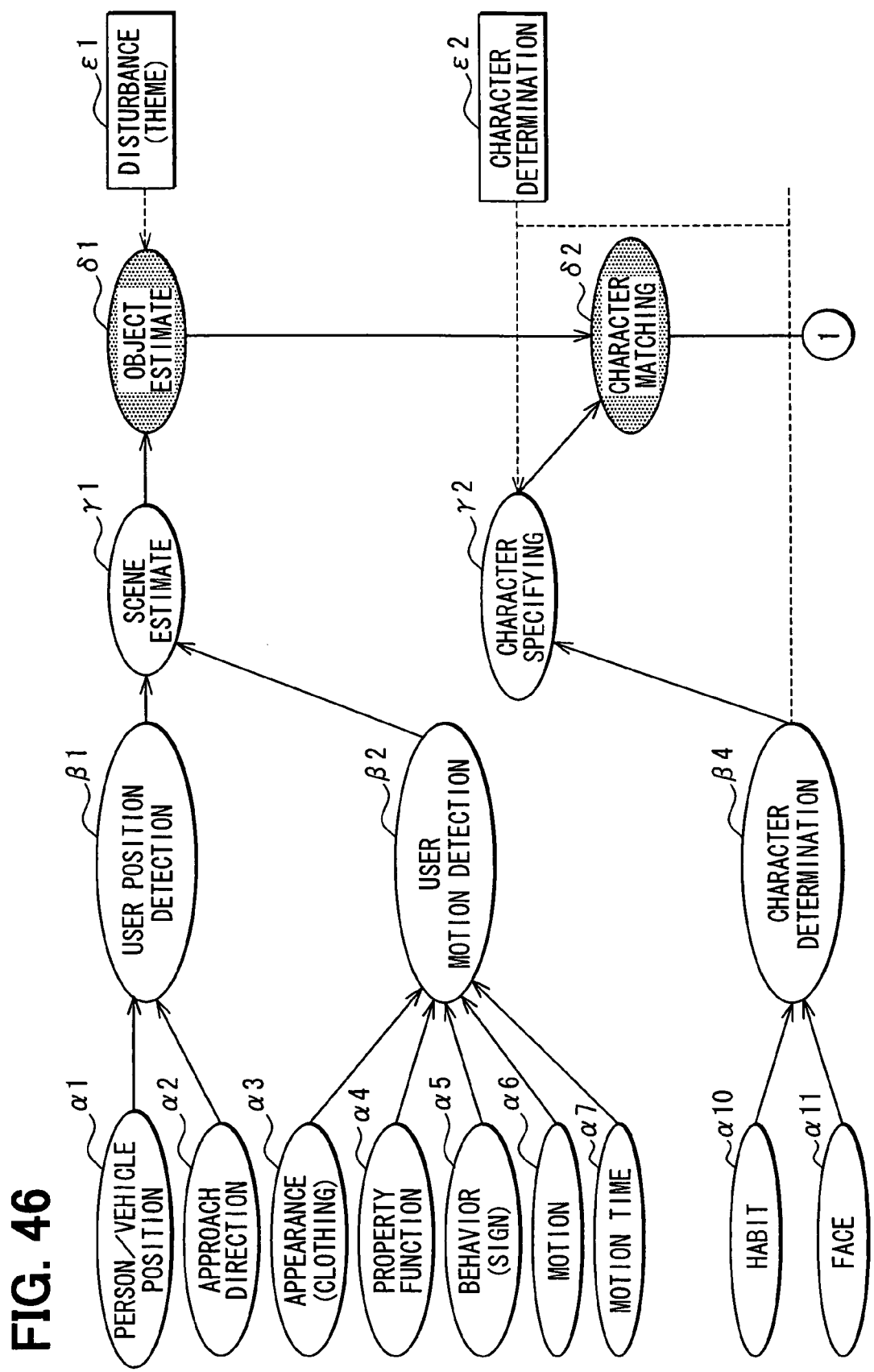
FIG. 46 is a flowchart showing an overall flow of a hospitality process in the vehicular user hospitality system.
Figure 47:
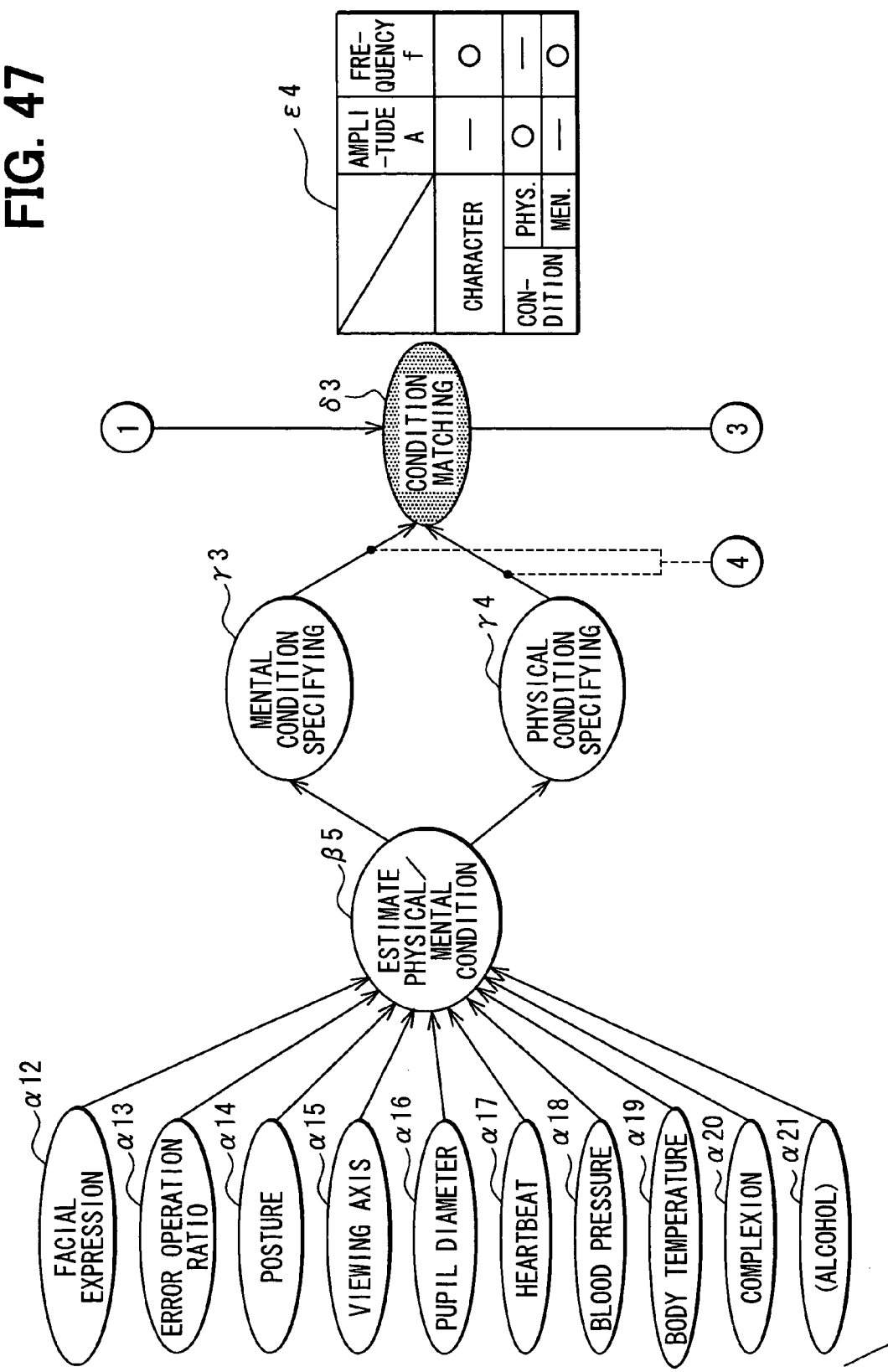
FIG. 47 is a flowchart following FIG. 46.
Figure 48:
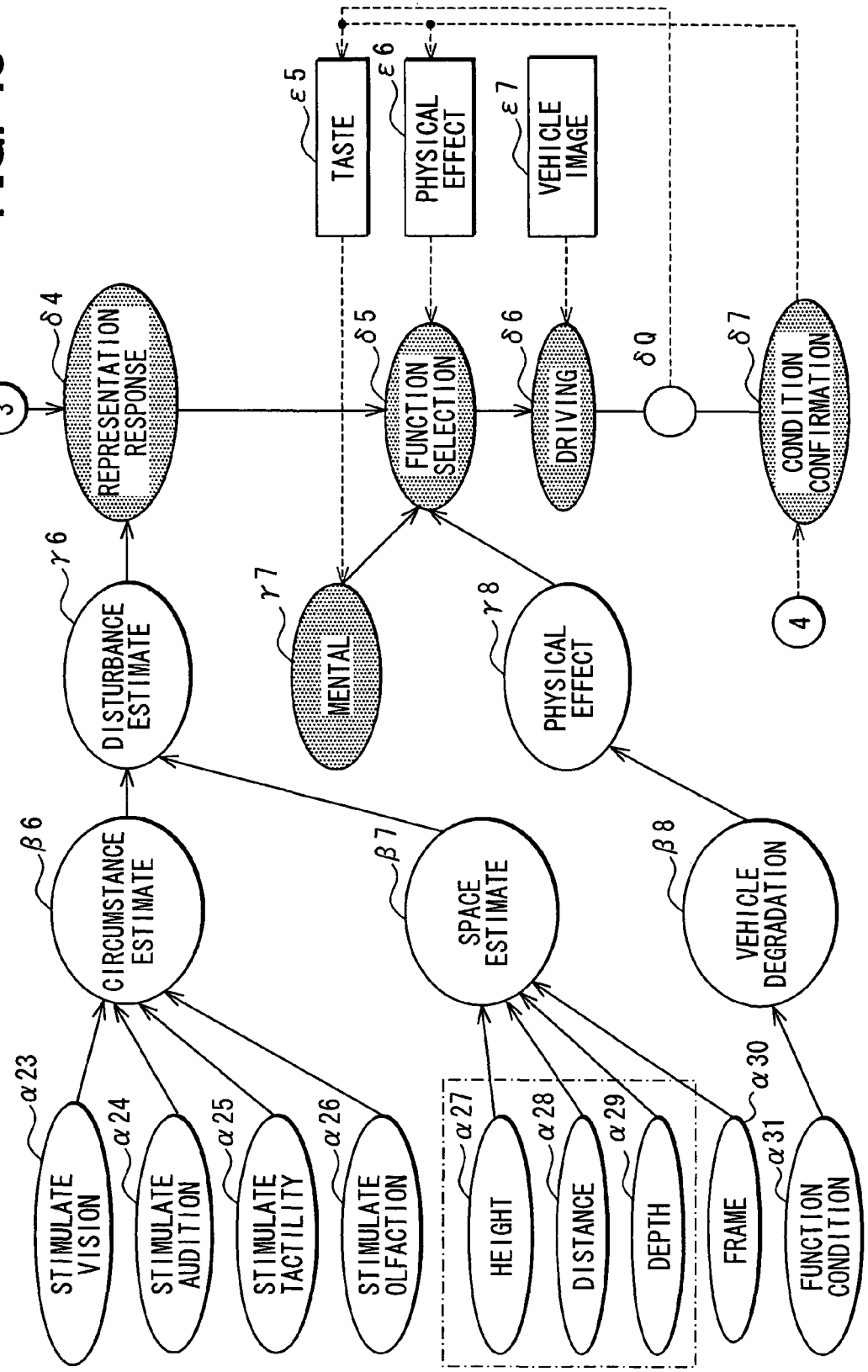
FIG. 48 is a flowchart following FIG. 47.

Next, operations of a vehicular user hospitality system (hereinafter called just a "system") 100 will be explained below. FIGS. 46 to 48 conceptually show an overall algorithm of a series of processes from the hospitality determination to the hospitality operation execution (these three drawings are to be read as one drawing by use of the numerals in the circles as connectors). A main hospitality process includes "object estimate (δ1)," "character matching (δ2)," "condition matching (δ3)," "representation response (δ4)," "function selecting (δ5)," "driving (δ6)," and "condition confirming (δ7)."

"FIGS. 46 to 48 are complementarily explained here for understanding the figures in more detail as follows.

Scene Estimate γ1

Whether the approach scene, door opening scene, getting-in scene, or the like is in progress, is specified.

Disturbance (theme) ε1

An item of the corresponding disturbance is set, but not used for detection.

"Safety," "easiness," and "comfort" are added to each scene. The requirement when a disturbance occurs is used for extracting disturbances related to the requirement. This algorithm quantifies the responses to the disturbances.

Character Determination β4

What the user considers important is extracted to determine the user's sense of value.

Character Specifying γ2

Appropriate values are set corresponding to the characters. The representation for the safety, easiness, and comfort is set. Each detail of the safety, easiness, comfort, and comfort is weighted. The priority of the safety, easiness, and comfort is fixed in this order.

Character Matching δ2

For example, red light is used for a person of the A type.

Physical/Mental Condition Estimate β5

The physical/mental condition of a user is specified from an input into an interface, an attribute, and a change of a vital reaction in response to a disturbance. The mental/physical factors are separated in accordance with a contribution ratio.

Mental Condition Specifying γ3

A frequency is changed in accordance with a mental condition. For example, a switch to a blue light is made in case of excitation. A mental stress resistance is determined in accordance with an appropriate value corresponding to the mental condition.

Physical Condition Specifying γ4

A physical stress resistance is determined in accordance with an appropriate value corresponding to the physical condition. An amplitude is changed in accordance with a physical condition. Stimulation is decreased as the physical condition is worse.

Table ε4

The frequency is a default value. All the representations are made in accordance with an amplitude (strength) and frequency (change ratio).

A target value is determined in accordance with the conditions. The physical condition is shown by a peak of the input. The mental condition is shown by a frequency/wavelength.

Circumstance Estimate β6

The stimulation directly recognized by a user is specified.

Disturbance Estimate γ6

The disturbance stimulation is set to a numeral value comparable to an appropriate value obtained from the "character" and the "conditions." A type and level of the disturbance is determined.

Representation response δ4

A difference between a target value and a disturbance, the order and control amount of controlling safety, easiness, and comfort, are determined.

Space Estimate β7

Indirect stimulation is specified. An obstacle is specified. Oppression, alienation, and so on are specified.

Vehicle Degradation β8

Auto trouble shooting is executed.

Mental Condition Matching γ7

It is determined whether the selected function matches an interest of a user. The NG/OK and so on is extracted from an evaluation of the selected function by the user, and reflected by information about a taste of the user.

Physical Effect γ8

The physical effect γ8 is reflected by the determination about whether the function is normal.

Favorite ε5

Defaults are set for selecting functions.

Function Selecting δ5

The functions are arranged. The functions are selected in the descending order of levels of their effects. The selection reflects the taste of a user and whether the functions are normal.

Driving δ6

A representation suitable for an image of a vehicle is made (the image is a favorite of the user). The image is assumed to be a school of a tea ceremony."

Again, referring to FIG. 46, at first, in "object estimate (δ1)," a current scene is estimated in a user position detection (β1) and a user motion detection (β2). The user position detection (β1) is executed by grasping and specifying a relationship (α1) between a user and a vehicle. In this embodiment, an approach direction (α2) of the user is considered together. Fundamentally, the user motion detection (β2) is executed by use of outputs of the sensors (scene estimate information obtaining unit) for detecting motions uniquely defined to determine scenes, such as the opening and closing of the door and the seating on the seat (α6). As well as detecting a switch from the preparation scene to the drive/stay scene by use of a seating duration, a duration of a specified motion (α7) is considered.

Figure 3:
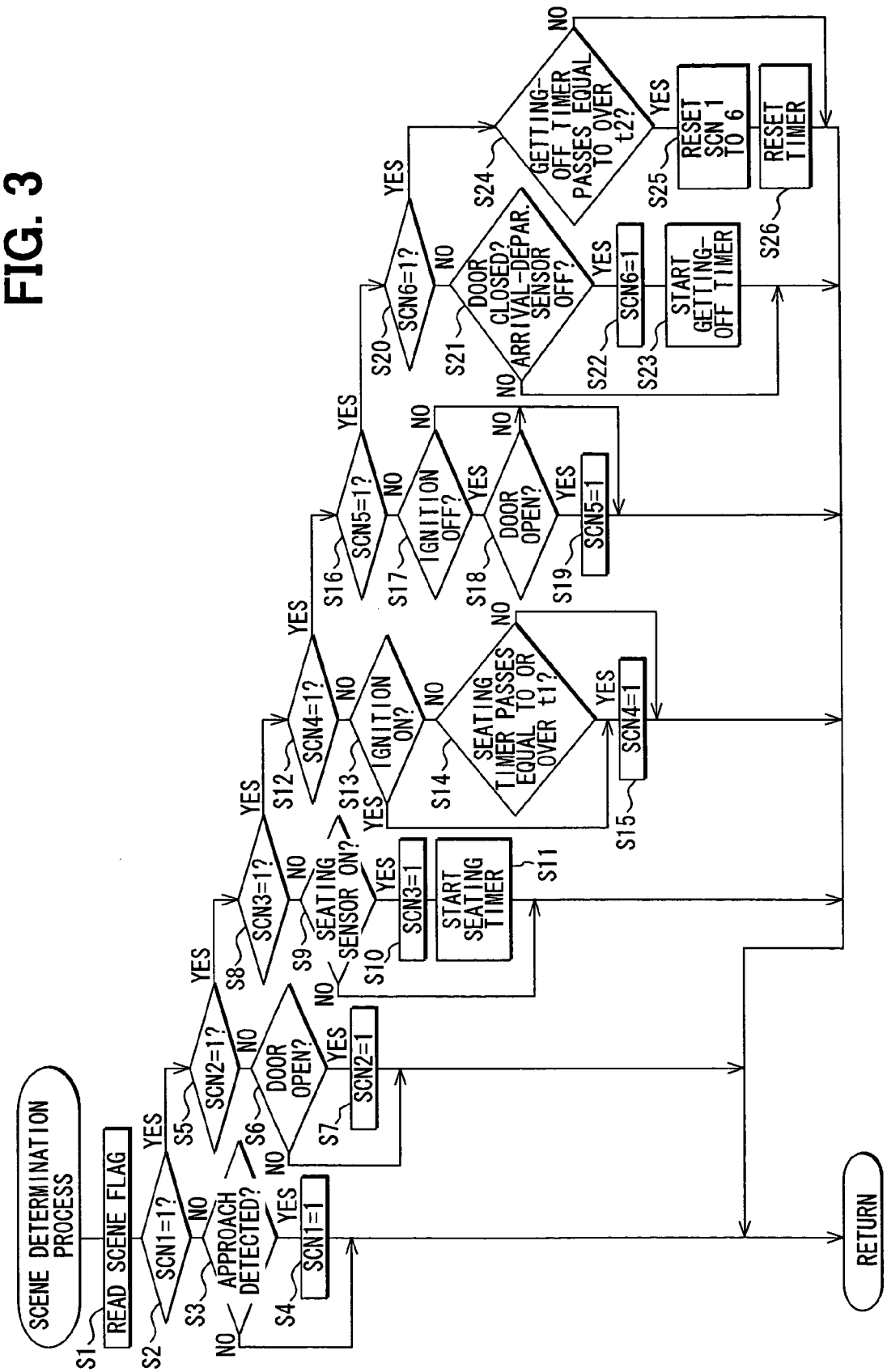
FIG. 3 is a flowchart showing a flow of a scene determination process.

FIG. 3 is a flowchart showing a flow of a process for determining the scene. The process is executed repeatedly in a predetermined cycle while the vehicle is used. First in S1, the scene flag 350 of FIG. 5 is read. In S2, S5, S8, S12, S16, and S20, which scene is in progress is determined from a state of the scene flag 350. In the scene flag 350, flags are set from a flag of a time-sequentially preceding scene. A flag of a following scene is not set solely by bypassing the flag of the preceding scene.

In S2 to S4, the approach scene is specified. First in S2, a flag SCN1 of the approach scene is confirmed not to be "1" (namely, the approach scene is not in progress). In S3, from position information specified by the vehicle GPS 533 (FIG. 1) and user GPS 554 (mobile phone 1: FIG. 15), it is determined whether the user approaches inside a predetermined distance (for example, 50 m or smaller) to the vehicle. When the user approaches inside the predetermined distance, it is determined that the switch to the approach scene is made and SCN1 is set to "1" in S4.

In S5 to S7, the getting-in scene is specified. In S5, a flag SCN2 of the getting-in scene is confirmed not to be "1." In S6, from input information from the door courtesy switch 537, it is determined whether the door is opened. When the door is opened, it is determined that the switch to the getting-in scene is made, and SCN2 is set to "1" in S7. Because the current scene is SCN=1, namely, confirmed to be the approach scene, it can be easily determined that the door opening in this situation is made in getting in the vehicle.

In the approach scene and getting-in scene, when the user approaches the vehicle to get in and drive the vehicle, the hospitality operation may be executed on the premise that the user gets in the vehicle, as described above. The user may approach the vehicle, e.g., to confirm a property left in the vehicle, not to get in and drive the vehicle. In such a case, although the user approaches the vehicle, the user may not move to get in the vehicle for long time (for example, the user just looks inside the vehicle, or the user does not move while gripping a handle of the door, and the user does not start opening the door). At a timing of the switch from the preceding scene to the following scene, a voice of a question for confirming an object of the user in the following scene is outputted from, e.g., a speaker. In accordance with answer information (voice input through a microphone) to the question from the user, a hospitality operation in the following scene can be executed. One example is shown below.

When the user approaches the vehicle, and stops in front of the door and does not move, the hospitality control section forwards the hospitality control process just before the switch to the getting-in scene. When the user does not open the door for a predetermined time, a question such as "Won't you get in? I'm disappointed." is outputted from a speaker directing outside the vehicle. The user answers "I'm just looking for a lost property. I'll come again. Don't be disappointed." The hospitality determination section analyzes the content of the answer, and starts the hospitality operation module for confirming a lost property in response to a keyword "lost property." For example, together with a message such as "Look inside. I'll turn on the inner light," the vehicle interior light is turned on lighter than usual. The window is opened by the power window mechanism so that the inside of the vehicle is easy to confirm.

In S8 to S11, the preparation scene is specified. In S8, a flag SCN3 for the preparation scene is confirmed not to be "1." In S9, it is determined whether the user is seated on the seat, from the input information from the seating sensor 520. When the seating of the user is detected, the switch to the preparation scene is determined to be made, and SCN3 is set to "1" in S10. In this stage, only the complete of the seating is detected. The preparation stage where the user switches to driving or staying in the vehicle completely, is only specified. In S11, a seating timer used for determining the switch to the drive/stay scene starts.

In S12 to S15, the drive/stay scene is specified. In S12, a flag SCN4 for the drive/stay scene is confirmed not to be "1," and it is determined whether the user starts the engine in accordance with the input information from the ignition switch 538. When the engine starts, the switch to the drive/stay scene is made immediately. The process jumps to S15 to set SCN4 to "1." On the other hand, even when the engine does not start, but when the seating timer passes for a predetermined time (t1), the user is determined to get in and stay in the vehicle (e.g., for the purpose other than driving). The process goes to S15 to set SCN4 to "1" (when t1 does not pass, the process skips S15 to continue the preparation scene).

In S16 to S19, the getting-off scene is specified. In S16, a flag SCN5 for the getting-off scene is confirmed not to be "1." In S17, it is determined whether the user stops the engine in accordance with the input information from the ignition switch 538. When the engine stops, the process goes to S18. It is determined whether the user opens the door in accordance with the input information of the door courtesy switch 537. When the door is opened, the switch to the getting-off scene is determined to be made. In S19, SCN5 is set to "1."

In S20 to S23, the separation scene is specified. In S20, a flag SCN6 for the separation scene is confirmed not to be "1." In S21, in accordance with the ignition switch 538 and input information about the seating sensor 520, it is determined whether the user closes the door while separating from the seat. When Yes, the process goes to S22 to set SCN6 to "1." In S23, the getting-off timer is started. In S20, when SCN6 is 1 (the separation scene is in progress), the process goes to S24 or further. A time t2 required for the hospitality process in the getting-off scene is measured by the getting-off timer. When t2 already passes in S24, a scene flag is reset for the next hospitality process. In S26, the seating timer and the getting-off timer are reset.

Referring to FIG. 46 again, when the scene is determined in γ1, the hospitality content in the scene is determined. This determination is made in reference to the hospitality determination table 360 in FIG. 2. As described above, the multiple hospitality genres are set in each scene, and ramified hospitality themes are set in each genre. As described above, various genres and hospitality themes are set in view of a direction of the hospitality requested by a user. For example, the user requests "safety," "easiness," and "comfort" in using the vehicle. When the request is not achieved due to some factor, the factor is specified as a disturbance. The final object of the system is such that any response, namely, the hospitality operation, is executed to the disturbance for achieving the above requests. In accordance with a type of disturbance, the hospitality genres and hospitality themes are defined. The genres are defined in accordance with the "disturbances" commonly found in each scene. Specifically, ST1 for uplifting a user; ST2 for relaxing the user and providing ease to the user; ST3 for eliminating anxiety and tension; ST4 for reducing physical burden of the user; and ST5 for assisting the user adequately in accordance with physical condition of the user are set as the genres.

In FIG. 2, the hospitality themes belonging to the expectation/uplifting genre ST1 and the relaxing/easing genre ST2 are selected alternatively (one of these genre is selected exclusively) in accordance with a character and mental condition of the user. The hospitality themes of the genres other than the genres ST1 and ST2 are selected in each scene simultaneously. The hospitality operations belonging to the themes are executed in parallel in the corresponding scene.

On the other hand, different hospitality themes belonging to each genre are set in the scenes. The themes of the genres in each scene are shown in FIG. 2. Some themes are set across the multiple scenes. For example, OBJ331 "I want to know the situation of the destination" are set across the preparation and drive/stay scenes.

The hospitality determination table 360 is used in accordance with a flow shown in FIG. 4 (this is the main portion extracted from the main hospitality processes shown in δ1 to δ6 of FIGS. 46 to 48). In S101, the scene flag is read. In S102, what scene is in progress is specified. In S103, the hospitality themes are read corresponding to the specified scene. The hospitality functions (hospitality operation devices) belonging to the themes are selected in reference to the function selection tables 371, 372 exampled in FIGS. 7A to 13B. In S105, the hospitality applications for operating the extracted functions actually are selected from the theme application library 351 of FIG. 6.

Referring to FIG. 46 again, as compensation items in case of specifying the scene, a user's appearance detection (α3: for example, in case of the approach, the appearance can be grasped from a taken image of the user by use of the vehicle exterior camera 518 (FIG. 1)), a property detection (α4: such as baggage), a gesture detection (α5: the gesture is detected as a sign of a motion directly related to the scene estimate), and so on can be executed additionally. These detections contribute to the hospitality theme determination in each scene effectively.

Next, in δ2, the hospitality content is matched with a character of a user. Especially, in accordance with the after-mentioned user character determination process and the determined character, each hospitality process is weighted appropriately. Namely, to match the hospitality operation with a character of each user, a combination of the multiple hospitality operations is customized properly or a level of the hospitality operation is changed. To specify the character, a character determination process β4 or ϵ2 is required. The process ϵ2 is, e.g., a questionnaire process for obtaining a character type from an input by a user. The process β4 determines more analytically a character classification from a motion, act, thought pattern, or facial expression of the user. An example of the latter for determining the character classification from statistics of music selection is shown in the after-mentioned embodiment. Like α10, a habit related to the character determination can be extracted from a motion of the user. Like α11, the character determination can be made from a face of the user.

In FIG. 47, the hospitality content is matched with the user mental/physical condition in δ3. A detail example of this process is described later. In accordance with detection information of the biological condition detection unit, the mental/ physical condition information reflecting the mental and physical condition of the user is obtained. In accordance with the obtained information, the mental or physical conditions of the user are estimated. The biological condition detection unit can use an infrared sensor 519 (complexion: α20), a face camera 521 (facial expression: α112, posture: α14, line of sight: α15, and pupil diameter: α16), a pulse sensor 524$b$ (pulse: α17), and so on. Additionally, sensors for detecting a history of the operations (502$w$, 530, 531, 532; error operation ratio: α13), a blood pressure sensor (α18), an expiration sensor (alcohol: α21, for example, when alcohol is detected in expiration, the engine cannot be started), a seating sensor 520 (the pressure sensor measures a weight distribution on the seat and detects small weight shifts to determine loss of calm in driving, and detects a biased weight to determine a level of fatigue of a driver).

The object of the process is as follows. An output from the biological condition detection unit is replaced with a numeral parameter showing the mental and physical conditions (β5). In accordance with the numeral parameter and its time change, the mental and physical conditions of the user (γ3, γ4) are estimated. Each hospitality process is weighted accurately. Namely, to match the hospitality operations with the estimated user mental and physical conditions, a combination of the multiple hospitality operations is customized, or a level of the hospitality operation is changed. When a character of the user differs as described above, the hospitality operation matching the character is preferably executed from the hospitality operations for the same scene and same theme. A type and level of even the hospitality for the same user is preferably adjusted in accordance with the mental and physical conditions.

For example, in case of the lighting, a color of the lighting requested by the user often differs in accordance with a character of the user (for example, an active user requests red, and a gentle user requests blue). A required quantity of the lighting often differs in accordance with the physical condition of the user (in case of poor physical condition, a light quantity is decreased to restrict a stimulation by the lighting). In the former, a frequency or wavelength (a waveform is shortened in the order of red, green, blue) is adjusted as the hospitality in the latter, an amplitude of the light is adjusted as the hospitality. The mental condition is a factor related to both. To further uplifting a little cheerful mental condition, a red light can be used (frequency adjustment). Without changing a color of the light, the brightness can be changed (amplitude adjustment). To calm a too much excited condition, a blue light can be used (frequency adjustment). Without changing a color of the light, the brightness can be decreased (amplitude adjustment). Because music contains various frequency elements, more complex processes are needed. To increase an awakening effect, a sound wave in a high sound area between about several hundred Hz and 10 kHz is emphasized. To calm the mood of the user, the so-called α wave music in which a center frequency of a fluctuation of a sound wave is superimposed to a frequency (7 to 13 Hz: Schumann resonance) of the brain wave when relaxed (α wave) is used, for example. The control pattern can be grasped in accordance with the frequency or amplitude, as well.

With respect to the brightness and the level of the sound wave in the vehicle, an appropriate level can be set as a numeral in each hospitality theme of each scene in view of a character and mental and physical conditions. As shown in FIGS. 7A, 7B, 8A, 8B, 9A, 9B, a control appropriate value setting table 371$a$ is provided to the function selection table 371 for each theme.

The control appropriate value setting table 371$a$ is prepared to each hospitality theme of each scene, and contains control appropriate values to be set for the multiple hospitality operation devices used in the themes. Within a range of a value (for example, required lighting level and sound wave level) corresponding to a range of an operation output of the hospitality operation device, an appropriate value for each theme of each scene is found in advance through, e.g., experiments. The value is registered to the control appropriate value setting table 371$a$. Because the control appropriate value has a personal difference, an average of appropriate values of multiple persons and a representative value such as a mode or median may be registered to the control appropriate value setting table 371$a$.

In δ4 of FIG. 48, a hospitality representation response process is executed. For example, from an output of the illumination sensor 539 (visual stimulation: α23) and sound pressure sensor (audio stimulation: α24), information (disturbance stimulation) about what level of the stimulation a user receives is obtained (environment estimate: β6). By converting the disturbance stimulation to a value comparable to the appropriate value obtained from the personality (character) and the mental and physical condition, a numeral estimate of the disturbance is executed (γ6). As disturbance stimulations to be specified, a tactility stimulation (α25: for example, the pressure sensor 523 mounted to the steering-wheel) and a smell stimulation (α26: the smell sensor), and so on can be used. With respect to the disturbance stimulation, an indirect stimulation from a space surrounding the user, for example, a height (α27), a distance (α28), a depth (α29), physical frames (α30) of the user and passengers, and so on can be considered.

In δ5, the function selection process is executed. The hospitality functions (hospitality operation devices) shown in the function selection tables 371, 372 are used in the descending order of the priority so that differences between the disturbance stimulations and appropriate values are decreased. Then, in δ6, each hospitality operation device is driven.

Information about whether the user likes a content or level of the actually selected hospitality function is estimated from an output of the above biological condition detection unit (δ7) or from answer information by the user (a direct input about liking or an estimate using an input operation for avoiding unwanted music and lighting may be used)(δQ). The information is fed back, so that a type of a learning effect can be provided to the hospitality operation control (δQ, δ7 to ε5, ε6 and γ7). Namely, a function of a hospitality adjustment instruction unit for instructing adjustment of a control condition of the hospitality operation in accordance with the response information from the user who has received the hospitality operation, is provided. In this embodiment, a program routine for achieving the function is stored in the ROM of the hospitality determination section 2.

In this case, after the drive step of δ6, a condition confirming process for δ7 is executed. The condition confirming process uses the same process as the mental condition estimate and physical condition estimate executed in γ3 and γ4 to monitor how these conditions change after the hospitality driving. The result is fed back to the function selection process of δ5. When the result of the monitoring shows that the estimated mental or physical condition is improved, an instruction is made so that the currently selected hospitality operation is maintained or enhanced further. When the result of the monitoring shows that the estimated mental or physical condition becomes worse, an instruction is made so that the currently selected hospitality operation is restricted or cancelled in some cases. When the mental or physical condition tends to settle near the normal condition, an instruction is made so that the condition is maintained stable.

On the other hand, in δQ, the user is questioned about a level of the satisfaction with the hospitality operation. The answer information (taste (ε5: I like it. I don't like it.), physical effect (ε6: hot, cold, or noisy)) is fed back to the hospitality operation. The voice of the question can be outputted from the speaker 515S (or can be displayed on the monitor 536 of FIG. 1). In each case, the question data are stored in, e.g., the storage device 535 of FIG. 1, corresponding to the hospitality operation IDs and control direction information, as shown in FIG. 73A. For example, when the hospitality operation ID corresponds to "air conditioner," and the control direction information corresponds to "increase of a set temperature," a content of the question information is set to, e.g., "Is it too hot?" When outputting the question, the hospitality operation used at the time is retrieved to read and output the question data of the corresponding ID sequentially.

The voice of the answer of the user can be inputted from, e.g., the microphone 522. The inputted voice is specified by a known voice conversion module, its meaning is analyzed by a known language analysis module, and the result of the answer to the question data is specified. In case of simple questions and answers, a keyword list of answer candidates to questions is produced. Whether a specified input voice contains the keywords or a keyword which means negative, can be analyzed to grasp the answer. For example, to the question "Is it hot?," keywords such as "yes," "hot," "not," "no," "cold," or "comfortable" are registered. When the answer "It's not hot." is specified, the keywords "hot" and "not" match the answer, so that the answer can be recognized as negative. The voice conversion module and language analysis module can be stored in the ROM of the hospitality determination section 2.

As function selection determination elements of another system, the following process is possible. A function condition of the hospitality operation device is detected (α31), and adjusted as degradation information of the vehicle (β8). It is determined whether the function condition contributes to normal or abnormal (γ8). The function contributing to normal can be actively used. The function contributing to abnormal can be avoided.

It is important that the concept of the hospitality operation be defined as a content matching an image of the vehicle for increasing the hospitality effect. With respect to a luxury vehicle, a smart hospitality representation for emphasizing its gentle and luxury appearance is effective. With respect to a sports vehicle and leisure vehicle, a cheerful representation is suitable.

Figure 28:
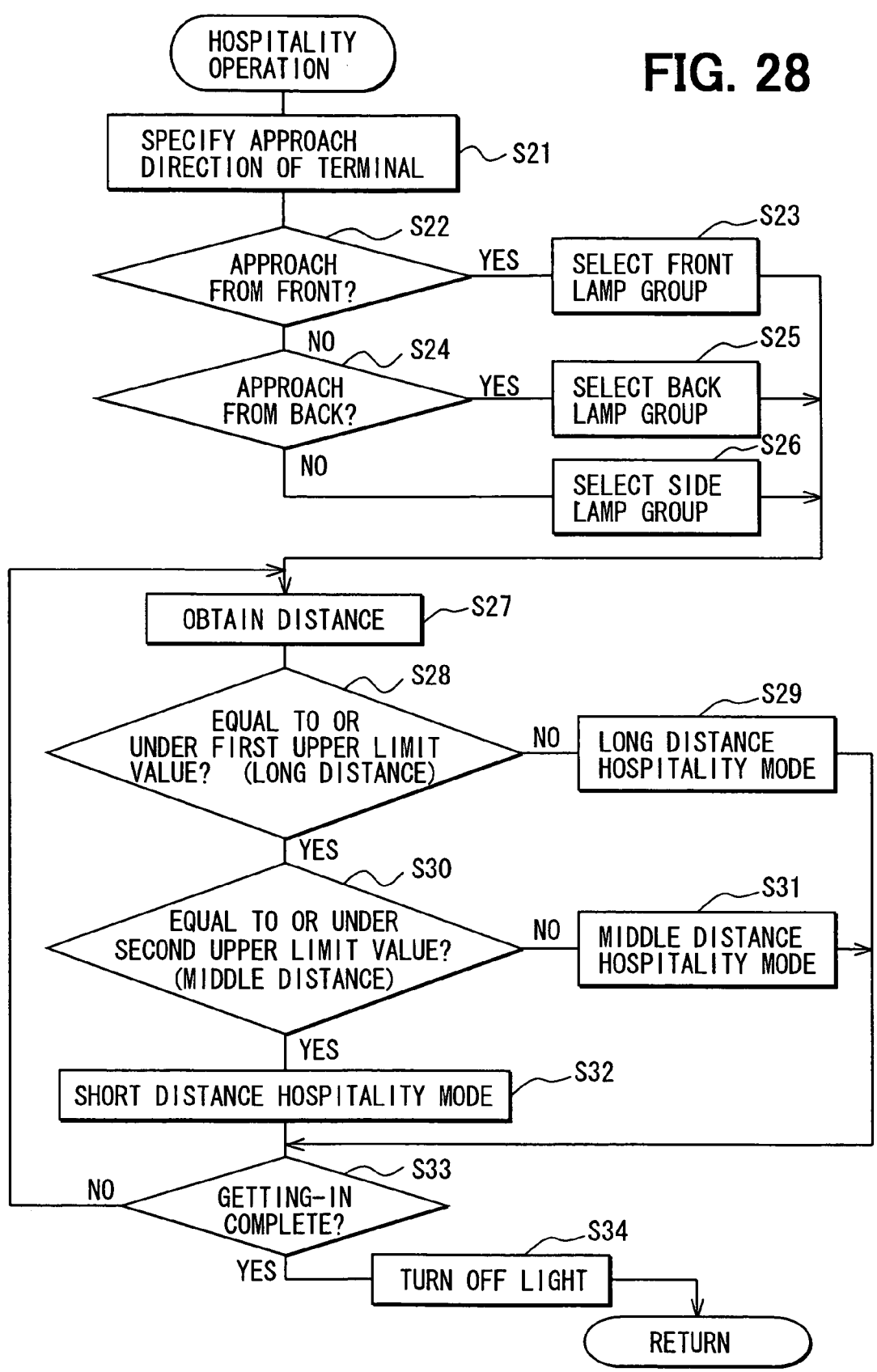
FIG. 28 is a flowchart showing a flow of a process of the hospitality operation when the user approaches the vehicle.

The representative example of each scene is explained below. FIG. 28 shows a flow of a process of the hospitality operation in the approach scene SCN1. The theme is "uplifting of a feeling about getting in a vehicle" of FIG. 2. In accordance with a character type of a user, the theme (OBJ111; for example, when the character type is "active SKC1" (FIG. 18)) belonging to the expectation/uplifting genre ST1, or the theme (OBJ211; for example, when the character type is "gentle SKC2" (FIG. 18)) belonging to the relaxing/easing genre ST2, is selected. Through the aftermentioned method, the mental or physical condition of the user is estimated, and reflected by the hospitality operation process. In this embodiment, as described later, "poor physical condition (slight or serious)," "distraction," and "excitation (anger)" are estimated as the physical or mental condition. In accordance with each condition, the hospitality operation is adjusted as shown in FIG. 67.

In S21 of FIG. 28, a direction of the approach to a vehicle by a user (namely, the user terminal device 1) is specified. In the vehicle, from position information of the GPS 533 and a history of a change of a traveling direction of the vehicle before parking, a position and direction of the vehicle can be specified. Therefore, in reference to the user position information (of the GPS 554) sent from the mobile phone 1, whether the user approaches the vehicle from the front, rear, or side, and how far the distance between the user and vehicle is, are recognized.

Figure 23:
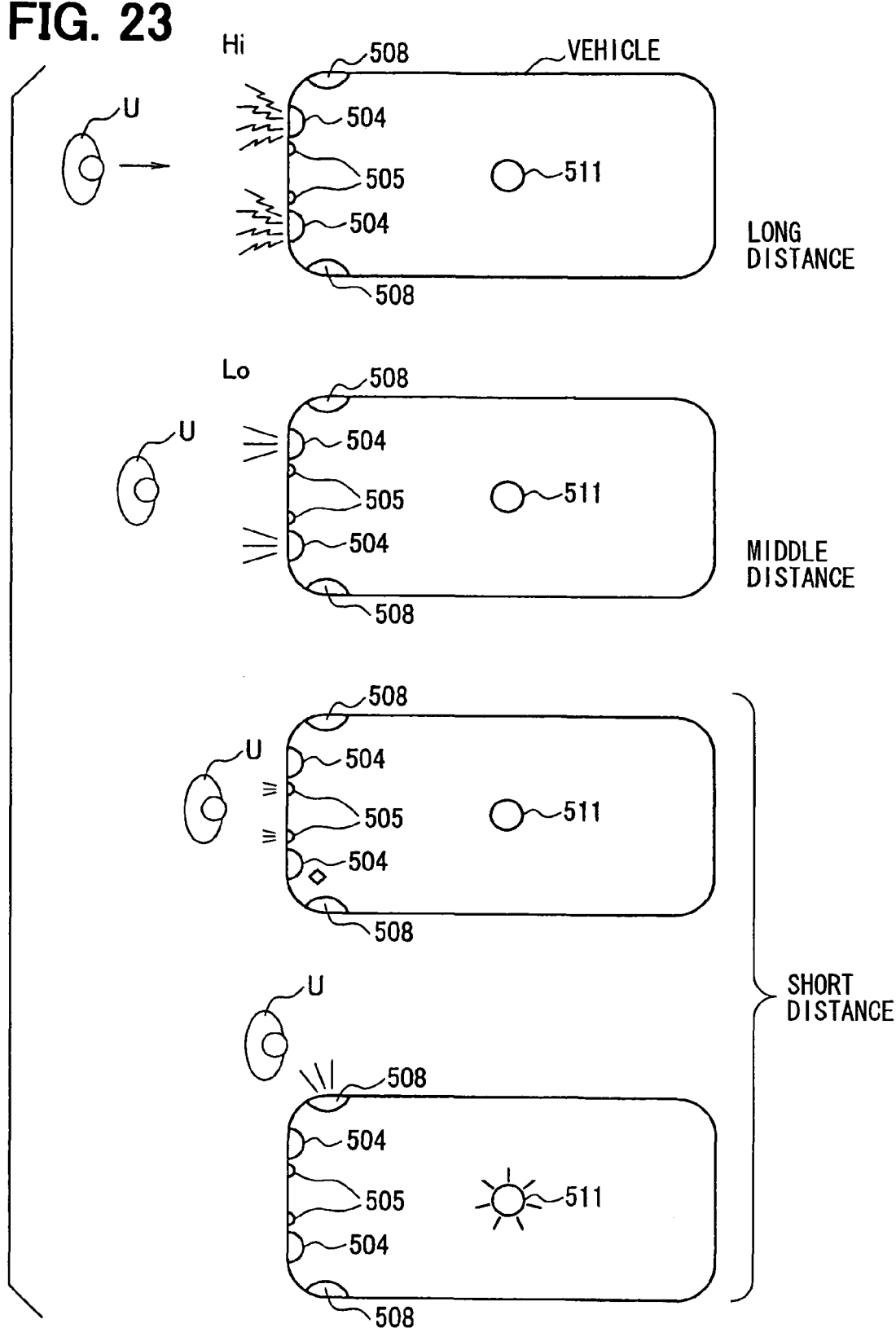
FIG. 23 is a view showing a first example of a hospitality operation when a user approaches a vehicle from frontward of a vehicle.
Figure 24:
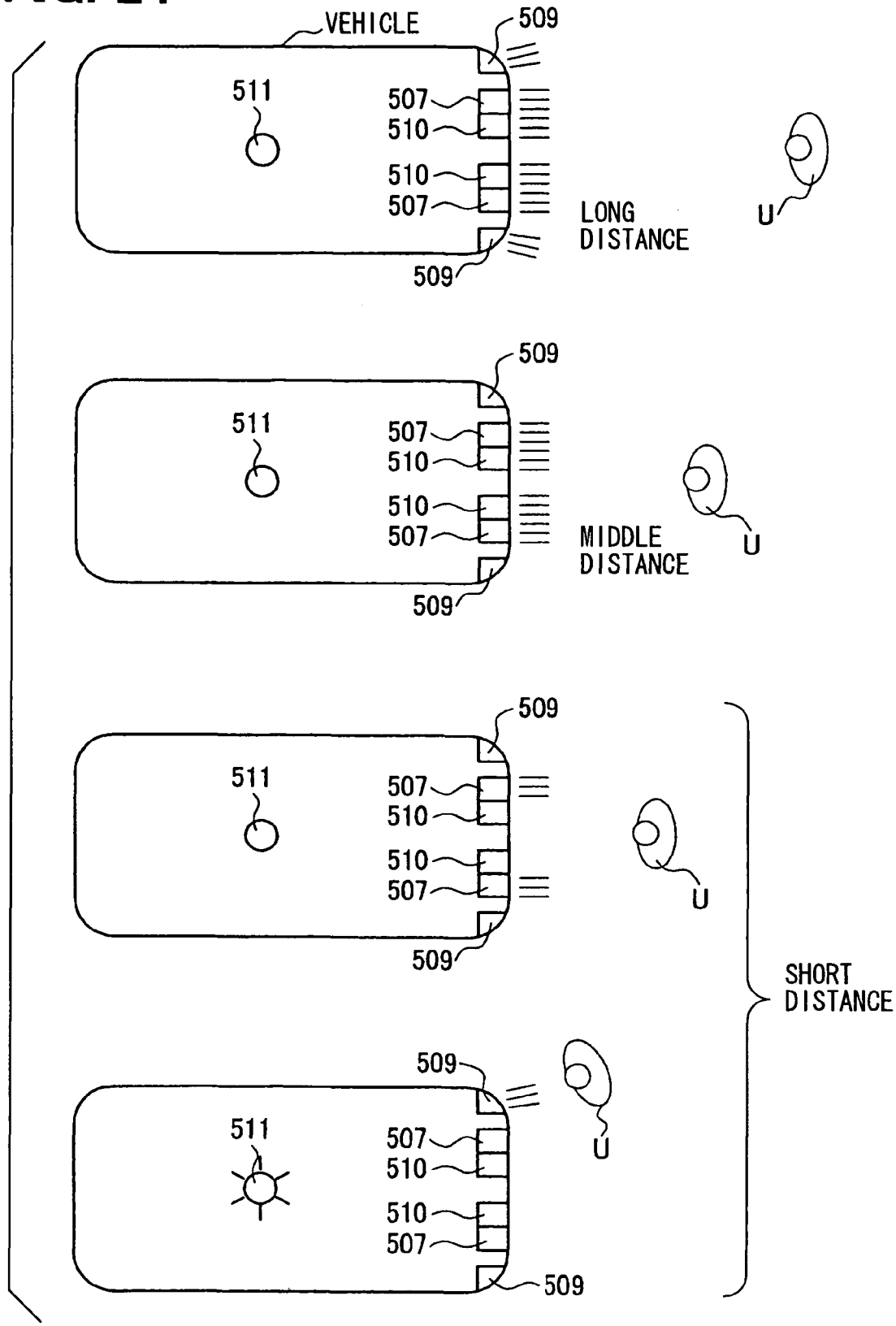
FIG. 24 is a view showing a second example of the hospitality operation when the user approaches the vehicle from rearward of the vehicle.
Figure 25:
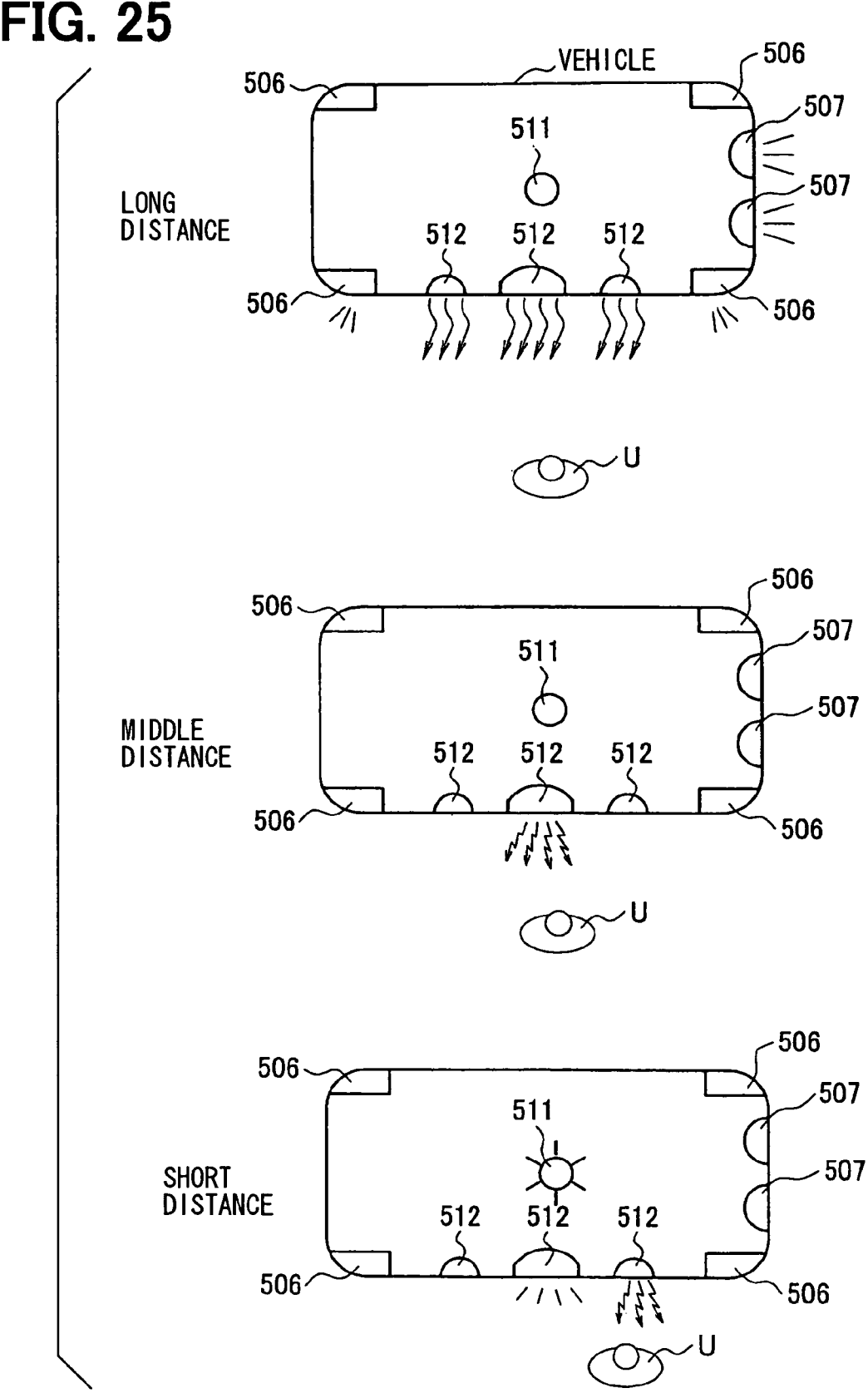
FIG. 25 is a view showing a third example of the hospitality operation when the user approaches the vehicle from sideward of the vehicle.

In S22, when the user approaches the vehicle from the front, the process goes to S23 to select a front lamp group. As shown in FIG. 23, as the front lamp group, in this embodiment, a head lamp 504, a fog lamp 505, and a cornering lamp 508 are used. When the user approaches the vehicle from the rear, the process goes from S24 to S25 to select a rear lamp group. As shown in FIG. 24, as the rear lamp group, in this embodiment, a tail lamp 507, a backup lamp 509, and a stop lamp 510 are used. In other cases, it is determined that the user approaches the vehicle from the side, and the process goes to S26 to select a side lamp group. As shown in FIG. 25, as the side lamp group, in this embodiment, a hazard lamp 506, a tail lamp 507, and an under-floor lamp 512 are used.

In S27, a distance between a user and vehicle is specified through the above method. When a distance between a user and vehicle is specified, and when the distance is over a first upper limit value (for example, set to equal to or over 20 m), the process goes to S29 to enter a long distance lighting mode. When the distance is over a second upper limit value (for example, set to equal to or over 5 m and under 20 m), the process goes to S31 to enter a middle distance lighting mode. In other cases (when the distance is under the second upper limit value), the process goes to S32 to enter a short distance lighting mode. The lighting of each lamp is controlled so that, as the user is far away from the vehicle (namely, in the order of the short distance lighting mode, the middle distance lighting mode, the long distance lighting mode), a total light quantity of the lamps (lighting) becomes great (when a beam angle relates to this lighting, a light quantity viewed by the user in front of the lighting is used: for example, when the lamp is directed higher to produce high beam, the viewed light quantity becomes great although the quantity of the light source does not change in both cases of high beam and low beam). Accordingly, the approach to the vehicle is lighted, so that the user can be effectively introduced to the vehicle safely.

FIG. 23 shows an example of the operation when a user U approaches a vehicle from the front. In the long distance lighting mode, the head lamp 504 is lighted in the high beam position. In the middle distance lighting mode, the head lamp 504 is in the low beam position, and its light quantity is decreased. Namely, at least one of a quantity of the light source (which can be adjusted by, e.g., driving voltage) and a beam angle is adjusted to change a viewed light quantity. On the other hand, in the short distance lighting mode, the fog lamp 505 or cornering lamp 508 having smaller light quantity is selected. When the user U approaches the front of the vehicle, the fog lamp 505 is lighted. When the user U moves to the side of the vehicle, the cornering lamp 508 on the corresponding side is lighted.

FIG. 24 shows an example of the operation when the user U approaches the rear of the vehicle. In the long distance lighting mode, the backup lamp 509, the tail lamp 507, and the stop lamp 510 are all lighted. In the middle distance lighting mode, only the tail lamp 507 and the stop lamp 510 are lighted to decrease the light quantity. Namely, the number of the lighted lamps in the multiple lamps is changed to change the total light quantity. In the short distance lighting mode, one of the backup lamp 509, the tail lamp 507, and the stop lamp 510 is lighted. When the user U approaches the center rear of the vehicle, only the tail lamp 507 (or only the stop lamp 510) is lighted. When the user U moves toward the side of the vehicle, the backup lamp 509 on the corresponding side is lighted.

FIG. 25 shows an example of the operation when the user U approaches the side of the vehicle. In the long distance lighting mode, the hazard lamp 506 and the multiple under-floor lamps 512 are all lighted. In the middle distance lighting mode, only the hazard lamp 506 in the lamps lighted in the long distance lighting mode is turned off to decrease the light quantity. In the short distance lighting mode, only one near the user U in the multiple under-floor lamps 512 is lighted. When the user approaches the center side of the vehicle, only the center under-floor lamp 512 is lighted. When the user U moves in the longitudinal direction of the vehicle, the under-floor lamp 512 on the corresponding side is lighted. When the user U approaches the vehicle, a lighting angle of the under-floor lamp 512 may be changed to change the lighting area so that the user U is introduced to the vehicle. In each case, in the short distance lighting mode, the interior light 511 is also lighted to offer hospitality to the user ready to get in the vehicle respectfully.

In a pattern imaging a destination to which the user travels from now, illumination is made. When the destination is the sea, lighting is effectively executed in the illumination pattern that an illumination of a blue light is gradually increased and then gradually decreased, the pattern being associated with the wave.

In this case, the above embodiment of the lighting has variations as shown in FIG. 67 in accordance with physical and mental conditions of the user. In case of "slightly poor condition," the less required light in the lights used for the illumination is decreased to increase the visibility when the user approaches the vehicle. In case of "serious physical condition," a white or warm dark light is used to decrease a psychological burden. In case of "distraction," to awake the user, the lighting is flashed (for example, a stimulating wavelength of a primary color such as red and blue is effectively used). In case of "excitation," a blue light is effectively used to calm the extremely excited mental condition.

Figure 26:
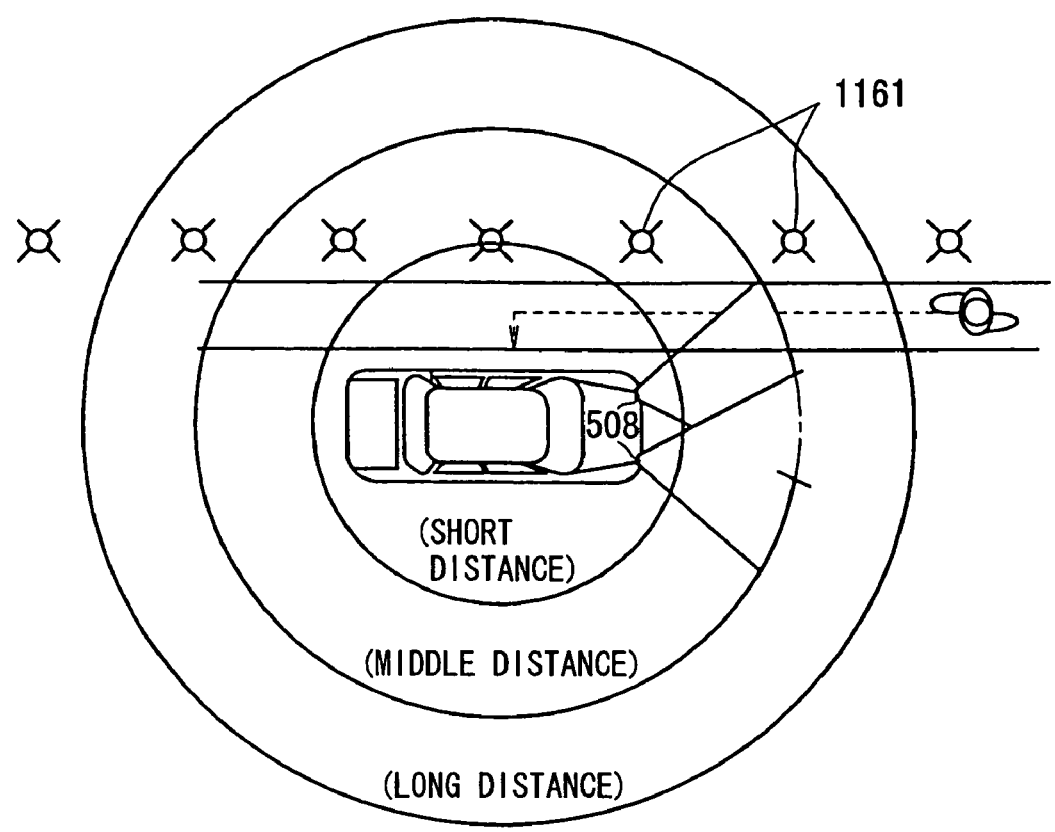
FIG. 26 is a view showing a forth example of the hospitality operation when the user approaches the vehicle in a parking area.
Figure 27:
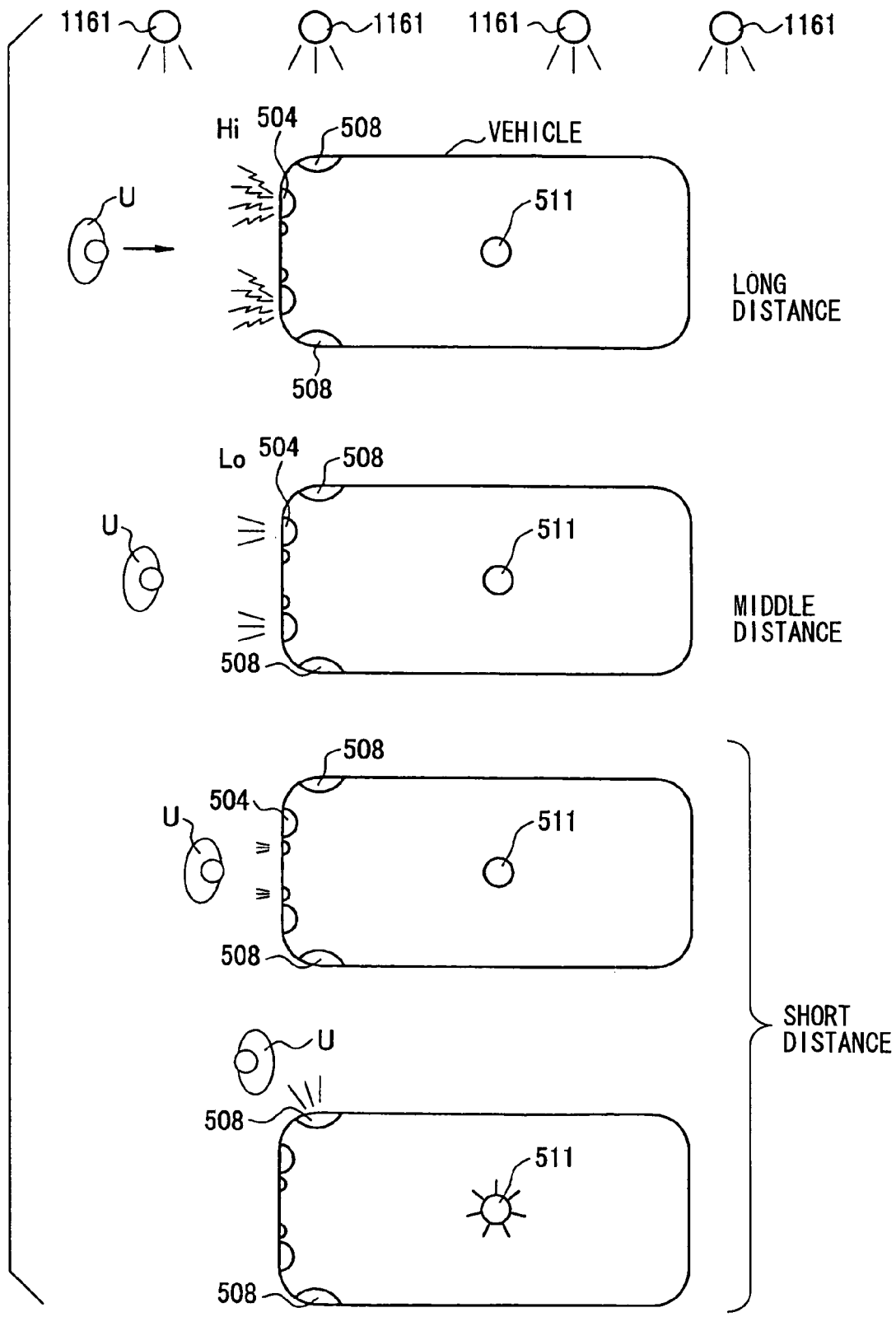
FIG. 27 is a view showing a fifth example of the hospitality operation when the user approaches the vehicle in a parking area.

When, as the hospitality operation device controllable by a radio instruction from the user terminal device 1, a peripheral facility having a building light 1161 as shown in FIG. 26 is around a parking location of the vehicle, the hospitality operation for lighting the vehicle by use of the building light 1161 may be added. As shown in FIG. 27, in the long distance lighting mode, the vehicle of the user is lighted in the parking area in the night, so that the parking location is more visible, and a mood of the user is effectively uplifted. On the other hand, in the middle and long distance lighting modes, because the area around the vehicle is widely lighted, the effect for introducing or assisting the getting in the vehicle is increased. Accordingly, even when there is an obstacle on a path (under foot) to a position where the user gets in the vehicle, the obstacle can be found easily.

Figure 36:
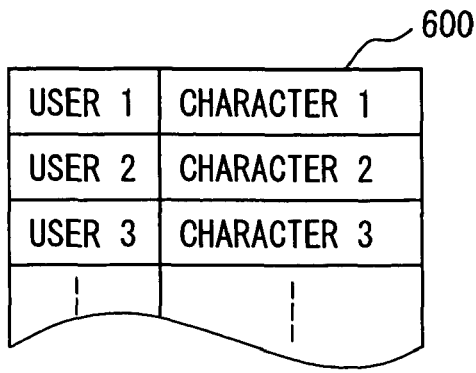
FIG. 36 is a conceptual diagram showing user registration information.

The character types are defined through the following method. Users of a vehicle can be previously registered in a user registration portion 600 (for example, the ROM of the hospitality determination section 2, and the ROM is preferably comprised of a rewritable flash ROM) and the storage device 535 as shown in FIG. 36. In this user registration portion 600, names of the users (or user IDs and personal identification numbers) and character types (see FIG. 18) are registered corresponding to each other. These character types are estimated in accordance with operation history information, which is obtained and accumulated as operation history information about a specified operation device while the user uses the vehicle. When the operation history information is accumulated insufficiently, such as just after the user starts using the vehicle, or when the character type is to be estimated without daring to collect the operation history information, the user is allowed to input character type information or information required to specify the character type information, as follows. Then, the character type may be determined in accordance with the input result.

Figure 37:
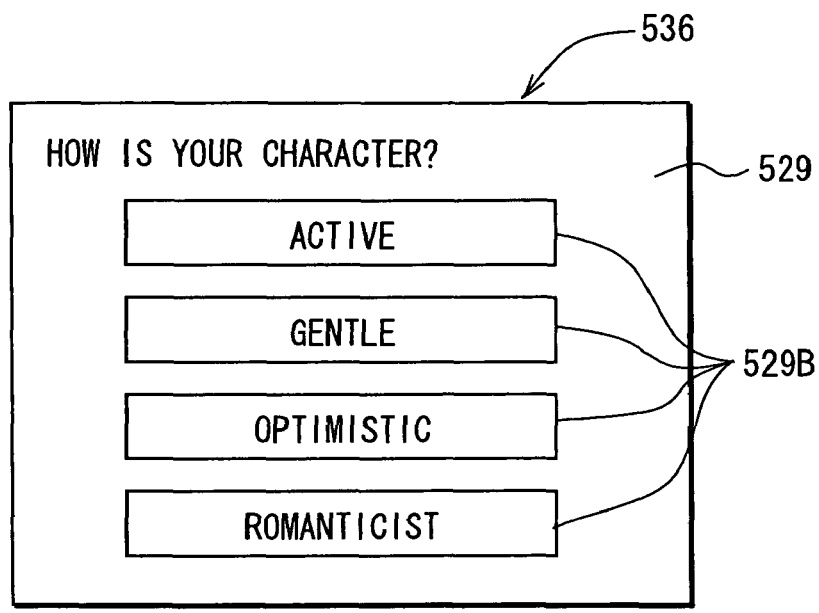
FIG. 37 is a view showing a first example of an input method for determining a character type.
Figure 38:
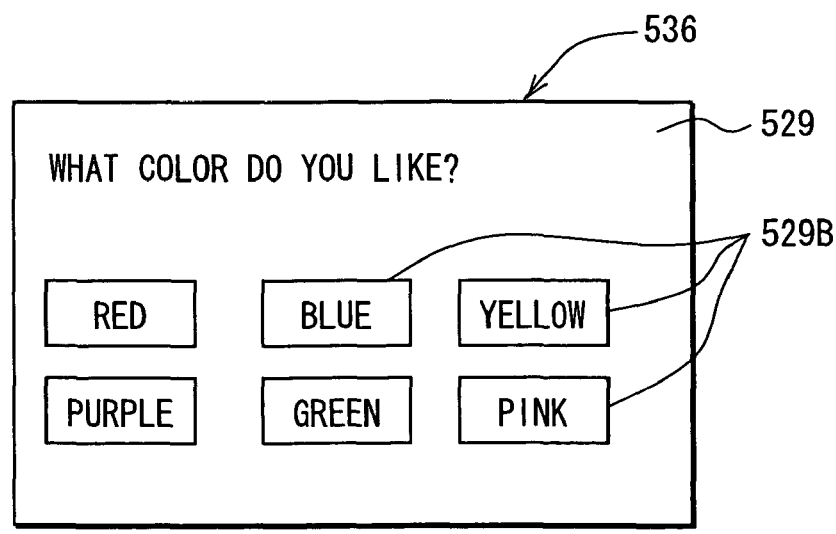
FIG. 38 is a view showing a second example of the input method for determining a character type.

In FIG. 37, the monitor 536 of FIG. 1 (which may be replaced by the monitor of the car navigation system 534) displays the character types. The user selects the character type matching the user, and inputs it from the input portion 529. The input portion is a touch panel superimposed on the monitor 536, where by touching a selection button 529B displayed and produced, a selection input is made. On the other hand, in FIG. 38, instead of a direct input of the character type, a questionnaire input for the character type determination is executed. Question items of the questionnaire are displayed on the monitor 536. The user selects from the answer choices (the selection buttons 529B form the choices, and by touching a corresponding position of the touch panel as an input portion 529 on the buttons, the selection input is made). By answering all the questions, in accordance with a combination of the answers, one character type is uniquely determined from the character type group.

The user registration input including names of the users is executed from the input portion 529. The names and determined character types are stored in the user registration portion 600. These inputs can be executed from the mobile phone 1. In this case, the input information is sent to the vehicle by radio. When a user buys a vehicle, the user registration input can be previously done by a dealer by use of the input portion 529 or a dedicated input tool.

Before the user uses the vehicle, the user authentication is required. Especially when multiple users are registered, a different character type is set to each user, and thus a content of the hospitality differs in accordance with each user. The simplest authentication is such that a user ID and personal identification number are sent from the mobile phone 1 to the hospitality determination section 2. The hospitality determination section 2 checks the sent user ID and personal identification number to the registered user IDs and personal identification numbers. The biometrics authentication such as verification of a photograph of a face by use of a camera provided to the mobile phone 1, voice authentication, and fingerprint authentication, can be used. On the other hand, when the user approaches the vehicle, a simple authentication using a user ID and personal identification number may be executed. After the user unlocks the door and gets in the vehicle, the biometrics authentication using, e.g., the face camera 521, the microphone 522, the retina camera 526, the iris camera 527, or the vein camera 528 may be executed.

After the user is authenticated and specified as described above, a character type (user biological condition information) corresponding to the user is obtained by the hospitality determination section 2, and the hospitality operation device and operation pattern corresponding to the character type are selected. As described above, when the specified character type is, "active SKC1," the theme OBJ111 belonging to the expectation/uplifting genre ST1 is selected. When the specified character type is "gentle SKC2," the theme OBJ211 belonging to the relaxing/easing genre ST2 is selected. The flow of the process is the same as the other scenes.

The examples of the function selection tables are explained below in reference to FIGS. 7A to 13B. The function selection tables are formed as two-dimensional matrix. In the tables, the vertical axis shows the operation objects determined in accordance with a disturbance on the user (part of the objects are not dependent on the disturbance), and the horizontal axis shows types of the hospitality operation devices usable for the scenes and themes. In a cell corresponding to each hospitality operation device prepared for each operation object, an order of the hospitality operation device preferentially used for the operation object, is specified as a numeral. The greater the numeral is, the higher the priority is. The numeral "0" shows the hospitality operation device is not used. At the right end of each table, to assist the understanding, the disturbance types relating to the operation objects and names of the units detecting the disturbances are also described.

FIGS. 7A, 7B shows the function selection table 371 and control appropriate value setting table 371a corresponding to the theme OBJ111 for expectation/uplifting. The operation objects are as follows.

Vehicle exterior brightness

The disturbance type is "decrease of vehicle exterior light quantity," which is detected by the vehicle exterior light quantity sensor (because the approach scene is the target, the sensor can be provided to an outer facility such as a parking area, as well as to the vehicle. In this case, the detection information of the sensor is obtained via communications). When the vehicle exterior light quantity detected by the sensor is under a predetermined threshold, the disturbance condition of "decrease of vehicle exterior light quantity" can be determined to occur.

Capture of outer light, generation of interior light

The disturbance is "decrease of vehicle interior light quantity," which is detected by the illumination sensor 539 (FIG. 1). When the vehicle exterior light quantity detected by the sensor is under a predetermined threshold, the disturbance condition of "decrease of vehicle interior light quantity" can be determined to occur.

Shield of outside, cancel of noise

The disturbance type is "increase of vehicle interior noise," which is detected by the noise detection microphone 2011 of FIG. 44. In accordance with a level of the vehicle interior noise detected by this sensor, the noise canceller 1001B executes an audio process for decreasing the vehicle interior noise independently by use of the above-described operation.

Vehicle interior environment

The disturbance type is "increase/decrease of room temperature," which is detected by a room temperature sensor 563 and sunshine sensor 564 (FIG. 1). When the room temperature departs from an appropriate temperature (or a factor of the departure (for example, increase and decrease of the sunshine quantity and a change of intake air temperature) occurs), the disturbance relating to "increase/decrease of room temperature" is determined to occur.

With respect to the entertainment elements and information provision, the hospitality operation is selected in accordance with a taste of the user. The disturbances do not relate to this selection basically. In this case, in accordance with an estimate result of the mental or physical condition of the user, the estimate being executed through the after-mentioned algorithm, the hospitality operation can be selected accurately.

A functional priority of the vehicle exterior light, vehicle interior light, window shield (power shield), and car audio is high. For impressive uplifting, a preset value of an exterior lighting level for the illumination by the vehicle exterior light, a set value of the vehicle interior light, and a voice output level (music sound level about a music output) from the car audio system 515 and mobile phone 1, are set high in the control appropriate value setting table 371a. To approximate an illumination detection level of the illumination sensor 539 of FIG. 1 and a sound pressure detection level of the sound pressure sensor 540 of FIG. 1 to the set values, the hospitality control section 3 controls drive output levels of the lights 504 to 512 and car audio system 515. A voice output level of the mobile phone 1 is set to a corresponding value in response to radio instruction. Even when an estimated mental condition corresponds to the distraction, the representation for the expectation/uplifting sometimes improves the concentration for driving effectively.

On the other hand, FIGS. 8A, 8B show the function selection table 371 and control appropriate value setting table 371a corresponding to the theme OBJ211 for the relaxing/easing. The operation objects or disturbance types are the same as those in FIGS. 7A, 7B. The functional priority is set in the same way as the expectation/uplifting. A set value of the exterior lighting level, a set value of the vehicle interior lighting, and a music sound level in the control appropriate value setting table 371a are set lower than those of the theme OBJ111 of the expectation/uplifting. The milder representation including the lighting colors and music selection is executed. Even when the estimated mental or physical condition corresponds to the poor physical condition or excitation, the mild representation is also effective.

Specific processes are as follows. Namely, when a user approaches the vehicle to get in the vehicle, different operations by the lighting devices (FIGS. 23 to 25: numerals 504, 505, 507, 509, 510, 511, and 512: these devices function as the lighting devices for lighting the appearance of the vehicle (leaking light of the interior light 511 lights the appearance indirectly)) can be executed in accordance with an obtained character type (user biological condition information) of the user. When the theme OBJ111 for expectation/uplifting is selected, the representations for uplifting the approach to the vehicle by the user impressively are executed. For example, the lighting quantity or the number of flashes of the lighting devices relating to the hospitality is increased, the head lamp 504 is switched to high beam, and the lighting quantity of the red tail lamp 507 is increased. On the other hand, when the theme OBJ211 for the relaxing/easing is selected, soft representations are executed as follows. The lighting quantity of the lighting devices relating to the hospitality is decreased slightly. The impressive flash lighting is avoided. The lighting fades in to increase the light quantity gradually. The side under-floor lamp 512 for lighting the feet, interior light 511, and head lamp 504 are sequentially lighted to make the vehicle appear gradually. When the red tail lamp 507 is not used, the overall lighting color can be changed in comparison to the lighting pattern for the "active" character type. Instead of incandescent lamps and halogen lamps, light emitting diodes can form the lighting devices including the head lamp and tail lamp.

Next, when the user approaches the vehicle, the speaker (voice output portion) 311 provided to the mobile phone 1 (user terminal device) can be used as the hospitality operation device, instead of the above lighting devices. In this case, the communications device 4 of the vehicle detects the approach of the user, and makes the speaker 311 output the hospitality voice in accordance with a character type corresponding to the user (namely, the obtained user biological condition information). In this embodiment, the hospitality voice data is the music source data. The hospitality voice data may be data of sound effects and human voices (so-called ring voices). The hospitality voice data may be stored in the storage device 535 of the vehicle as shown in FIG. 1. Only the required data may be sent to the mobile phone 1 via the communications device 4. The hospitality voice data may be stored in a sound data flash ROM 316b of the mobile phone 1. The latter case is explained below.

First, when a user is authenticated and specified, a character type corresponding to the user is specified. The list of IDs of the hospitality voice data stored in the sound data flash ROM 316b is obtained from the mobile phone 1. Next, the music source data corresponding to the specified character type is selected from the list. To uplift the user as the user approaches the vehicle, multiple pieces of the music source data having different song mode codes are selected (for example, MIDI data is used).

The representation which differs in accordance with the distance is made, as well as the hospitality process using the lighting (the flow is the same as that in FIG. 28). A priority of the song mode codes is set corresponding to a level of uplifted mental condition of the user. A song is selected so that, as the distance becomes shorter, the uplifted mental condition is increased further. Specifically, as the user approaches the vehicle, a level of uplifted mental condition becomes higher. The song mode codes are determined in the order: "healing and α wave" or "mild and soothing" (for long distance), "refreshing" (for middle distance), "uplifting" (for short distance). In accordance with a taste of a user, the reverse code order to the above order is also possible so that the user is first uplifted, and then calmed down as the user approaches the vehicle.

Figure 31:
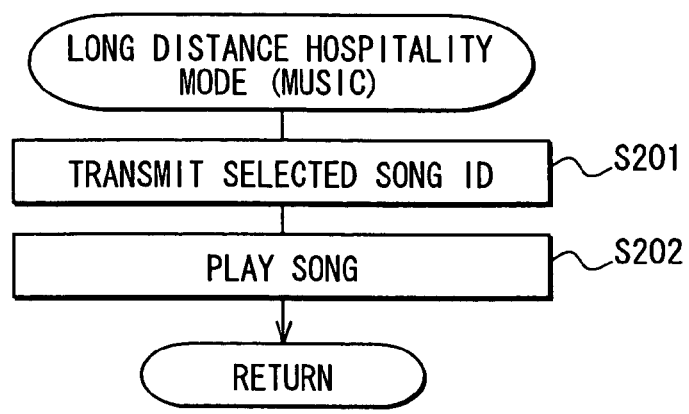
FIG. 31 is a flowchart showing a flow of a process in a long distance hospitality mode using music.
Figure 32:
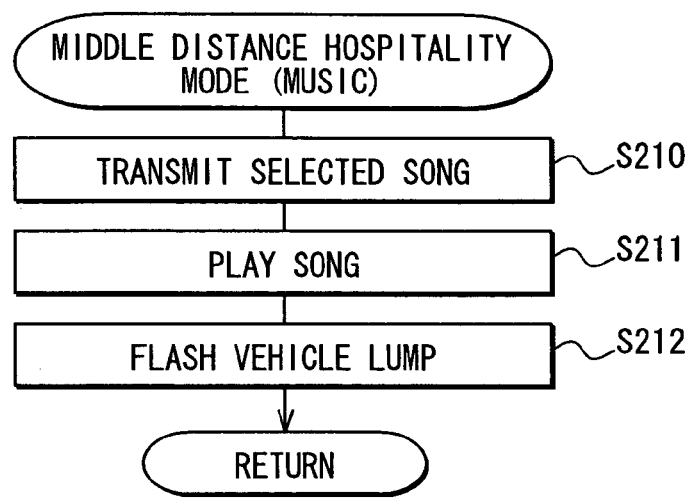
FIG. 32 is a flowchart showing a flow of a process in a middle distance hospitality mode using music.
Figure 33:
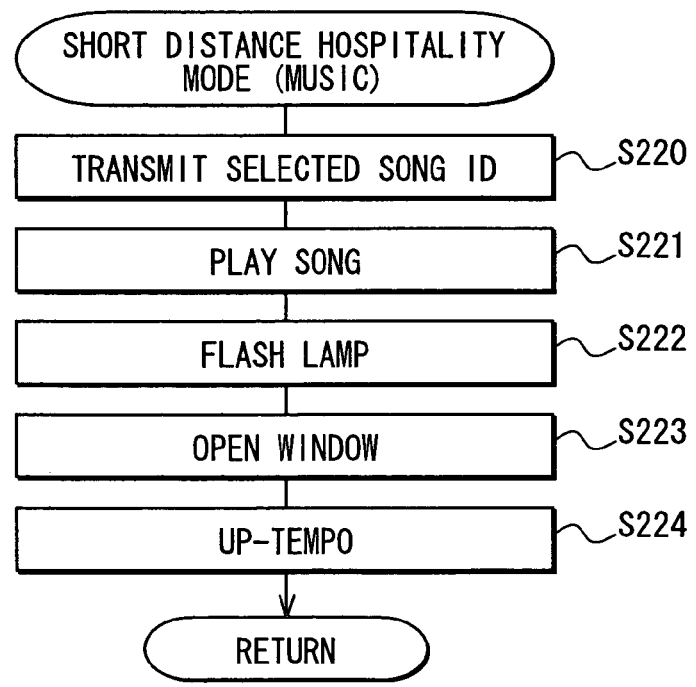
FIG. 33 is a flowchart showing a flow of a process in a short distance hospitality mode using music.

As shown in FIG. 31, in the long distance hospitality mode, an ID (song ID) of music source data having a song mode code of "healing and α wave" or "mild and soothing" is sent to the mobile phone 1 (S201). In the mobile phone 1, music source data corresponding to the ID is selected and starts being played (S202). Next, in the middle distance hospitality mode shown in FIG. 32, an ID (song ID) of music source data having a song mode code of "refreshing" is sent to the mobile phone 1 (S210). The mobile phone 1 selects and plays the music source data corresponding to the ID. As described above, the vibrator unit 354 and LED unit 355 are driven in synchronization with the music to uplift the hospitality using sound output further (S211). The lighting devices may blink in synchronization with the music (S212).

When the user approaches the vehicle to ready to get in the vehicle, the short distance hospitality mode starts to provide the most uplifting representation. Namely, the processes in S220 to S222 are almost the same as the middle distance hospitality mode. However, in S220 to S222, the music source data of "uplifting" is selected. On the other hand, the music source data of the same ID is selected, and starts being played in the car audio system 515. In this case, when the window is opened by the power window mechanism, and the music source data is outputted in synchronization with the play of the mobile phone 1, the uplifting can be more effective (S223). In this case, in the vehicle, a tone code of a main melody portion of MIDI data is decreased (or increased) by such a degree that a consonant tone is formed, in comparison to a main melody portion on the mobile phone 1, and outputted. Then, the outputs of the mobile phone 1 and car audio system 515 can be harmonized with each other. When the output timing of the main melody portion of the MIDI data is delayed (or preceded) by the predetermined number of beats with respect to the main melody portion on the mobile phone 1, the troll effect can be achieved between the outputs of the mobile phone 1 and car audio system 515.

In S224, the heartbeat sensor 342 of the mobile phone 1 reads a heart rate of the user, and a tempo code of the MIDI data is changed to increase the tempo in proportion to the heart rate. Accordingly, the outputted music is made uptempo, so that the uplifting effect can be increased. In the theme OBJ211 for the relaxing/easing, the last impressive uplifting process for the short distance can be avoided.

With respect to the relationship between the music and estimated mental or physical condition, a music mainly comprised of low sound instead of stimulated high sound is played in case of poor physical condition, or the sound volume is lowered and the tempo is set slow in case of relatively serious physical condition. In case of excitation, a tempo of the music is effectively set slow. In case of distraction, the volume is raised, and the music effective in awaking the mood (such as free jazz, hard rock, heavy metal, and avant-garde music) is played effectively.

As shown in FIG. 2, in the approach scene SCN1, "obtaining of vehicle position (OBJ311)" and "confirming of lost property and lock (OBJ312)" are set in the anxiety/tension releasing genre ST3, and "smooth loading of baggage (OBJ411)" is set in the physical burden decreasing genre ST4. The hospitality processes for these genres are executed in parallel to the hospitality processes of the themes OBJ111 and OBJ211 for uplifting the mood.

FIG. 10 shows the content of the function selection table 371 corresponding to the theme "obtaining of vehicle position (OBJ311)." The operation object or disturbance type is as follows.

Notification of vehicle position

The disturbance type is "long distance between vehicle and user." The distance is detected by use of positioning information of the vehicle GPS 533 and mobile phone GPS 554. When the distance is over a predetermined threshold, the disturbance type of "long distance between vehicle and user" is determined to occur.

Vehicle interior environment

The disturbance type is "increase/decrease of room temperature," and the same as the operation object "vehicle interior environment." The collection of information relates to the selection of the hospitality operation in accordance with a taste of the user, but does not relate to the disturbance basically. In this case, in accordance with an estimate result of mental or physical condition of the user by use of the aftermentioned algorithm, the appropriate hospitality operation can be selected.

The vehicle GPS 533, mobile phone 1, mobile phone GPS 554, horn 502, and vehicle exterior lights (or vehicle interior lights) are selected as the hospitality operation devices. The operations are as follows. Positional information is notified to the mobile phone 1, and displayed on the monitor 308 (FIG. 14) in a form of a map together with positional information of the mobile phone GPS 554. Accordingly, a relative position between the user and vehicle can be grasped. When the user approaches inside a predetermined distance to the vehicle, a position of the vehicle is notified to the user by use of whistle and siren of the horn 502 and the lighting of the vehicle exterior lights (or vehicle interior lights).

On the other hand, in "confirming of lost property and lock (OBJ312)," a voice of a message for prompting the confirmation of precautions before traveling is outputted (voice data can be stored in the ROM of the hospitality control section 3, and outputted by use of voice output hardware of the car audio system). The messages for promoting the confirmation of the precautions are as follows, as actual examples. "Did you carry a license and wallet?" "Did you carry a passport?" (When a destination set in the car navigation system is an airport.) "Did you lock the entrance?" "Did you close the back windows?" "Did you turn off the interior air conditioner?" "Did you turn off the gas?"

Next, time changes of a facial expression (which can be taken by the vehicle exterior camera 518) of the user approaching the vehicle and a body temperature (which can be measured by the infrared sensor 519) of the user are measured. From waveforms of the time changes, the mental or physical condition of the user can be estimated. As described above, when the estimated mental condition is normal, the hospitality operation of the expectation/uplifting genre ST1 can be selected. When the estimated mental condition is unstable or in anger (or excitation) (or when the physical condition is poor), the hospitality operation of the relaxing/easing genre ST2 can be selected.

Figure 56:
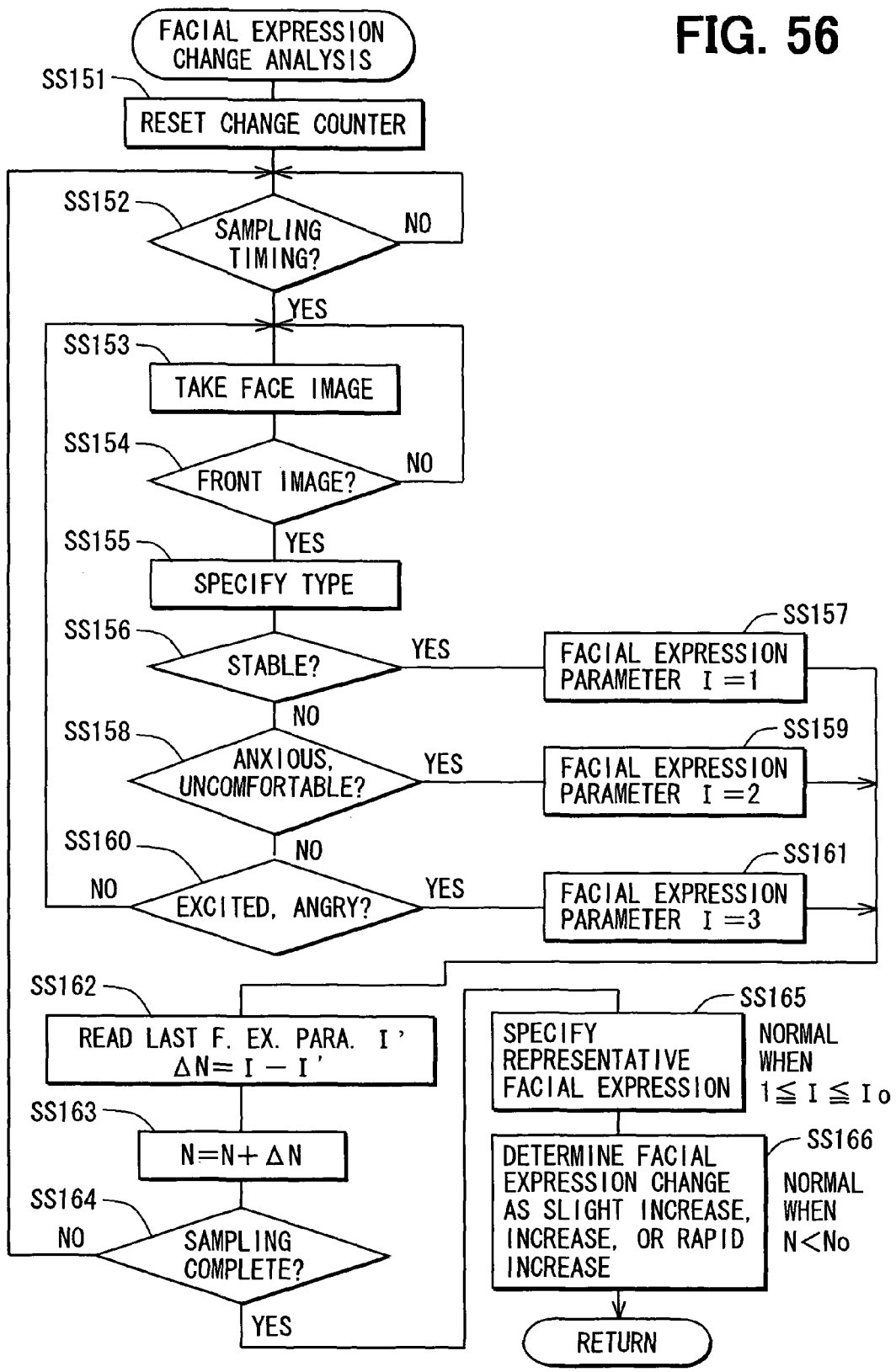
FIG. 56 is a flowchart showing one example of a facial expression analysis algorithm.

FIG. 56 shows one example of a flowchart of a facial expression change analysis process. In SS151, a change counter N is reset. In SS152, when a sampling timing comes, the process goes to SS153 to take a face image. The face image is taken repeatedly until the front image in which a facial expression can be specified is obtained (SS154 to SS153). When the front image is obtained, the front image is sequentially compared to master images (contained in biological authentication master data 432 in the storage device 535) to specify a facial expression type (SS155). When the specified facial expression type is "stable," a expression parameter I is set to "1" (SS156 to SS157). When the specified facial expression type is "anxious and displeasure," the expression parameter I is set to "2" (SS158 to SS159). When the specified facial expression type is "excitation and anger," the expression parameter I is set to "3" (SS160 to SS161).

In SS162, the last obtained facial expression parameter I' is read to calculate its change value ΔN. In SS163, the change value is added to the change counter N. The above process is repeated until a determined sampling period ends (SS164 to SS152). When the sampling period ends, the process goes to SS165. In SS165, an average value I of the facial expression parameter I (made to be an integer) is calculated. The mental condition corresponding to the facial expression value can determined. The greater a value of the change counter N is, the greater the facial expression change is. For example, a threshold is set in a value of N. From a value of N, a change of the facial expression can be determined as "small change," "increase," "slight increase," and "rapid increase."

Figure 53:
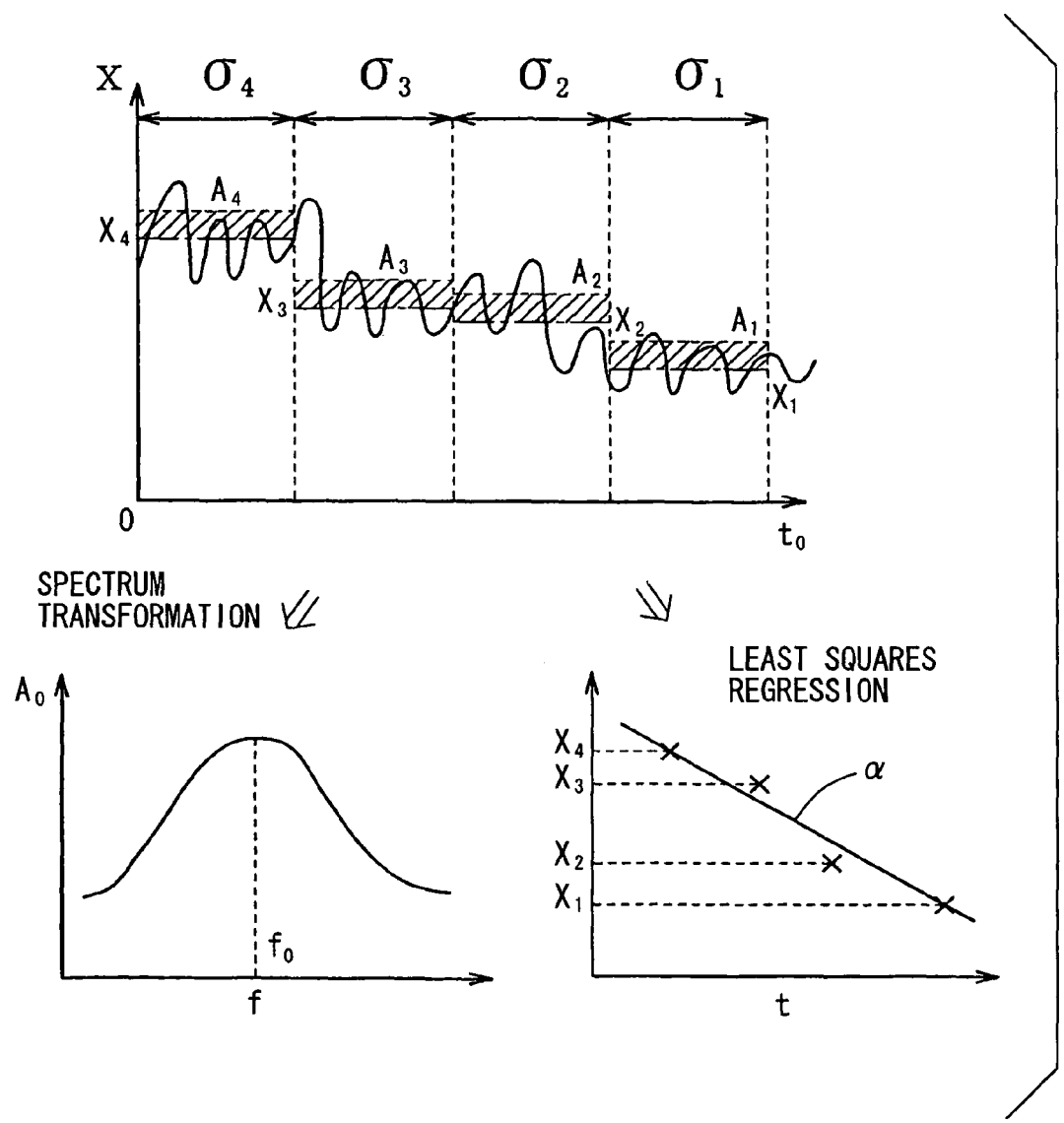
FIG. 53 is a view showing examples of a waveform analysis method.

On the other hand, FIGS. 54A, 54B show one example of a flowchart of a body temperature waveform analysis process. In a sampling routine, each time that a sampling timing comes at a predetermined interval, a body temperature detected by the infrared sensor 519 is sampled, and its waveform is recorded. In a waveform analysis routine, waveforms of body temperatures sampled during the nearest predetermined period are obtained in SS53. The known fast Fourier transformation is applied to the waveforms in SS54 to obtain a frequency spectrum in SS54. A center frequency of the spectrum (or peak frequency) f is calculated in SS55. In SS56, as shown in FIG. 53, the waveform is divided into the predetermined number of sections σ1, σ2, and so on, and in SS57, an average value of the body temperature in each section is calculated. In the respective sections, by use of the average values of the body temperatures as waveform center lines, integrated amplitudes A1, A2, and so on (each obtained by integrating an absolute value of the waveform change on the basis of the center line, and dividing the integral value by use of each section width σ1, σ2, and so on) are calculated. In SS59, the integrated amplitudes A in the sections are averaged, and the average is determined as a representative value of the waveform amplitudes.

The information sampling program for obtaining the waveforms, including the following processes, is scheduled to start at predetermined intervals for only the biological condition detection unit relating to the specified scene. Not shown in the figures, the sampling is not repeated without limit. After the sampling period defined for obtaining samplings required for the waveform analysis, the repetition ends.

In SS60, it is checked whether a frequency f is over an upper limit value fu0. When the frequency f is over the upper limit value fu0, a change of the monitored body temperature is determined to be "rapid." In SS62, it is checked whether the frequency f is under a lower limit value fL0 (>fu0). When the frequency f is under the lower limit value fL0 (>fu0), a change of the monitored body temperature is determined to be "slow." When fu0≧f≧fL0, the process goes to SS64. In SS64, the monitored body temperature is determined to be "normal." Next, the process goes to SS65. In SS65, an integrated amplitude A (average value) is compared to a threshold A0. When A>A0, the monitored body temperature is determined to "change." When A≦A0, the monitored body temperature is determined to be "maintained (stable)."

By use of the determination results of time changes of the obtained biological condition parameters, specific mental or physical condition of the user is determined (estimated). For example, a determination table 1601 is stored in the storage device 535. As shown in FIG. 51, in the determination table 1601, each of multiple specified conditions corresponds to a combination of time changes of biological condition parameters to be detected by the multiple biological condition detection units for determining that each specified condition is established.

In this embodiment, as the specified conditions, "distraction," "poor physical condition," and "excitation" are determined. Specifically, the "poor physical condition" is divided into multiple levels, "slightly poor physical condition" and "serious physical condition." The total four basic specified conditions are defined. The "distraction" and "excitation" can be divided into multiple levels to estimate more detailed mental or physical condition. In this embodiment, a combination of time changes of the biological condition parameters is uniquely defined for each combined condition where a physical condition and mental condition ("distraction" and "excitation") are combined.

The estimate accuracies of the combined conditions are improved. When the user experiences discomfort due to, e.g., nonconformity of the hospitality operation and a shortage or excess of its level, the user often shows the same biological condition as the slightly poor physical condition. In this embodiment, the "discomfort" and "slightly poor physical condition" are integrated with each other as a specified condition (of course, for example, by changing thresholds of the related parameters, each may be specified separately).

As the biological condition parameters, "blood pressure," "body temperature," "skin resistance," "facial expression," "posture," "line of sight," "pupil (scale)," and "steering," including the parameters used in the subsequent scenes, are used. The sensor or camera to be selected even for obtaining the same target biological condition parameter is changed in accordance with the scene.

As described above, in this approach scene, a facial expression of the user, taken by the vehicle exterior camera 518, and a body temperature of the user, measured by the infrared sensor 519, can be used as the biological condition parameter. In the determination table 1601, in case of distraction, a change of the facial expression increases rapidly, and in case of poor physical condition and excitation, a change of the facial expression tends to increase. These cases can be recognized to be different from a normal condition, but each mental or physical condition is difficult to recognize in detail. In case of distraction, a body temperature does not change widely (almost the same as a normal condition). In case of poor physical condition, a body temperature changes slowly. In case of excitation, a body temperature changes rapidly. Accordingly, by combining these parameters with each other, "distraction," "poor physical condition," and "excitation" can be recognized separately.

Figure 65:
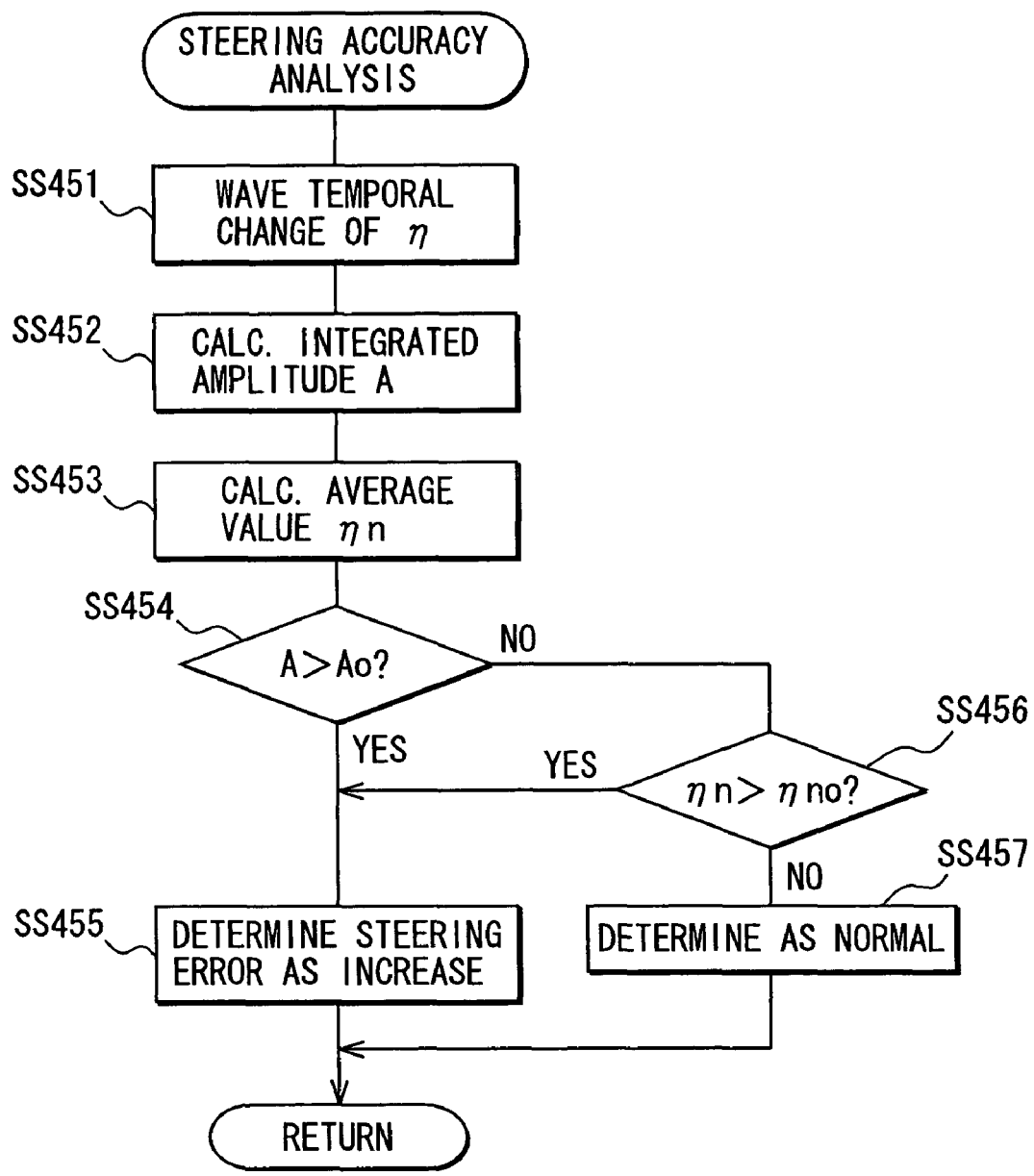
FIG. 65 is a flowchart showing one example of a steering accuracy analysis process using the traveling monitor data.
Figure 66:
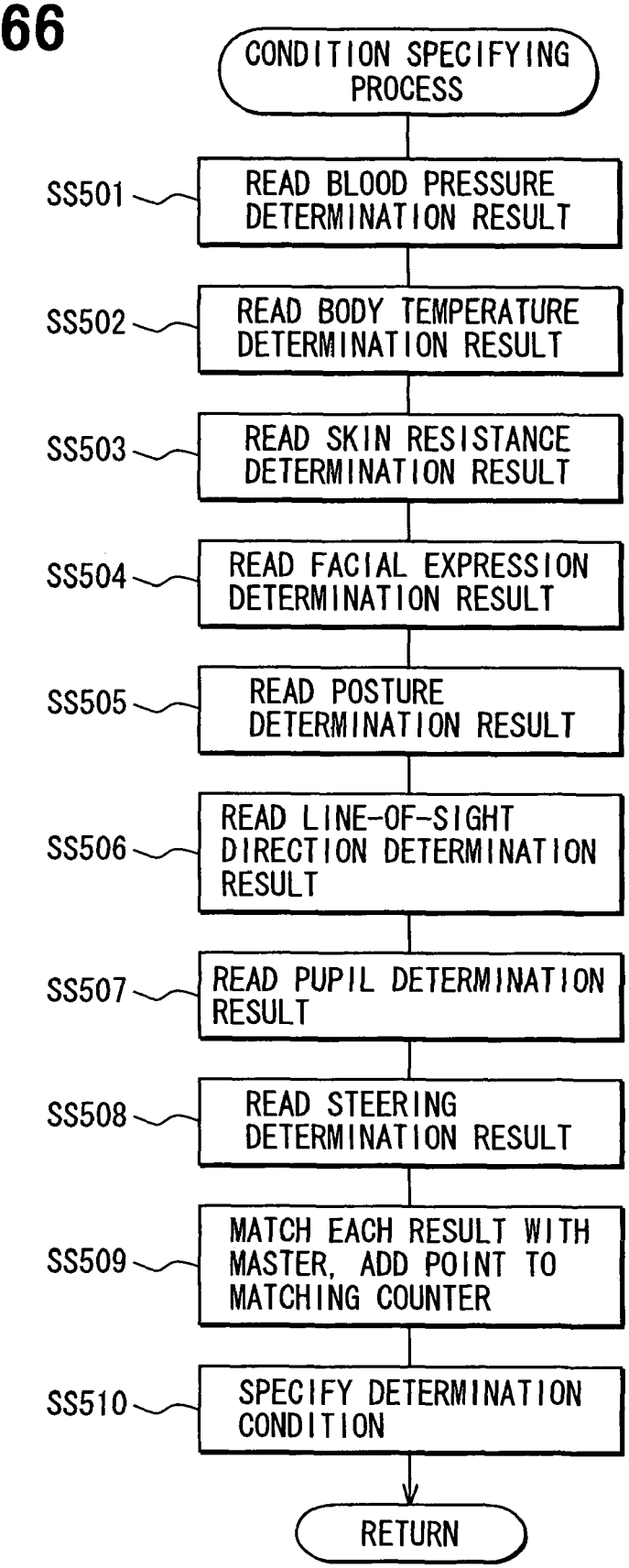
FIG. 66 is a flowchart showing one example of a condition specifying process.

A process in this case are shown in FIG. 66 (this can be determined under the same concept regardless of the scenes, and the basically same flow is made in the after-mentioned drive scene). Basically, the multiple biological condition parameters (facial expression and body temperature) are matched with matched information on the determination table. The specified condition corresponding to the matched combination is specified as a current specified condition. In SS501 to SS508, determination results (for example, "rapid decrease" and "increase") of the time changes of the biological condition parameters obtained through the analysis processes shown in the flowcharts of FIGS. 54A to 57B, 60A to 62B, or 64, 65, are read. In SS509, the matched information showing how each biological parameter in the determination table 1601 changes to determine that each specified condition is established, is matched with the above determination results. A matching counter of the specified condition whose matched information matches the determination result is incremented. In this case, for example, only the specified condition whose matched information matches the determination results about all the biological parameters, may be used. When many biological condition parameters are referenced, the matched information rarely matches the determination results about the biological parameters. The physical or mental condition of the user cannot be estimated flexibly. A point (N) of the matching counter is used as a "matching degree," and the specified condition having the highest point, namely, the highest matching degree, is determined as a current specified condition (SS510).

In FIG. 51, like the case where an average blood pressure level is determined to "change," the same biological condition parameter sometimes contributes to the establishment of the multiple specified conditions ("distraction" or "excitation") positively. In this case, the matching counter of each specified condition is incremented. For example, the average blood pressure level is determined to "change," the four matching counter values N1, N4, N12, and N13 are incremented.

As described above, in most cases, it is determined whether the matched information matches the determination results, in comparison with thresholds of the biological condition parameters (such as frequency or amplitude). When the matching is determined in binary (white or black), information about a deviation between an instruction value of an actual parameter and a threshold is buried. When the matching is determined in accordance with a value near the threshold, the determination is "gray." In comparison to the case where the matching is determined in accordance with a value far from the threshold (for example, the value is over the threshold considerably), it is fundamentally preferable that the parameter less contribute to the determination result.

Instead of the addition to the matching counter only when the matched information and determined result match with each other completely, when the matched information and determine result do not match each other completely, but the near result is obtained within a predetermined range, this result is added to the matching counter. For example, when the matched information is "rapid increase," and the determination result is "rapid increase," three points are added. When the matched information is "rapid increase," and the determination result is "increase," two points are added. When the matched information is "rapid increase," and the determination result is "slight increase," one point is added.

As a more accurate method, the following method is exampled. As shown in FIG. 51, the sum (v or μ) of deviations between the biological condition parameters and thresholds used for the determinations is used in each specified condition. In accordance with the sum of the deviations, the specified condition can be determined. The case where the specified condition having the highest sum of the deviations is determined as the final condition estimate result, is exampled below. Because the determination method changes in accordance with a definition of the deviation, the determination method is not limited to the following case. The specified condition can be determined also by use of the N. The explanation is made further in detail below. First, a concept of calculating a deviation of each biological condition parameter is shown in expressions 1.

Expressions 1
X: parameter used for determination
$X_0$: determination threshold
abnormality (positive) determination in case of $X>X_0$ $$\Delta\mu = \frac{X - X_0}{X_0} \quad (1)$$

abnormality (positive) determination in case of $X<X_0$ $$\Delta\mu = \frac{X_0 - X}{X_0} \quad (2)$$

sum of deviation points for abnormality determination $$\mu = \Sigma\Delta\mu \quad (3)$$

normality determination in case of $X<X_0$ $$\Delta v = \frac{X_0 - X}{X_0} \quad (4)$$

normality determination in case of $X>X_0$ $$\Delta v = \frac{X - X_0}{X_0} \quad (5)$$

sum of deviation points for normality determination $$v = \Sigma\Delta v \quad (6)$$

A value of the biological condition parameter is generalized and shown by X, and a threshold used for the determination is $X_0$. It is determined whether X contributes to the establishment of the specified condition positively in accordance with magnitude relation between X and $X_0$. When a blood pressure in FIGS. 52A, 52B is exampled, a frequency f and amplitude A of a blood pressure time change waveform are adopted as the biological condition parameter X. With respect to the amplitude A, a threshold is $A_0$. When $A>A_0$, an average blood pressure level is determined to be "change," which is one of abnormal conditions. In this case, as shown in FIG. 51, the amplitude A contributes to the establishment of two specified conditions "distraction" and "excitation" positively.

On the other hand, two thresholds, an upper limit value fu0 and a lower limit value fL0, are set for the frequency f. When f>fu0, a blood pressure change is determined as "rapid," which is one of the abnormal condition. Also in this case, as shown in FIG. 51, the frequency f contributes to the establishment of two specified conditions, "distraction" and "excitation" positively. On the other hand, when f<fL0, a blood pressure change is determined as "slow," which is one of the abnormal conditions. In this case, the frequency f contributes to the establishment of two specified conditions, "slightly poor physical condition/displeasure" and "serious physical condition" positively. In both cases, the magnitude relation between the parameters positively contributing to the establishment of the specified conditions and their thresholds is reversed.

On the other hand, when the specified condition does not correspond to either of the abnormal conditions, the specified condition is to be determined as normal (which case is determined as "normal" is shown in FIGS. 52A, 52B, 54A to 57B, 60A to 62B, and 65). For example, in FIGS. 52A, 52B, an average blood pressure level is determined as normal (constant) when A>A$_0$, a blood pressure change is determined as normal (constant) when fu0>fL0.

In this embodiment, a value of a deviation to be calculated is defined so that the deviation is directed to be plus when the deviation is directed to positively contribute to the establishment of a specified condition. A difference between X and X$_0$ calculated in accordance with the definition is used as a value of the deviation. When X>X$_0$ is directed to be positive contribution, deviations $\Delta\mu$, $\Delta v$ are calculated by use of expression (1) or (5) of the expressions 1 (for example, f when the blood pressure change is determined as "rapid" or A when the average blood pressure level is determined as "normal"). When X<X$_0$ is directed to be positive contribution, deviations $\Delta\mu$, $\Delta v$ are calculated by use of expression (2) or (4) of the expressions 1 (for example, f when the blood pressure change is determined as "slow"). To divide the specified condition into an abnormal condition and normal condition, the former is provided with "$\mu$," and the latter is provided with "$v$."

When the parameter is between the upper limit threshold and lower limit threshold, the case where the establishment of the specified condition is positive (for example, f when the blood pressure change is determined as "normal") is treated as follows. Namely, a deviation needs to be calculated for the upper limit value by use of the expression (2), and a deviation needs to be calculated for the lower limit value by use of the expression (4). In this case, because the validity of the positive establishment of the specified condition becomes higher as the parameter is positioned nearer the center of a section between the upper limit value and lower limit value, the defined deviation may be used so that the parameter becomes greater as the parameter is positioned nearer a center value between the section. For example, when a calculation value of a deviation by use of the expression (2) with respect to the upper limit value is $\Delta\mu 1$, and when a calculation value of a deviation by use of the expression (2) with respect to the lower limit value is $\Delta\mu 2$, a synthesis deviation $\Delta\mu s$ calculated by $\Delta\mu s=(\Delta\mu 1\times\Delta\mu 2)^{1/2}$ (geometric average of $\Delta\mu 1$ and $\Delta\mu 2$) can be used.

As described above, deviations $\Delta v$, $\Delta\mu$ calculated for each parameter are added to counters $v0$, $\mu 1$, $\mu 2$, and so on which sum deviation points in each specified condition (expressions 1: expressions (4), (6) or expression (7), (8) of FIG. 77). The specified condition (abnormal or normal condition) having the highest sum of the deviation points is determined as the condition estimate result.

In the above example, the contributions of the parameters when the specified condition is determined are used equally. The contributions may be divided into large ones and small ones, and weighted differently. For example, in FIG. 51, when "distraction" is specified, and when a detection accuracy of a change of the facial expression suffers from a problem, the weight factor when the parameters relating to "facial expression" are added to the matching counter can be made smaller than that of the blood pressure and skin resistance. The addition expressions in the case where the weight factor when the deviations $\Delta v$, $\Delta\mu$ are added to the matching counter are used, are shown as expressions (9), (10) of FIG. 77. A set value of the weight factor differs in accordance with a user. The weight factor can be set for each user. Uniform weight factors may be set for the parameters regardless of the specified conditions. To achieve a control having a higher accuracy, the weight factor of each parameter can be changed in accordance with the specified condition (in this case, the weight factors form a two-dimensional array).

The condition specifying result table 472 of FIG. 77 (stored in the RAM of the hospitality determination section 2 or in the storage device 535) shows which piece of the matched information is matched with each parameter or how high a calculation value of the deviation showing the matching level is, and the estimate result of a mental or physical condition (one of the specified conditions of FIG. 51) in accordance with the matched piece of the information and the calculation value. In this table, a contribution of each parameter to the condition estimate result, and the calculation results of the above deviations are shown. The contributions to the condition estimate result are provided for distinguishing between the parameters (in FIG. 77, blood pressure change, body temperature change, facial expression, posture change, change of a line of sight and its pattern) positively contributing to the estimate result of the specified condition (in FIG. 77, slightly poor physical condition) and the parameters not contributing to the estimate result.

Specifically, when the condition estimate result is "abnormal condition (slightly poor physical condition)," the parameters positively contributing to this condition estimate result are provided with "2." The parameters negatively contributing to the condition estimate result of "normal condition" are provided with "0." A third condition (hereinafter also called a neutral condition) showing "abnormal condition" which is not "normal" different from the condition estimate result, is provided with "1." Information for recognizing the positive contributions to the condition estimate result forming "abnormal condition" and the negative contributions to the result, particularly, information for recognizing whether the negative contribution shows "normal condition" or "abnormal condition" different from the condition estimate result, is stored as contribution information for the condition determination. When the condition estimate result is "normal condition," the parameter positively contributing to "normal condition" is provided with "0," and the parameter negatively contributing to "normal condition" (namely, showing somewhat "abnormal condition") is provided with "1."

With respect to the mental or physical condition estimated and monitored as described above, when point values contributing to the respective specified conditions (including normal condition) are near each other, the condition estimate result is determined in accordance with the magnitude relation of the point values. Accordingly, the decrease of an accuracy of the estimate result cannot be avoided. To compensate for this, when a difference between the points of the higher positioned specified conditions is equal to or under a predetermined level, a question for confirming a condition is outputted to a user by use of voice or a screen display. In accordance with the answer information, it is possible to compensate for the condition estimate result.

Specifically, confirmation question information corresponding to each specified condition in each scene is stored in, e.g., the storage device 535. When the point difference between the higher positioned specified conditions is equal to or under a predetermined level, a question for confirming whether either of these specified conditions is the actual specified condition, is outputted. For example, a question for confirming the specified condition having the highest points is easy for the user to understand, and thus a clear answer can be obtained easily. Accordingly, this question is effective. When the condition estimate result is finally determined in reference to the question result, thresholds or weight factors of parameters of the determined specified condition and of a specified condition competing with the determined specified condition in points, are corrected and changed by the after-mentioned algorithm so that the parameters of the determined specified condition are prioritized. Accordingly, the same questions can be effectively prevented from being repeated. The examples are shown below.

(When a point value of normal condition is slightly over a point value of slightly poor physical condition) (Question) "You don't look well. Are you all right?" (or "Is it my imagination?") (Answer) "I'm all right." The normal condition is determined as the estimate result. (After that, thresholds or weight factors of parameters of the normal condition and of a condition competing with the normal condition in points are corrected and changed by the after-mentioned algorithm so that the parameters of the normal condition are prioritized.)

(When a point value of slightly poor physical condition is slightly over a point value of normal condition) (Question) "You look pale. Do you take a break before traveling?" (Answer) "No, I'm all right." The normal condition is determined as the estimate result. (After that, until points of the parameters of the normal condition exceed points of the parameters of the slightly poor physical condition, thresholds or weight factors of the related parameters are corrected and changed by the after-mentioned algorithm.)

(When a point value of excitation (angry) condition is slightly over a point value of slightly poor physical condition) (Question) "What's wrong? You are in a bad mood." (Answer) "I feel a little sick." The slightly poor physical condition is determined as the estimate result. (After that, until points of the parameters of slightly poor physical condition exceed points of the parameters of the excitation (angry) condition, thresholds or weight factors of the related parameters are corrected and changed by the after-mentioned algorithm.)

(When a point value of the slightly poor physical condition is slightly over a point value of excitation (angry) condition) (Question) "What's wrong? Do you have a cold?." (Answer) "Don't bug me. I'm fine." The excitation (angry) condition is determined as the estimate result. (After that, until points of the parameters of excitation (angry) condition exceed points of the parameters of the slightly poor physical condition, thresholds or weight factors of the related parameters are corrected and changed by the after-mentioned algorithm.)

The process for compensating for the condition estimate can be executed after and before the hospitality operation in each scene starts. In the latter case, a direction of the hospitality operation to be started is corrected to a direction requested by a user at the initial step. The result of the hospitality can be prevented from separating from the request of the user considerably.

Next, the hospitality process in the getting-in scene SCN2 can be executed as continuation of the process in the approach scene SCN1 (FIG. 2, OBJ121, OBJ221). When a user gets in a vehicle, and the seating sensor 520 detects the user, the hospitality control section 3 sends an instruction to stop playing music to the mobile phone 1 wirelessly. Then, the hospitality operation in the mobile phone 1 ends. On the other hand, themes for the anxiety/tension releasing genre ST3 are "comfort in vehicle" (OBJ321: for example, a suitable temperature is maintained in the vehicle by use of a prior operation by an air conditioner) and "security in case of getting in vehicle, avoiding of trouble" (OBJ322). These themes are achieved by the under-foot lighting by the under-floor lamp 512 of FIG. 1 and the collision restriction mode for an obstacle and door by the door assist mechanism 541 of FIG. 40.

In the hospitality theme "easy getting-in" (OBJ421), a burden for opening and closing the door can be reduced through a basic operation of the door assist mechanism 541. Because the detailed explanation of the operation of the door assist mechanism 541 has been done, the door assist mechanism 541 is not explained here. When the poor physical condition is estimated, a burden on the user can be reduced further by use of a stronger assist force of the door assist mechanism 541 than the usual assist force. In the structure of FIG. 41, the total torque of the outer operation force and positive assist force is reflected by a torque detection voltage Vst. Because the door assist driving by the motor 1010 is fed back so that the torque detection voltage Vst approaches Vref1, the assist force increases automatically as the force for opening the door by the user in poor physical condition decreases. When the poor physical condition is estimated, Vref1 is changed to increase, so that the assist force can be enhanced. In this case, part of voltage dividing resistors for determining Vref is made changeable. When the poor physical condition is estimated, Vref1 can be increased by changing values of the voltage dividing resistors.

In the theme "easy loading of baggage" (OBJ422), when the user has big baggage and is estimated to be in the poor physical condition, the door is opened automatically to a predetermined position to make the operating of the door unnecessary without assisting the user to open the door. Accordingly, the loading of the baggage is assisted. It is effective to show a position of the trunk, and to open automatically the cover for assisting the loading.

Next, the preparation scene SCN3 and drive/stay scene SCN4 are explained. In the themes (OBJ131, OBJ141, and OBJ231, OBJ241) of the expectation/uplifting genre ST1 and relaxing/easing genre ST2, the operation of the vehicle interior light 511 and the play of the car audio system 515, executed from the approach scene SCN1 and getting-in scene SCN2, are continued mainly (the lighting color or lighting pattern and music selection (or volume) are changed). In the preparation scene SCN3, to calm the mood, the light having a lowered lighting quantity, and the music selection for the refreshing ST3 or mild and soothing SF of FIG. 18 can be set. When the user starts driving, the lighting quantity can be increased to awake the driver sharply, and the music selection for the uplifting and activating AG can be done, for example. As described above, when the mental and physical condition is estimated to be abnormal, the light driving pattern and music selection are prioritized in consideration of this condition, as well as in the approach scene.

FIG. 13 shows a setting example of the function selection table 372 relating to the themes OBJ141, OBJ142 of the expectation/uplifting genre ST1. The operation object or disturbance type is the same as FIG. 7. The vehicle exterior lights (five in the night, zero in daytime (do not operate)), vehicle interior lights, closing operation of the power window mechanism, noise canceller, car audio system, and video output device such as a DVD player are selected as the hospitality operation devices. To decrease a noise level in the vehicle, a full closing of the window by the closing operation of the power window mechanism, and the operation of the noise canceller 1001B shown in FIGS. 44, 45 contribute considerably. As described above, the noise canceller 1001B saves specified required sounds such as the car audio system 515, conversations in the vehicle, or required vehicle-exterior sounds (emphasis sounds) to be noted or recognized as danger, and cancels noise elements other than the required sounds, by use of the setting of the adaptive filter. Accordingly, the user can listen music under more silent environment, and does not miss the required vehicle-exterior sounds. As shown in FIG. 67, in case of the poor physical condition, it can be effective to save the specified required sounds (alert/important sounds), and to equalize mainly low sound of the audio output.

In the control appropriate value setting table 371a, the vehicle interior lighting level and sound music level are set relatively high. When young persons who like noisy environment are targeted, vehicle interior noise such as wind noise may contribute to the ambience in the vehicle. The adaptive filter has the limit to pick up the required vehicle-exterior sounds more or less. Accordingly, because the music sound level in the vehicle is set relatively high, the decrease of the noise level (the higher the value is, the more it is silent) is rather restricted. A set value of the music sound level can be controlled by adjusting the output volume of the car audio system 515 so that a detection level of the sound pressure sensor 540 of FIG. 1 approaches a target value. On the other hand, a set value of the noise level can be controlled by setting a target level of the remaining noise elements detected by the error detection microphone 2012 of FIG. 44 to a finite value showing a level of the noise to be saved, not to zero.

FIGS. 9A, 9B show a setting example of the function selection table 371 and control appropriate value setting table 371a relating to the themes OBJ241, OBJ242 of the relaxing/easing genre ST2. The operation objects or disturbance types are the same as FIG. 11. The selected hospitality operation devices are the same as the expectation/uplifting genre ST1. The lighting level and music sound level are set lower than those of the expectation/uplifting genre ST1. The decrease of the noise level is set higher than that of the expectation/uplifting genre ST1. As described above, this hospitality is effective as the representation for cooling down the user in the poor physical condition or in excitation.

When the music in the approach scene SCN1 and getting-in scene SCN2 is played by MIDI, the playing using MPEG3 song database 515b (FIG. 17) is selected, because MIDI is not enough to enjoy full-scale music. In this case, the hospitality determination section 2 (FIG. 1) selects the music source data corresponding to a character type of the user.

When the user does not like the song automatically selected by the hospitality determination section 2, the user can always select his or her favorite song by use of an input from the operation portion 515d. When the user selects a song, the user specifying information (user name or user ID), an ID of the selected music source data, the above hospitality reference data RD (character type code, age code, sex code, genre code, and song mode code) correspond to each other, and are stored in the music selection history data 403 (stored in the storage device 535 of FIG. 1), as shown in FIG. 20. In this embodiment, a date of the music selection and a sex and age of the user are also stored.

In the music selection history data 403, statistics information 404 (stored in the storage device 535 of FIG. 1) of the music selection history is produced for each user, as shown in FIG. 21. In the statistics information 404, the music selection data is counted for each character type code (SKC), and what character type corresponds to the most frequently selected song is specified as a numeral parameter. The simplest process is such that a character type corresponding to the most frequently selected song is specified as a character of the user. For example, when the number of the music selection histories stored in the statistics information 404 reaches a predetermined level, the character type initially set from the input by the user may be replaced with the character type obtained from the statistics information 404 as described above.

The types of the characters of users are complicated actually. The taste in music is not simple enough to correspond to the same character type. In accordance with a life environment of the user (for example, whether the user is satisfied or stressed), the character and taste may change in a short term. In this case, it is natural that the taste in music also changes, and the character type obtained from the statistics changes. In this case, as shown in FIG. 21, when the statistics information 404 about the music selection is produced for only the nearest predetermined period (for example, one to six months), instead of obtaining the statistics of the music selection histories without limit, the short-term change of the character type can be reflected by the statistics result. As a result, a content of the hospitality using music can be changed flexibly in accordance with a condition of the user.

Even the same user does not always select the music corresponding to the same character type, but may select the music corresponding to another character type. In this case, when the user selects from only songs belonging to the character type where the songs are most frequently selected by the user, a situation undesirable for switching a mood of the user may occur. Music selection probability expectation values are assigned to the respective character types in accordance with music selection frequencies shown by the statistics information 404. Songs can be selected randomly from the character types weighted in accordance with the expectation values. Accordingly, with respect to the music source in which the user is interested more or less (namely, selected by the user), songs are selected in the descending order of the selection frequency across the multiple character types. The user can sometimes receive the hospitality using the music not corresponding to the character type of the user. This is a good switch of the mood. Specifically, a random number table including the predetermined number of random values is stored. The numbers of the random values are assigned to the respective character types in accordance with the music selection frequency. Next, a random number is generated by a known random number generation algorithm. It is checked to which character type the obtained random number value is assigned, so that the character type to be selected can be specified.

In the statistics information 404, music selection frequencies in accordance with the music genre (JC), age (AC), and sex (SC) are counted. As well as in the above method in case of the character types, the music source data belonging to the genre, age group, or sex where songs are frequently selected, can be preferentially selected. Accordingly, the hospitality music selection more matching the taste of the user is possible. The multiple character types can be assigned to one music source data.

Figure 30A:
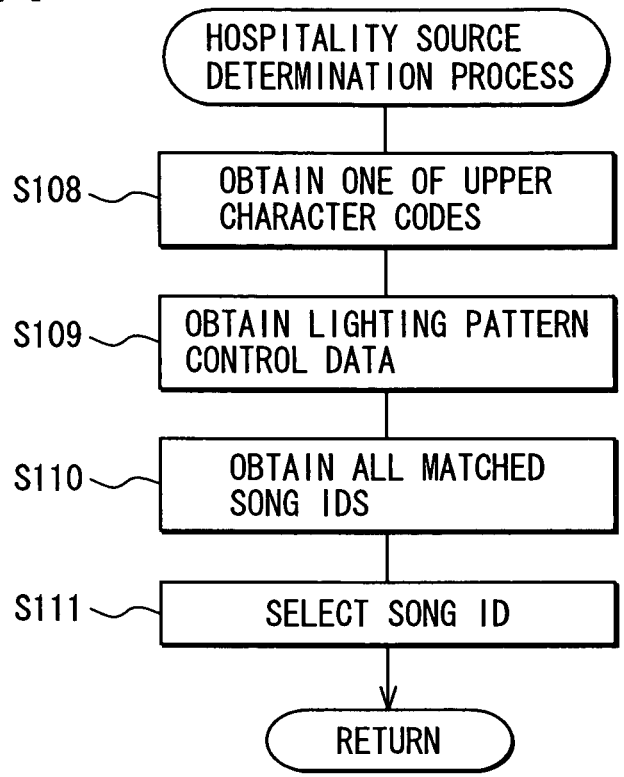
FIG. 30A is a flowchart showing one example of a hospitality source determination process.
Figure 30B:
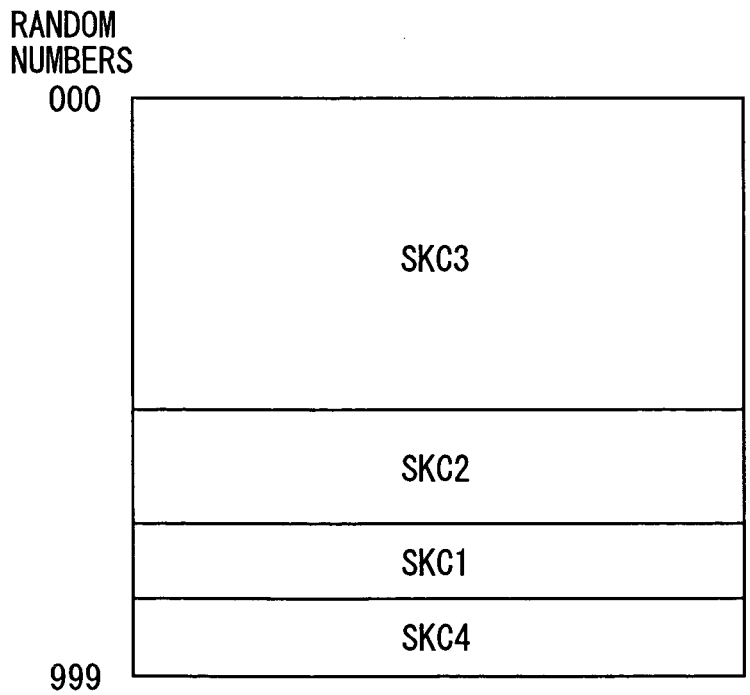
FIG. 30B is a table for random numbers.

FIG. 30A is a flowchart showing one example of the process. As shown in FIG. 21, when the music selection frequency statistics for each character type is obtained, random numbers on the random number table (in FIG. 30B) are assigned to the respective character types in proportion to the respective music selection frequencies. Next, in S108 of the flowchart, one arbitrary random number value is generated, and a character type code corresponding to the obtained random number value is selected on the random number table. Next, in S109, from the lighting control data group of FIG. 19, the lighting pattern control data corresponding to the character code is selected. In S110, all the music source data corresponding to the genre, age group, and sex having the highest music selection frequency in FIG. 21, are extracted from the music source data corresponding to the obtained character type (as well as in case of the determination of the character type, the genre, age, and sex of the music selection may be selected by use of the random numbers assigned in proportional to the frequency of each genre, age, and sex). When multiple pieces of music source data are extracted, an ID of one of the music source data may be selected by use of a random number, as well as in S111. Additionally, the list of the music source data is shown on the monitor 536 (FIG. 1), and the user selects the music source data manually by use of the operation portion 515d (FIG. 17). In accordance with the selected lighting control data, the lighting of the lighting device in the vehicle which is being driven by the user (or in which the user stays) is controlled. The music is played in the car audio system by use of the selected music source data.

The other hospitality themes assigned to the preparation scene SCN3 or drive/stay scene SCN4 are explained below. The theme "situation of destination/route" is set across both scenes. For example, in the preparation scene SCN3 (OBJ331), as shown in the function selection table 371 of FIG. 12, the vehicle GPS 533 and car navigation system 534 are selected as the hospitality operation devices. When a destination is set, a situation of the destination and route is obtained via the radio communications network 1170, and displayed on the monitor of the car navigation system 534, as the hospitality operation. The operation object or disturbance type for "vehicle interior brightness" or "vehicle interior environment" is the same as the other function selection tables. With respect to the entertainment elements and information provision, the hospitality operation is selected in accordance with a taste of the user, regardless of disturbances. In this case, in accordance with an estimate result of the mental or physical condition of the user by use of the after-mentioned algorithm, the appropriate hospitality operation can be selected. On the other hand, "vehicle interior accommodation" does not relate to disturbances. On the other hand, when a positional relationship between the user and the steering wheel or seat can be specified by use of a user detection sensor 565 separately provided (FIG. 1), a disturbance can be determined to occur when the positional relationship is not in an accurate condition. To reduce the disturbance, a position of the steering wheel and a longitudinal position and height of the seat can be adjusted as the hospitality operation.

In the drive/stay scene, a character type of the user can be estimated by use of information other than the music selection history of the music sources. For example, driving history data of each user is stored. In accordance with an analysis result of the driving history data, the character type of the user can be specified. The specifying process is explained below. As shown in FIG. 22, the operations which tend to be executed when the user feels stressed in driving are predetermined as stress reflection operations. The corresponding detection unit detects the stress reflection operations. The detection result is stored and accumulated as a stress reflection operation statistics data in the storage unit 405 (FIG. 1: in the storage device 535). In accordance with the result of the stored data, a character type of the user is estimated. The following embodiment is focused on how to restrict the influence of the character elements unfavorable for driving a vehicle.

In this embodiment, as the stress reflection operations, horn operations (when the user blows the horn many times impatiently), the frequency of brakes (when the user brakes many times due to a too short distance to a vehicle in front), and the frequency of lane changing (when the user changes lanes frequently to pass a vehicle in front: the lane changing can be detected from the operation of the turn signal and the steering angle after the operation of the turn signal) are selected. A horn switch 502a, brake sensor 530, turn signal switch 502w, and acceleration sensor 532 operate as the stress reflection operation detection units. Every time each operation is executed, the corresponding counter in the stress reflection operation statistics data storage unit 405 is counted up, and the frequency of the operations is recorded. These operations can reflect a tendency toward "dangerous driving."

A speed of a running vehicle is detected by the vehicle speed sensor 531. The acceleration is detected by the acceleration sensor 532. An average speed $V_N$ and average acceleration $A_N$ are calculated, and stored in the stress reflection operation statistics data storage unit 405. The average acceleration $A_N$ is obtained only while the acceleration increases by equal to or over a predetermined level. The average acceleration AN is not used for calculating the average value during the low speed traveling where the acceleration changes small. Accordingly, a value of the average acceleration AN reflects whether the user likes to depress the accelerator frequently in case of, e.g., passing, or to start suddenly. A traveling distance is calculated from an output integration value of the vehicle speed sensor 531, and stored in the stress reflection operation statistics data storage unit 405.

The stress reflection operation statistics is produced for a general way section and express way section separately (this distinction is possible by referencing the traveling information of the car navigation system 534). In case of traveling on an express way, when vehicles travel smoothly, a user who drives normally does not blow the horn, depress the brake, and change lanes many times. The number of the detections of these stress reflection operations on the express way is to be weighted greater than that on the general way section.

The average speed and average acceleration on the express way section are naturally higher than those on the general way section. This influence can be decreased by taking statistics on the express way section and general way section separately.

One example of an algorithm for determining a character by use of the stress reflection operation statistics is shown below. The algorithm is not limited to the following. Values of the number of horns Nh, the number of brakes $N_B$, and the number of lane changes $N_{LC}$ on the ordinary way section (shown by a suffix "O") are multiplied by a weighting factor α, and the values on the express way section (shown by a suffix "E") are multiplied by a weighting factor β (α<β: one of the factors may be fixed to 1, the other may be a relative value), and added. The added value is divided by a travel distance L as a converted number (shown by a suffix "Q"). The values of the average speeds and average accelerations in the ordinary road section and express way section are weighted by the weighting factors, and added, and calculated as converted average speeds and converted average accelerations. A value obtained by adding all the values is a character estimate parameter ΣCh. In accordance with the value ΣCh, the character is estimated.

Figure 29:
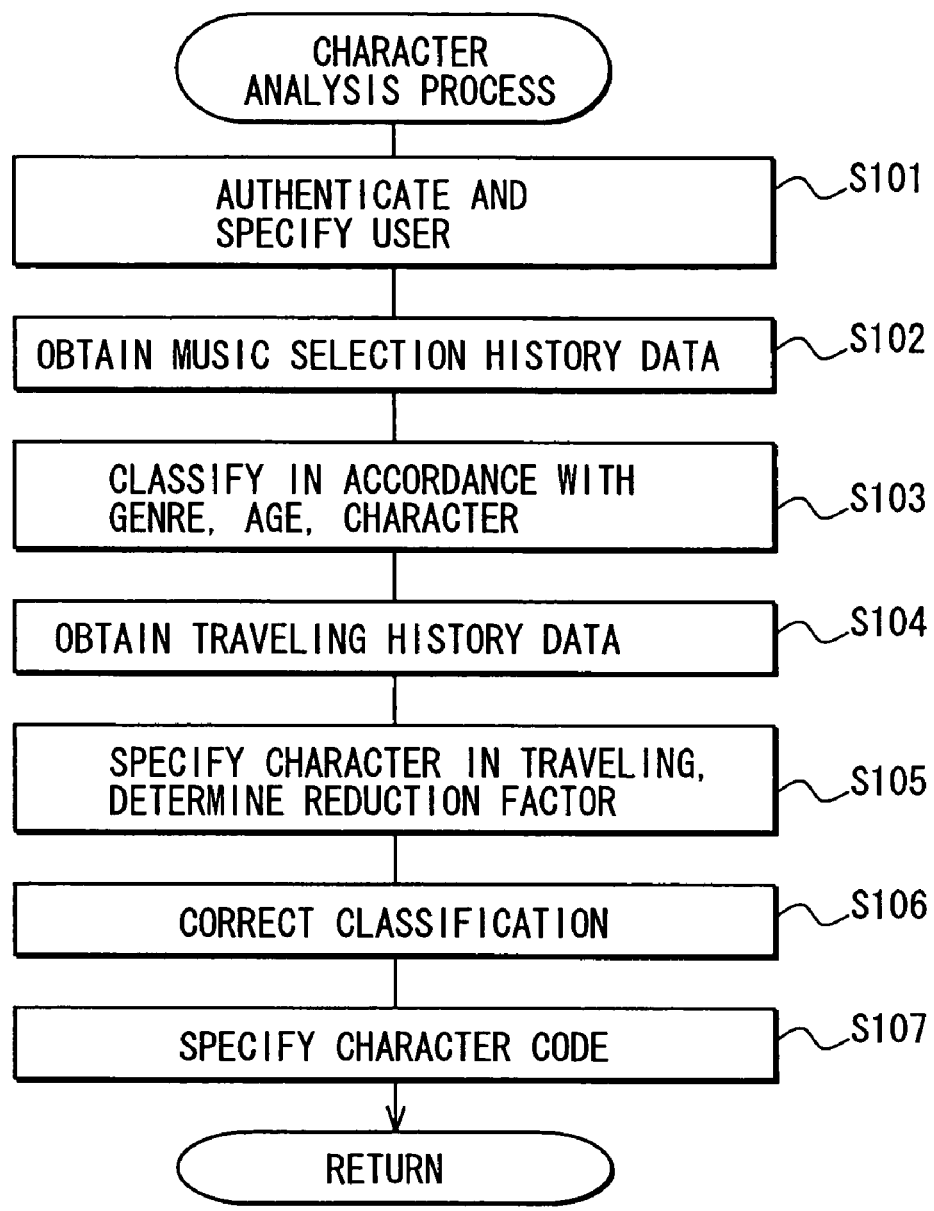
FIG. 29 is a flowchart showing a flow of a process of analyzing characters.

In this embodiment, a range of the value ΣCh is divided into multiple sections A1, A2, A3, and A4. The character types are assigned to the sections. Contraction factors δ1, δ2, and δ3 (these are over 0 and under 1) are defined corresponding to the section including the calculated value ΣCh. FIG. 29 shows one example of a flow of a specific character analysis process using this. As described above, a user authentication is done in S101. In S102, the music selection history data 403 is obtained. In S103, the music selection statistics information 404 of FIG. 21 is produced. Next, in S104, the information (traveling history) accumulated in the stress reflection operation statistics data storage unit 405 of FIG. 22 is read. In S105, through the above method, a value ΣCh is calculated. A character type is specified corresponding to the value ΣCh. Then, a contraction factor δ is obtained. In S106, the character type where songs are most frequently selected is specified in the music selection statistics information 404, and multiplied by the contraction factor δ to contract an apparent frequency. Accordingly, for example, when ΣCh about an "active" user becomes high, this means that a tendency toward a dangerous driving is increased due to the active character such that ΣCh becomes high. The frequency of selecting the music which promotes the dangerous driving can be restricted by being multiplied by the contraction factor δ. Accordingly, the user can be introduced to safety driving. When ΣCh about a "gentle" user becomes low, a frequency of selecting songs corresponding to "gentle" is multiplied by the contraction factor δ, and thus restricted. A frequency of selecting active songs increases relatively. Accordingly, the user can receive moderate stimulation and drive smart, enhancing safety.

Next, when the user is driving, the mental and physical condition further needs to be considered, in addition to the character. When a user (driver) is seated on the driver's seat, more sensors and cameras can be used as the biological condition detection units for obtaining the biological parameters. Specifically, the infrared sensor 519, seating sensor 520, face camera 521, microphone 522, pressure sensor 523, blood pressure sensor 524, body temperature sensor 525, iris camera 527, and skin resistance sensor 545 of FIG. 1 can be used. These biological condition detection units can grasp vital reaction of the user who is driving, variously. The hospitality determination section 2 estimates mental and physical condition of the user from the time change information of the biological condition parameters detected by the biological condition detection units, and executes the hospitality operation matching the condition, as well as described in detail in the embodiment of the approach scene.

Figure 34:
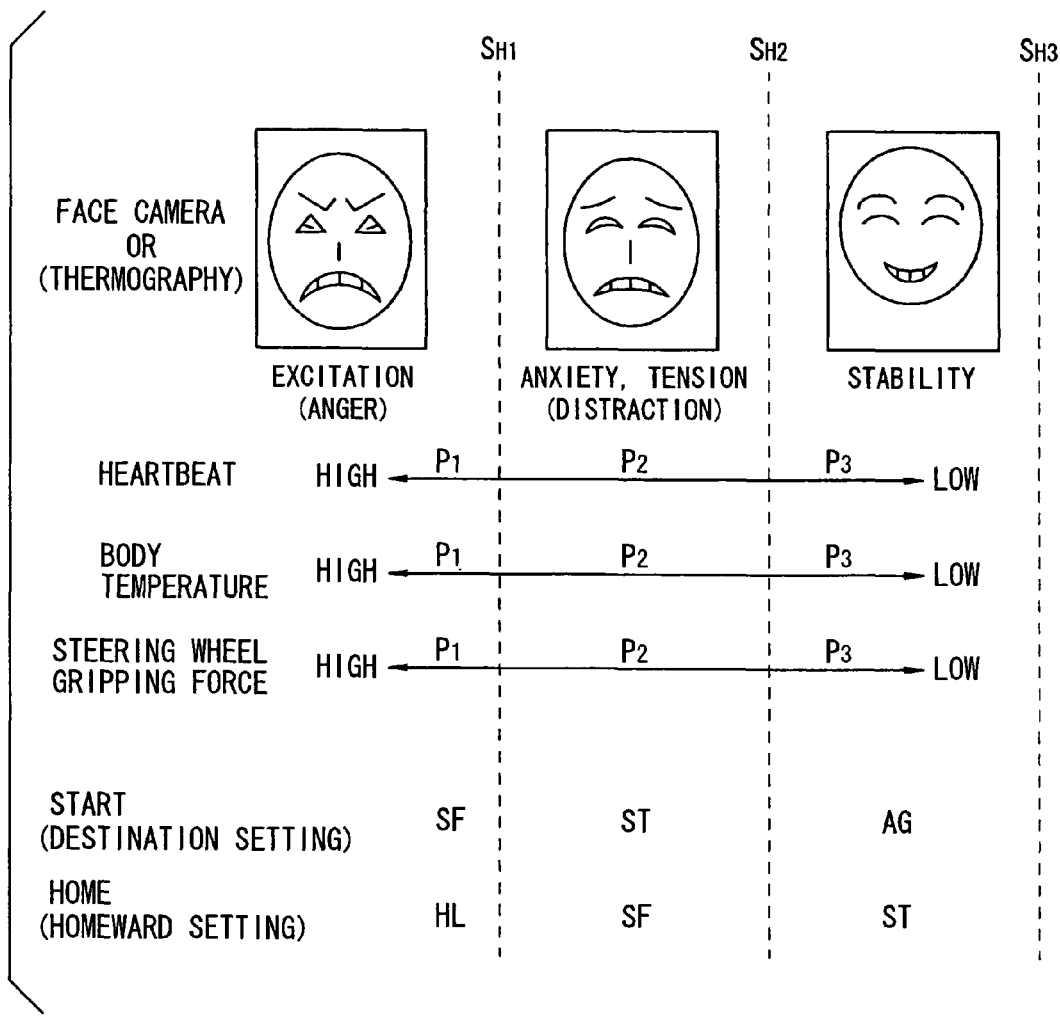
FIG. 34 is a view showing estimate of mental/physical condition using detection information from a biological condition detection unit, and an example of determined song mode codes.

As well as described above, information about a facial expression can be obtained from a still image of the face taken by the face camera 521. As shown in FIG. 34, by comparing the image of the whole face (or part of the face: for example, eyes or the mouth) to master images of various mental or physical conditions, whether the user is angry, calm, good humored (for example, exhilarated), bad humored (for example, disappointed or sad), or anxious or tensioned, can be estimated. Instead of using a master image unique to a user, positions and shapes of a face, eyes (irises), mouth, and nose are extracted as a facial feature amount common to all users. The feature amount is compared to standard feature amounts previously measured and stored in case of various mental and physical conditions, so that the same determination as above can be made. Types of faces are classified by characters by use of the feature amounts, and matched with the character types, so that a character type of the user can be specified.

In accordance with information about motions of the body, such as a moving image of the user taken by the face camera 521 (for example, wiggling motion or contorted face) and about the conditions detected by the pressure sensor 523 (for example, the user releases his or her hand from the steering wheel frequently), whether the user who is driving is bad humored, can de determined.

The body temperature can be detected and specified by the body temperature detection units such as the body temperature sensor 525 mounted to the steering wheel and a thermography of the face obtained by the infrared sensor 519. By use of the same algorithm as shown in FIGS. 54A, 54B, a speed of the body temperature changing and a change or maintenance of the average body temperature level can be determined. A normal body temperature of the user is registered in advance. The body temperature detection units measure the temperature shift from the normal body temperature (particularly to a higher temperature), so that a slighter body temperature change, a slighter emotional swing due to the change, and so on can be detected.

FIGS. 55A, 55B show one example of a flowchart of a skin resistance change waveform analysis process. In the sampling routine, each time a sampling timing determined at a predetermined interval comes, a skin resistance value detected by the skin resistance sensor 545 is sampled, and its waveform is recorded. In the waveform analysis routine, the skin resistance value sampled during the nearest predetermined interval is obtained as a waveform in SS103, a known fast Fourier transformation process is applied to the waveform in SS104 to obtain a frequency spectrum, and a center frequency (or peak frequency) f of the spectrum is calculated in SS105. In SS106, as shown in FIG. 53, the waveform is divided into the predetermined number of sections σ1, σ2, and so on, and an average skin resistance value is calculated in SS107. In each section, by use of the average skin resistance value as a waveform center line, the integrated amplitudes A1, A2, and so on are calculated. In SS109, the integrated amplitude A in each section is plotted to a time t, and by use of least-square regression, an inclination α is obtained.

In SS110, it is checked whether a frequency f is over an upper limit threshold fu0, and when the frequency f is over the upper limit threshold fu0, a skin resistance change being monitored is determined to be "rapid." In SS112, it is checked whether the frequency f is under an lower limit threshold fL0 (>fu0), and when the frequency f is over the lower limit threshold fL0, the skin resistance change being monitored is determined to be "slow." When fu0≧f≧fL0, the process goes to SS114, and the skin resistance change being monitored is determined to be "normal." Next, in SS115, an absolute value of the inclination α is compared to a threshold α0. When |α|≦α0, a skin resistance level being monitored is determined to be "constant." When |α|>α0, and a sign of α is plus, the skin resistance level being monitored is determined to "increase." When |α|>α0, and a sign of α is minus, the skin resistance level being monitored is determined to "decrease."

As shown in FIG. 51, when a change of the skin resistance detection value is fast and the change is in the "increasing" direction, the mental condition can be estimated to be in "distraction." With respect to the poor physical condition, a slightly poor physical condition is not so reflected by a time change of the skin resistance. When the poor physical condition progresses, a change of the skin resistance value increases slowly, so that the change is effective to estimate a "serious poor physical condition." When the skin resistance value decreases fast, the condition can be estimated to be in "excitation (anger)" quite accurately.

Next, FIGS. 57A, 57B show one example of a flowchart of a posture signal waveform analysis process. In the sampling routine, each time the sampling timing determined at a predetermined interval comes, the posture signal value (Vout) explained in FIG. 58 is sampled, and its waveform is recorded (SS201, SS202). In the waveform analysis routine, the posture signal value sampled during the nearest predetermined interval in SS203 is obtained as a waveform. In SS204, the known fast Fourier transformation process is applied to the waveform to obtain a frequency spectrum. In SS205, a center frequency (or a peak frequency) f is calculated. In SS206, as shown in FIG. 53, the waveform is divided into the predetermined number of sections σ1, σ2, and so on. In SS207, an average posture signal value in each section is calculated. In each section, by use of the average posture signal value as a waveform center line, integrated amplitudes A1, A2, and so on are calculated. In SS209, the integrated amplitudes A in the sections are averaged, and determined as a representative value of a waveform amplitude. In SS210, a variance $\Sigma^2$ of the integrated amplitudes A is calculated.

In SS211, it is checked whether a frequency f is over an upper limit threshold fu0. When the frequency f is over the upper limit threshold fu0, a posture change speed being monitored is determined to be "increase." In SS213, it is checked whether the frequency f is under a lower limit threshold fL0 (>fu0). When the frequency f is under the lower limit threshold fL0, the posture change speed being monitored is determined to be "decrease." When fu0≧f≧fL0, the process goes to SS215, and the posture change speed being monitored is determined to be "normal." Next, in SS216, an average value An of the integrated amplitudes A is compared to a predetermined threshold, and a posture change amount is determined to be one of "small change," "slight increase," or "rapid increase" (as the average value An is greater, the posture transition amount tends to increase). In SS217, when a value of a variance $\Sigma^2$ of A is over the threshold, the posture change tends to increase or decrease.

Because the change of the posture shows a quite different tendency in accordance with a change of the basic specified conditions ("poor physical condition," "distraction," and "excitation"), the change is a particularly effective parameter to distinguish the basic specified conditions. In the normal condition, a user who is driving maintains an appropriate posture and a sense of tension required for driving. When the poor physical condition occurs, the user sometimes changes the posture obviously to soften the pain. The posture change amount tends to increase slightly. When the poor physical condition progresses further (or the user feels sleepy extremely), the posture becomes unstable to shake, and the posture change tends to increase and decrease. Because the posture change at this time is uncontrollable and unstable, a speed of the posture change decreases considerably. In case of the distraction, the posture change increases and decreases loosely, but the body can be controlled, so that a difference is seen in that the posture change speed does not decrease considerably. In case of the excitation, the user becomes restless and nervous, so that the posture change increases rapidly, and the change speed becomes high.

FIGS. 60A, 60B show one example of a flowchart of a process for analyzing a waveform of an angle of a line of sight. In the sampling routine, each time a sampling time determined at a predetermined interval comes and a face image is taken, positions of a pupil and center of the face are specified in SS252, and a difference from a front direction of the pupil relative to the center position of the face is calculated, so that an angle θ of the line of sight can be obtained. In the waveform analysis routine, a line-of-sight angle value sampled during the nearest predetermined interval is obtained as a waveform, the known fast Fourier transformation process is applied to the waveform to obtain a frequency spectrum in SS255, and a center frequency (or peak frequency) f of the spectrum is calculated in SS256. In SS257, as shown in FIG. 53, the waveform is divided into the predetermined number of sections σ1, σ2, and so on. In SS258, an average line-of-sight angle value in each section is calculated. In SS259, by use of the average line-of-sight angle value as a waveform center line, integrated amplitudes A1, A2, and so on are calculated in each section. In SS260, the integrated amplitudes A in the sections are averaged, and determined as a representative value An of the waveform amplitudes. In SS261, a variance $\Sigma^2$ of the integrated amplitudes A is calculated.

In SS262, it is checked whether the frequency f is over an upper limit threshold fu0. When the frequency f is over the upper limit threshold fu0, a change speed of a line-of-sight angle θ being monitored is determined to be "increase." In SS264, it is checked whether the frequency f is under a lower limit threshold fL0 (>fu0). When the frequency f is under the lower limit threshold fL0, a change speed of the line-of-sight angle θ being monitored is determined to be "decrease." When fu0≧f≧fL0, the process goes to SS266, and a change speed of the line-of-sight angle θ being monitored is determined to be "normal." Next, in SS267, the average value An of the integrated amplitudes A is compared to a predetermined value, and a change amount of the line-of-sight angle θ is determined to be one of "small change," "slight increase," and "fast increase" (as the average value An is greater, the change amount of the line-of-sight angle θ tends to increase). In SS268, when a variance $\Sigma^2$ of A is equal to or over a threshold, a change of the line-of-sight angle θ tends to increase and decrease, namely, the line-of-sight is determined to be in "changing" condition (namely, the eyes rove)

In case of the distraction, a change amount of the line-of-sight angle θ increases rapidly and the eyes rove. Accordingly, the change amount is an important determining factor to estimate the distraction. In case of the poor physical condition, the line-of-sight change amount decreases in accordance with a degree of the poor physical condition. Accordingly, the change amount is an important determining factor to estimate the poor physical condition. The line-of-sight change amount decreases in case of the excitation. In case of the poor physical condition, when a change occurs in a visual range, it is difficult for the line-of-sight to follow the change, and the line-of-sight change speed decreases. In case of the excitation, the line-of-sight sharply responds to, and stares at, e.g., a change in a visual range, namely, a speed of the line-of-sight change which sometimes occurs is very high. The poor physical condition and excitation can be distinguished.

FIGS. 61A, 61B show one example of a flowchart of a pupil diameter change analysis process. In the sampling routine, each time a sampling timing determined at a predetermined interval comes, an iris of a user is taken by the iris camera 527 (FIG. 1) in SS302, and a pupil diameter is determined on the image in SS303. In the analysis routine, the pupil diameter d sampled during the nearest predetermined interval is obtained as a waveform in SS304. In SS305, as shown in FIG. 53, the waveform is divided into the predetermined number of sections σ1, σ2, and so on. In SS306, an average pupil diameter value dn in each section is calculated. In SS307, in each section, by use of the average pupil diameter value as a waveform center line, integrated amplitude A1, A2, and so on are calculated. In SS308, an average value An of the integrated amplitudes in the sections is calculated. In SS309, a variance $\Sigma^2$ of the integrated amplitudes A is calculated.

In SS310, it is checked whether the average pupil diameter value dn is over a threshold d0. When the average pupil diameter value dn is over the threshold d0, the process goes to SS311 to determine that "the pupil opens." When the average pupil diameter value dn is not over the threshold d0, the process goes to SS312 to check whether the variance $\Sigma^2$ of the integrated amplitudes A is over a threshold $\Sigma^2 0$. When the variance S2 of the integrated amplitudes A is over the threshold $\Sigma^2 0$, it is determined that "a diameter of the pupil changes." When the variance $\Sigma^2$ of the integrated amplitudes A is not over the threshold $\Sigma^2 0$, the pupil is determined to be "normal."

As shown in FIG. 51, the pupil diameter d changes in accordance with the mental condition of the user. Particularly, in accordance with whether the pupil is in a specific condition, it can be estimated whether the user is in excitation, accurately. When the pupil diameter changes, the user can be estimated to be in distraction.

In this system, a steering condition of a driver is also used as a biological condition parameter for estimating a mental or physical condition of the driver. The steering is sampled and evaluated only in straight traveling. When a steering angle can be estimated to be naturally greater in case of, e.g., turning right or left or changing lanes, it is preferable that the steering is not monitored and evaluated (the steering by the driver in normal might be determined to be unstable). For example, when the turn signal is lighted, during the turn signal lighting period and a predetermined period before and after the anticipated steering (for example, about five seconds before the lighting and about ten seconds after the lighting), the steering may not be evaluated.

FIGS. 62A, 62B show one example of a flowchart of a steering angle waveform analysis process. In the sampling routine, at each regular sampling timing, in SS352, a current steering angle $\phi$ is read (for example, $\phi=0$ degree in the straight neutral condition, defined as a deflection angle to the right or left (for example, the angle in the right direction is positive, and the angle in the left direction is negative)). In a steering accuracy analysis routine, a steering angle value sampled during the nearest regular period is obtained as a waveform in SS353, the known fast Fourier transformation process is applied to the waveform to obtain a frequency spectrum in SS354, and a center frequency f of the spectrum (or peak frequency) is calculated in SS355. In SS356, as shown in FIG. 53, the waveform is divided into the predetermined number of sections $\sigma 1$, $\sigma 2$, and so on. In SS357, an average steering angle value in each section is calculated. In SS358, in each section, by use of the average steering angle value as a waveform center line, integrated amplitudes A1, A2, and so on are calculated. In SS359, a variance $\Sigma^2$ of the integrated amplitudes A is calculated.

In SS360, it is checked whether the frequency f is over an upper limit threshold fu0. When the frequency f is over the upper limit threshold fu0, the process goes to SS361 to determine that a changing speed of the steering angle $\phi$ being monitored "increases." In SS362, it is checked whether the frequency f is over a lower limit threshold fL0 (>fu0). When the frequency f is over the lower limit threshold fL0, a changing speed of the steering angle $\phi$ being monitored is determined to "decrease." When fu0$\geq$f$\geq$fL0, the process goes to SS264 to determine that the steering angle $\phi$ being monitored is "normal." Next, in SS365, the variance $\Sigma^2$ of the integrated amplitudes of the changing waveform of the steering angle f is over a threshold $\Sigma^2 0$. When the variance $\Sigma^2$ is over the threshold $\Sigma^2 0$, a steering error is determined to "increase" (SS366). When the variance $\Sigma^2$ is not over the threshold $\Sigma^2 0$, the steering error is determined to be "normal" (SS367).

Figure 63:
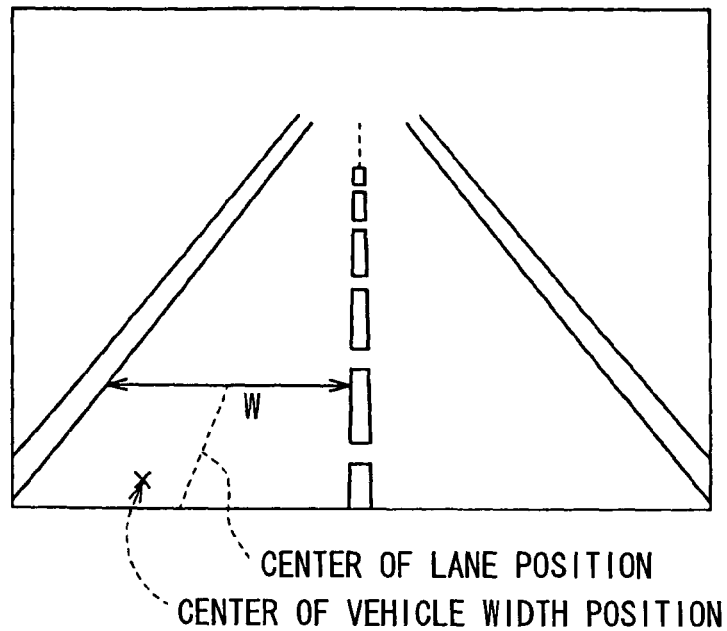
FIG. 63 is an image of a traveling monitor image.
Figure 64:
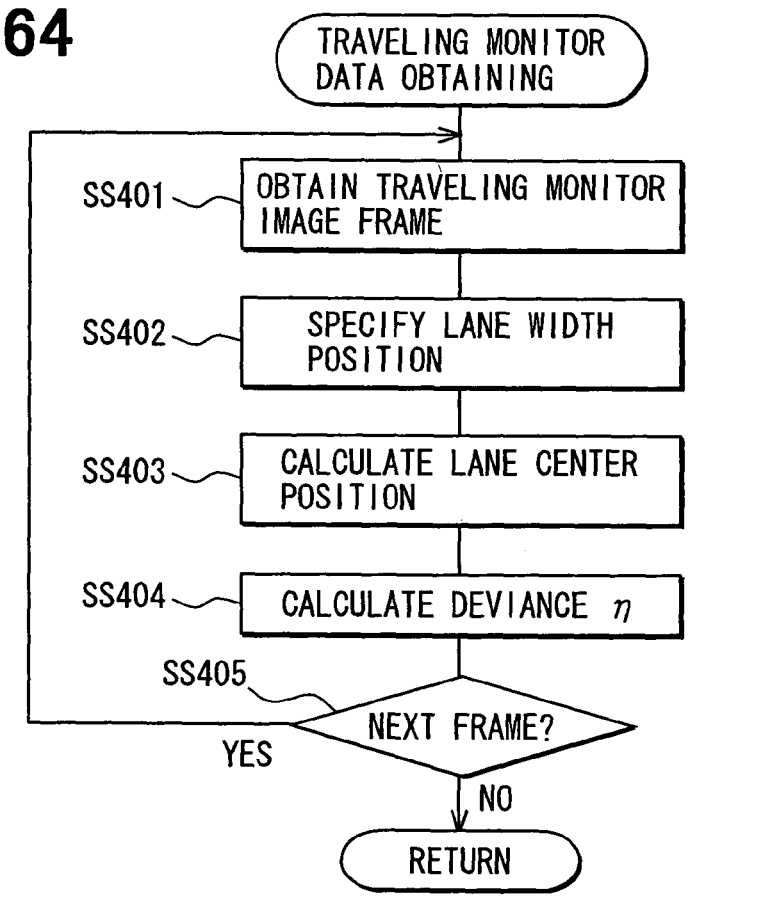
FIG. 64 is a flowchart showing one example of a traveling monitor data obtaining process.

The steering error can be detected from a monitoring image of a traveling monitor camera 546 of FIG. 1, as well as from the above steering angle. The traveling monitor camera 546 can be mounted to the front center (for example, the center of a front grill) of the vehicle, and takes a front visual range in the traveling direction, as shown in FIG. 63. When the mounting position of the camera relative to the vehicle is determined, a vehicle width center position (vehicle standard position) is determined in the traveling direction on the taking visual range. For example, by distinguishing a road shoulder line, a center line, or a lane separating line on the image, the center position of the lane where the user is in traveling can be specified on the image. When an offset of the vehicle width center position from the lane center position is found, whether the vehicle driven by the user can keep the center of the lane can be monitored. FIG. 64 is a flowchart showing an example of a flow of the process. In SS401, a frame of the travel monitoring image is obtained. In SS402, lane side edge lines of the road shoulder line and the white line (or an orange line of the no-passing zone) showing center line or lane separating line are extracted by a known image processing, and specified as lane width positions. In SS403, a position dividing a distance between the edge lines into two is used as a lane center position to execute the calculation. On the other hand, in SS404, the vehicle width center position is plotted on the image frame, and an offset amount T from the lane center position in the road width direction is calculated. This process is repeated for image frames loaded at predetermined intervals, and the offset amounts Ti are recorded as a time change waveform (SS405 to SS401).

The steering accuracy analysis process in this case can be executed along a flow shown in FIG. 65, for example. In SS451, an integrated amplitude A relative to a center line of a waveform during the nearest predetermined period is calculated. In SS453, an average value $\eta n$ of an offset amount $\eta$ from the lane center position is calculated. In SS454, the integrated amplitude A is compared to a predetermined threshold A0. When the integrated amplitude A is over the predetermined threshold A0, the process goes to SS455 to determine that a steering error "increases." When the integrated amplitude A is over the predetermined threshold A0, an offset amount $\eta$ oscillates relative to time considerably, showing a tendency of a type of unstable traveling. In the case where a tendency to move toward the corner continues because the vehicle cannot keep traveling on the lane center, an offset amount $\eta$ becomes great. The tendency is to be determined as abnormal even when the integrated amplitude A is under the threshold A0. Therefore, in this case, the process goes to SS456. When the average value Tin of the offset amounts is over the threshold $\eta n 0$, the process goes to SS455 to determine that the steering error "increases." On the other hand, when the average value $\eta n$ of the offset amounts is under the threshold $\eta n 0$, the process goes to SS457 to determine that the steering error is "normal."

With respect to the steering speed (response to the steering), the known fast Fourier transformation process is applied to the waveform to obtain a frequency spectrum. A center frequency (or peak frequency) f of the spectrum is calculated. From f, a tendency of the steering speed can be determined. In this case, it is checked whether the frequency f is over an upper limit value fu0. When the frequency f is over the upper limit value fu0, the steering speed is determined to "increase." In SS362, it is checked whether the frequency f is under a lower limit value fL0 (>fu0). When the frequency f is under the lower limit value fL0, the steering speed is determined to "decrease." When fu0$\geq$f$\geq$fL0, the steering speed is determined to be "normal."

As shown in FIG. 51, by detecting the increase of the steering error, the driver can be estimated to be in the distraction or excitation. On the other hand, in case of the serious physical condition (including drowsiness), normal steering is prevented. Accordingly, from a tendency of the increase of the error, the condition can be estimated. On the other hand, the response to the steering tends to be delayed in case of the poor physical condition or distraction. From the decrease of the steering speed, the poor physical condition or distraction can be estimated. In the excitation, the driver tends to turn the steering wheel from impatience. From the increase of the steering speed, the excitation can be estimated.

In the traveling, the process for specifying the specified condition along a flow of FIG. 66 is executed. In this case, many biological condition parameters are referenced. The points of the matching counter are considered as a "matching degree." The condition having the highest points is effectively determined as the specified condition. As described above, the addition to the matching counter is executed such that, when the approximate result can be obtained within a determined range although the specified information and the determination result are not matched with each other completely, the result can be added to the matching counter while the result is limited to lower points than that of the perfect matching.

When the specified condition can be specified, many specific examples can be considered as the hospitality control corresponding to the condition. For example, in the theme "setting of proper driving environment" OBJ441, as shown in the function selection table 371 in FIG. 12, the car navigation system 534 (for outputting video), the car audio system 515, the air conditioner 514, the vehicle interior light 511, a steering wheel adjustment unit, and a seat adjustment unit are selected as the hospitality operation devices. As described above, in accordance with the mental and physical condition of the driver (user), the music selection is changed, and the lighting color or lighting quantity in the vehicle is adjusted. The steering wheel adjustment unit and seat adjustment unit are such that, for example, a position of the steering wheel and longitudinal position of the seat or an angle of the back rest are automatically adjusted. For example, when a sense of tension is determined to be released, the back rest is raised and the seat is moved forward, and a position of the steering wheel is raised, so that the driver can concentrate on driving. When the driver is determined to be tired, an angle of the back rest is effectively adjusted slightly so that movement of the driver showing displeasure is decreased.

The modes other than the above ones are as follows. In case of excitation (when the mood of the driver is determined to be excited too much or the driver is determined to feel anger and stress): Still and comfortable music is played to calm the mood of the driver. A temperature of the air conditioner is decreased, slow (longer cycle than that in the after-mentioned distraction) rhythm vibration is generated by the seat vibrator 550, so that the driver is relaxed. When the driver is assumed to feel discomfort due to overtaking, cutting-in, flashing, horn blowing, and so on from the following vehicle, a voice message for calming the driver, such as "How rude! But forget it. You are very wise." is outputted. When the speed exceeds a speed limit (vehicle speed detection) or is about to exceed a speed limit: a voice message for prompting the speed reduction, such as "Don't be in a hurry. You have spare time. Safety driving is cool." is outputted. In case of distraction: Strong vibrations are generated by the steering wheel vibrator 551 and seat vibrator 550 like an impulse to promote concentration. The ammonia generation portion 549 generates strong smell for awaking. In case of poor physical condition (when fatigue and disease (such as fever) are recognized): The safety driving such as speed reduction and the stop and rest are promoted. When approaching a railroad crossing and red signal, caution information is outputted by use of voice. In the worst case, a notification, e.g., for stopping driving, is outputted and displayed on the monitor. The direction generation portion generates a fragrance for relaxing. With respect to sleepiness, the same hospitality operation as the distraction is effective. In case of disappointment (facial expression, body temperature): A joyful music is played, and a red light is selected to uplift the mood.

More specific cases are explained by use of music selection for driving as examples. The above character type codes are used such that a specified character of a user is provided with music sources having a character type code matching the character of the user, namely, such that the character of the user matches the character type code of the selected music source. On the other hand, the song mode codes are used such that a song code provided to the music source does not always match the specified mental and physical condition of the user. For example, the mild and soothing music source and the healing and $\alpha$-wave music source are used for calming the too much uplifted mental condition. The song mode codes are used so that the mental condition of the user approaches a target value of a mental condition. When an uplifting level of the mental condition of the user can be parameterized, the song mode codes are prioritized corresponding to the uplifting levels. The music selection can be done so that a song mode code is selected in accordance with a parameter of the uplifting level of the mental condition. Specifically, when it is determined that, as a parameter of the mental condition uplifting level becomes high, the mental condition is uplifted, the song mode codes are prioritized in the order: "uplifting," "refreshing," "mild and soothing," "healing and $\alpha$-wave." As a parameter of the mental condition uplifting level is higher, the higher-prioritized song mode code is selected so that the music selection is done to calm the too much uplifted mood. On the other hand, the song mode code is selected so that the music selection is done to uplift the disappointed mood. In the former case, an effect for restricting the too fast speed due to, e.g., the excitation can be obtained. In the latter case, an effect for awaking the user and increasing the attention of the user can be obtained. Both cases contribute to the safety driving. On the other hand, when the physical condition decreases, it is preferable that radical music selection for making the user be tired is avoided if possible.

For example, as shown in FIG. 34, when the mental condition of the user is divided into three levels, excitation (anger), distraction (anxiety and tension), and stability, the song mode codes correspond to the respective mental condition levels uniquely. In this embodiment, "anger" corresponds to "mild and soothing" (SF), "anxiety and tension" corresponds to "refreshing" (ST), "stability" corresponds to "uplifting and activating" (AG) (first setting).

In case of traveling to a destination separated by over a predetermined distance by use of the car navigation system 534, the driver is tired on the homeward route. Accordingly, a level of the song mode code is made low so that the driver on the homeward route is more calmed than on the outward route (second setting). In FIG. 34, on the homeward route, "healing and $\alpha$-wave" (HL) corresponds to "anger," "mild and soothing" (SF) corresponds to "anxiety and tension," and "refreshing" (ST) corresponds to "stability."

Figure 35:
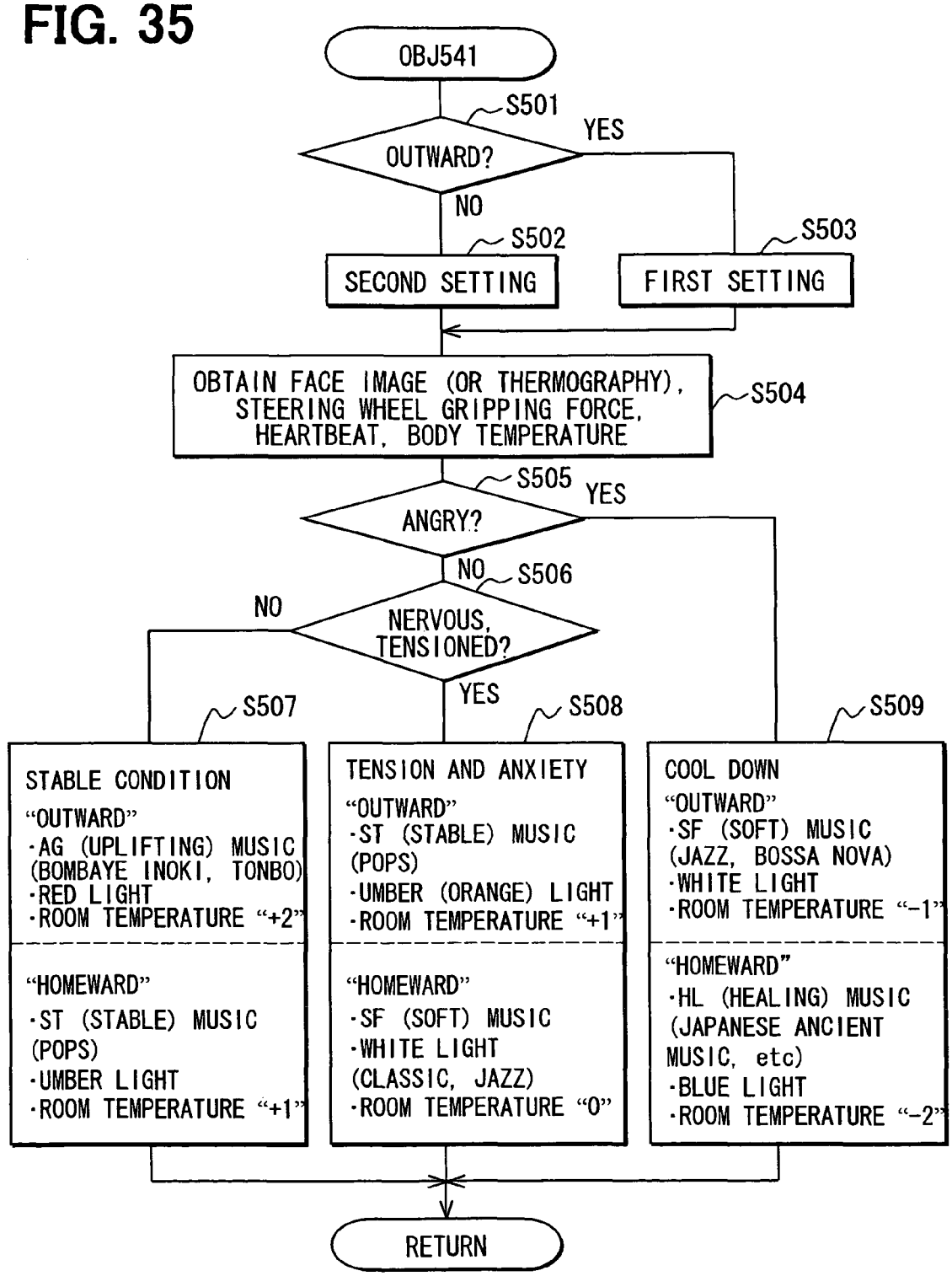
FIG. 35 is a flowchart showing an example of a hospitality process in traveling.

FIG. 35 shows a flowchart of the process. In S501, it is determined whether the traveling is on the outward or homeward route. In S502, S503, a level of the song mode code is set corresponding to the determined route. In S504, the detection condition of the biological condition portions is read. In S505, S506, the mental condition is estimated. In case of "stability," the process of S507 is executed. In case of "anxiety and tension," the process of S508 is executed. In case of "anger," the process of S509 is executed. The music selection corresponding to each mental condition is done to play the music (the character type is determined through the above method, and a song is selected from the music source group corresponding to the character type). While playing music, the interior lights and air conditioner are controlled in accordance with the mode corresponding to each mental condition. For example, in case of "stability" on the "outward" route, the uplifting music (AG) is played, the red lights are used, and a room temperature is set a little high. On the "homeward" route, to relax the driver, refreshing (or stable) music is played, the umber lights are used, and a room temperature is set a little lower than that on the outward route.

In case of "tension and anxiety" on the "outward" route, to relax the driver, refreshing (or stable) music is played, umber lights are used, and a room temperature is set a little lower than that on the outward route. On the homeward route, soothing music (SF) is played, white lights are used, and a room temperature is a little decreased further. In case of "anger" on the "outward" route, to cool down the driver soon, easing music (SF) is played, white lights are used, and a room temperature is further decreased. On the "homeward" route, the healing music (HL) is played, and blue lights are selected. To soothe fatigue of the driver, the room temperature is set higher than that in case of "anger" on the "outward" route so that the room temperature does not decrease.

An example for retrieving a detour destination is explained. The destination database of FIG. 81 is used. The character type codes are used such that a destination corresponding to a character type code matching a specified character of a user is presented from retrieved destinations. Sub genres can be used as follows. A content of a sub genre corresponding to the destination does not always match specified mental and physical conditions of the user. A certain mental condition is set as a target value. A mental condition of a user is approximated to the target value. For example, a relaxing and soothing destination is selected for a user in a too-much excited mental condition, and the user is guided to the selected destination where the user can be calmed. When it is determined by measuring, e.g., an elapsed time that the user is bored increasingly (when a mental energy is about to run short), an adjacent sightseeing spot, an amusement facility, and so on, can be retrieved and outputted for a change of pace. When the user is in good physical condition, a method for retrieving, e.g., an "energetic spot" can be exampled. When the user is not in good physical condition, a method for retrieving, e.g., a "relaxing and soothing spot" can be exampled.

Figure 96:
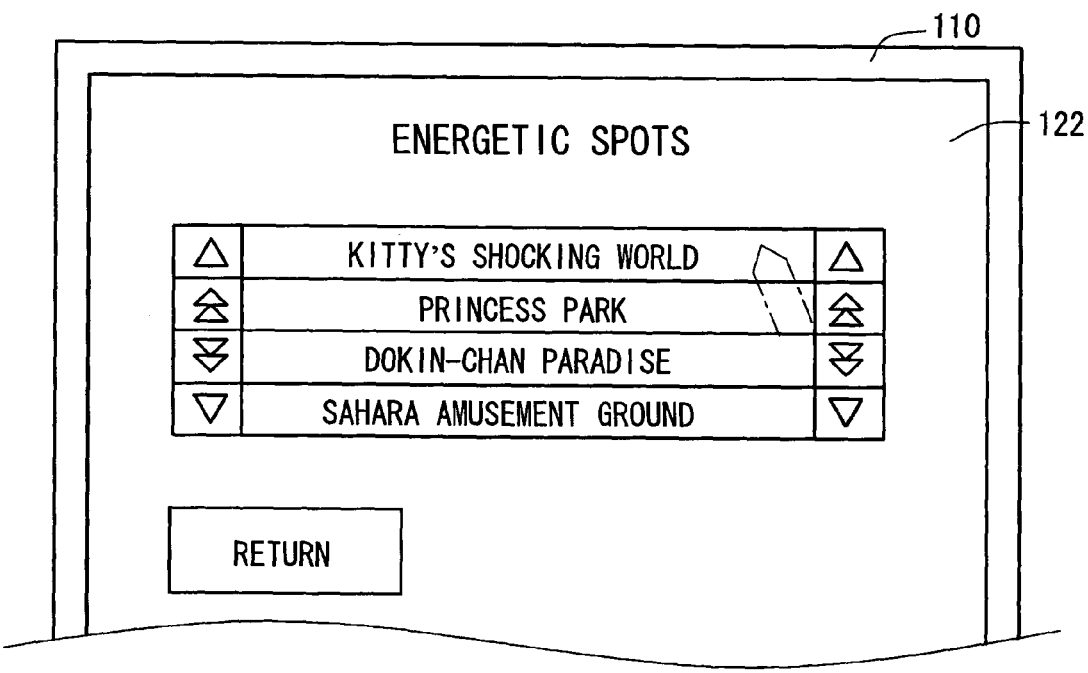
FIG. 96 is an explanatory view showing a fifth example of a result of retrieving a destination in the car navigation system.
Figure 97:
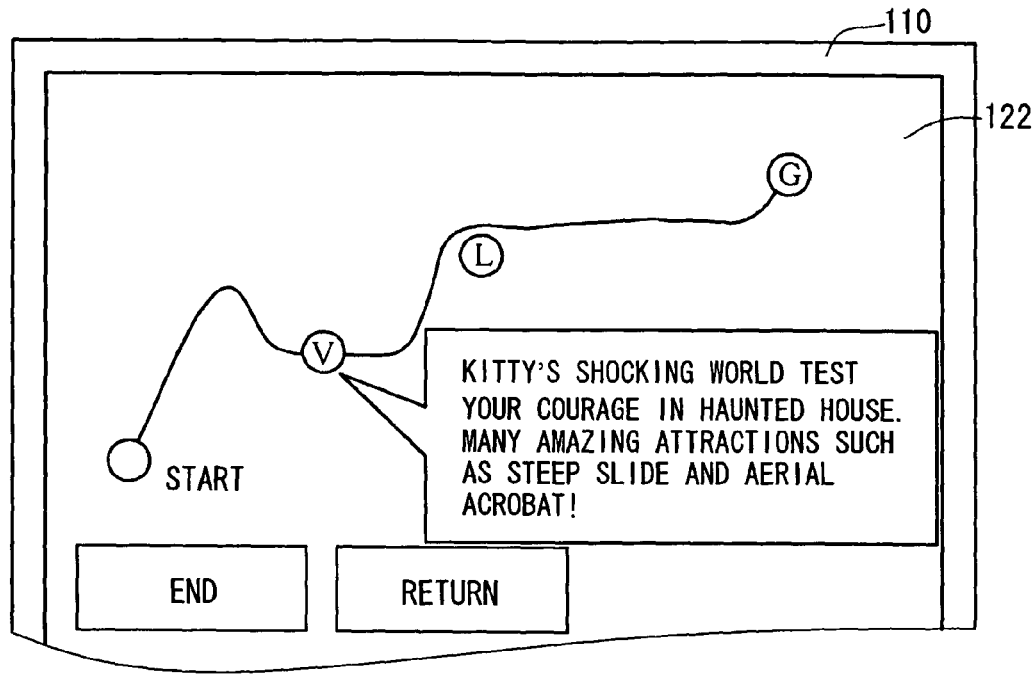
FIG. 97 is an explanatory view showing a fourth example of a screen of a guide map to a destination.
Figure 98:
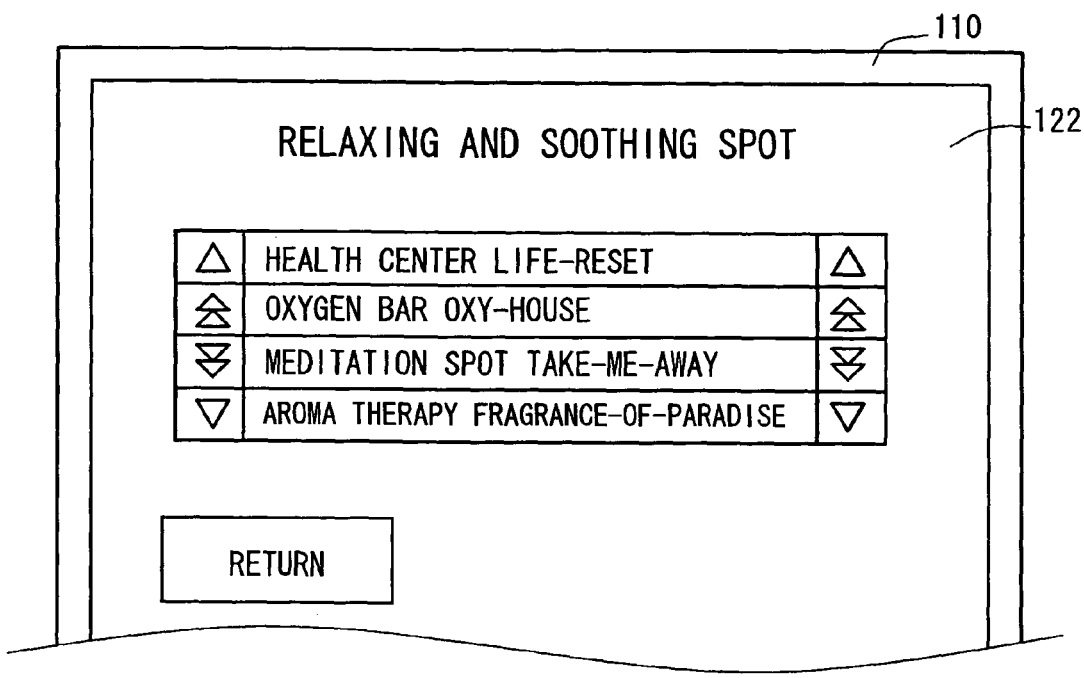
FIG. 98 is an explanatory view showing a sixth example of a result of retrieving a destination in the car navigation system.
Figure 99:
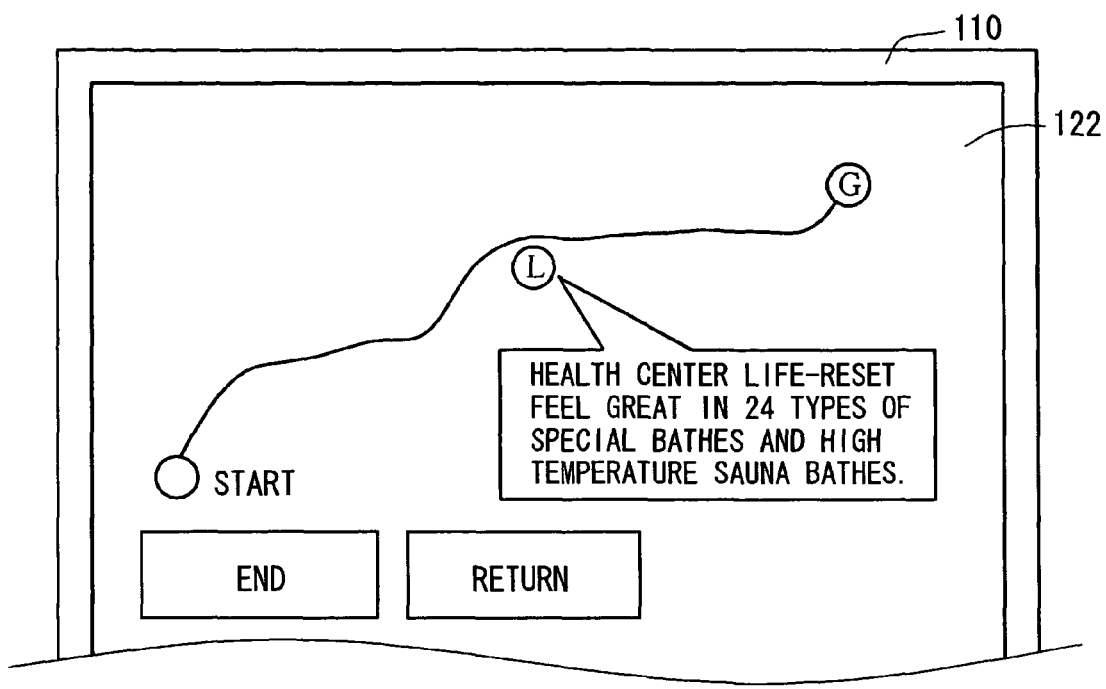
FIG. 99 is an explanatory view showing a fifth example of a screen of a guide map to a destination.

FIG. 96 is an example of an output on the monitor 110 when the energetic spots are retrieved. FIG. 98 is an example of an output on the monitor 110 when the relaxing and soothing spots are retrieved. In both cases, by touching a soft button corresponding to a desired destination, the destination can be inputted and selected from the touch panel 122. As shown in FIG. 97 or 99, the screen is switched, and the selected destination is displayed on the screen (because the flow of this display is a known method in the car navigation system, the detailed explanation is omitted: the destination is determined by selecting "end (or start guide)"). At this time, as shown in FIG. 81, in the destination database 21d, content information is corresponded to each facility (destination), and stored. As shown in FIG. 97 or 99, content information about the selected destination is displayed on the screen (or expressed through voice output), so that the content information can be confirmed before determining the destination. This content confirmation serves to assist the selection.

Returning to FIG. 2, in the getting-off scene SCN5 and separation scene SCN6, the following hospitality operations are possible. For example, in the theme "uplifting of feeling of arriving on destination" (OBJ151, OBJ161, OBJ251, OBJ261), music and lights suitable for the destination are used for rewarding the arrival of the user. Additionally, a message such as "We arrived on the recreation ground. Enjoy it." can be outputted. In the theme "confirmation of lost property on leaving vehicle" (OBJ351), messages for preventing property from being left in the vehicle and for preventing a baby from being left in the vehicle are outputted (this operation can be continued in the separation scene SCN6 by use of the mobile phone 1). In the themes "securing of safety and avoidance of trouble on getting off vehicle" (OBJ352) and "getting off vehicle easily" (OBJ451, OBJ551), as well as on getting in the vehicle, the operations for assisting the opening and closing of the door by use of the door assist mechanism 541 and for preventing the door from colliding with an obstacle can be executed. In the separation scene, by use of the vehicle exterior camera 518, the traffic condition around the vehicle is monitored. When an oncoming vehicle and following vehicle approach the user, a message for alerting the user by use of the mobile phone 1 can be outputted.

Next, even after the hospitality operation starts in each scene, the detection of the biological condition parameters and the monitoring of the physical or mental condition in accordance with the waveform analysis are continued. The above condition confirmation process (FIG. 48: δ7 or δQ) is executed. The process is executed below in detail. As described above, the basic hospitality process is selected in each scene and each theme from the function selection table 371 shown in FIGS. 7A to 12 in the order of the priority. A control appropriate value for each hospitality operation device is provided to the control appropriate value setting table 371a corresponding to the function selection table 371. The value is used as a default value for starting the control. On the other hand, in the condition matching process of δ3, by use of the determination table 1601 of FIG. 51, the mental or physical condition is specified. In accordance with the specified mental or physical condition, from the image shown in FIG. 67, the additional adjustment (correction) is applied to a control appropriate value of each hospitality operation device. A different default preset value can be set in accordance with a user. In this case, as shown in FIG. 73A, a default set value of each user is stored as user default setting data 434, corresponding to user specifying information (for example, user ID). When a user of the vehicle can be specified, the corresponding default set data may be read and set at any time.

The function selection table 371 and control appropriate value setting table 371a are basically provided to each scene or theme. To explain specific examples in the drive scene more understandably, main hospitality operations are extracted from various hospitality themes in the drive scene. The hospitality operations and corresponding control appropriate values are shown in FIGS. 13A, 13B as the overall function selection table 372 and control appropriate value setting table 471a.

The "lighting level" means that as the value is greater, the lighting quantity is greater. A preset value for the "lighting color" corresponds to the lighting color index of FIG. 72. The "air conditioner setting" means that as the value is greater, the preset room temperature is higher. The "seat vibration" is defined by an amplitude and frequency of a vibration output. As the value is greater, the amplitude or frequency is higher (when the frequency is high, the seat vibrates like impulses, and when the frequency is low, the seat vibrates to relax the user at a loose long cycle ). The "fragrance" means that as the value is greater, the output amount of fragrance from the fragrance generation portion is greater. The "awakening" means that as the value is greater, the output amount of ammonia from the ammonia generation portion is greater. The "music sound level" means that as the value is greater, the output sound volume from the car stereo is greater. The "loading of required sounds" is a set value for the noise canceller. This means that as the value is greater, the noise canceller loads required sounds at a higher level by use of the above mechanism. The "output of warning sound" means that an output volume of a warning sound (by use of, e.g., the car stereo or buzzer) outputted in case of abnormality is higher.

Especially, to respond to emergency and abnormality (including poor physical condition of the user), on the function selection table 371, the operations of the noise canceller (e.g., for loading required sounds), the car audio (for outputting a warning sound), and the awakening (by use of ammonia) are provided with a higher operation priority. This setting is temporary in case of emergency and abnormality. The response to emergency and abnormality may be delayed when an appropriate value is changed after the response of the user. Accordingly, as shown in FIGS. 70A, 70B, it is preferable that a specific control appropriate value setting table 471b is provided separately for emergency and abnormality, and the control appropriate value setting table 471a for normal and the specific control appropriate value setting table 471b are switched as needed.

Figure 13B:
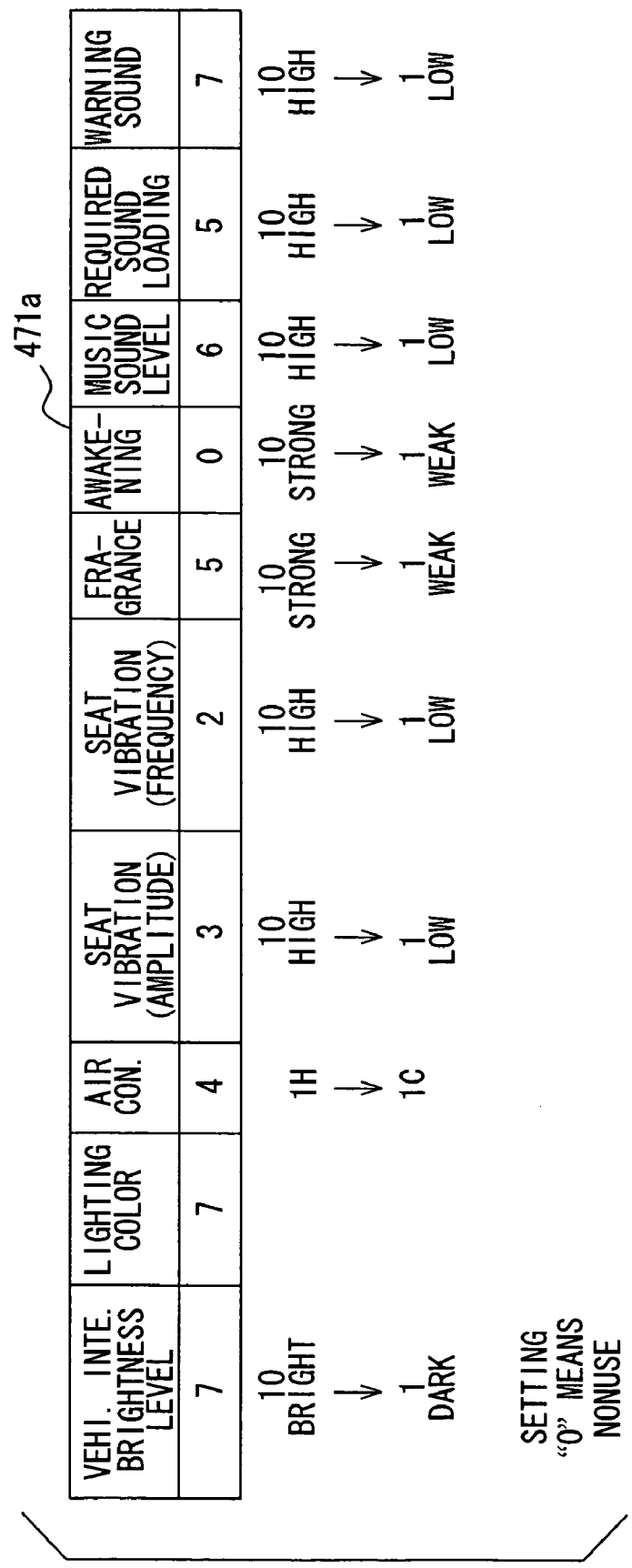

For example, in case of emergency, as is clear in comparison to FIGS. 13A, 13B, a setting when the lighting color is changed from "7" (relaxing pale orange) to "6" (white) to increase visibility such as a warning display. A level of loading outer required sounds is raised (from "5" to "6"). An output level of the warning sound is raised (from "7" to "9"). The control appropriate value setting table 471b when the serious physical condition occurs as an abnormality is exampled as an abnormality. A level of loading outer required sounds is raised further (from "5" to "8"). A setting is also made for generating ammonia for awakening (from "0" to "7").

Figure 74:
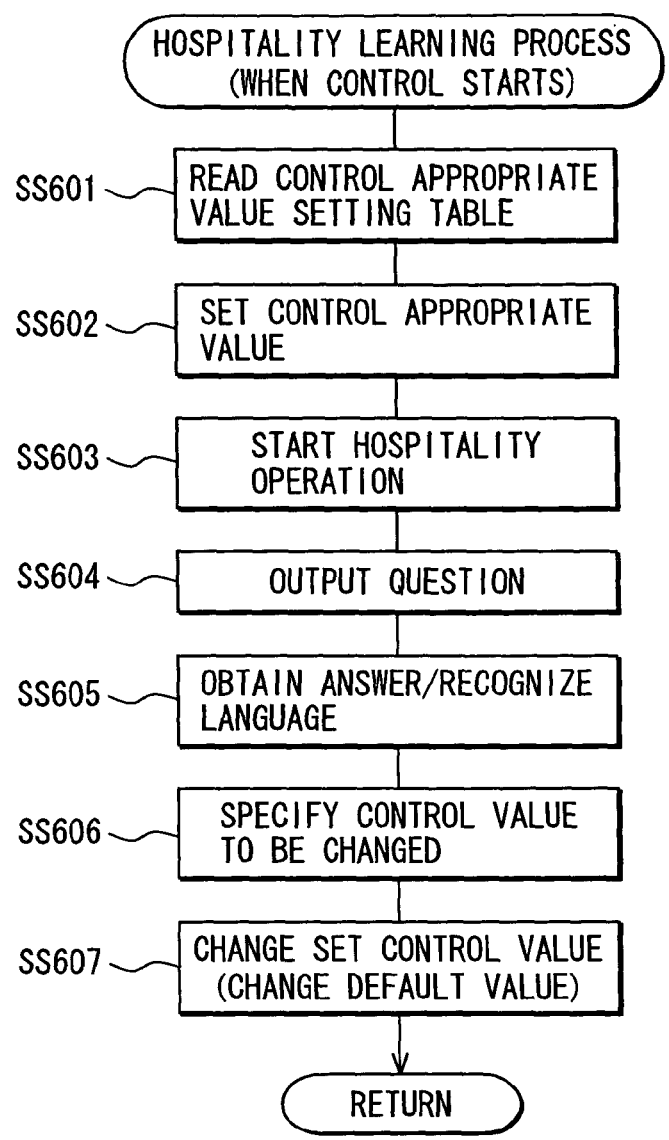
FIG. 74 is a flowchart showing a flow of a process of changing a default control setting value by use of a question interaction method.

Returning to FIGS. 13A, 13B, when a control appropriate value of each hospitality operation device is set as a default in accordance with the control appropriate value setting table 471a, the hospitality operation is started once in accordance with the setting. A flow of the process in this case is shown in FIG. 74. In SS601, the content of the control appropriate value setting table 471a is read. In SS602, a control appropriate value is set for each hospitality operation device in accordance with the content. In SS603, the hospitality operation is started in accordance with the set value.

In SS604, a question is outputted to a user. As described above, an ID and control direction corresponding to the hospitality operation device currently in operation are specified. The question data of FIG. 73A corresponding to the ID and control direction is retrieved and outputted. In SS605, an answer to the question is obtained from the user, and its content is analyzed. In FIG. 69, examples of the questions and of inputs of answers are shown. Questions about an air conditioner, fragrance, and music sound level are examined. Questions about efficacy of the air conditioner (here, summer is assumed), taste of the fragrance, and sound volume setting are made. The answers from the user means: (1) "The efficacy of the air conditioner is weak. It's hot." (2) "The fragrance is too strong. I don't like it." (3) "Raise the sound volume higher." The question for obtaining an overall impression about a level of relaxing is made. The answer is: (4) "I'm a little nervous. I'm not relaxed enough."

In SS606, from the content of the above answers, a control value to be changed is specified. In FIG. 69, a preset temperature of the air conditioner, an output amount of the fragrance, and a sound volume of the car stereo are the control values to be changed. The lighting color, the lighting level (lighting quantity), and the amplitude of the seat vibration are selected as the control values to be changed. In SS607, to satisfy the taste of the user, specified from the answers, each control set value is changed. In FIG. 69, the temperature setting of the air conditioner is decreased (from "4" to "3") for (1), the output amount of the fragrance is decreased (from "5" to "4") for (2), and the music sound level is increased (from "6" to "7") for (3). The light and seat vibration are adjusted for (4). Specifically, the lighting color is changed from white ("6") to gentle warm color (pale orange: "7"), and the lighting level is decreased (from "7" to "6"). The vibration amplitude of the seat vibrator is decreased (from "3" to "2"), emphasizing a comfortable feeling.

Part or all of the corrected control appropriate value group can be registered as new default values, which can be used as initial settings of the hospitality operations when the user uses the vehicle in the future.

The summary of an object of the system in this embodiment is "to meet a potential or obvious request generated in a scene where a user exists, by selecting and executing an optimum function," for example. However, when certain conditions are satisfied without intention of a user, the user may enter an unexpected scene. This is because a situation of the user changes (or the user changes his or her mind: for example, sudden idea) in accordance with, e.g., time (time instant) and disturbance. In this case, it is effective that a next scene can be estimated from the change of this situation, and the user can be guided to this scene casually.

For example, when the user feels "hungry," the user is made to recognize that "I can eat a (favorite) delicious food, so that" means for "full stomach" of the hospitality functions prepared in the system is started. In the ultimate sense, a service that the system itself cooks food for the user can be considered. It is more reasonable that a position of the user at a current time (or a future time) is specified, and the user is timely guided to an eating facility within a predetermined distance from the current position. In this case, as described later, the car navigation system incorporated in the hospitality system functions effectively. When the user feels tired or bored, it is effective that the user is guided to a spot for change of pace on a detour route. In the above assumption, it is highly possible that physical and mental conditions finally related to an obvious request are not recognized by the user at the first step. In this case, to make the user notice such potential physical and mental condition, it is effective that a condition of the user is previously confirmed.

As described above, the system determines the above situation of the user in accordance with biological characteristic information of the user. This information is detected or acquired by the system. Concretely, information about physical or mental condition of the user directly analyzed and estimated by use of an output result of the biological condition detecting portion through the above method, can be used as the above biological characteristic information. Additionally, physical and mental conditions estimated from, e.g., a time instant and an elapsed time without using the biological condition detecting portion can be used as the above biological characteristic information.

For example, as shown in FIG. 82, a situation of the user can be systemized conceptually. First, "energy" maintains "physical function" and "mental function," and is a factor for a source of activities. The "energy" is a virtual parameter which can be supplied from eating. Without the supply, the "energy" is consumed over time in one direction. The consumed "energy" can be recovered by the supply (as described in the law of energy conservation, a person cannot generate the "energy" by himself or herself). As disturbance which has a bad influence upon a body and mentality, "stress" can be grasped. The influence due to the energy consumption and extreme stress is accumulated in the user as "damage." It is important that a "situation" of the user, the "situation" having "*" in FIG. 82, is determined accurately from the biological characteristic information so as to offer the hospitality to the user comfortably.

Figures 83, 84:
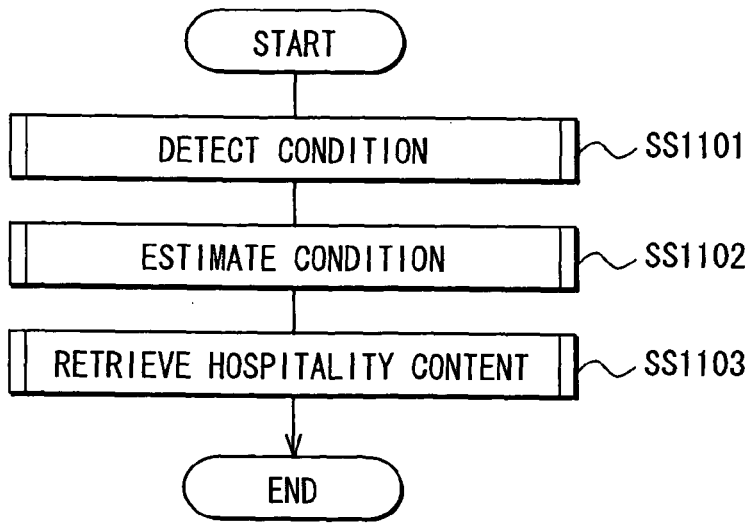
FIG. 83 is a diagram illustrating various supply forms.
FIG. 84 is a flowchart showing a flow of a main process in which a hospitality function or information (content) is retrieved and operated in accordance with a detection result of the condition.

The above "stress" and "damage" can be analyzed and estimated by use of an output result of the biological condition detecting portion as shown in FIG. 51. On the other hand, the "energy" can be grasped as a physical condition (particularly, hunger) and mental condition (boredom) estimated from, e.g., a time instant and an elapsed time. For example, as shown in FIG. 83, a supply mode of the energy is assumed. The following properties (body: eating/drinking, mentality: information) show what energy is supplied at each place. In view of "mental room," "mental energy" can be grasped by a numerical value. When information (mainly, entertainment) which has a high possibility of increasing the mental room is provided to the user, the "mental energy" is supplied to the user. Satisfaction from buying something can be a source of the mental energy.

On the other hand, a factor which directly controls energy of a body is eating. Basically, as described above, when the user is assumed to be hungry, a function for guiding the user to an adjacent eating facility immediately by use of the car navigation system becomes important. When correlation based on mental or physical condition is used as additional data, one-rank-higher hospitality becomes possible. In this case, contrasts between tendencies of the eating facilities need to be defined (for example, image such as "heavy←→plain" and "sweet←→spicy") in accordance with the correlation. The contrasts are corresponded to the conflicting mental or physical conditions. For example, the correspondences are, e.g., "physical fatigue→plain, sweet" and "good physical condition→heavy, spicy." Many psychological facts about relationship between mental condition and eating preference have emerged. Without mentioning an example of "intemperateness due to stress," it must be taken into consideration that the hospitality is not oriented to a thought for satisfying a request of the user without limit.

In the entertainment information, correlations such as "cheerful←→gentle" and "exciting←→calming" can be imagined. As described above, it can be said that the entertainment information is "mental energy" which can be supplied more effectively, e.g., by selecting a music source. On the other hand, as information about correlations with places, "sight" and "detour spot" can be exampled. As one example method, when mental stability is spoiled due to stress, or when boredom is assumed due to a long driving time, a spot such as a beauty spot and a historic spot which exists near a route to a destination (within a predetermined distance) is retrieved. Then, the user suggests and selects the spot as a detour route.

Basic operations of the system considering the above idea is explained below as an overview flow. FIG. 84 is the overall flow. In SS1101, in accordance with the method described above in detail, a condition is detected by the various biological condition detecting portions (sensors). In SS1102, a physical or mental condition (condition to be specified) is specified (refer to, e.g., the process of FIG. 66). In SS1103, a hospitality function or hospitality information (content) corresponding to the specified condition is retrieved, and started.

Figure 85:
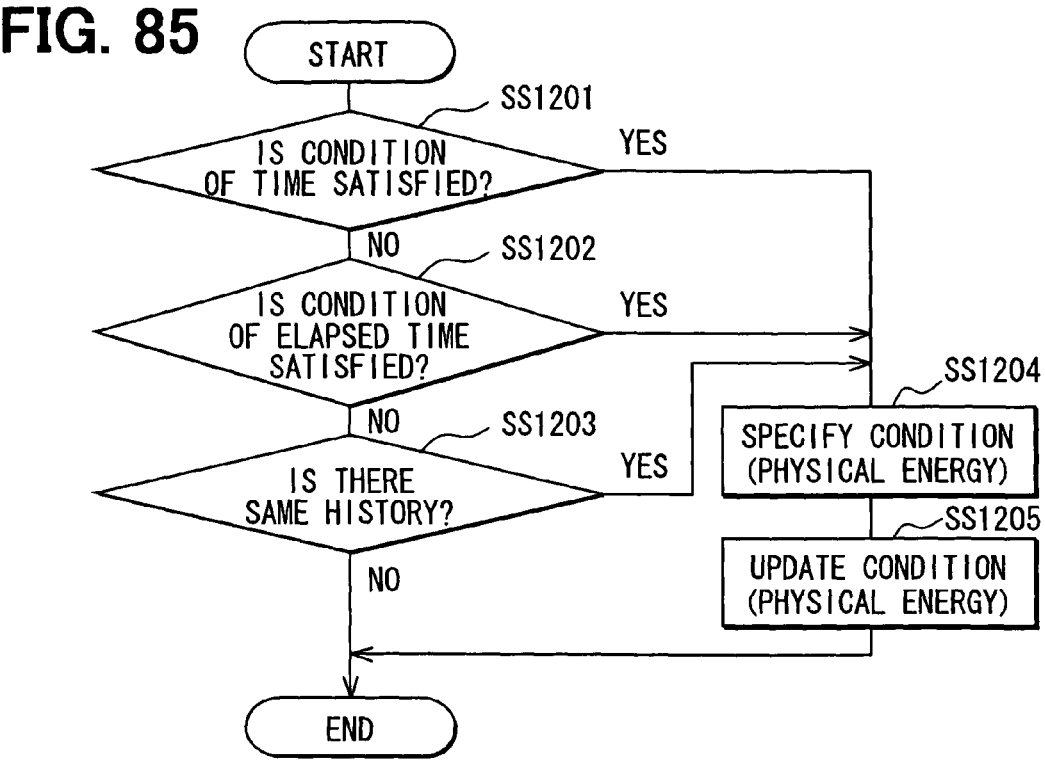
FIG. 85 is a flowchart for estimating a condition of energy of a body.

Next, the physical energy can be estimated in accordance with a time instant and an elapsed time (and with, e.g., a history of activities and a schedule of the user). On the other hand, the mental energy can be grasped, for example, when frequencies of changes of a line-of-sight, an attitude, and a facial expression decrease. FIG. 85 is a flow for estimating a condition of the physical energy. In SS1201, a current time is measured by timing means (for example, a calendar clock 153 of FIG. 80 can be used). Because a user eats usually at a predetermined time, it is determined whether a current time is in a meal time. When a predetermined meal time has come, the flow goes to a condition specifying process SS1204 or later.

In SS1202, a time elapsed after the user has got in a vehicle is determined. In other words, running-out of the energy due to the elapsed time is determined. When a predetermined time has elapsed, the process goes to the condition specifying process SS1204 or later. In SS1204, a value of the energy is calculated by use of a predetermined algorithm. In SS1205, the value is updated as a latest energy value. The updated energy condition is used in a condition detection step of FIG. 84. Users eat at different times (for example, when eating habit is irregular, or when a user is, e.g., a night worker and eats at a different time from a time at which ordinary persons eat). To respond to this situation, a tendency of temporal energy consumption of the user is stored as a history. In SS1203, it can be determined whether the latest history up to the running-out of the energy matches a recorded history, and the shortage of the physical energy can be determined more accurately.

Figure 86:
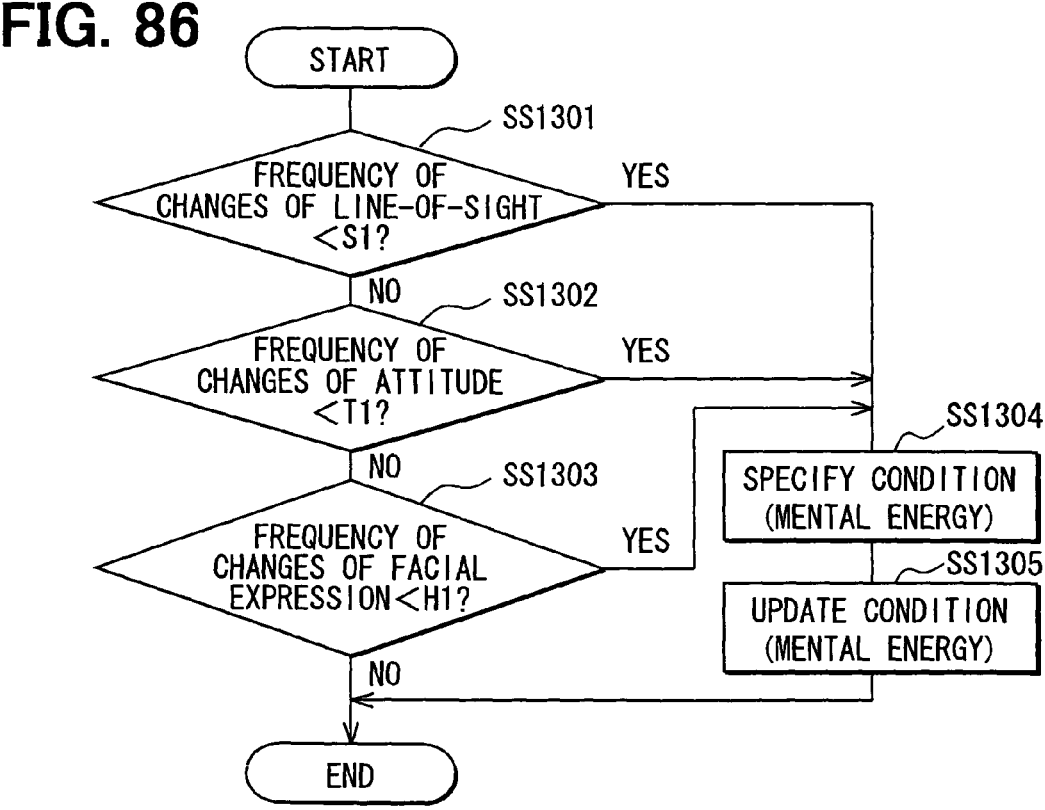
FIG. 86 is a flowchart for estimating a condition of energy of a mentality.

FIG. 86 is a flow for detecting a condition of mental energy. In SS1301, SS1302, and SS1303, it is determined whether the frequency of changes of a line-of-sight, attitude, and facial expression are equal to or under predetermined values, respectively. This is because, when a user is depressed, the user tends to be mentally inactive, the line-of-sight tends to be fixed (not fixed), the attitude does not move, and the facial expression tends to be fixed. To grasp feature of this condition, these pieces of the biological characteristic information are used. When the determination is YES at least in one of these steps, the flow goes to SS1304 to determine that the mental energy comes short. In SS1305, a condition of the consumption of the mental energy is updated. The above process can be replaced with a process for outputting an estimated result of the mental condition through, e.g., the flow of FIG. 66 as a numerical value of the mental energy. For example, in accordance with a definition predetermined by use of a value of the reference counter, a value of the mental energy may be calculated. As shown in FIG. 85, the above method for the determination about the running-out of the mental energy can be replaced with a method using a determination flow by use of a time instant or an elapsed time (the mental energy increases because of satisfaction after meal, and the mental energy decreases as boredom increases over time).

Physical and mental conditions are specified, and corresponded to the properties as shown in FIG. 83. Then, a content to be offered to the user is retrieved. When the mental energy is consumed, entertainment information is provided to the user. When the physical energy is consumed, the user is guided to eating. In reference to a result of the physical or mental condition estimated by the biological condition detecting portion, genres of the above entertainment information and eating facilities can be selected. For example, when the user is in good physical condition, an eating facility serving meat or heavy foods can be selected. When the user is in poor physical condition, an eating facility serving noodles or plain foods can be selected.

Figure 87:
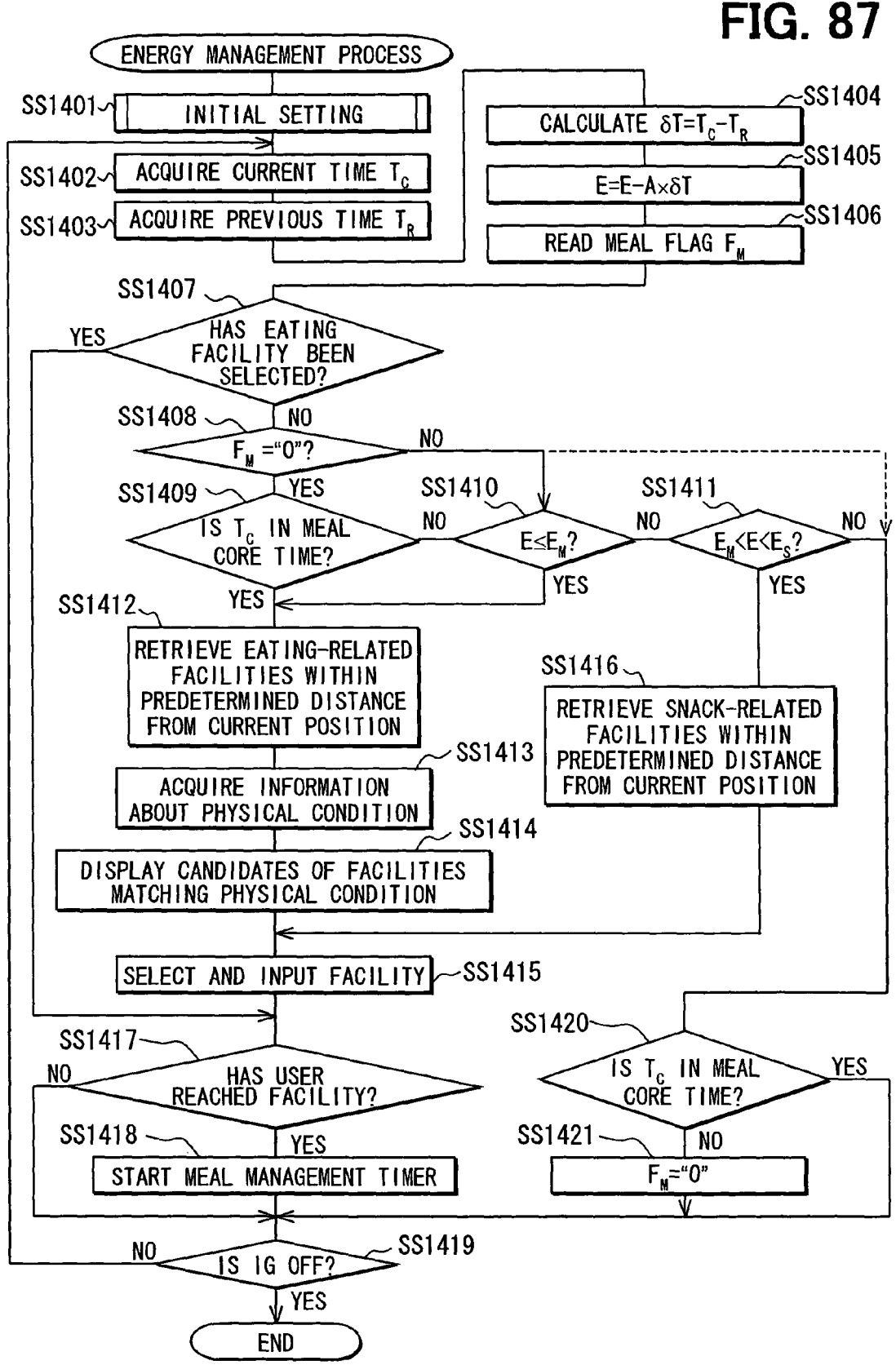
FIG. 87 is a flowchart showing a detailed process algorithm for estimating a condition of the energy of the body.
Figure 88:
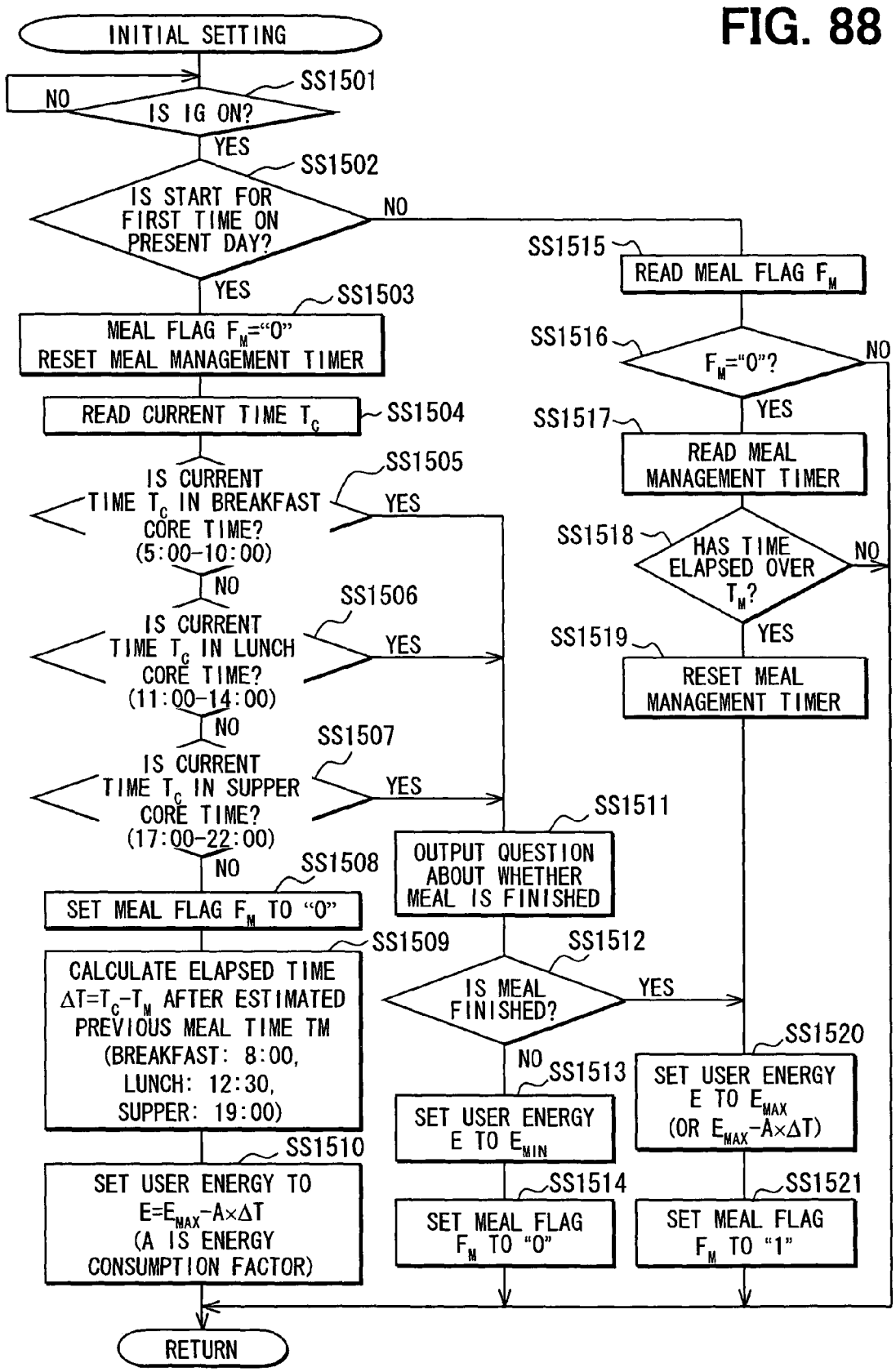
FIG. 88 is a flowchart following FIG. 87.

FIG. 87 is an example showing a more detailed process for managing the physical energy (energy management process: the information ECU 51 of the car navigation system 534 repeats this process at predetermined time intervals each time an IG signal is turned ON). This energy engagement process in SS1401 is an initial setting process for setting a user energy when a user starts using a vehicle. FIG. 88 shows the initial setting process in detail. In SS1501, it is determined whether an ignition switch is ON. In SS1502, it is determined whether the ignition switch is turned on for the first time on a day (this is possible by monitoring a time by use of the calendar clock 153). When the determination is YES, the flow goes to SS1503 to reset a meal flag $F_M$ (meal confirming information) and a meal management timer (meal determination timing means). When the meal flag $F_M$ is "0," the user has not yet eaten. When the meal flag $F_M$ is "1," the user has already eaten.

In SS1504, a current time $T_C$ is acquired from the calendar clock 153. In SS1505 to SS1507, it is determined whether the current time $T_C$ is in a breakfast core time (5:00 to 10:00, a standard breakfast time is, e.g., 8:00), a lunch time (11:00 to 14:00, a standard lunch time is, e.g., 12:30), or a supper time (17:00 to 22:00, a standard supper time is, e.g., 19:00). Time ranges in which ordinal persons eat probably are determined as the above meal core times. In accordance with whether the current time $T_C$ is in the meal core times, it is determined whether a timing for a meal guide comes.

When the current time $T_C$ is not in any meal core time, it is determined that the user does not eat after meal in the previous meal core time. Then, the flow goes to SS1508 to set the meal flag $F_M$ to "0." In SS1509, a standard time $T_M$ of the previous meal core time is defined as an estimate meal time. Then, an elapsed time $\Delta T = T_C - T_M$ up to the current time is calculated. In SS1509, the user energy E is calculated by use of $E_{max} - A \times \Delta T$ (A is an energy consumption factor), and set.

$E_{max}$ is defined as a value of an energy obtained when a user who is hungry eats to have a feeling of a full stomach. $E_{max}$ may be set arbitrarily. In this case, the energy consumption factor A showing an energy consumption amount per unit time needs to be defined so that $E_{max}$ decreases to a predetermined minimum energy $E_{min}$ just before the next meal. For example, after the user has finished lunch at the standard time 12:30, the user starts having supper at 18:30, which is thirty minutes (during the meal time) before the standard supper time. When the minimum energy $E_{min}$ just before the supper is defined as 0.4 $E_{max}$, the energy consumption factor A may be defined as 0.1 $E_{max}$. In the cycle of breakfast, lunch, and supper, meal intervals and degrees of hungry differ. Therefore, in accordance with in which meal interval the current time is, values of $E_{max}$, $E_{min}$, and A can be set differently.

On the other hand, when the current time $T_C$ is in any one of the meal core times, the flow goes to SS1511. In this case, the user may get in the vehicle after meal, or may get in the vehicle without meal, and think of eating out somewhere soon after starting driving. This is not known until questioning the user about meal (usually, a guest who has come at mealtime is asked about meal).

In SS1511, a question for confirming whether the user has finished meal, is outputted. This question may use voice or characters outputted to the monitor 110. The answer may use voice directly (voice recognition is required to grasp content of the answer), or may be inputted manually from an input portion such as the touch panel 122. When the answer is "meal is not finished yet," the flow goes to SS1513 to set the user energy to $E_{min}$. Then, in SS1514, the meal flag is set to $F_M$="0" (meal is not finished yet). When the answer is "meal has been finished," the flow goes to SS1520 to set the user energy to $E_{max}$ (which may be subtracted by an energy consumption amount $A \times \Delta T$ corresponding to an elapsed time after the standard time). Then, in SS1521, the meal flag is set to $F_M$="1" (meal has been finished).

In SS1502, a case where the engine start detected in SS1501 is not the first engine start on a day, corresponds to a case where the user parks the vehicle on the way of a route to a destination, separates from the vehicle for some business, returns to the vehicle, and starts the engine. In this case, the user may park the vehicle for a meal. As well as in SS1511, a question about whether the user has finished meal can be done. Then, it can be determined from the answer whether the user has finished a meal. It may be uncomfortable that the question about meal is done mechanically in each parking. In this embodiment, in SS1515, a content of the meal flag $F_M$ is read. When the content is "1," the processes up to SS1521 are done in the previous cycle, and a value of the energy is updated. Therefore, the flow ends without doing anything.

As described later in the main process of FIG. 87, when the content is "0," an eating facility is set in the car navigation system as a destination. It can be easily determined from a current position of the vehicle whether the user has parked the vehicle at the eating facility. As described later, the meal management timer starts a timing process when an arrival of the user at the eating facility is confirmed. In SS1517, a state of the meal management timer is read. In SS1518, when a value of a measurement time of the meal management timer is equal to or over $T_M$ corresponding to a finish of meal, the flow goes to SS1519 to reset the meal management timer. Then, the flow goes to SS1520 to execute the above process for determining that meal is finished. On the other hand, when a value of a measurement time of the meal management timer is under $T_M$ (the value includes zero), a value of the energy has been updated. Then, the flow ends without doing anything.

In FIG. 87, when an initial setting for the user energy ends as described above, the current time $T_C$ is acquired in SS1402. In SS1403, a previous time $T_R$ (for example, a time acquired as the current time $T_C$ in the previous cycle) is acquired. In SS1404, the time difference $\delta T = T_C - T_R$ is calculated. In SS1405, the user energy E is subtracted by an energy consumed during $\delta T$, and updated. In SS1406, the meal flag $F_M$ is read.

In SS1407, it is determined whether a destination of an eating facility is set in the car navigation system and the guide starts. When the determination is NO, a value of the meal flag $F_M$ is confirmed. When the confirmation is "0 (meal is not finished)," the flow goes to SS1409 to determine whether the current time $T_C$ is in the above meal core times. When the current time $T_C$ is in the above meal core time, the flow goes to SS1412 to retrieve eating facilities within a predetermined distance from the current position on the destination database. In SS1413, a result of determination of the physical condition is acquired through the process of FIG. 66. Then, eating facilities matching the physical condition are listed and displayed as candidates. In SS1415, the user selects a desired eating facility in reference to the candidates. The eating facilities are classified in accordance with meal types, breakfast, lunch, and supper. The eating facilities matching a current meal core time can be selected and retrieved.

Figure 89:
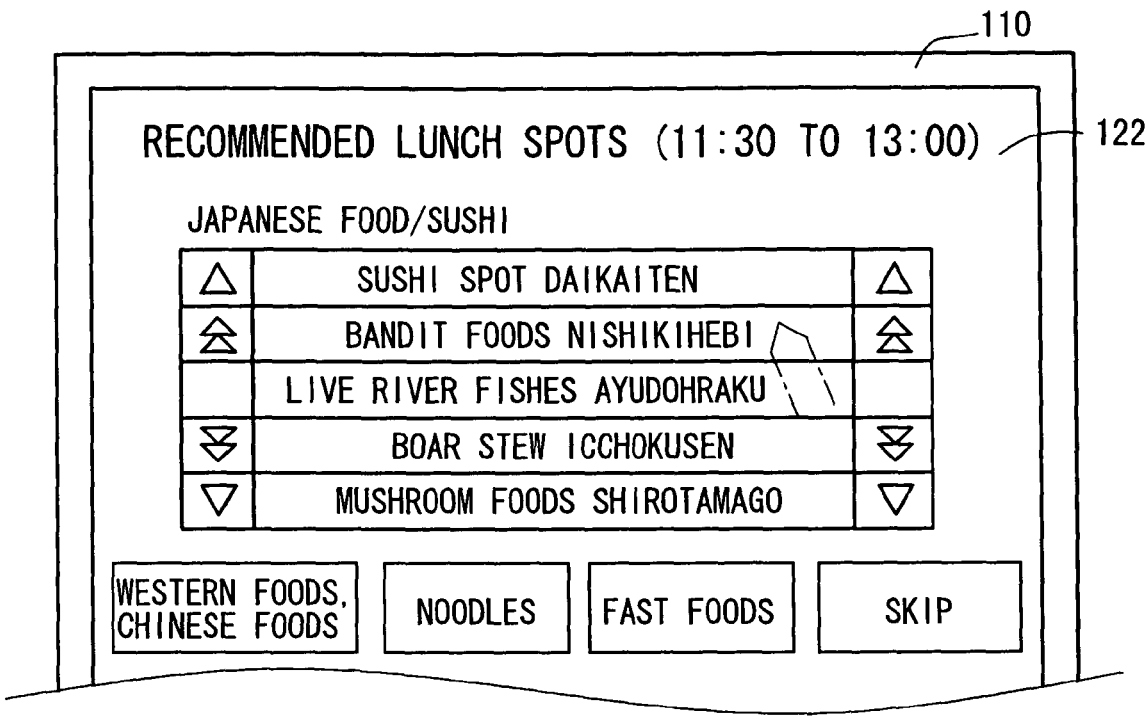
FIG. 89 is an explanatory view showing a first example of a result of retrieving a destination in the car navigation system.
Figure 90:
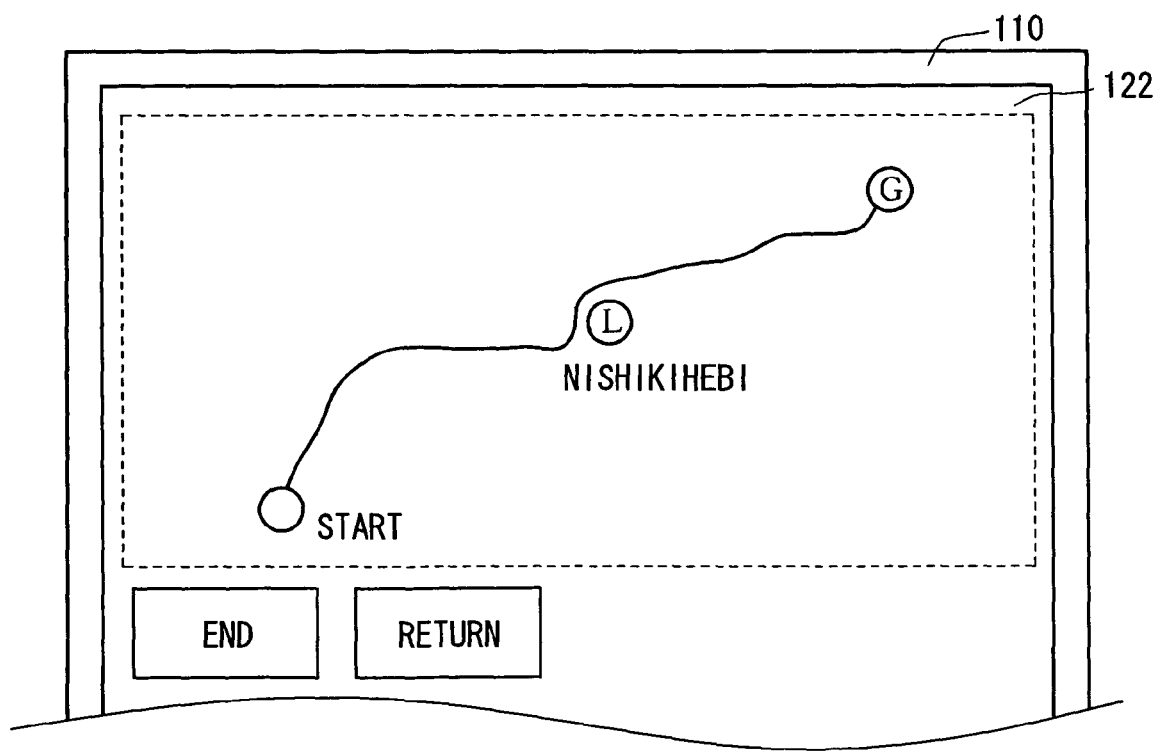
FIG. 90 is an explanatory view showing a first example of a screen of a guide map to a destination.
Figure 91:
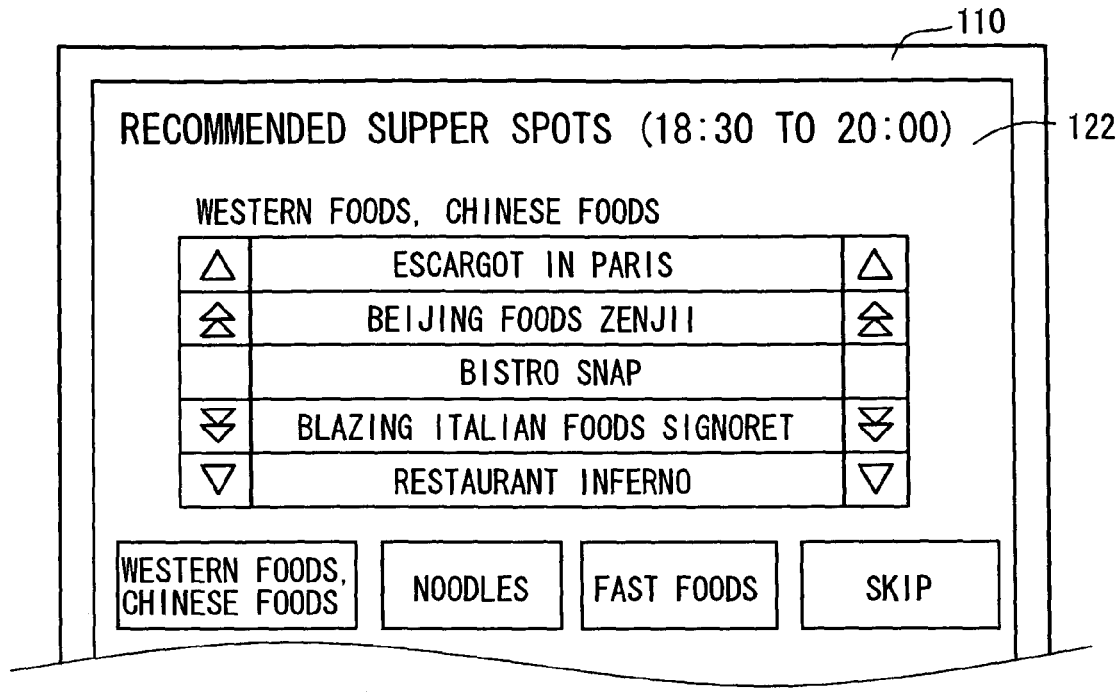
FIG. 91 is an explanatory view showing a second example of a result of retrieving a destination in the car navigation system.

The candidates can be outputted in accordance with genres of adjacent eating spots without referring to the physical condition. FIG. 89 is an example of the output in this case, where adjacent eating facilities for lunch, classified by the sub classification code of Japanese food/sushi, are retrieved and outputted. A retrieval result when the genre is changed by use of the soft button on the screen (western foods and Chinese foods, noodles, fast foods, and so on), can be outputted. By touching a corresponding soft button, a desired eating facility can be inputted and selected from the touch panel 122. Then, as described in FIG. 90, the screen changes, where the selected eating facility is displayed on the map as a routing point. FIG. 91 is a result of retrieved and outputted eating facilities for supper.

Figure 92:
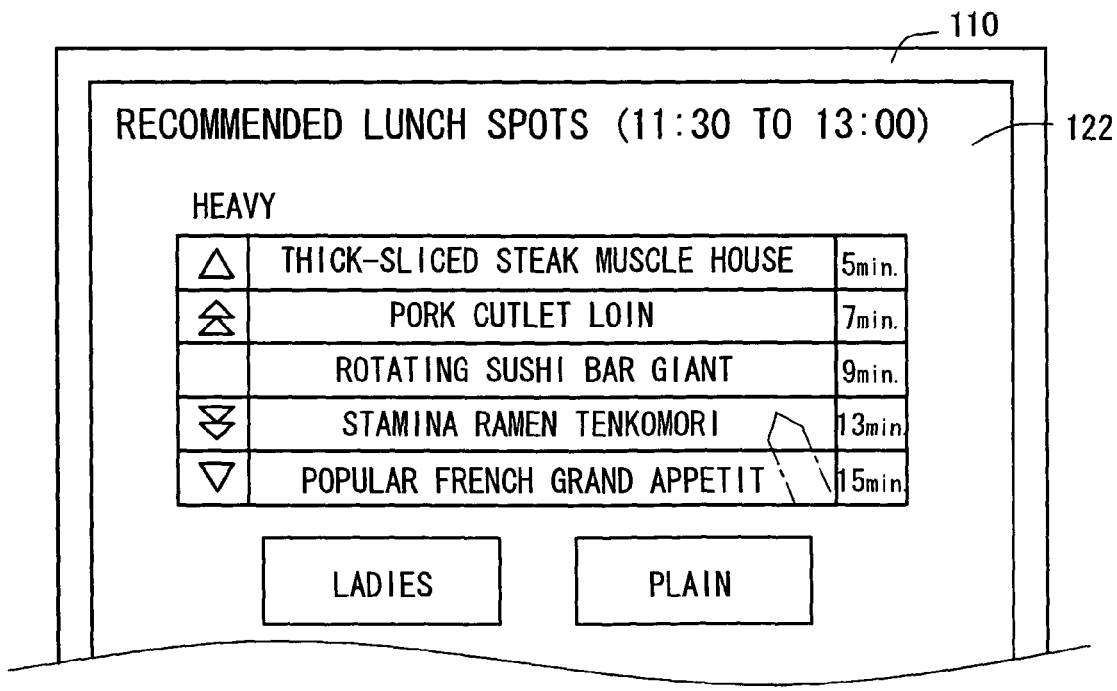
FIG. 92 is an explanatory view showing a third example of a result of retrieving a destination in the car navigation system.
Figure 93:
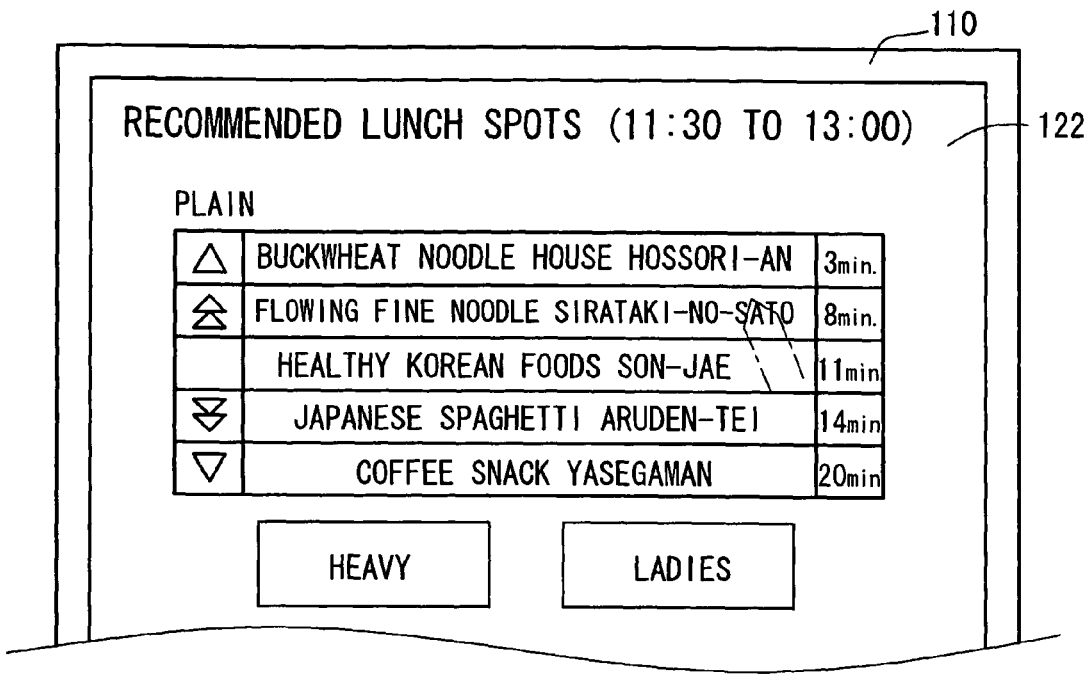
FIG. 93 is an explanatory view showing a fourth example of a result of retrieving a destination in the car navigation system.

FIG. 92 is a retrieval result in consideration of a user in a good physical condition, where eating facilities for "heavy" lunch are retrieved and outputted. To refer to eating facilities of other sub classifications ("ladies" and "plain" are examplesed), the corresponding soft buttons are formed. To select from the soft buttons, a retrieval list for the eating facilities of the selected sub classification is displayed. FIG. 93 is a result of retrieved and outputted eating facilities for "plain" lunch when the user is determined to be in poor condition. In this embodiment, in accordance with a distance from a current position to a corresponding facility, an estimated required time is also calculated and displayed (the distance may be displayed).

Figure 94:
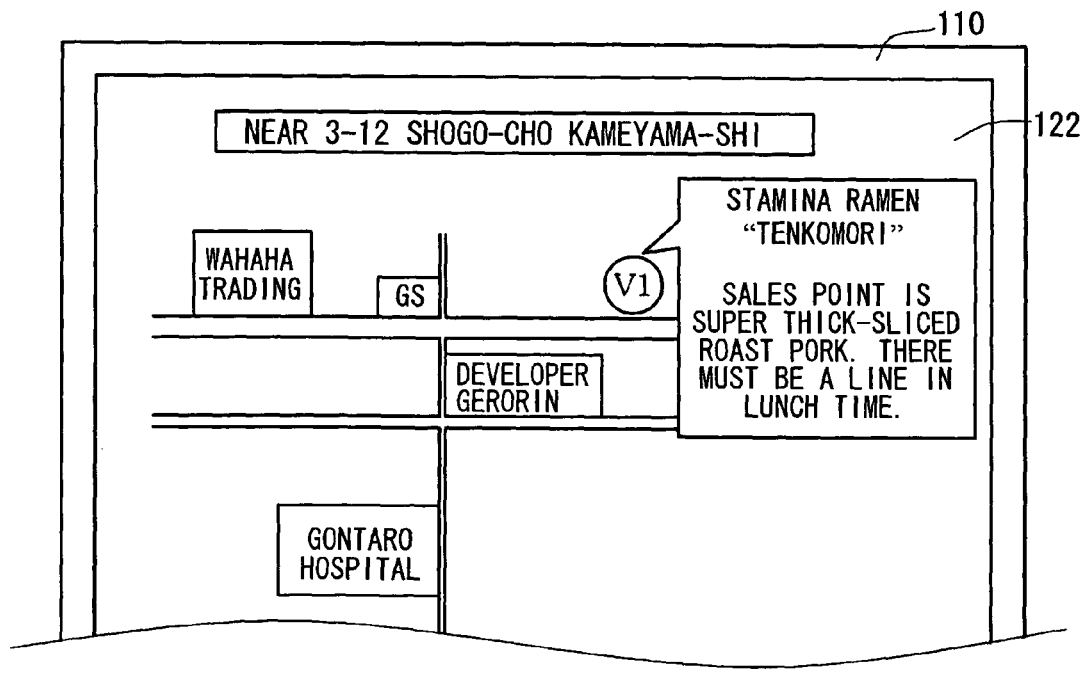
FIG. 94 is an explanatory view showing a second example of a screen of a guide map to a destination.
Figure 95:
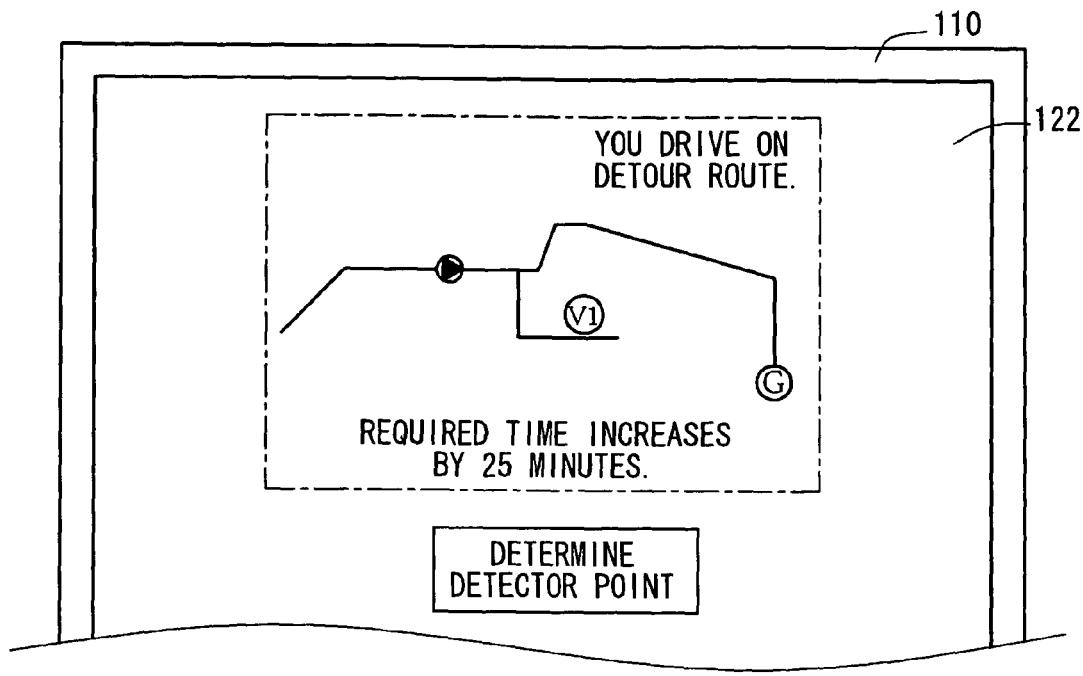
FIG. 95 is an explanatory view showing a third example of a screen of a guide map to a destination.

As shown in FIG. 94, when the facility is near the current position, the displayed scale may be expanded, and switched to a detailed route guide screen. In FIG. 94, content information about the selected facility (destination) is also outputted on the screen. As described in FIG. 95, when the selected facility (destination) is separated from a main route to a final destination to some degree, the displayed scale can be expanded to show to what degree the user detours together with the main route. FIG. 95 shows an example where an additional required time is calculated from a detour distance from the main route when the user detours, and displayed.

When an eating facility as a destination has been set in SS1407 (the previous cycle), the flow skips the processes up to SS1415. When the meal flag $F_M$ is "1" (meal is finished) in SS1408, or when the current time $T_C$ is not in the meal core times in SS1409, the flow goes to SS1410 to determine a current value of the energy E. Many people feel hungry in a vehicle more than usual. Thus, they have snack between long interval between lunch and supper. When a user drives for long time in the midnight after supper, the user may want to have midnight snack, because there is lots of time until next breakfast. When the user eats at an irregular time for some reason, a meal may be required outside meal core times. A hungry situation which cannot be estimated from a total time is determined from a value of the energy E based on an elapsed time after meal. When the user is determined to be hungry, the process for guiding the user to an eating facility is executed.

In this embodiment, a threshold $E_M$, $E_S$ ($E_M<E_S$) of the energy E are set in multiple steps. When the energy E is smaller than the lower first threshold $E_M$ in SS1410, the user is guided to an authentic eating facility (for example, including a service area) in SS1412 to SS1415. When the energy E is between the higher second threshold $E_S$ and the lower first threshold $E_M$ (SS1411), the user is guided to a snack facility (for example, a parking area, convenience store, and fast food shop such as a hamburger shop) in SS1416. When the energy E is higher than a threshold (the second threshold $E_S$) at which eating is determined to be unnecessary, the user is not guided to an eating facility. When a current time is outside the meal core times in SS1420, the meal flag $F_M$ is reset to "0" (meal is not finished).

When a facility is set as a destination as described above, the user continues driving in accordance with a guide display through the known process of the car navigation program. In SS1417, it is determined whether the user reaches the selected facility. When the user has reached the selected facility, the flow goes to SS1418 to start the meal management timer (when the user has not reached the selected facility yet, the flow skips SS1418). When the IG signal maintains ON in SS1419, the flow returns to SS1402 to repeat SS1402 or later. When the IG signal is OFF, the energy management process in the cycle ends. As described above, the meal management timer starts after the user has reached an eating facility. It is determined that meal has been finished when a predetermined time has elapsed at a time that the engine starts next time (the IG signal is turned ON), in the processes of SS1516 to 1520 of FIG. 88.

Figure 75:
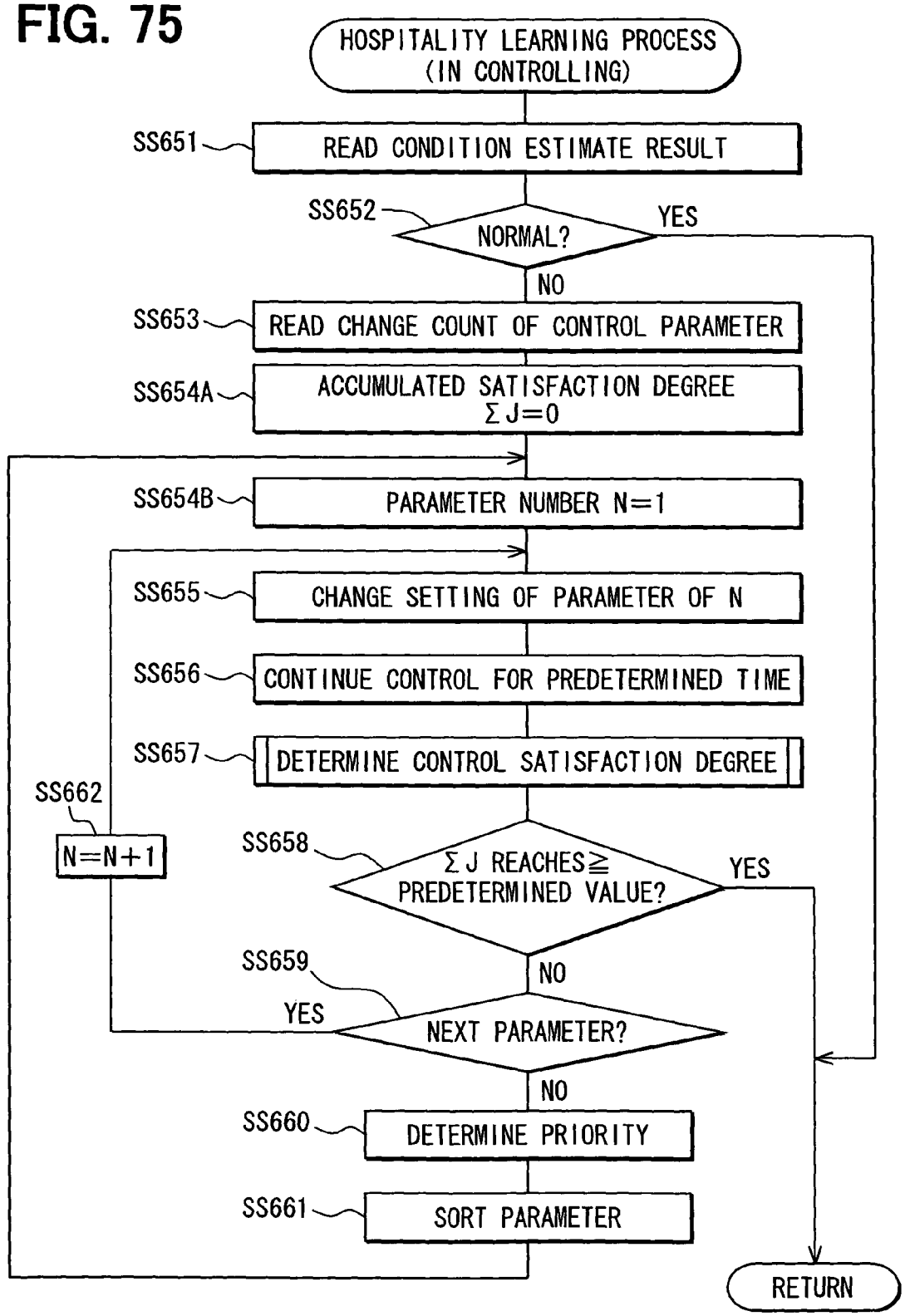
FIG. 75 is a flowchart showing an example of a hospitality operation adjustment process.

Next, FIG. 75 is a flowchart showing a condition confirmation process and an adjustment process of the hospitality operation in accordance with the confirmation result. As described above, after the hospitality operation is started, the detection of the biological condition parameters, and the monitoring of the physical or mental condition in accordance with the waveform analysis of the parameters are continued. In SS651, the latest condition estimate result is read.

This process is executed by referencing the current condition of the condition specifying result table 472. In SS652, when the condition estimate result is normal, the process ends (namely, the hospitality operation is continued in accordance with the current setting condition).

On the other hand, when the condition estimate result is not normal, namely, the condition is somewhat abnormal, the process goes to SS653. By referencing the hospitality control amount setting table 441 shown in FIG. 68 (stored in the ROM or storage device (as a storage unit) 535 of the hospitality determination section 2), the control amount of the hospitality operation device is changed and adjusted. In the hospitality control amount setting table 441, the contents are determined corresponding to the adjustment image of the control appropriate values of the hospitality operation devices of FIG. 67. Specifically, the preset values are changed as follows (refer to the control appropriate value setting table 471a of FIG. 13B).

When the estimated condition is "slightly poor physical condition (or displeasure)," the process is as follows. "An output of the less required light in the lights is decreased to increase the visibility when the user approaches the vehicle." An output of the red light is decreased (in FIG. 72, on the basis of white ("6"), the lighting color index is changed in the direction of blue (for example, "−1")). "Specified required sounds (warning sounds or important sounds) are saved, and mainly the low sound range of the audio output is equalized." A set value of loading the required sounds is increased (for example, "+3"). As shown in FIG. 71, with respect to the audio setting, not only the control appropriate value of the sound volume level but a control appropriate value of the tone setting can be changed. A set value of the low sound is increased relative to a set value of the high sound (for example, low sound "+1," high sound "−1": the high sound may not be changed). "One or both of temperature and humidity is changed to increase, so that the discomfort is eased." The temperature setting of the air conditioner is increased (for example, "+1"), and a humidifier (not shown in FIGS. 13A, 13B) is started. The current settings of the other hospitality operation devices (for example, vibration and fragrance) are maintained.

When the estimated condition is "serious physical condition," the process is as follows. "The lighting is set a little dark by use of white or warm color." In FIG. 72, on the basis of white ("6"), the lighting color index is changed in the red direction (for example, "+1"). The lighting level is decreased (for example, "−1"). "A slow song is played at a small sound level." A slow song is selected, and the sound volume setting level is decreased (for example, "−1": when the condition is not improved, the sound volume is zero finally, or the audio operation may be stopped). The air conditioning is maintained not to stimulate the condition. Unnecessary hospitality operations are stopped (for example, the vibration of the seat vibrator). To improve the physical condition by use of aroma therapy effect, an output of the fragrance is increased (for example, "+1").

In case of the serious physical condition, a hospitality operation for making the user stop driving is executed effectively in accordance with the scenes. The exampled operations are as follows. In the approach scene, the door lock is not released. After the user gets in the vehicle, a voice message for prompting the user to stop driving is outputted. A speed limiter starts to restrict a speed over a predetermined speed.

When the estimated condition is "distraction," the process is as follows. The operations for awaking the user (driver) are executed particularly. "By use of a flashing light and a stimulated wavelength, the user is alerted." On the basis of white ("6"), the lighting color index is changed in the blue direction (for example, "−1"). Alternatively, the lighting color index is changed in the primary color based direction (red, blue, and green). The lighting level is also increased (for example, "−1"). As shown in FIG. 71, a set value is set for the lighting pattern. For example, continuous lighting can be switched to periodic lighting for generating flash light. "A warning sound is outputted." The warning sound is outputted immediately. The setting sound volume is increased (for example, "+1"). The air conditioning is maintained, or the set temperature is decreased for awakening (for decreasing sleepiness). The seat vibrator or steering wheel vibrator is made to generate impulse vibration. Specifically, the set frequency is increased (for example, "+3"). The amplitude is increased(for example, "+3"). The output of the fragrance is stopped (set value "0"). The ammonia for awakening is outputted.

When the estimated condition is "excitation (anger, nervous)," the process is as follows. The mental condition of the user is calmed and eased particularly. "A blue light is used." On the basis of white ("6"), the lighting color index is changed in the blue direction (for example, "−1"). "A song effective for relieving the excitation, such as a soothing song, is selected." The music selection method has been explained above. A set temperature of the air conditioning is deceased to calm the mental condition (for example, "−1"). "The operation of the seat vibrator or steering wheel is eased." The frequency and amplitude are decreased (for example, "−1"). The direction is maintained, or the output of the fragrance is increased to stabilize the mental condition by use of aroma therapy (for example, "+1").

Returning to FIG. 75, the control amounts of the hospitality operation devices are changed and adjusted on the hospitality control amount setting table 441 in accordance with only the parameters (control set values) specifically instructed to be changed. When the multiple parameters exist, all the parameters may be changed at one time, and may be reflected by the hospitality operations. In this embodiment, to confirm a contribution (effect) due to a change of each parameter separately, settings of the multiple parameters are changed sequentially. The order of changing set values of the parameters (namely, the priority of the adjustment of the hospitality operations) follows the priority set in the function selection tables 371, 372 (FIG. 7A to 13B).

In SS654A, an after-mentioned accumulated satisfaction degree ΣJ is initialized. In SS654B, a number N of a parameter to be changed is initialized. In SS655, a number N of a parameter is changed in accordance with an instruction value of the hospitality control amount setting table 441. In SS656, in a condition of the changed setting, the hospitality operation is continued for a predetermined time (hereinafter called a trial hospitality operation). In SS657, a satisfaction degree (called a "control satisfaction degree") of the user at the hospitality operation is determined. Namely, in reference to the satisfaction degree of the user at the hospitality operation as feedback information, the hospitality control amount is changed.

Figure 76:
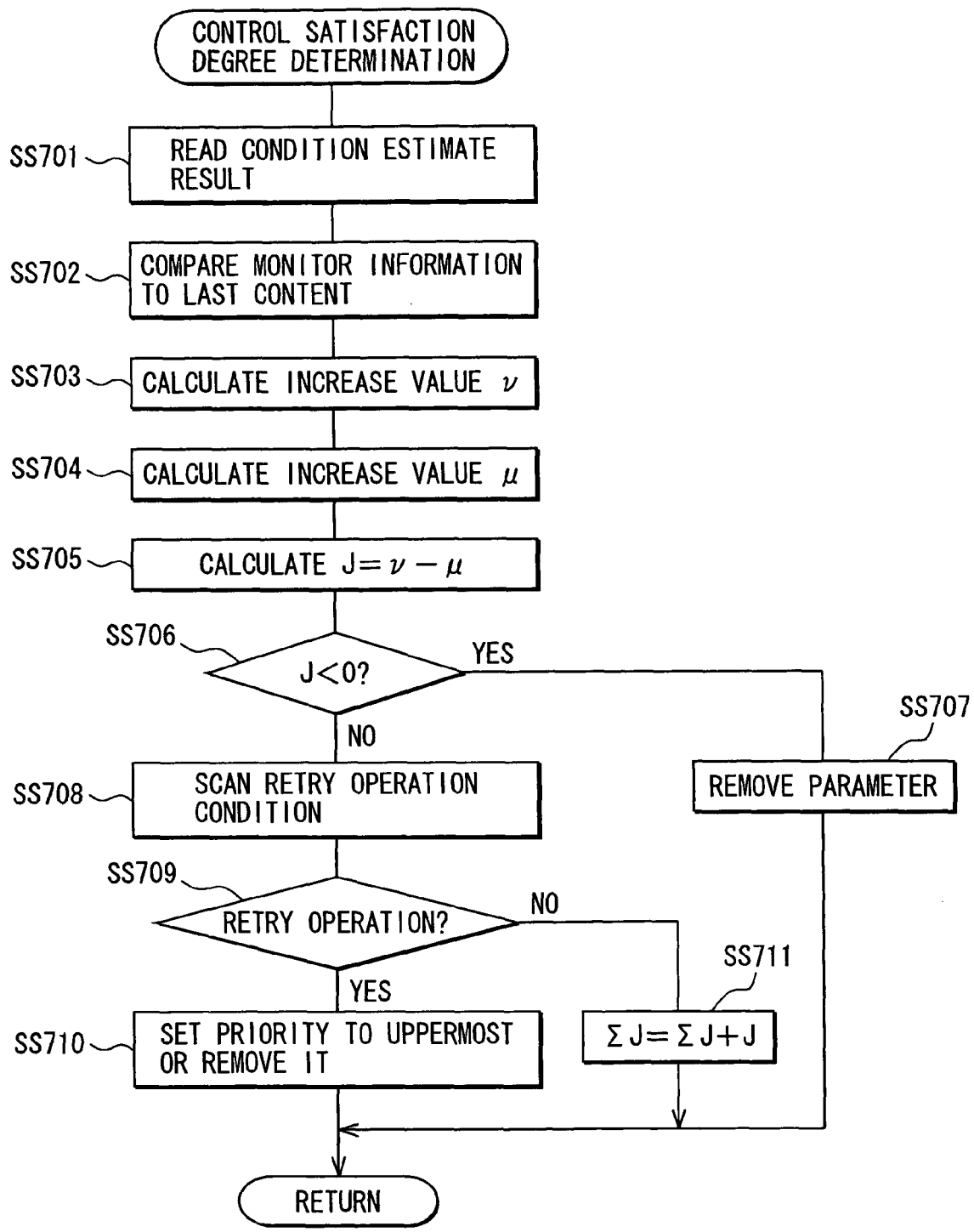
FIG. 76 is a flowchart showing a flow of a control satisfaction degree determination process.

FIG. 76 shows one example of a determination process of the control satisfaction degree. In SS701, to check whether the estimated condition changes in accordance with the trial hospitality operation in SS656, the process accesses the condition specifying result table 472 (FIG. 77) to confirm a content of the monitoring information. In SS702, the content of the monitoring information is compared to the previous content (the previous condition specifying result table 472 may be backed up in the RAM or storage device 535 of the hospitality determination section 2).

In SS703, an increase value of a parameter showing "normal" is calculated. Specifically, the increase value ν is calculated as a sum (expression (7) of FIG. 77) of an increase value Δν of parameters whose contribution to the condition determination is "0." As a simpler value, the sum number of the parameters whose contribution to the condition determination is "0" may be calculated. When the increase value ν is great, the previously estimated "abnormal condition" is released as a result of the trial hospitality operation, and the condition is closer to the normal condition than the previous one. When the increase value ν is small, the condition becomes worse (when a degree of the worse is great, the increase value may become minus).

In SS704, an increase value of a parameter positively contributing to a current condition estimate result ("abnormal condition") is calculated. Specifically, the increase value μ is calculated as a sum (expression (8) of FIG. 77) of increase values Δμ of parameters whose contribution to the condition determination is "2." As a simple value, the sum number of the parameters whose contribution to the condition determination is "2" may be calculated. When the increase value l is great, the previous estimated "abnormal condition" becomes worse as a result of the trial hospitality operation. When the increase value μ is small, the "abnormal condition" is in the released direction (when the released degree is great, the increase value may be minus).

In view of releasing the "abnormal condition," the increase value μ contributes reversely to the increase value ν. The satisfaction degree J when the setting of the parameter is changed is calculated in accordance with the increase value μ and the increase value ν. The satisfaction degree J is calculated as J=ν−μ (when μ and ν are always maintained plus, a ratio between μ and ν (for example, μ/ν) can be used instead). As J is greater, the condition is improved more considerably in accordance with this change if the setting of the parameter. In SS706, it is checked whether this value becomes minus. When J is minus, the condition of the user becomes worse in accordance with the change of the setting of the parameter. In SS707, the parameter is removed from the parameters to be changed (after that, the parameter is returned to the previous value, and maintained, or the hospitality operation relating to the parameter may be stopped).

On the other hand, when the satisfaction degree J is plus in SS706, this change of the parameter setting is effective for improving the condition of the user. The basic process is such that, in SS711, the satisfaction degree J is added to the accumulated satisfaction ΣJ. In this embodiment, before that, whether a retry operation by the user is executed to the operation input portion of the hospitality operation device corresponding to the parameter, is taken into consideration. Specifically, in SS708, a condition of a retry operation by the user executed to the operation input portion of the hospitality operation device corresponding to the parameter is scanned. When the retry operation is not confirmed in SS709, the process goes to SS711.

When the retry operation is confirmed, the process goes to SS710. When the retry operation is positive relative to this change of the parameter setting, the future change of the setting of the parameter is prioritized uppermost. On the other hand, when the retry operation is negative, the parameter is removed from the parameters to be changed. For example, when the user executes a retry operation for decreasing a set temperature of the air conditioner further after the set temperature is decreased, the change of a set temperature of the air conditioner is prioritized uppermost in the future basic cycle. On the other hand, when the user increases the set temperature, a set temperature of the air conditioner is not changed in the future basic cycle. Then, the control satisfaction degree determination process ends.

Returning to FIG. 75, in SS658, it is checked whether the accumulated satisfaction degree $\Sigma J$ reaches a threshold. When the accumulated satisfaction degree $\Sigma J$ reaches the threshold, the process ends. The full marks of the accumulated satisfaction degree $\Sigma J$ can be calculated, for example, from a sum of assumed upper limit values of the values $v$ when all the parameters are "normal condition." A threshold of the accumulated satisfaction degree $\Sigma J$ may be determined in accordance with whether the degree $\Sigma J$ reaches a predetermined ratio on the basis of the full marks.

On the other hand, when the accumulated satisfaction degree $\Sigma J$ does not reach the threshold, the process goes to SS659 to check whether there is a parameter to be changed in the next setting. When there is the parameter, one is added to the parameter number N (SS662). Returning to SS655, the process to SS658 is repeated for the parameter as well. When there is no parameter to be changed, all the parameters to be changed are changed. Returning to SS654B, N is initialized to enter the next cycle, where the same process as above is repeated. In this case, in SS660, an adjustment of the parameter corresponding to the greater value J is prioritized higher. In SS710 of FIG. 76, the parameter prioritized uppermost in response to the retry operation is prioritized regardless of the value J. In SS661, in accordance with the priority, the parameter numbers are sorted. Accordingly, in the next basic cycle, the parameters are adjusted in the new order. The hospitality operation adjustment process of FIG. 75 is started automatically, e.g., at predetermined intervals, and repeated so that the accurate hospitality operation can be continued stably.

Next, one of factors influencing the above condition estimate process is a threshold set for each parameter (X0 in the expressions 1: for example, fu0, fL0, A0, α0, I0, N0, An0, $\Sigma^2 0$, d0, and ηn0 of FIGS. 52A, 52B, 54A, 54B, 55A, 55B, 56, 57A, 57B, 60A, 60B, 61A, 61B, 62A, 62B, and 65). Many thresholds of the parameters are difficult to set at one time, and influenced easily by a individual difference of a user to be monitored. It is more preferable that a process for correcting the thresholds as needed is incorporated into the hospitality operation adjustment process.

Figure 78:
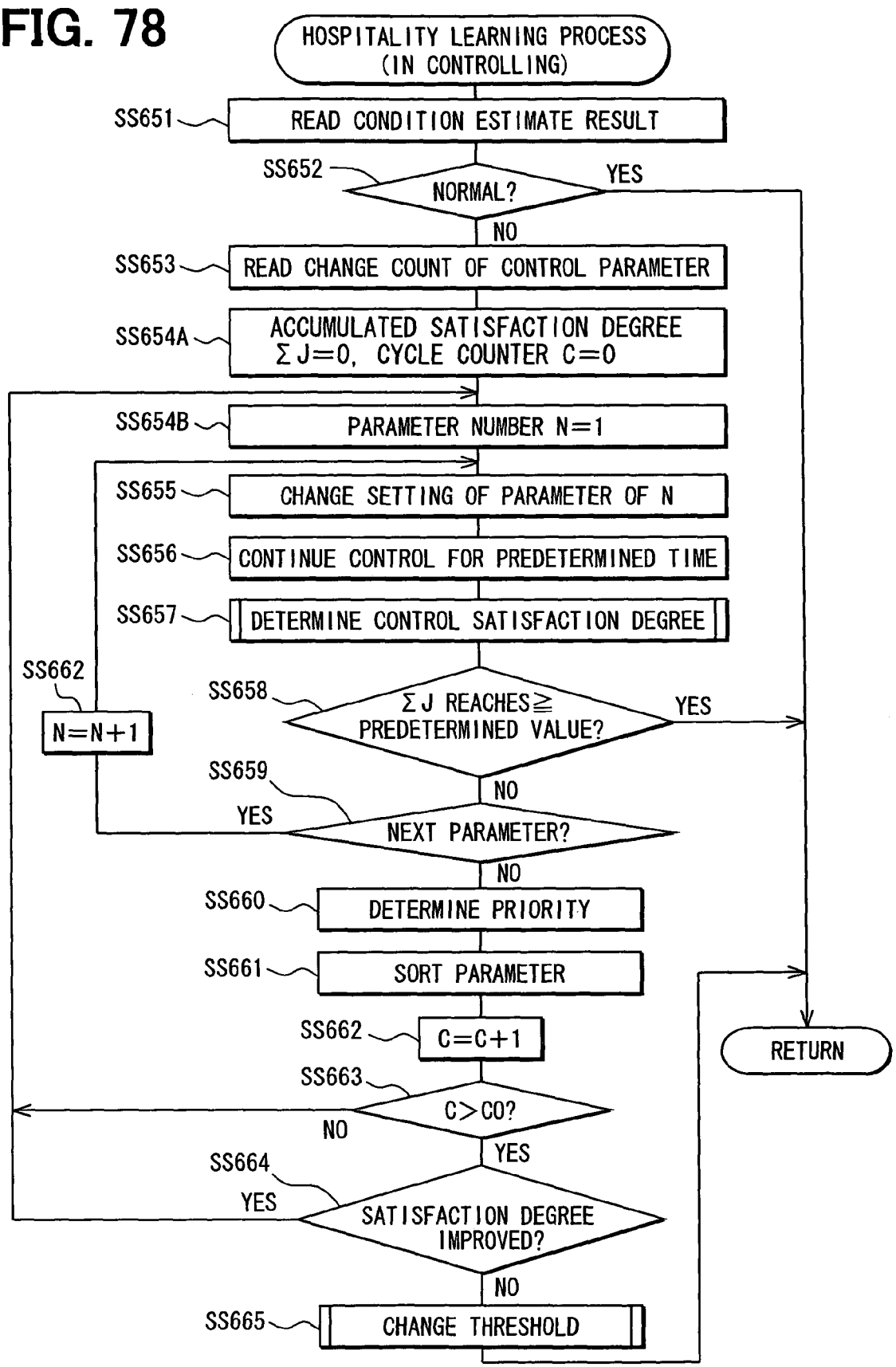
FIG. 78 is a flowchart showing an example of a flow of a hospitality operation adjustment process including a threshold changing process.

FIG. 78 is a flowchart showing an example where a step of correcting the thresholds is incorporated into the process of FIG. 75. A difference between this step and the process of FIG. 75 is mainly explained below. In this process, a threshold is corrected when no improvement of equal to or over a predetermined level is seen in the condition estimate result of the user even after the basic cycle of the hospitality operation adjustment process is repeated predetermined times. In SS654A, a process for initializing a cycle counter C for correcting thresholds is added. In the step to SS661, a step for adjusting related parameters cycles one time, so that the hospitality operation adjustment process for one cycle ends.

In FIG. 75, until the accumulated satisfaction degree $\Sigma J$ is equal to or over a predetermined level, the cycle of the hospitality operation adjustment process is repeated. In the process of FIG. 78, when the satisfaction degree $\Sigma J$ is not improved to equal to or over the predetermined level even after this cycle is repeated predetermined times, the process shifts to the threshold change process in SS665. Namely, each time the cycle is repeated one time, the cycle counter C for the threshold adjustment is incremented (SS662B). When a value of C is equal to or under a defined value C0, the process returns to SS654B to enter the next basic cycle. When a value of C is over the defined value C0, the process goes to SS664. When the satisfaction degree $\Sigma J$ is improved to equal to or over the predetermined level (which is set smaller than a final target value of the satisfaction degree $\Sigma J$ relating to a determination of the end of the adjustment process in SS658), the process returns to SS654B to enter the next basic cycle process.

Figure 79:
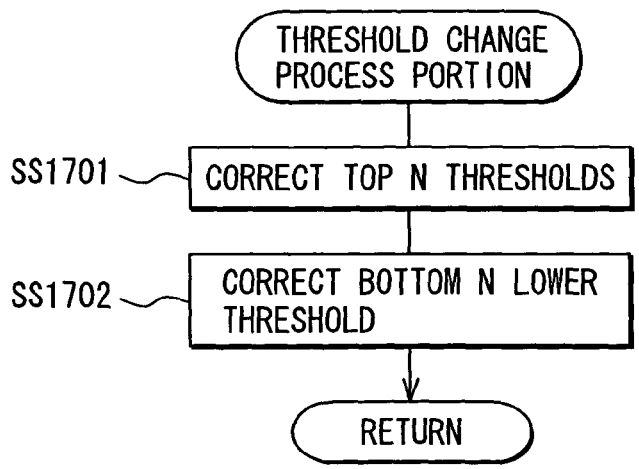
FIG. 79 is a flowchart showing an example of a flow of the threshold changing process.

On the other hand, when the satisfaction degree $\Sigma J$ is improved insufficiently, the threshold change process is executed in SS665. FIG. 79 shows one example of the threshold change process. When a threshold needs to be changed, it is highly possible that the mental or physical condition estimated to be established is wrong. Therefore, to correct this situation, thresholds of a group of parameters positively contributing to the current estimated "abnormal condition" are preferably changed to decrease the contribution ratios in the descending order of the contribution ratios. Thresholds of a group of parameters positively contributing to the current estimated "normal condition" are preferably changed to increase the contribution ratios in the ascending order of the contribution ratios. As the contribution ratio, a deviation $\Delta\mu$ or $\Delta v$ from each parameter, explained above, can be used.

In FIG. 79, in SS1701, the top n thresholds having greater $\Delta\mu$ in thresholds of a group of parameters positively contributing to the "abnormal condition" are decreased by a predetermined amount so that $\Delta\mu$ decreases. In SS1702, the bottom n thresholds having greater $\Delta v$ in thresholds of a group of parameters showing the "normal condition" are decreased by a predetermined amount so that $\Delta v$ increases. The n may be one or more (in this case, all the corresponding parameters may be corrected).

Only one of SS1701 and SS1702 can be executed. Particularly, to correct the situation where the currently estimated "abnormal condition" is wrong, it is preferable that SS1701 is executed essentially. In this case, SS1702 can be abbreviated. When the process returns to the hospitality operation adjustment process of FIG. 78 after SS1701 is executed, thresholds of parameters forming a backbone for determining the abnormal condition are changed, and the priority of the parameters is decreased forcibly. When the thresholds are corrected rightly, parameters reflecting an actual physical or mental condition in the remaining parameters are provided with the opportunity to be prioritized higher.

On the other hand, SS1702 relates to a process for correcting thresholds of a group of parameters showing "normal condition." The current condition is estimated to be the "abnormal condition." When this estimate reflects the correct mental or physical condition, a group of parameters showing "normal condition" is unqualified basically as ones used for estimating the mental or physical condition. However, in this case, the estimated "abnormal condition" does not reflect the correct mental or physical condition. Accordingly, at least some of a group of the parameters showing "normal condition" are possibly parameters adapted for estimating an actual mental or physical condition. The parameters having small Δv less contribute to the accumulated satisfaction degree, so that the parameters are possibly buried in the current hospitality operation process. The lower n number of thresholds having greater Δv in thresholds of a group of the parameters showing the "normal condition" is corrected by a predetermined amount so that Δv increases. Accordingly, some of the lower prioritized parameters showing the "normal condition" can be prioritized higher.

Instead of changing the thresholds as described above (or together with the change of the thresholds), weighting factors shown in FIG. 77 are changed. In this case, in SS1701 of FIG. 79, in a group of the parameters positively contributing to the "abnormal condition," top n weighting factors corresponding to greater Δμ may be decreased by a predetermined amount. In SS1702, in a group of the parameters positively contributing to the "normal condition," bottom n weighting factors corresponding to smaller Δv may be increased by a predetermined amount.

The default data of each threshold common to each user is prepared, and mounted, e.g., by a dealer of vehicles. The data is provided with the above threshold change process, so that the data is customized unique to each user. As shown in FIG. 73A, a group of the customized thresholds are stored corresponding to the user specifying information, as the user mental or physical condition determination threshold 435. In the future, when a user of the vehicle is specified, a group of the thresholds corresponding to the user are read, and set as default values. Even when the user of the vehicle changes together with the above user default setting data 434, the hospitality operations are adjusted by use of the control default values and thresholds unique to the user. For example, when multiple users share the vehicle, the hospitality operations are adapted for each user, so that every user can use the vehicle comfortably.

Multiple sets of the biological condition detection units (FIG. 1: sensor and camera group 518 to 528) used for the hospitality determination are provided corresponding to multiple seats of the vehicle. Mental and physical conditions of each user seated on each seat can be detected separately. In this case, the hospitality determination section 2 can determine operations of the hospitality operation devices in accordance with the mental and physical conditions of the multiple users corresponding to the sets of the biological condition detection units. In this case, the operations of the hospitality operation devices can be determined so that the user corresponding to the estimated worst mental and physical conditions (for example, serious physical condition) is prioritized.

Data items unique to each user (such as user ID or personal identification number 401, biometrics master data 432, user default setting data 434, user mental or physical condition determination threshold 435, and stress reflection operation statistics data in the storage unit 405) are shown in data 440 for various hospitality determinations (in FIG. 73A). Some of the data items can be stored in a data server 561 of a management center 560 which can communicate with the vehicle, instead of in the storage device in the vehicle such as the storage device 535. Then, the unique data may be obtained as needed in accordance with a request from the vehicle, and used. Accordingly, the security problem such as the case where the vehicle is misused by a stranger can be decreased. When the user switches to another vehicle provided with a hardware infrastructure of this vehicular user hospitality system, the data unique to each user is obtained from the management center 560. Accordingly, even in another vehicle, the same hospitality as the former vehicle can be provided, so that a more flexible system structure can be achieved.

Each or any combination of processes, steps, or means explained in the above can be achieved as a software unit (e.g., subroutine) and/or a hardware unit (e.g., circuit or integrated circuit), including or not including a function of a related device; furthermore, the hardware unit can be constructed inside of a microcomputer.

Furthermore, the software unit or any combinations of multiple software units can be included in a software program, which can be contained in a computer-readable storage media or can be downloaded and installed in a computer via a communications network.

It will be obvious to those skilled in the art that various changes may be made in the above-described embodiments of the present invention. However, the scope of the present invention should be determined by the following claims.

What is claimed is:

1. A system for providing vehicular hospitality information, said system comprising:
a data acquisition unit located in a user's vehicle and configured to acquire user biological characteristic information based on a temporal change in a biological condition of the user;
a memory configured to store hospitality information to assist the user;
a data retrieval unit configured to retrieve hospitality information corresponding to the acquired user biological characteristic information;
an information output unit located on said vehicle and configured to output the retrieved hospitality information to the user; and
an estimator configured to estimate a user's current biological condition by (a) defining the user's biological condition as an energy value that is consumed over time in one direction without supply and (b) calculating the estimated current energy value based on the detected temporal change of the biological condition;
wherein the data retrieval unit is configured to retrieve hospitality information corresponding to the estimated current energy value and which promotes improvement of the energy value.

2. The system of claim 1, wherein:
the data retrieval unit comprises a vehicle navigation apparatus;
the memory includes a destination database for setting a travel destination in the vehicle navigation apparatus,
the destination database stores classification information respectively relating corresponding destination information to user biological characteristic information;
the data retrieval unit retrieves a travel destination classified by the classification information as related to the acquired user biological characteristic information; and
the information output unit outputs the retrieved travel destination on a display screen of the vehicle navigation apparatus.

3. The system of claim 2, wherein:
the acquired user biological characteristic information comprises hunger information reflecting a user's degree of hunger, and
the data retrieval unit retrieves from the destination database at least one eating-possible facility destination within a predetermined range of the vehicle's current location where eating is possible when the acquired hunger information satisfies a predetermined condition.

4. The system of claim 3, further comprising:
timing means; and
means for determining a predetermined meal time in accordance with time information from the timing means,
wherein the data acquisition unit determines a coming meal time as hunger information.

5. The system of claim 3, further comprising:
means for timing an elapsed time after a user meal,
wherein the data acquisition unit utilizes the elapsed time as hunger information.

6. The system of claim 1, wherein:
the estimator estimates the user's biological condition in accordance with amplitude of the waveform of a temporal change in the biological condition.

7. The system of claim 1, wherein: the estimator estimates the user's biological condition in accordance frequency of a waveform of a temporal change in the biological condition.

8. The system of claim 1, wherein:
a detected temporal change of a user's body temperature is used as the temporal change in the user's biological condition.

9. The system of claim 1, wherein:
a detected temporal change of at least one of (i) a facial expression and (ii) a line-of-sight of the user is used as the temporal change in the user's biological condition.

10. The system of claim 1, wherein:
a temporal change of the biological condition is detected while the user is driving.

11. The system of claim 10, wherein:
a temporal change of a first biological condition of one or more of (i) blood pressure, (ii) heart rate, (iii) body temperature, (iv) skin resistance, and (v) perspiration is acquired as the temporal change of the user's biological condition.

12. The system of claim 11, wherein:
a user's mental condition is estimated as abnormal when a waveform frequency of the first biological condition is equal to or greater than a predetermined level.

13. The system of claim 10, wherein:
a detected temporal change of a second biological condition of at least one of (i) an attitude, (ii) a line-of-sight, and (iii) a facial expression of the user who is driving is acquired as the temporal change of the biological condition.

14. The system of claim 13, wherein:
a user's physical condition is estimated as abnormal when a waveform amplitude of the second biological condition is equal to or less than a predetermined level.

15. The system of claim 13, wherein:
a user's mental condition is estimated to be abnormal when a waveform frequency of the second biological condition is (a) equal to or greater than a predetermined level, or (b) equal to or less than a predetermined level.

16. The system of claim 13, wherein:
a temporal change of a pupil size of the user is detected as the temporal change of the biological condition, and
a user's physical condition is estimated to be abnormal when the detected pupil size changes by an amount equal to or greater than a predetermined level.

17. The system of claim 16, wherein:
a user's mental condition is estimated to be abnormal when the detected pupil size is enlarged by an amount equal to or greater than a predetermined level.

18. The system of claim 13, wherein:
a user's mental condition or physical condition is estimated in accordance with a combination of temporal changes of biological condition parameters detected by a plurality of detectors.

19. The system of claim 1, wherein:
the acquired user biological information comprises hunger information reflecting a degree of the user's hunger,
the data retrieval unit retrieves from the destination database at least one eating-possible facility destination within a predetermined range of the vehicle's current location where eating is possible when the acquired hunger information satisfies a predetermined condition, and
the displayed hospitality information about the eating-possible facility provides a respectively corresponding predetermined quality classification of the estimated physical condition of the eating-possible facility.

20. The system of claim 19, wherein:
the provided quality classification data distinguishes the retrieved eating-possible facility between eating-possible facilities serving low-calorie foods and eating-possible facilities serving plain foods.

21. A system for providing vehicular hospitality information as in claim 1, wherein:
said data acquisition unit is configured to acquire user biological characteristic information reflecting the user's mental condition and the user's physical condition;
said data retrieval unit is configured to retrieve hospitality information in accordance with a predetermined correlation between two pieces of the user biological characteristic information and the stored hospitality information;
the memory is further configured to store classification information related to at least one of (i) the mental condition, and (ii) the physical condition, and respectively corresponding hospitality information;
the estimator is configured to estimate a user's mental or physical condition by (a) defining the user's mental or physical condition as an energy value that is consumed over time in one direction without supply, and (b) calculating the estimated current energy value based on the detected temporal change of the biological condition; and
the retrieval unit is further configured to find the classification information corresponding to the estimated mental or physical condition, and retrieve, from the memory, hospitality information which is classified by the classification information and which improves the energy value.

22. A system for providing vehicular hospitality information as in claim 1, wherein
said data acquisition unit is configured to acquire user biological characteristic information reflecting a user's mental condition and the user's physical condition;
said data retrieval unit is configured to classify the acquired user biological characteristic information into at least two or more of (i) energy, (ii) stress, and (iii) damage to estimate a user's condition, and thereby to retrieve hospitality information matching the user biological characteristic information in accordance with a predetermined correlation between the estimated user's condition and the stored hospitality information; and
the memory is further configured to store classification information related to at least one of (i) the mental condition, and (ii) the physical condition, and respectively corresponding hospitality information;

the estimator is configured to estimate a user's mental or physical condition by (a) defining the user's mental or physical condition as an energy value that is consumed over time in one direction without supply and (b) calculating the estimated current energy value based on detected temporal change of the biological condition value; and the data retrieval unit is further configured to find the classification information corresponding to the estimated mental or physical condition, and retrieve hospitality information which is classified by the classification information and which improves the energy value.

23. A system for providing vehicular hospitality information as in claim 1, wherein:

said data acquisition unit is configured to acquire a user's character and user biological characteristic information reflecting at least one of (i) a mental condition and (ii) a physical condition;

the memory is further configured to store classification information related to at least one of (i) the character, (ii) the mental condition, and (iii) the physical condition, and respectively corresponding hospitality information;

the estimator is configured to estimate a user's mental or physical condition by (a) defining the user's mental or physical condition as an energy value that is consumed over time in one direction without supply and (b) calculating the estimated current energy value based on the detected temporal change of the biological condition value; and the data retrieval unit is further configured to find the classification information corresponding to the estimated mental or physical condition, and retrieve hospitality information which is classified by the classification information and which improves the energy value.

24. A system for providing vehicular hospitality information as in claim 1, wherein:

said data acquisition unit is configured to acquire the user's character and user biological characteristic information reflecting at least one of (i) a mental condition and (ii) a physical condition;

said data retrieval unit is configured to retrieve hospitality information matching corrected user's preference data acquired by correcting default user's preference data which is set based on character data acquired by the data acquisition unit, by use of user biological characteristic information acquired by the data acquisition unit from the stored hospitality information, in accordance with a predetermined correlation between the user biological characteristic information and the stored hospitality information, and the memory is further configured to store classification information related to at least one of (i) the character, (ii) the mental condition, and (iii) the physical condition, and respectively corresponding hospitality information;

a user's mental or physical condition is estimated by (a) defining the user's mental or physical condition as an energy value that is consumed over time in one direction without supply and (b) calculating the energy value based on the detected temporal change of the biological condition value; and the data retrieval unit is further configured to find the classification information corresponding to the estimated mental or physical condition, and retrieve hospitality information which is classified by the classification information and which improves the energy value.

25. The system of claim 3, further comprising:

an engine start detection unit configured to detect starting of an engine of the vehicle; and a meal-finish determination unit configured to determine, when an engine start is detected, whether the user finished a meal during an engine stop just prior to the engine start, wherein:

the estimator calculates as the energy value a user's physical energy value, which is consumed over time and supplied when it is determined that the meal was finished during the engine stop, using a predetermined algorithm based on the hunger information; and the data retrieval unit determines that the user is in a hungry state when the physical energy value becomes smaller than a predetermined threshold value, and retrieves the eating-possible facility from the destination database.

26. The system of claim 25, further comprising:

a destination arrival determination unit configured to determine whether the vehicle has arrived at the destination;

a time measurement unit configured to measure an elapsed time since arriving at the destination;

an engine determination unit configured to determine whether an engine start detected by the engine start detection unit is a first time for engine start in a day;

a meal information storage unit configured to store meal-finish confirmation information which indicates whether the user finished a meal; and an update unit configured to update the meal-finish confirmation information into a meal finished status when it is determined that the meal was finished during the engine stop, wherein:

the meal-finish determination unit determines that the meal was finished during the engine stop just prior to the engine start under a predetermined condition being satisfied when a first to fifth states take place simultaneously, the first state is that the vehicle arrived at the destination, the second state is that the destination is an eating-possible facility, the third state is that an elapsed time since arriving at the eating-possible facility is equal to or greater than a predetermined threshold time corresponding to a finish of the meal, the fourth state is that the engine start detected after arriving at the eating-possible facility is not the first time of the day, and the fifth state is that the meal-finish confirmation information indicates that the meal was not finished before the engine start; and the update unit updates the meal-finish confirmation information from a meal not-finished status to a meal finished status.

27. The system of claim 25, wherein:

the predetermined threshold value of the physical energy value is provided with a first threshold value and a second threshold value higher than the first threshold value;

the data retrieval unit retrieves an eating-possible facility, which corresponds to the physical energy state in each of a first case and a second case, from the destination database, the first case being a case that the physical energy value comes to be smaller than the first threshold value, the second case being a case that the physical energy value comes to be in between the first threshold value and the second threshold value.

* * * * *